United States Patent
Hiroki et al.

(10) Patent No.: US 10,377,737 B2
(45) Date of Patent: Aug. 13, 2019

(54) 1,2,3-TRIAZOLE DERIVATIVE AND INSECTICIDE AND ACARICIDE CONTAINING SAID DERIVATIVE AS ACTIVE INGREDIENT

(71) Applicant: HOKKO CHEMICAL INDUSTRY CO., LTD., Tokyo (JP)

(72) Inventors: Hidekatsu Hiroki, Kanagawa (JP); Yuta Kobayashi, Kanagawa (JP); Jun Suzuki, Kanagawa (JP); Shinji Onoue, Kanagawa (JP); Katsuhiko Iwasaki, Kanagawa (JP); Akihito Ootaka, Kanagawa (JP); Hayato Doi, Kanagawa (JP); Eiko Matsuo, Kanagawa (JP); Miwa Onoue, Kanagawa (JP); Asako Okimoto, Kanagawa (JP)

(73) Assignee: HOKKO CHEMICAL INDUSTRY CO., LTD., Tokyo (JP)

( * ) Notice: Subject to any disclaimer, the term of this patent is extended or adjusted under 35 U.S.C. 154(b) by 0 days.

(21) Appl. No.: 15/993,211

(22) Filed: May 30, 2018

(65) Prior Publication Data

US 2018/0290986 A1 Oct. 11, 2018

Related U.S. Application Data

(63) Continuation of application No. PCT/JP2016/085601, filed on Nov. 30, 2016.

(30) Foreign Application Priority Data

Nov. 30, 2015 (JP) ................................. 2015-233791

(51) Int. Cl.
| | |
|---|---|
| C07D 401/04 | (2006.01) |
| C07D 403/10 | (2006.01) |
| C07D 401/14 | (2006.01) |
| C07D 413/10 | (2006.01) |
| C07D 249/06 | (2006.01) |
| A01N 43/82 | (2006.01) |
| A01N 43/647 | (2006.01) |
| A61K 31/4439 | (2006.01) |
| A61K 31/4192 | (2006.01) |

(52) U.S. Cl.
CPC ......... *C07D 401/04* (2013.01); *A01N 43/647* (2013.01); *A01N 43/82* (2013.01); *A61K 31/4192* (2013.01); *A61K 31/4439* (2013.01); *C07D 249/06* (2013.01); *C07D 401/14* (2013.01); *C07D 403/10* (2013.01); *C07D 413/10* (2013.01)

(58) Field of Classification Search
None
See application file for complete search history.

(56) References Cited

U.S. PATENT DOCUMENTS

| | | |
|---|---|---|
| 2011/0021539 A1 | 1/2011 | Schwarz et al. |
| 2012/0190687 A1 | 7/2012 | Schwarz et al. |
| 2013/0012547 A1 | 1/2013 | Jung et al. |
| 2015/0189880 A1 | 7/2015 | Maehata et al. |
| 2015/0246911 A1 | 9/2015 | Takahashi et al. |
| 2015/0336895 A1 | 11/2015 | Maehata et al. |
| 2016/0002260 A1 | 1/2016 | Tanabe et al. |
| 2016/0021886 A1 | 1/2016 | Yonemura et al. |
| 2016/0278379 A1 | 9/2016 | Hallenbach et al. |
| 2016/0280668 A1 | 9/2016 | Hallenbach et al. |
| 2016/0297765 A1 | 10/2016 | Hallenbach et al. |
| 2016/0302414 A1 | 10/2016 | Jung et al. |
| 2016/0368915 A1 | 12/2016 | Tanabe et al. |
| 2017/0027173 A1 | 2/2017 | Jung et al. |
| 2017/0144988 A1 | 5/2017 | Hallenbach et al. |
| 2018/0160686 A1* | 6/2018 | Aoyama ............. C07D 401/14 |

FOREIGN PATENT DOCUMENTS

| | | |
|---|---|---|
| EP | 2 955 178 | 12/2015 |
| EP | 2 955 179 | 12/2015 |
| EP | 2 963 022 | 1/2016 |
| EP | 3 312 162 | 4/2018 |
| JP | 2012-188418 | 10/2012 |
| JP | 2013-522263 | 6/2013 |
| JP | 2015-3906 | 1/2015 |
| WO | 2010/136145 | 12/2010 |
| WO | 2011/113756 | 9/2011 |
| WO | 2012/175474 | 12/2012 |
| WO | 2013/191188 | 12/2013 |
| WO | 2014/002754 | 1/2014 |
| WO | 2014/021468 | 2/2014 |
| WO | 2014/104407 | 7/2014 |
| WO | 2014/123205 | 8/2014 |
| WO | 2014/123206 | 8/2014 |
| WO | 2014/132971 | 9/2014 |
| WO | 2014/132972 | 9/2014 |

(Continued)

OTHER PUBLICATIONS

International Search Report dated Feb. 28, 2017 in International (PCT) Application No. PCT/JP2016/085601.

Hohloch et al., "Copper (I) Complexes of Normal and Abnormal Carbenes and Ther Use as Catalysts for the Huisgen [3+2] Cycloaddition between Azides and Alkynes", European Journal of Inorganic Chemistry, No. 20, 2011, pp. 3067-3075.

Xu et al., "Copper-Catalyzed Trifluoromethylthiolation of Aryl Halides with Diverse Directing Groups", Organic Letters, vol. 16, 2014, pp. 3942-3945.

Schweinfurth et al., "Heterobimetallic Cu-dppf (dppf =1,1'-Bis(diphenylphosphino)ferrocene) Complezes with "Click" Derived Ligends: A combined Structural, Electrochemical, Spectroelectochemical, and Theoretical Study", Organometallics, vol. 32, No. 20, 2013, pp. 5834-5842.

(Continued)

*Primary Examiner* — Bethany P Barham
*Assistant Examiner* — Barbara S Frazier
(74) *Attorney, Agent, or Firm* — Wenderoth, Lind & Ponack, L.L.P.

(57) ABSTRACT

The present invention provides a 1,2,3-triazole derivative and an insecticide or acaricide containing the 1,2,3-triazole derivative as an active ingredient.

2 Claims, No Drawings

(56) References Cited

FOREIGN PATENT DOCUMENTS

| WO | 2014/142292 | 9/2014 | | |
|---|---|---|---|---|
| WO | 2014/148451 | 9/2014 | | |
| WO | 2014/157600 | 10/2014 | | |
| WO | 2015/000715 | 1/2015 | | |
| WO | 2015/002211 | 1/2015 | | |
| WO | 2015/067646 | 5/2015 | | |
| WO | 2015/067648 | 5/2015 | | |
| WO | 2015/068719 | 5/2015 | | |
| WO | 2015/144826 | 10/2015 | | |
| WO | 2015/144895 | 10/2015 | | |
| WO | 2016/008830 | 1/2016 | | |
| WO | 2016/204270 | 12/2016 | | |
| WO | WO-2016204270 A1 * | 12/2016 | ........... | C07D 401/14 |
| WO | 2017/050751 | 3/2017 | | |

OTHER PUBLICATIONS

Extended European Search & Report dated Apr. 1, 2019 in European Patent Application No. 16870727.1.

* cited by examiner

1,2,3-TRIAZOLE DERIVATIVE AND INSECTICIDE AND ACARICIDE CONTAINING SAID DERIVATIVE AS ACTIVE INGREDIENT

TECHNICAL FIELD

The present invention relates to a novel 1,2,3-triazole derivative and an insecticide or acaricide containing the derivative as an active ingredient.

BACKGROUND ART

Heretofore, in the agricultural/horticultural field, insecticides or acaricides intended to control various pests are used in practice. However, conventional general-purpose insecticides or acaricides are not always satisfied in terms of efficacy, spectrum, residual effectiveness, etc. As well, the societal requirements such as reduction in the number of applications or the rate of application are not sufficiently fulfilled.

In addition, appearance of pests having gained resistance to conventional general-purpose insecticides or acaricides also becomes a problem. For example, in the cultivation of vegetables, fruit trees, ornamental flowers, teas, wheat/barley, etc., it is becoming difficult to control pests having gained resistance to insecticides or acaricides of various systems, for example, organophosphorus agents (e.g., fenitrothion, malathion, prothiofos, DDVP) and pyrethroid-based (e.g., permethrin, cypermerin, fenvalerate, cyhalothrin), benzoylurea-based (e.g., diflubenzuron, teflubenzuron, chlorfluazuron) and nereistoxin-based (e.g., cartap, bensultap) insecticides or acaricides.

Furthermore, although there are insecticides or acaricides to which pests have not yet gained resistance (for example, organic halogen-based agrochemicals such as DDT and BHC, and chlorinated cyclic diene-based agrochemicals such as aldrin, dieldrin, endrin, heptachlor and benzoepin), these are disadvantageous in view of toxicity, environmental pollution, etc. Accordingly, it is keenly demanded to develop a novel insecticide or acaricide exhibiting a sufficient control effect with a small dosage also on various pests having gained resistance to agricultural/horticultural insecticides or acaricides that have been conventionally used for general purposes.

As to a 1,2,3-triazole derivative exhibiting an insecticidal or acaricidal activity, for example, Patent Document 1 describes a 1,2,3-triazole derivative having an insecticidal or acaricidal activity against various pests but discloses none of the 1,2,3-triazole derivative according to the present invention. In addition, although a compound analogous to the present invention is described in Patent Documents 2 to 18, there is absolutely no description of the 1,2,3-triazole derivative of the present invention in which the 1,2,3-triazole ring is substituted at the 1-position with a 2-alkyl thio group, a 2-alkylsulfinyl group or a 2-alkylsulfonyl group and substituted with a phenyl group that may be substituted with other substituent.

BACKGROUND ART LITERATURE

Patent Document

Patent Document 1: WO 2011/113756
Patent Document 2: WO 2015/144895
Patent Document 3: WO 2015/144826
Patent Document 4: WO 2015/068719
Patent Document 5: JP-A-2015-003906
Patent Document 6: WO 2015/002211
Patent Document 7: WO 2015/000715
Patent Document 8: WO 2014/157600
Patent Document 9: WO 2014/148451
Patent Document 10: WO 2014/142292
Patent Document 11: WO 2014/132972
Patent Document 12: WO 2014/132971
Patent Document 13: WO 2014/123206
Patent Document 14: WO 2014/123205
Patent Document 15: WO 2014/104407
Patent Document 16: WO 2014/021468
Patent Document 17: WO 2014/002754
Patent Document 18: WO 2013/191188

SUMMARY OF THE INVENTION

Problems that the Invention is to Solve

An object of the present invention is to provide a novel 1,2,3-triazole derivative and an insecticide or acaricide containing the same.

Means for Solving the Problems

As a result of many intensive studies to attain the object above, the present inventors have found that a 1,2,3-triazole derivative represented by the following formula (1) has an insecticidal or acaricidal activity, and accomplished the present invention.

Accordingly, a first aspect of the present application relates to a 1,2,3-triazole derivative represented by the following formula (1) (in the present description, sometimes referred to as "compound of the present invention"), and a second aspect relates to an insecticide or acaricide characterized by containing a 1,2,3-triazole derivative represented by formula (1) as an active ingredient.

More specifically, the present inventors have found that the above-described problems can be solved by the following configurations.

<1> A 1,2,3-triazole derivative represented by the following formula (1):

[Chem. 1]

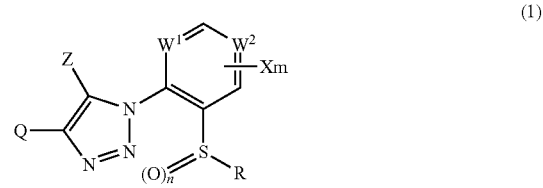

wherein in the formula (1):
R represents a C1-C6 alkyl group or a C1-C6 haloalkyl group;
n represents an integer of 0 to 2;
each of $W^1$ and $W^2$ independently represents CH or a nitrogen atom;
X represents a hydrogen atom, a halogen atom, a cyano group, a nitro group, an amino group, a hydroxyl group, a carboxyl group, a C1-C6 alkyl group that may be substituted with a hydroxyl group or a cyano group, a C3-C6 cycloalkyl group that may be substituted with a cyano group, a (C1-C6 alkoxy)C1-C6 fluoroalkyl group, a C1-C6 alkoxy group, a C1-C6 alkylsulfonyloxy group, a (C1-C6 alkoxy)C1-C6 alkoxy group, a C1-C6 haloalkyl group that may be substituted with a cyano group, a C1-C6 haloalkoxy group, a C1-C6 alkylcarbonyl group, a C1-C6 haloalkylsulfonyloxy group, a C1-C6 alkylthio group, a C1-C6 alkylsulfinyl group, a C1-C6 alkylsulfonyl group, a C1-C6 haloalkylthio group, a C1-C6 haloalkylsulfinyl group, a C1-C6 haloalkylsulfonyl group, a C1-C6 alkylamino group, a (C1-C6 alkoxy)carbonyl group, a di(C1-C6 alkyl)amino group, a (C1-C6 alkyl)carbonylamino group, a (C1-C6 alkyl)carbonyl(C1-C6 alkyl)amino group, an N—(C1-C6 alkyl)carbamoyl group, an N,N'-di(C1-C6 alkyl)carbamoyl group, a pentafluorosulfanyl group, a triazolyl group that may be substituted with a C1-C6 alkyl group, an oxadiazolyl group that may be substituted with a C1-C6 alkyl group, a tetrazolyl group that may be substituted with a C1-C6 alkyl group, a (tetrazolyl that may be substituted with a C1-C6 haloalkyl group)C1-C6 alkyl group, a benzoyl group that may be substituted with a halogen atom, an arylsulfonyl group that may be substituted with a halogen atom, an arylsulfinyl group that may be substituted with a halogen atom, an arylthio group that may be substituted with a halogen atom, an arylamino group that may be substituted with a halogen atom, an aryloxy group that may be substituted with a halogen atom, or an aryl group that may be substituted with a halogen atom;

m represents an integer of 1 to 4 and when m represents an integer of 2 or more, respective X may be the same or different;

Q represents a phenyl group, a pyridyl group, a thiazolyl group, a quinolyl group, a benzoxazolyl group, a benzothiazolyl group or a benzimidazolyl group, each of which may be substituted with one or more groups selected from the group consisting of a halogen atom, a cyano group, a nitro group, a carboxyl group, a C1-C6 alkyl group that may be substituted with a hydroxyl group or a cyano group, a C3-C6 cycloalkyl group that may be substituted with a cyano group, a C1-C6 alkoxy group, a C1-C6 haloalkyl group that may be substituted with a cyano group, a C1-C6 haloalkyl group {substituted with an N-carbamoyl group (that may be substituted with a C1-C6 alkyl group)}, a C1-C6 haloalkyl group {substituted with an N-arylcarbamoyl group (that may be substituted with a halogen atom or a C1-C6 alkyl group)}, a C1-C6 haloalkoxy group, a C1-C6 alkylthio group, a C1-C6 haloalkylthio group, a C1-C6 alkoxycarbonyl group, a C1-C6 alkylsulfinyl group, a C1-C6 alkylsulfonyl group, a C1-C6 alkylcarbonyl group, a C1-C6 haloalkylcarbonyl group, a pentafluorosulfanyl group, an N—(C1-C6 alkyl)carbamoyl group, an N—(C1-C6 haloalkyl)carbamoyl group, an N-(phenyl)carbamoyl group that may be substituted with a halogen atom or a C1-C6 alkyl group, an N-(pyridyl)carbamoyl group that may be substituted with a halogen atom or a C1-C6 alkyl group, an N,N'-di(C1-C6 alkyl)carbamoyl group, an N—(C1-C6 alkylcarbonyl)amino group, an N—(C1-C6 haloalkylcarbonyl)amino group, an N—(C1-C6 alkoxycarbonyl)amino group, an N—(C1-C6 haloalkoxycarbonyl)amino group, a C1-C6 alkylsulfonylamino group in which the nitrogen atom may be substituted with a C1-C6 alkyl group, a C1-C6 haloalkylsulfonylamino group in which the nitrogen atom may be substituted with a C1-C6 alkyl group, a phenylsulfonylamino group in which the nitrogen atom may be substituted with a C1-C6 alkyl group and the phenyl group may be substituted with a halogen atom or a C1-C6 alkyl group, a (C1-C6 alkyl)aminosulfonyl group in which the nitrogen atom may be substituted with a C1-C6 alkyl group, a phenyl group that may be substituted with a halogen atom or a C1-C6 alkyl group, a phenoxy group that may be substituted with a halogen atom or a C1-C6 alkyl group, and a benzoyl group that may be substituted with a halogen atom; and Z represents a hydrogen atom, a halogen atom, a cyano group, an amino group, a carboxyl group, a carbamoyl group, a C1-C6 alkyl group, a C3-C6 cycloalkyl group, a C1-C6 alkoxy group, a (C1-C6 alkoxy)C1-C6 alkyl group, a C1-C6 haloalkyl group, a C1-C6 alkylthio group, a C1-C6 haloalkylthio group, a C1-C6 alkylamino group, a di(C1-C6 alkyl)amino group, a C1-C6 alkoxycarbonyl group, a (C1-C6 alkyl)carbonylamino group, an N—(C1-C6 alkyl)carbamoyl group, an N—(C1-C6 haloalkyl)carbamoyl group, an N-(phenyl)carbamoyl group that may be substituted with a halogen atom or a C1-C6 alkyl group, an N,N'-di(C1-C6 alkyl)carbamoyl group, a (C1-C6 haloalkyl)carbonylamino group, an N,N'-di(C1-C6 alkyl)carbonylamino group, an arylcarbonylamino group that may be substituted with a halogen atom or a C1-C6 alkyl group.

<2> The 1,2,3-triazole derivative according to <1>, wherein in formula (1):

R is a C1-C6 alkyl group;

$W^1$ and $W^2$ are CH;

X is a hydrogen atom, a halogen atom, a cyano group, a C1-C6 alkyl group that may be substituted with a cyano group, a C3-C6 cycloalkyl group that may be substituted with a cyano group, a C1-C6 alkoxy group, a C1-C6 haloalkyl group that may be substituted with a cyano group, a C1-C6 haloalkoxy group, a C1-C6 alkylcarbonyl group, a C1-C6 alkylthio group, a C1-C6 alkylsulfinyl group, a C1-C6 alkylsulfonyl group, a C1-C6 haloalkylthio group, a C1-C6 haloalkylsulfinyl group, a C1-C6 haloalkylsulfonyl group, a C1-C6 alkylamino group, a (C1-C6 alkoxy)carbonyl group, a di(C1-C6 alkyl)amino group, a (C1-C6 alkyl)carbonylamino group, a (C1-C6 alkyl)carbonyl(C1-C6 alkyl)amino group, an N—(C1-C6 alkyl)carbamoyl group, an N,N'-di(C1-C6 alkyl)carbamoyl group, a pentafluorosulfanyl group, or an aryl group that may be substituted with a halogen atom;

Q is a phenyl group or a pyridyl group, each of which may be substituted with one or more groups selected from the group consisting of a halogen atom, a cyano group, a nitro group, a C1-C6 alkyl group that may be substituted with a cyano group, a C3-C6 cycloalkyl group that may be substituted with a cyano group, a C1-C6 alkoxy group, a C1-C6 haloalkyl group that may be substituted with a cyano group, a C1-C6 haloalkoxy group, a C1-C6 alkylthio group, a C1-C6 haloalkylthio group, a C1-C6 alkoxycarbonyl group, a C1-C6 alkylsulfinyl group, a C1-C6 alkylsulfonyl group, a C1-C6 alkylcarbonyl group, a C1-C6 haloalkylcarbonyl group, a pentafluorosulfanyl group, a (C1-C6 alkyl)aminosulfonyl group in which the nitrogen atom may be substituted with a C1-C6 alkyl group, a phenyl group that may be substituted with a halogen atom or a C1-C6 alkyl group, a phenoxy group that may be substituted with a halogen atom or a C1-C6 alkyl group, and a benzoyl group that may be substituted with a halogen atom; and Z is a hydrogen atom, a halogen atom, a cyano group, a C1-C6 alkyl group, a C3-C6 cycloalkyl group, or a C1-C6 haloalkyl group.

<3> The 1,2,3-triazole derivative according to <1>, wherein in formula (1):

R is an ethyl group;

$W^1$ and $W^2$ are CH;

X is a hydrogen atom, a halogen atom, a cyano group, a C1-C6 alkyl group that may be substituted with a cyano group, a C3-C6 cycloalkyl group that may be substituted with a cyano group, a C1-C6 alkoxy group, a C1-C6 haloalkyl group that may be substituted with a cyano group, a C1-C6 haloalkoxy group, a C1-C6 alkylcarbonyl group, a C1-C6 alkylthio group, a C1-C6 alkylsulfinyl group, a C1-C6 alkylsulfonyl group, a C1-C6 haloalkylthio group, a C1-C6 haloalkylsulfinyl group, a C1-C6 haloalkylsulfonyl group, a C1-C6 alkylamino group, a (C1-C6 alkoxy)carbonyl group, a di(C1-C6 alkyl)amino group, a (C1-C6 alkyl)carbonylamino group, a (C1-C6 alkyl)carbonyl(C1-C6 alkyl)amino group, an N—(C1-C6 alkyl)carbamoyl group, an N,N'-di(C1-C6 alkyl)carbamoyl group, a pentafluorosulfanyl group, or an aryl group that may be substituted with a halogen atom;

Q is a phenyl group that may be substituted with one or more groups selected from the group consisting of a halogen atom, a cyano group, a nitro group, a C1-C6 alkyl group that may be substituted with a cyano group, a C3-C6 cycloalkyl group that may be substituted with a cyano group, a C1-C6 alkoxy group, a C1-C6 haloalkyl group that may be substituted with a cyano group, a C1-C6 haloalkoxy group, a C1-C6 alkylthio group, a C1-C6 haloalkylthio group, a C1-C6 alkoxycarbonyl group, a C1-C6 alkylsulfinyl group, a C1-C6 alkylsulfonyl group, a C1-C6 alkylcarbonyl group, a C1-C6 haloalkylcarbonyl group, a pentafluorosulfanyl group, a (C1-C6 alkyl)aminosulfonyl group in which the nitrogen atom may be substituted with a C1-C6 alkyl group, a phenyl group that may be substituted with a halogen atom or a C1-C6 alkyl group, a phenoxy group that may be substituted with a halogen atom or a C1-C6 alkyl group, and a benzoyl group what may be substituted with a halogen atom; and Z is a hydrogen atom, a halogen atom, or a C1-C6 alkyl group.

<4> The 1,2,3-triazole derivative according to <1>, wherein in formula (1):

R is an ethyl group;

$W^1$ and $W^2$ are CH;

X is a hydrogen atom, a halogen atom, a cyano group, a C1-C6 alkyl group that may be substituted with a cyano group, a C3-C6 cycloalkyl group that may be substituted with a cyano group, a C1-C6 alkoxy group, a C1-C6 haloalkyl group that may be substituted with a cyano group, a C1-C6 haloalkoxy group, a C1-C6 alkylcarbonyl group, a C1-C6 alkylthio group, a C1-C6 alkylsulfinyl group, a C1-C6 alkylsulfonyl group, a C1-C6 haloalkylthio group, a C1-C6 haloalkylsulfinyl group, a C1-C6 haloalkylsulfonyl group, a C1-C6 alkylamino group, a (C1-C6 alkoxy)carbonyl group, a di(C1-C6 alkyl)amino group, a (C1-C6 alkyl)carbonylamino group, a (C1-C6 alkyl)carbonyl(C1-C6 alkyl)amino group, an N—(C1-C6 alkyl)carbamoyl group, an N,N'-di(C1-C6 alkyl)carbamoyl group, a pentafluorosulfanyl group, or an aryl group that may be substituted with a halogen atom;

Q is a pyridyl group that may be substituted with one or more groups selected from the group consisting of a halogen atom, a cyano group, a C1-C6 alkyl group that may be substituted with a cyano group, a C3-C6 cycloalkyl group that may be substituted with a cyano group, a C1-C6 alkoxy group, a C1-C6 haloalkyl group that may be substituted with a cyano group, a C1-C6 haloalkoxy group, a C1-C6 alkylthio group, a C1-C6 haloalkylthio group, a C1-C6 alkylsulfinyl group, a C1-C6 alkylsulfonyl group, a C1-C6 alkylcarbonyl group, a C1-C6 haloalkylcarbonyl group, and a pentafluorosulfanyl group; and Z is a hydrogen atom, a halogen atom, or a C1-C6 alkyl group.

<5> An insecticide or acaricide containing the 1,2,3-triazole derivative according to any one of <1> to <4> as an active ingredient.

Effect of the Invention

The novel 1,2,3-triazole derivative of the present invention represented by formula (1) provides excellent insecticide or acaricide effects.

MODE FOR CARRYING OUT THE INVENTION

The 1,2,3-triazole derivative according to the compound of the present invention, the production method thereof, and the insecticide or acaricide containing the derivative as an active ingredient are described specifically below.

Here, the carbon number specified in each group below excludes carbon in the cyano group in the case of having a cyano group. In addition, the carbon number excludes also carbonyl carbon in a carbonyl-containing group such as C1-C6 alkylcarbonyl group and (C1-C6) alkoxycarbonyl group.

Incidentally, in the case where $W^1$ or W2 in formula (1) represents CH, when X is bonded to $W^1$ or $W^2$, hydrogen atom in $W^1$ or W2 is replaced by X.

In the 1,2,3-triazole derivative represented by formula (1) of the present invention, examples of the halogen atom represented by X and Z include fluorine, chlorine, bromine, and iodine.

The C1-C6 alkyl group represented by R and Z may be either linear or branched, and examples thereof include a methyl group, an ethyl group, an n-propyl group, an isopropyl group, an n-butyl group, an isobutyl group, a sec-butyl group, a tert-butyl group, a 1-pentyl group, an isoamyl group, a neopentyl group, a 2-pentyl group, a 3-pentyl group, a 2-methylbutyl group, a tert-pentyl group, and a 1-hexyl group.

The C1-C6 alkyl group that may be substituted with a hydroxyl group or a cyano group, represented by X, may be either linear or branched, and examples thereof include a methyl group, an ethyl group, an n-propyl group, an isopropyl group, an n-butyl group, an isobutyl group, a sec-butyl group, a tert-butyl group, a 1-pentyl group, an isoamyl group, a neopentyl group, a 2-pentyl group, a 3-pentyl group, a 2-methylbutyl group, a tert-pentyl group, a 1-hexyl group, a hydroxymethyl group, a cyanomethyl group, a 2-methylcyanomethyl group, a 2,2-dimethylcyanomethyl group, a 2-ethyl-2-methylcyanomethyl group, a 2,2-diethylcyanomethyl group, and a 2-cyanoethyl group.

Examples of the C3-C6 cycloalkyl group represented by Z include a cyclopropyl group, a cyclobutyl group, a cyclopentyl group, and a cyclohexyl group.

Examples of the C3-C6 cycloalkyl group that may be substituted with a cyano group, represented by X, include a cyclopropyl group, a cyclobutyl group, a cyclopentyl group, a cyclohexyl group, a 1-cyanocyclopropyl group, and a 2-cyanocyclopropyl group.

Examples of the (C1-C6 alkoxy)C1-C6 fluoroalkyl group represented by X include a 1-methoxy-2,2,2-trifluoroethyl group, a 1-ethoxy-2,2,2-trifluoroethyl group, a 2-methoxy-1,1,1,3,3,3-hexafluoro-isopropyl group, and a 2-ethoxy-1,1,1,3,3,3-hexafluoroisopropyl group.

The C1-C6 alkoxy group represented by X and Z may be either linear or branched, and examples thereof include a methoxy group, an ethoxy group, an n-propyloxy group, an isopropyloxy group, an n-butyloxy group, an isobutyloxy group, a sec-butyloxy group, a tert-butyloxy group, a 1-pentyloxy group, an isoamyloxy group, a neopentyloxy group, a 2-pentyloxy group, a 3-pentyloxy group, a 2-methylbutyloxy group, a tert-pentyloxy group, and a hexyloxy group.

The C1-C6 alkylsulfonyloxy group represented by X may be either linear or branched, and examples thereof include a methylsulfonyloxy group, an ethylsulfonyloxy group, a propylsulfonyloxy group, an isopropylsulfonyloxy group, an n-butylsulfonyloxy group, an isobutylsulfonyloxy group, a sec-butylsulfonyloxy group, a tert-butylsulfonyloxy group, a 1-pentylsulfonyloxy group, an isoamylsulfonyloxy group, a neopentylsulfonyloxy group, a 2-pentylsulfonyloxy group, a 3-pentylsulfonyloxy group, a 2-methylbutylsulfonyloxy group, a tert-pentylsulfonyloxy group, and 1-hexylsulfonyloxy group.

The (C1-C6 alkoxy)C1-C6 alkoxy group represented by X may be either linear or branched, and examples thereof include a methoxymethoxy group, a methoxyethoxy group, an ethoxymethoxy group, an ethoxyethoxy group, a methoxypropoxy group, an ethoxypropoxy group, an n-propoxymethoxy group, an isopropoxymethoxy group, an n-butoxymethoxy group, a sec-butoxymethoxy group, a tert-butoxymethoxy group, a 1-pentyloxymethoxy group, and a 1-hexyloxymethoxy group.

The (C1-C6 alkoxy)C1-C6 alkyl group represented by Z may be either linear or branched, and examples thereof include a methoxymethyl group, a methoxyethyl group, an ethoxymethyl group, an ethoxyethyl group, an n-propoxymethyl group, an isopropoxymethyl group, an n-butoxymethyl group, a sec-butoxymethyl group, a tert-butoxymethyl group, a 1-pentyloxymethyl group, and a 1-hexyloxymethyl group.

The C1-C6 haloalkyl group that may be substituted with a cyano group, represented by X may be either linear or branched, and examples thereof include a monofluoromethyl group, a monochloromethyl group, a difluoromethyl group, a trifluoromethyl group, a 2,2,2-trifluoroethyl group, a 2-chloroethyl group, a 1-fluoroethyl group, a 2-fluoroethyl group, a 6-fluorohexyl group, a heptafluoroisopropyl group, a 1,1,1,3,3,3-hexafluoro-isopropyl group, and a (cyano)difluoromethyl group.

The C1-C6 haloalkyl group represented by R and Z may be either linear or branched, and examples thereof include a monofluoromethyl group, a difluoromethyl group, a trifluoromethyl group, a 2,2,2-trifluoroethyl group, a 2-chloroethyl group, a 1-fluoroethyl group, a 2-fluoroethyl group, a 6-fluorohexyl group, and a heptafluoroisopropyl group.

Examples of the C1-C6 haloalkoxy group represented by X include a trifluoromethoxy group, a 2,2,2-trifluoroethoxy group, a 2-chloroethoxy group, and a 1,1,2,2-tetrafluoroethoxy group.

The C1-C6 alkylcarbonyl group represented by X may be either linear or branched, and examples thereof include an acetyl group, an ethylcarbonyl group, an n-propylcarbonyl group, an isopropylcarbonyl group, an n-butylcarbonyl group, an isobutylcarbonyl group, a sec-butylcarbonyl group, tert-butylcarbonyl group, a 1-pentylcarbonyl group, and a 1-hexylcarbonyl group.

Examples of the C1-C6 haloalkylsulfonyloxy group represented by X include a difluoromethylsulfonyloxy group, a trifluoromethylsulfonyloxy group, a chloromethylsulfonyloxy group, a trichloromethylsulfonyloxy group, and 2-chloroethylsulfonyloxy group.

The C1-C6 alkylthio group represented by X and Z may be either linear or branched, and examples thereof include a methylthio group, an ethylthio group, an n-propylthio group, an isopropylthio group, an n-butylthio group, an isobutylthio group, a sec-butylthio group, a tert-butylthio group, a 1-pentylthio group, an isoamylthio group, a neopentylthio group, a 2-pentylthio group, a 3-pentylthio group, a 2-methylbutylthio group, a tert-pentylthio group, and a 1-hexylthio group.

The C1-C6 alkylsulfinyl group represented by X may be either linear or branched, and examples thereof include a methylsulfinyl group, an ethylsulfinyl group, an n-propylsulfinyl group, an isopropylsulfinyl group, an n-butylsulfinyl group, an isobutylsulfinyl group, a sec-butylsulfinyl group, a tert-butylsulfinyl group, a 1-pentylsulfinyl group, an isoamylsulfinyl group, a neopentylsulfinyl group, a 2-pentylsulfinyl group, a 3-pentylsulfinyl group, a 2-methylbutylsulfinyl group, a tert-pentylsulfinyl group, and a 1-hexylsulfinyl group.

The C1-C6 alkylsulfonyl group represented by X may be either linear or branched, and examples thereof include a methylsulfonyl group, an ethylsulfonyl group, an n-propylsulfonyl group, an isopropylsulfonyl group, an n-butylsulfonyl group, an isobutylsulfonyl group, a sec-butylsulfonyl group, a tert-butylsulfonyl group, a 1-pentylsulfonyl group, an isoamylsulfonyl group, a neopentylsulfonyl group, a 2-pentylsulfonyl group, a 3-pentylsulfonyl group, a 2-methylbutylsulfonyl group, a tert-pentylsulfonyl group, and a 1-hexylsulfonyl group.

Examples of the C1-C6 haloalkylthio group represented by X and Z include a monofluoromethylthio group, a difluoromethylthio group, a trifluoromethylthio group, a 2,2,2-trifluoroethylthio group, and a 2,2,2-trichloroethylthio group.

Examples of the C1-C6 haloalkylsulfinyl group represented by X include a monofluoromethylsulfinyl group, a difluoromethylsulfinyl group, a trifluoromethylsulfinyl group, a 2,2,2-trifluoroethylsulfinyl group, and a 2,2,2-trichloroethylsulfinyl group.

Examples of the C1-C6 haloalkylsulfonyl group represented by X include a monofluoromethylsulfonyl group, a difluoromethylsulfonyl group, a trifluoromethylsulfonyl group, a 2,2,2-trifluoroethylsulfonyl group, and a 2,2,2-trichloroethylsulfonyl group.

The C1-C6 alkylamino group represented by X and Z may be either linear or branched, and examples thereof include a methylamino group, an ethylamino group, an isopropylamino group, an isobutylamino group, a 1-pentylamino group, and a 1-hexylamino group.

The (C1-C6 alkoxy)carbonyl group represented by X and Z may be either linear or branched, and examples thereof include a methoxycarbonyl group, an ethoxycarbonyl group, an n-propoxycarbonyl group, an isopropoxycarbonyl group, an n-butoxycarbonyl group, a sec-butoxycarbonyl group, a tert-butoxycarbonyl group, and an n-hexyloxycarbonyl group.

The di(C1-C6 alkyl)amino group represented by X and Z may be either linear or branched, and examples thereof include a dimethylamino group, a diethylamino group, an N-ethyl-N'-methylamino group, a di(isopropyl)amino group, a di(n-butyl)amino group, a di(n-pentyl)amino group, and a di(n-hexyl)amino group.

The (C1-C6 alkyl)carbonylamino group represented by X and Z may be either linear or branched, and examples thereof include an acetylamino group, an ethylcarbonylamino group, an n-propylcarbonylamino group, an isopropylcarbonylamino group, and a tert-butylcarbonylamino group.

The (C1-C6 alkyl)carbonyl(C1-C6 alkyl)amino group represented by X may be either linear or branched, and examples thereof include an N-(methyl)acetylamino group, an N-(ethyl)-n-propylcarbonylamino group, an N-(ethyl) isopropylcarbonylamino group, and an N-(ethyl)-tert-butylcarbonylamino group.

The N—(C1-C6 alkyl)carbamoyl group represented by X and Z may be either linear or branched, and examples thereof include an N-methylcarbamoyl group, an N-ethylcarbamoyl group, an N-(n-propyl)carbamoyl group, an N-isopropylcarbamoyl group, and an N-(n-hexyl)carbamoyl group.

The N,N'-di(C1-C6 alkyl)carbamoyl group represented by X and Z may be either linear or branched, and examples thereof include an N,N'-dimethylcarbamoyl group, an N,N'-diethylcarbamoyl group, an N-ethyl-N'-methylcarbamoyl group, and an N-ethyl-N'-isopropylcarbamoyl group.

The triazolyl group that may be substituted with a C1-C6 alkyl group, represented by X, may be either linear or branched, and examples thereof include a 1,2,4-triazol-3-yl group, a 1-methyl-1,2,4-triazol-3-yl group, a 1-ethyl-1,2,4-triazol-3-yl group, a 1-(n-propyl)-1,2,4-triazol-3-yl group, and a 1-isopropyl-1,2,4-triazol-3-yl group.

The oxadiazolyl group that may be substituted with a C1-C6 alkyl group, represented by X, may be either linear or branched, and examples thereof include a 1,2,4-oxadiazol-3-yl group, a 5-methyl-1,2,4-oxadiazol-3-yl group, a 5-ethyl-1,2,4-oxadiazol-3-yl group, a 5-(n-propyl)-1,2,4-oxadiazol-3-yl group, and a 5-isopropyl-1,2,4-oxadiazol-3-yl group.

The tetrazolyl group that may be substituted with a C1-C6 alkyl group, represented by X, may be either linear or branched, and examples thereof include a tetrazol-5-yl group, a 1-methyltetrazol-5-yl group, a 1-ethyltetrazol-5-yl group, a 1-(n-propyl)-tetrazol-5-yl group, a 1-isopropyltetrazol-5-yl group, a 2-methyltetrazol-5-yl group, a 2-ethyltetrazol-5-yl group, a 2-(n-propyl)-tetrazol-5-yl group, and a 2-isopropyltetrazol-5-yl group.

Examples of the (tetrazolyl that may be substituted with a C1-C6 haloalkyl group)C1-C6 alkyl group, represented by X, include a (5-trifluoromethyltetrazol-2-yl)methyl group and a (5-pentafluoroethyltetrazol-2-yl)methyl group.

Examples of the benzoyl group that may be substituted with a halogen atom, represented by X, include a benzoyl group, a 2-fluorobenzoyl group, a 3-fluorobenzoyl group, a 4-fluorobenzoyl group, a 2-chlorobenzoyl group, a 3-chlorobenzoyl group, a 4-chlorobenzoyl group, a 2-bromobenzoyl group, a 3-bromobenzoyl group, a 4-bromobenzoyl group, a 2-iodobenzoyl group, a 3-iodobenzoyl group, a 4-iodobenzoyl group, a 2,4-dichlorobenzoyl group, a 2,6-dichlorobenzoyl group, a 3,4-dichlorobenzoyl group, and a 3,5-dichlorobenzoyl group.

Examples of the arylsulfonyl group that may be substituted with a halogen atom, represented by X, include a phenylsulfonyl group, a 2-fluorophenylsulfonyl group, a 3-fluorophenyl sulfonyl group, a 4-fluorophenyl sulfonyl group, a 2-chlorophenylsulfonyl group, a 3-chlorophenylsulfonyl group, a 4-chlorophenylsulfonyl group, a 2-bromophenylsulfonyl group, a 3-bromophenylsulfonyl group, a 4-bromophenylsulfonyl group, a 2-iodophenylsulfonyl group, a 3-iodophenylsulfonyl group, a 4-iodophenylsulfonyl group, a 2,4-dichlorophenylsulfonyl group, a 2,6-dichlorophenylsulfonyl group, a 3,4-dichlorophenylsulfonyl group, a 3,5-dichlorophenylsulfonyl group, a 2-pyridylsulfonyl group, a 5-chloro-2-pyridylsulfonyl group, a 5-trifluoromethyl-2-pyridylsulfonyl group, a 3-chloro-5-trifluoromethyl-2-pyridylsulfonyl group, a 3-pyridylsulfonyl group, a 6-chloro-3-pyridylsulfonyl group, and a 4-pyridylsulfonyl group.

Examples of the arylsulfinyl group that may be substituted with a halogen atom, represented by X, include a phenylsulfinyl group, a 2-fluorophenylsulfinyl group, a 3-fluorophenylsulfinyl group, a 4-fluorophenylsulfinyl group, a 2-chlorophenylsulfinyl group, a 3-chlorophenylsulfinyl group, a 4-chlorophenylsulfinyl group, a 2-bromophenylsulfinyl group, a 3-bromophenylsulfinyl group, a 4-bromophenylsulfinyl group, a 2-iodophenylsulfinyl group, a 3-iodophenylsulfinyl group, a 4-iodophenylsulfinyl group, a 2,4-dichlorophenylsulfinyl group, a 2,6-dichlorophenylsulfinyl group, a 3,4-dichlorophenylsulfinyl group, a 3,5-dichlorophenylsulfinyl group, a 2-pyridylsulfinyl group, a 5-chloro-2-pyridylsulfinyl group, a 5-trifluoromethyl-2-pyridylsulfinyl group, a 3-chloro-5-trifluoromethyl-2-pyridylsulfinyl group, a 3-pyridylsulfinyl group, a 6-chloro-3-pyridylsulfinyl group, and a 4-pyridylsulfinyl group.

Examples of the arylthio group that may be substituted with a halogen atom, represented by X, include a phenylthio group, a 2-fluorophenylthio group, a 3-fluorophenylthio group, a 4-fluorophenylthio group, a 2-chlorophenylthio group, a 3-chlorophenylthio group, a 4-chlorophenylthio group, a 2-bromophenylthio group, a 3-bromophenylthio group, a 4-bromophenylthio group, a 2-iodophenylthio group, a 3-iodophenylthio group, a 4-iodophenylthio group, a 2,4-dichlorophenylthio group, a 2,6-dichlorophenylthio group, a 3,4-dichlorophenylthio group, a 3,5-dichlorophenylthio group, a 2-pyridylthio group, a 5-chloro-2-pyridylthio group, a 5-trifluoromethyl-2-pyridylthio group, a 3-chloro-5-trifluoromethyl-2-pyridylthio group, a 3-pyridylthio group, a 6-chloro-3-pyridylthio group, and a 4-pyridylthio group.

Examples of the arylamino group that may be substituted with a halogen atom, represented by X, include a phenylamino group, a 2-fluorophenylamino group, a 3-fluorophenylamino group, a 4-fluorophenylamino group, a 2-chlorophenylamino group, a 3-chlorophenylamino group, a 4-chlorophenylamino group, a 2-bromophenylamino group, a 3-bromophenylamino group, a 4-bromophenylamino group, a 2-iodophenylamino group, a 3-iodophenylamino group, a 4-iodophenylamino group, a 2,4-dichlorophenylamino group, a 2,6-dichlorophenylamino group, a 3,4-dichlorophenylamino group, a 3,5-dichlorophenylamino group, a 2-pyridylamino group, a 5-chloro-2-pyridylamino group, a 5-trifluoromethyl-2-pyridylamino group, a 3-chloro-5-trifluoromethyl-2-pyridylamino group, a 3-pyridylamino group, a 6-chloro-3-pyridylamino group, and a 4-pyridylamino group.

Examples of the aryloxy group that may be substituted with a halogen atom, represented by X, include a phenoxy group, a 2-fluorophenoxy group, a 3-fluorophenoxy group, a 4-fluorophenoxy group, a 2-chlorophenoxy group, a 3-chlorophenoxy group, a 4-chlorophenoxy group, a 2-bromophenoxy group, a 3-bromophenoxy group, a 4-bromophenoxy group, a 2-iodophenoxy group, a 3-iodophenoxy group, a 4-iodophenoxy group, a 2,4-dichlorophenoxy group, a 2,6-dichlorophenoxy group, a 3,4-dichlorophenoxy group, a 3,5-dichlorophenoxy group, a 2-pyridyloxy group, a 5-chloro-2-pyridyloxy group, a 5-trifluoromethyl-2-pyridyloxy group, a 3-chloro-5-trifluoromethyl-2-pyridyloxy group, a 3-pyridyloxy group, a 6-chloro-3-pyridyloxy group, and a 4-pyridyloxy group.

Examples of the aryl group that may be substituted with a halogen atom, represented by X, include a phenyl group, a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2,4-dichlorophenyl group, a 2,6-dichlorophenyl group, a 3,4-dichlorophenyl group, a 3,5-dichlorophenyl group, a 2-pyridyl group, a 5-chloro-2-pyridyl group, a 5-trifluoromethyl-2-pyridyl group, a 3-chloro-5-trifluoromethyl-2-pyridyl group, a 3-pyridyl group, a 6-chloro-3-pyridyl group, and a 4-pyridyl group.

Examples of the N—(C1-C6 haloalkyl)carbamoyl group represented by Z include an N-(2,2,2-trifluoroethyl)carbamoyl group and an N-(3,3,3-trifluoropropyl)carbamoyl group.

The N,N'-di(C1-C6 alkyl)carbonylamino group represented by Z may be either linear or branched, and examples thereof include an N,N'-diacetylamino group, an N-acetyl-N'-ethylcarbonylamino group, an N,N'-diethylcarbonylamino group, an N-acetyl-N'-(n-propyl)carbonyl amino group, and an N-acetyl-N'-isopropylcarbonylamino group.

Examples of the N-(phenyl)carbamoyl group that may be substituted with a halogen atom or a C1-C6 alkyl group, represented by Z, include an N-(phenyl)carbamoyl group, an N-(2-chlorophenyl)carbamoyl group, an N-(3-chlorophenyl)carbamoyl group, an N-(4-chlorophenyl)carbamoyl group, an N-(2-methylphenyl)carbamoyl group, an N-(3-methylphenyl)carbamoyl group, and an N-(4-methylphenyl)carbamoyl group.

Examples of the (C1-C6 haloalkyl)carbonylamino group represented by Z include a trifluoromethylcarbonylamino group, a (2,2,2-trifluoroethyl)carbonylamino group, and a (3,3,3-trifluoropropyl)carbonyl amino group.

Examples of the arylcarbonylamino group that may be substituted with a halogen atom or a C1-C6 alkyl group, represented by Z, include a benzoylamino group, a 2-chlorobenzoylamino group, a 3-chlorobenzoylamino group, a 4-chlorobenzoylamino group, a 2-methylbenzoylamino group, a 3-methylbenzoylamino group, and a 4-methylbenzoylamino group.

Examples of the phenyl group represented by Q, which may be substituted with one or more groups selected from the group consisting of a halogen atom, a cyano group, a nitro group, a carboxyl group, a C1-C6 alkyl group that may be substituted with a hydroxyl group or a cyano group, a C3-C6 cycloalkyl group that may be substituted with a cyano group, a C1-C6 alkoxy group, a C1-C6 haloalkyl group that may be substituted with a cyano group, a C1-C6 haloalkyl group {substituted with an N-carbamoyl group (that may be substituted with a C1-C6 alkyl group)}, a C1-C6 haloalkyl group {substituted with an N-arylcarbamoyl group (that may be substituted with a halogen atom or a C1-C6 alkyl group)}, a C1-C6 haloalkoxy group, a C1-C6 alkylthio group, a C1-C6 haloalkylthio group, a C1-C6 alkoxycarbonyl group, a C1-C6 alkylsulfinyl group, a C1-C6 alkylsulfonyl group, a C1-C6 alkylcarbonyl group, a C1-C6 haloalkylcarbonyl group, a pentafluorosulfanyl group, an N—(C1-C6 alkyl)carbamoyl group, an N—(C1-C6 haloalkyl)carbamoyl group, an N-(phenyl)carbamoyl group that may be substituted with a halogen atom or a C1-C6 alkyl group, an N-(pyridyl)carbamoyl group that may be substituted with a halogen atom or a C1-C6 alkyl group, an N,N'-di(C1-C6 alkyl)carbamoyl group, an N—(C1-C6 alkylcarbonyl)amino group, an N—(C1-C6 haloalkylcarbonyl)amino group, an N—(C1-C6 alkoxycarbonyl)amino group, an N—(C1-C6 haloalkoxycarbonyl)amino group, a C1-C6 alkylsulfonylamino group in which the nitrogen atom may be substituted with a C1-C6 alkyl group, a C1-C6 haloalkylsulfonylamino group in which the nitrogen atom may be substituted with a C1-C6 alkyl group, a phenylsulfonylamino group in which the nitrogen atom may be substituted with a C1-C6 alkyl group and the phenyl group may be substituted with a halogen atom or a C1-C6 alkyl group, a (C1-C6 alkyl)aminosulfonyl group in which the nitrogen atom may be substituted with a C1-C6 alkyl group, a phenyl group that may be substituted with a halogen atom or a C1-C6 alkyl group, a phenoxy group that may be substituted with a halogen atom or a C1-C6 alkyl group, and a benzoyl group that may be substituted with a halogen atom, include a phenyl group, a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 2-methylphenyl group, a 3-methylphenyl group, a 4-methylphenyl group, a 2-cyclopropylphenyl group, a 3-cyclopropylphenyl group, a 4-cyclopropylphenyl group, a 2-methoxyphenyl group, a 3-methoxyphenyl group, a 4-methoxyphenyl group, a 3-trifluoromethoxyphenyl group, a 4-cyanophenyl group, a 4-phenoxyphenyl group, a 2-(trifluoromethyl)phenyl group, a 3-(trifluoromethyl)phenyl group, a 4-(trifluoromethyl)phenyl group, a 3-pentafluorosulfanylphenyl group, a 3,5-dichlorophenyl group, a 2-chloro-4-(trifluoromethyl)phenyl group, a 3-(trifluoromethyl)-4-chlorophenyl group, a 3,5-bis(trifluoromethyl)phenyl group, a 2,5-bis(trifluoromethyl)phenyl group, a 2,4-bis(trifluoromethyl)phenyl group, a 3,4-bis(trifluoromethyl)phenyl group, a 4-(perfluoroisopropyl)phenyl group, a 2-chloro-3,5-bis(trifluoromethyl)phenyl group, a 2-fluoro-3,5-bis(trifluoromethyl)phenyl group, a 3-chloro-5-(trifluoromethyl)phenyl group, a 3-fluoro-5-(trifluoromethyl)phenyl group, a 3-bromo-5-(trifluoromethyl)phenyl group, a 3-methyl-5-(trifluoromethyl)phenyl group, a 3-acetyl-5-(trifluoromethyl)phenyl group, a 3-trifluoroacetyl-5-(trifluoromethyl)phenyl group, a 3-cyano-5-(trifluoromethyl)phenyl group, a 3-cyanomethyl-5-(trifluoromethyl)phenyl group, a 3-cyclopropyl-5-(trifluoromethyl)phenyl group, a 3-(1-cyanocyclopropyl)-5-(trifluoromethyl)phenyl group, a 3-trifluoromethoxy-5-(trifluoromethyl)phenyl group, a 3-methylthio-5-(trifluoromethyl)phenyl group, a 3-methylsulfinyl-5-(trifluoromethyl)phenyl group, a 3-methylsulfonyl-5-(trifluoromethyl)phenyl group, a 3-trifluoromethylthio-5-(trifluoromethyl)phenyl group, a 3-methoxycarbonyl-5-(trifluoromethyl)phenyl group, a 3-ethoxycarbonyl-5-(trifluoromethyl)phenyl group, a 3-methylcarbamoyl-5-(trifluoromethyl)phenyl group, a 3-(N-methylcarbamoyl)difluoromethyl-5-(trifluoromethyl)phenyl group, a 3-(N-phenylcarbamoyl)difluoromethyl-5-(trifluoromethyl)phenyl group, a 3-phenylaminocarbonyl-5-(trifluoromethyl)phenyl group, a 3-(2-pyridylamino)carbonyl-5-(trifluoromethyl)phenyl group, a 3-(3-pyridylamino)carbonyl-5-(trifluoromethyl)phenyl group, a 3-(4-pyridylamino)carbonyl-5-(trifluoromethyl)phenyl group, a 3-(tert-butoxycarbonylamino)-5-(trifluoromethyl)phenyl group, a 3-(trifluoroacetylamino)-5-(trifluoromethyl)phenyl group, a 3-(trifluoromethylsulfonylamino)-5-(trifluoromethyl)phenyl group, a 3-phenyl-5-(trifluoromethyl)phenyl group, a 3-phenoxy-5-(trifluoromethyl)phenyl group, a 3-cyanodifluoromethyl-5-(trifluoromethyl)phenyl group, a 4-tert-butylphenyl group, a 4-biphenyl group, a 4-chloro-3,5-bis(trifluoromethyl)phenyl group, a 4-methyl-3,5-bis(trifluoromethyl)phenyl group, a 3-{N-(4-chlorophenyl)carbamoyl}-5-(trifluoromethyl)phenyl group, a 3-carbamoyldifluoromethyl-5-(trifluoromethyl)phenyl group, a 3-trifluoromethyl-5-(methylaminocarbonyldifluoromethyl)phenyl group, a 3-benzoyl-5-(trifluoromethyl)phenyl group, a 3-trifluoromethyl-5-{(N-phenylcarbamoyl)difluoromethyl}phenyl group, a 3-(1,1'-difluoroethyl)-5-(trifluoromethyl)phenyl group, a 2-fluoro-5-(trifluoromethyl)phenyl group, and a 3-carboxyl-5-(trifluoromethyl)phenyl group.

Examples of the pyridyl group represented by Q, which may be substituted with one or more groups selected from the group consisting of a halogen atom, a cyano group, a nitro group, a carboxyl group, a C1-C6 alkyl group that may be substituted with a hydroxyl group or a cyano group, a C3-C6 cycloalkyl group that may be substituted with a cyano group, a C1-C6 alkoxy group, a C1-C6 haloalkyl group that may be substituted with a cyano group, a C1-C6 haloalkyl group {substituted with an N-carbamoyl group (that may be substituted with a C1-C6 alkyl group)}, a C1-C6 haloalkyl group {substituted with an N-arylcarbamoyl group (that may be substituted with a halogen atom or a C1-C6 alkyl group)}, a C1-C6 haloalkoxy group, a C1-C6 alkylthio group, a C1-C6 haloalkylthio group, a C1-C6 alkoxycarbonyl group, a C1-C6 alkylsulfinyl group, a C1-C6 alkylsulfonyl group, a C1-C6 alkylcarbonyl group, a C1-C6 haloalkylcarbonyl group, a pentafluorosulfanyl group, an N—(C1-C6 alkyl)carbamoyl group, an N—(C1-C6 haloalkyl)carbamoyl group, an N-(phenyl)carbamoyl group that may be substituted with a halogen atom or a C1-C6 alkyl group, an N-(pyridyl)carbamoyl group that may be substituted with a halogen atom or a C1-C6 alkyl group, an N,N'-di(C1-C6 alkyl)carbamoyl group, an N—(C1-C6 alkylcarbonyl)amino group, an N—(C1-C6 haloalkylcarbonyl)amino group, an N—(C1-C6 alkoxycarbonyl)amino group, an N—(C1-C6 haloalkoxycarbonyl)amino group, a C1-C6 alkylsulfonylamino group in which the nitrogen atom may be substituted with a C1-C6 alkyl group, a C1-C6 haloalkylsulfonylamino group in which the nitrogen atom may be substituted with a C1-C6 alkyl group, a phenylsulfonylamino group in which the nitrogen atom may be substituted with a C1-C6 alkyl group and the phenyl group may be substituted with a halogen atom or a C1-C6 alkyl group, a (C1-C6 alkyl)aminosulfonyl group in which the nitrogen atom may be substituted with a C1-C6 alkyl group, a phenyl group that may be substituted with a halogen atom or a C1-C6 alkyl group, a phenoxy group that may be substituted with a halogen atom or a C1-C6 alkyl group, and a benzoyl group that may be substituted with a halogen atom, include a 2-pyridyl group, a 3-pyridyl group, a 4-pyridyl group, a 6-chloro-2-pyridyl group, a 2-chloro-3-pyridyl group, a 2-chloro-4-pyridyl group, a 6-bromo-2-pyridyl group, a 5-bromo-3-pyridyl group, a 2-bromo-4-pyridyl group, a 6-methyl-2-pyridyl group, a 4-methyl-2-pyridyl group, a 4-chloro-2-pyridyl group, a 4-cyano-2-pyridyl group, a 2-methyl-4-pyridyl group, a 2-trifluoromethyl-4-pyridyl group, a 6-cyclopropyl-3-pyridyl group, a 6-methoxy-2-pyridyl group, a 6-methoxy-3-pyridyl group, a 3-trifluoromethyl-2-pyridyl group, a 4-trifluoromethyl-2-pyridyl group, a 5-trifluoromethyl-2-pyridyl group, a 6-trifluoromethyl-2-pyridyl group, a 4-pentafluoroethyl-2-pyridyl group, a 5-pentafluoroethyl-3-pyridyl group, a 4-pentafluorosulfanyl-2-pyridyl group, a 4,6-bistrifluoromethyl-2-pyridyl group, a 2,5-bistrifluoromethyl-4-pyridyl group, a 3-chloro-5-trifluoromethyl-2-pyridyl group, a 3-cyano-4,6-bistrifluoromethyl-2-pyridyl group, a 3-chloro-4-trifluoromethyl-2-pyridyl group, a 4-trifluoromethyl-5-chloro-2-pyridyl group, a 4-trifluoromethyl-6-chloro-2-pyridyl group, a 4-trifluoromethyl-3-bromo-2-pyridyl group, a 4-trifluoromethyl-5-bromo-2-pyridyl group, a 4-trifluoromethyl-6-bromo-2-pyridyl group, a 3,5-dichloro-4-trifluoromethyl-2-pyridyl group, a 3-fluoro-4-trifluoromethyl-2-pyridyl group, a 4-trifluoromethyl-5-fluoro-2-pyridyl group, a 4-trifluoromethyl-6-fluoro-2-pyridyl group, a 3,5-difluoro-4-trifluoromethyl-2-pyridyl group, a 4-trifluoromethyl-6-methoxy-2-pyridyl group, a 4-trifluoromethyl-6-cyano-2-pyridyl group, a 4-trifluoromethyl-6-cyclopropyl-2-pyridyl group, a 4-trifluoromethyl-3-pyridyl group, a 5-trifluoromethyl-3-pyridyl group, a 6-trifluoromethyl-3-pyridyl group, a 2-fluoro-5-trifluoromethyl-3-pyridyl group, a 3-trifluoromethyl-4-pyridyl group, a 4-trifluoromethoxy-2-pyridyl group, a 5-trifluoromethoxy-2-pyridyl group, a 5-methylthio-2-pyridyl group, a 4-methylthio-2-pyridyl group, a 5-methylsulfinyl-2-pyridyl group, a 4-methylsulfinyl-2-pyridyl group, a 5-methylsulfonyl-2-pyridyl group, a 4-methylsulfonyl-2-pyridyl group, a 4-trifluoromethylthio-2-pyridyl group, a 4-trifluoromethyl sulfinyl-2-pyridyl group, a 4-trifluoromethyl sulfonyl-2-pyridyl group, a 3-N-methylcarbamoyl-2-pyridyl group, a 3-N-(2,2,2-trifluoroethyl)carbamoyl-2-pyridyl group, a 3-N,N'-dimethylcarbamoyl-2-pyridyl group, a 3-methyl sulfonylamino-2-pyridyl group, a 5-trifluoromethyl sulfonylamino-2-pyridyl group, a 5-phenyl sulfonyl amino-2-pyridyl group, and a 5-methyl aminosulfonyl-2-pyridyl group.

Examples of the thiazolyl group represented by Q, which may be substituted with one or more groups selected from the group consisting of a halogen atom, a cyano group, a nitro group, a carboxyl group, a C1-C6 alkyl group that may be substituted with a hydroxyl group or a cyano group, a C3-C6 cycloalkyl group that may be substituted with a cyano group, a C1-C6 alkoxy group, a C1-C6 haloalkyl group that may be substituted with a cyano group, a C1-C6 haloalkyl group {substituted with an N-carbamoyl group (that may be substituted with a C1-C6 alkyl group)}, a C1-C6 haloalkyl group {substituted with an N-arylcarbamoyl group (that may be substituted with a halogen atom or a C1-C6 alkyl group)}, a C1-C6 haloalkoxy group, a C1-C6 alkylthio group, a C1-C6 haloalkylthio group, a C1-C6 alkoxycarbonyl group, a C1-C6 alkylsulfinyl group, a C1-C6 alkylsulfonyl group, a C1-C6 alkylcarbonyl group, a C1-C6 haloalkylcarbonyl group, a pentafluorosulfanyl group, an N—(C1-C6 alkyl)carbamoyl group, an N—(C1-C6 haloalkyl)carbamoyl group, an N-(phenyl)carbamoyl group that may be substituted with a halogen atom or a C1-C6 alkyl group, an N-(pyridyl)carbamoyl group that may be substituted with a halogen atom or a C1-C6 alkyl group, an N,N'-di(C1-C6 alkyl)carbamoyl group, an N—(C1-C6 alkylcarbonyl)amino group, an N—(C1-C6 haloalkylcarbonyl)amino group, an N—(C1-C6 alkoxycarbonyl)amino group, an N—(C1-C6 haloalkoxycarbonyl)amino group, a C1-C6 alkylsulfonylamino group in which the nitrogen atom may be substituted with a C1-C6 alkyl group, a C1-C6 haloalkylsulfonylamino group in which the nitrogen atom may be substituted with a C1-C6 alkyl group, a phenylsulfonylamino group in which the nitrogen atom may be substituted with a C1-C6 alkyl group and the phenyl group may be substituted with a halogen atom or a C1-C6 alkyl group, a (C1-C6 alkyl)aminosulfonyl group in which the nitrogen atom may be substituted with a C1-C6 alkyl group, a phenyl group that may be substituted with a halogen atom or a C1-C6 alkyl group, a phenoxy group that may be substituted with a halogen atom or a C1-C6 alkyl group, and a benzoyl group that may be substituted with a halogen atom, include a 2-thiazolyl group, a 4-methylthiazol-2-yl group, a 4-trifluoromethylthiazol-2-yl group, a 4-chlorothiazol-2-yl group, a 4,5-dimethylthiazol-2-yl group, and a 5-trifluoromethylthiazol-2-yl group.

Examples of the quinolyl group represented by Q, which may be substituted with one or more groups selected from the group consisting of a halogen atom, a cyano group, a nitro group, a carboxyl group, a C1-C6 alkyl group that may be substituted with a hydroxyl group or a cyano group, a C3-C6 cycloalkyl group that may be substituted with a cyano group, a C1-C6 alkoxy group, a C1-C6 haloalkyl group that may be substituted with a cyano group, a C1-C6 haloalkyl group {substituted with an N-carbamoyl group (that may be substituted with a C1-C6 alkyl group)}, a C1-C6 haloalkyl group {substituted with an N-arylcarbamoyl group (that may be substituted with a halogen atom or a C1-C6 alkyl group)}, a C1-C6 haloalkoxy group, a C1-C6 alkylthio group, a C1-C6 haloalkylthio group, a C1-C6 alkoxycarbonyl group, a C1-C6 alkylsulfinyl group, a C1-C6 alkylsulfonyl group, a C1-C6 alkylcarbonyl group, a C1-C6 haloalkylcarbonyl group, a pentafluorosulfanyl group, an N—(C1-C6 alkyl)carbamoyl group, an N—(C1-C6 haloalkyl)carbamoyl group, an N-(phenyl)carbamoyl group that may be substituted with a halogen atom or a C1-C6 alkyl group, an N-(pyridyl)carbamoyl group that may be substituted with a halogen atom or a C1-C6 alkyl group, an N,N'-di(C1-C6 alkyl)carbamoyl group, an N—(C1-C6 alkylcarbonyl)amino group, an N—(C1-C6 haloalkylcarbonyl)amino group, an N—(C1-C6 alkoxycarbonyl)amino group, an N—(C1-C6 haloalkoxycarbonyl)amino group, a C1-C6 alkylsulfonylamino group in which the nitrogen atom may be substituted with a C1-C6 alkyl group, a C1-C6 haloalkylsulfonylamino group in which the nitrogen atom may be substituted with a C1-C6 alkyl group, a phenylsulfonylamino group in which the nitrogen atom may be substituted with a C1-C6 alkyl group and the phenyl group may be substituted with a halogen atom or a C1-C6 alkyl group, a (C1-C6 alkyl)aminosulfonyl group in which the nitrogen atom may be substituted with a C1-C6 alkyl group, a phenyl group that may be substituted with a halogen atom or a C1-C6 alkyl group, a phenoxy group that may be substituted with a halogen atom or a C1-C6 alkyl group, and a benzoyl group that may be substituted with a halogen atom, include a 2-quinolyl group, a 3-quinolyl group, a 4-quinolyl group, a 5-quinolyl group, a 6-quinolyl group, a 7-quinolyl group, a 8-quinolyl group, a 4-methyl-2-quinolyl group, a 4-trifluoromethyl-2-quinolyl group, a 8-trifluoromethyl-2-quinolyl group, a 4-chloro-6-quinolyl group, and a 4-cyano-8-trifluoromethyl-6-quinolyl group.

Examples of the benzoxazolyl group represented by Q, which may be substituted with one or more groups selected from the group consisting of a halogen atom, a cyano group, a nitro group, a carboxyl group, a C1-C6 alkyl group that may be substituted with a hydroxyl group or a cyano group, a C3-C6 cycloalkyl group that may be substituted with a cyano group, a C1-C6 alkoxy group, a C1-C6 haloalkyl group that may be substituted with a cyano group, a C1-C6 haloalkyl group {substituted with an N-carbamoyl group (that may be substituted with a C1-C6 alkyl group)}, a C1-C6 haloalkyl group {substituted with an N-arylcarbamoyl group (that may be substituted with a halogen atom or a C1-C6 alkyl group)}, a C1-C6 haloalkoxy group, a C1-C6 alkylthio group, a C1-C6 haloalkylthio group, a C1-C6 alkoxycarbonyl group, a C1-C6 alkylsulfinyl group, a C1-C6 alkylsulfonyl group, a C1-C6 alkylcarbonyl group, a C1-C6 haloalkylcarbonyl group, a pentafluorosulfanyl group, an N—(C1-C6 alkyl)carbamoyl group, an N—(C1-C6 haloalkyl)carbamoyl group, an N-(phenyl)carbamoyl group that may be substituted with a halogen atom or a C1-C6 alkyl group, an N-(pyridyl)carbamoyl group that may be substituted with a halogen atom or a C1-C6 alkyl group, an N,N'-di(C1-C6 alkyl)carbamoyl group, an N—(C1-C6 alkylcarbonyl)amino group, an N—(C1-C6 haloalkylcarbonyl)amino group, an N—(C1-C6 alkoxycarbonyl)amino group, an N—(C1-C6 haloalkoxycarbonyl)amino group, a C1-C6 alkylsulfonylamino group in which the nitrogen atom may be substituted with a C1-C6 alkyl group, a C1-C6 haloalkylsulfonylamino group in which the nitrogen atom may be substituted with a C1-C6 alkyl group, a phenylsulfonylamino group in which the nitrogen atom may be substituted with a C1-C6 alkyl group and the phenyl group may be substituted with a halogen atom or a C1-C6 alkyl group, a (C1-C6 alkyl)aminosulfonyl group in which the nitrogen atom may be substituted with a C1-C6 alkyl group, a phenyl group that may be substituted with a halogen atom or a C1-C6 alkyl group, a phenoxy group that may be substituted with a halogen atom or a C1-C6 alkyl group, and a benzoyl group that may be substituted with a halogen atom, include a 2-benzoxazolyl group, a 5-methylbenzoxazol-2-yl group, a 5-methoxybenzoxazol-2-yl group, a 5-fluorobenzoxazol-2-yl group, a 5-chlorobenzoxazol-2-yl group, a 5-bromobenzoxazol-2-yl group, a 5-trifluoromethylbenzoxazol-2-yl group, a 6-methylbenzoxazol-2-yl group, and a 6-fluorobenzoxazol-2-yl group.

Examples of the benzothiazolyl group represented by Q, which may be substituted with one or more groups selected from the group consisting of a halogen atom, a cyano group, a nitro group, a carboxyl group, a C1-C6 alkyl group that may be substituted with a hydroxyl group or a cyano group, a C3-C6 cycloalkyl group that may be substituted with a cyano group, a C1-C6 alkoxy group, a C1-C6 haloalkyl group that may be substituted with a cyano group, a C1-C6 haloalkyl group {substituted with an N-carbamoyl group (that may be substituted with a C1-C6 alkyl group)}, a C1-C6 haloalkyl group {substituted with an N-arylcarbamoyl group (that may be substituted with a halogen atom or a C1-C6 alkyl group)}, a C1-C6 haloalkoxy group, a C1-C6 alkylthio group, a C1-C6 haloalkylthio group, a C1-C6 alkoxycarbonyl group, a C1-C6 alkylsulfinyl group, a C1-C6 alkylsulfonyl group, a C1-C6 alkylcarbonyl group, a C1-C6 haloalkylcarbonyl group, a pentafluorosulfanyl group, an N—(C1-C6 alkyl)carbamoyl group, an N—(C1-C6 haloalkyl)carbamoyl group, an N-(phenyl)carbamoyl group that may be substituted with a halogen atom or a C1-C6 alkyl group, an N-(pyridyl)carbamoyl group that may be substituted with a halogen atom or a C1-C6 alkyl group, an N,N'-di(C1-C6 alkyl)carbamoyl group, an N—(C1-C6 alkylcarbonyl)amino group, an N—(C1-C6 haloalkylcarbonyl)amino group, an N—(C1-C6 alkoxycarbonyl)amino group, an N—(C1-C6 haloalkoxycarbonyl)amino group, a C1-C6 alkylsulfonylamino group in which the nitrogen atom may be substituted with a C1-C6 alkyl group, a C1-C6 haloalkylsulfonylamino group in which the nitrogen atom may be substituted with a C1-C6 alkyl group, a phenylsulfonylamino group in which the nitrogen atom may be substituted with a C1-C6 alkyl group and the phenyl group may be substituted with a halogen atom or a C1-C6 alkyl group, a (C1-C6 alkyl)aminosulfonyl group in which the nitrogen atom may be substituted with a C1-C6 alkyl group, a phenyl group that may be substituted with a halogen atom or a C1-C6 alkyl group, a phenoxy group that may be substituted with a halogen atom or a C1-C6 alkyl group, and a benzoyl group that may be substituted with a halogen atom, include a 2-benzothiazolyl group, a 5-methylbenzothiazol-2-yl group, a 5-methoxybenzothiazol-2-yl group, a 5-fluorobenzothiazol-2-yl group, a 5-chlorobenzothiazol-2-yl group, a 5-bromobenzothiazol-2-yl group, a 5-trifluoromethylbenzothiazol-2-yl group, a 6-trifluoromethylbenzothiazol-2-yl group, a 6-methylbenzothiazol-2-yl group, and a 6-fluorobenzothiazol-2-yl group.

Examples of the benzimidazolyl represented by Q, which may be substituted with one or more groups selected from the group consisting of a halogen atom, a cyano group, a nitro group, a carboxyl group, a C1-C6 alkyl group that may be substituted with a hydroxyl group or a cyano group, a C3-C6 cycloalkyl group that may be substituted with a cyano group, a C1-C6 alkoxy group, a C1-C6 haloalkyl group that may be substituted with a cyano group, a C1-C6 haloalkyl group {substituted with an N-carbamoyl group (that may be substituted with a C1-C6 alkyl group)}, a C1-C6 haloalkyl group {substituted with an N-arylcarbamoyl group (that may be substituted with a halogen atom or a C1-C6 alkyl group)}, a C1-C6 haloalkoxy group, a C1-C6 alkylthio group, a C1-C6 haloalkylthio group, a C1-C6 alkoxycarbonyl group, a C1-C6 alkylsulfinyl group, a C1-C6 alkylsulfonyl group, a C1-C6 alkylcarbonyl group, a C1-C6 haloalkylcarbonyl group, a pentafluorosulfanyl group, an N—(C1-C6 alkyl)carbamoyl group, an N—(C1-C6 haloalkyl)carbamoyl group, an N-(phenyl)carbamoyl group that may be substituted with a halogen atom or a C1-C6 alkyl group, an N-(pyridyl)carbamoyl group that may be substituted with a halogen atom or a C1-C6 alkyl group, an N,N'-di(C1-C6 alkyl)carbamoyl group, an N—(C1-C6 alkylcarbonyl)amino group, an N—(C1-C6 haloalkylcarbonyl)amino group, an N—(C1-C6 alkoxycarbonyl)amino group, an N—(C1-C6 haloalkoxycarbonyl)amino group, a C1-C6 alkylsulfonylamino group in which the nitrogen atom may be substituted with a C1-C6 alkyl group, a C1-C6 haloalkylsulfonylamino group in which the nitrogen atom may be substituted with a C1-C6 alkyl group, a phenylsulfonylamino group in which the nitrogen atom may be substituted with a C1-C6 alkyl group and the phenyl group may be substituted with a halogen atom or a C1-C6 alkyl group, a (C1-C6 alkyl)aminosulfonyl group in which the nitrogen atom may be substituted with a C1-C6 alkyl group, a phenyl group that may be substituted with a halogen atom or a C1-C6 alkyl group, a phenoxy group that may be substituted with a halogen atom or a C1-C6 alkyl group, and a benzoyl group that may be substituted with a halogen atom, include a 1-methyl-2-benzimidazolyl group, a 1,5-dimethyl-2-benzimidazolyl group, a 1-methyl-5-methoxy-2-benzimidazol-2-yl group, a 1-methyl-5-chloro-2-benzimidazol-2-yl group, a 1-methyl-5-bromobenzimidazol-2-yl group, a 1-methyl-5-trifluoromethylbenzimidazol-2-yl group, a 1-methyl-6-trifluoromethylbenzimidazol-2-yl group, a 1-methyl-6-chlorobenzimidazol-2-yl group, and a 1,6-dimethyl-2-benzimidazolyl group.

R in formula (1) is preferably a C1-C6 alkyl group, more preferably an ethyl group.

$W^1$ and $W^2$ in formula (1) are more preferably CH.

X in formula (1) is preferably a hydrogen atom, a halogen atom, a cyano group, a hydroxyl group, a carboxyl group, a C1-C6 alkyl group that may be substituted with a hydroxyl group or a cyano group, a C3-C6 cycloalkyl group that may be substituted with a cyano group, a (C1-C6 alkoxy)C1-C6 fluoroalkyl group, a C1-C6 alkoxy group, a (C1-C6 alkoxy)C1-C6 alkoxy group, a C1-C6 haloalkyl group that may be substituted with a cyano group, a C1-C6 haloalkoxy group, a C1-C6 alkylcarbonyl group, a C1-C6 haloalkylsulfonyloxy group, a C1-C6 alkylthio group, a C1-C6 alkylsulfinyl group, a C1-C6 alkylsulfonyl group, a C1-C6 haloalkylthio group, a C1-C6 haloalkylsulfinyl group, a C1-C6 haloalkylsulfonyl group, a C1-C6 alkylamino group, a (C1-C6 alkoxy)carbonyl group, a di(C1-C6 alkyl)amino group, a (C1-C6 alkyl)carbonylamino group, a (C1-C6 alkyl)carbonyl(C1-C6 alkyl)amino group, an N—(C1-C6 alkyl)carbamoyl group, an N,N'-di(C1-C6 alkyl)carbamoyl group, a pentafluorosulfanyl group, a triazolyl group that may be substituted with a C1-C6 alkyl group, an oxadiazolyl group that may be substituted with a C1-C6 alkyl group, a tetrazolyl group that may be substituted with a C1-C6 alkyl group, a (tetrazolyl that may be substituted with a C1-C6 haloalkyl group)C1-C6 alkyl group, a benzoyl group that may be substituted with a halogen atom, an arylsulfonyl group that may be substituted with a halogen atom, an arylsulfinyl group that may be substituted with a halogen atom, an arylthio group that may be substituted with a halogen atom, an arylamino group that may be substituted with a halogen atom, an aryloxy group that may be substituted with a halogen atom, or an aryl group that may be substituted with a halogen atom, more preferably a hydrogen atom, a halogen atom, a cyano group, a hydroxyl group, a carboxyl group, a C1-C6 alkyl group that may be substituted with a hydroxyl group or a cyano group, a C3-C6 cycloalkyl group that may be substituted with a cyano group, a (C1-C6 alkoxy)C1-C6 fluoroalkyl group, a C1-C6 alkoxy group, a (C1-C6 alkoxy)C1-C6 alkoxy group, a C1-C6 haloalkyl group that may be substituted with a cyano group, a C1-C6 haloalkoxy group, a C1-C6 alkylcarbonyl group, a C1-C6 haloalkylsulfonyloxy group, a C1-C6 alkylthio group, a C1-C6 alkylsulfinyl group, a C1-C6 alkylsulfonyl group, a C1-C6 haloalkylthio group, a (C1-C6 alkoxy)carbonyl group, an N—(C1-C6 alkyl)carbamoyl group, a pentafluorosulfanyl group, a triazolyl group that may be substituted with a C1-C6 alkyl group, an oxadiazolyl group that may be substituted with a C1-C6 alkyl group, a tetrazolyl group that may be substituted with a C1-C6 alkyl group, a (tetrazolyl that may be substituted with a C1-C6 haloalkyl group)C1-C6 alkyl group, a benzoyl group that may be substituted with a halogen atom, an arylsulfonyl group that may be substituted with a halogen atom, an arylsulfinyl group that may be substituted with a halogen atom, an arylthio group that may be substituted with a halogen atom, an arylamino group that may be substituted with a halogen atom, an aryloxy group that may be substituted with a halogen atom, or an aryl group that may be substituted with a halogen atom, still more preferably a hydrogen atom, a halogen atom, a cyano group, a C3-C6 cycloalkyl group that may be substituted with a cyano group, a C1-C6 alkoxy group, a C1-C6 haloalkyl group that may be substituted with a cyano group, a C1-C6 haloalkoxy group, a C1-C6 haloalkylsulfonyloxy group, a C1-C6 haloalkylthio group, a (C1-C6 alkoxy)carbonyl group, a pentafluorosulfanyl group, a triazolyl group that may be substituted with a C1-C6 alkyl group, an oxadiazolyl group that may be substituted with a C1-C6 alkyl group, a tetrazolyl group that may be substituted with a C1-C6 alkyl group, or an aryl group that may be substituted with a halogen atom.

Q in formula (1) is preferably a phenyl group or a pyridyl group, each of which may be substituted with one or more groups selected from the group of substituents above, more preferably a phenyl group or a pyridyl group, each of which may be substituted with one or more groups selected from the group consisting of a halogen atom, a cyano group, a nitro group, a carboxyl group, a C1-C6 alkyl group that may be substituted with a hydroxyl group or a cyano group, a C3-C6 cycloalkyl group that may be substituted with a cyano group, a C1-C6 alkoxy group, a C1-C6 haloalkyl group that may be substituted with a cyano group, a C1-C6 haloalkyl group {substituted with an N-carbamoyl group (that may be substituted with a C1-C6 alkyl group)}, a C1-C6 haloalkyl group {substituted with an N-arylcarbamoyl group (that may be substituted with a halogen atom or a C1-C6 alkyl group)}, a C1-C6 haloalkoxy group, a C1-C6 alkylthio group, a C1-C6 haloalkylthio group, a C1-C6 alkoxycarbonyl group, a C1-C6 alkylsulfinyl group, a C1-C6 alkylsulfonyl group, a C1-C6 alkylcarbonyl group, a C1-C6 haloalkylcarbonyl group, a pentafluorosulfanyl group, an N-(phenyl)carbamoyl group that may be substituted with a halogen atom or a C1-C6 alkyl group, a (C1-C6 alkyl)aminosulfonyl group in which the nitrogen atom may be substituted with a C1-C6 alkyl group, a phenyl group that may be substituted with a halogen atom or a C1-C6 alkyl group, a phenoxy group that may be substituted with a halogen atom or a C1-C6 alkyl group, and a benzoyl group that may be substituted with a halogen atom.

The phenyl group that may be substituted with one or more groups selected from the group of substituents above is preferably a phenyl group that may be substituted with one or more groups selected from the group consisting of a halogen atom, a cyano group, a carboxyl group, a C1-C6 alkyl group that may be substituted with a hydroxyl group or a cyano group, a C3-C6 cycloalkyl group that may be substituted with a cyano group, a C1-C6 alkoxy group, a C1-C6 haloalkyl group that may be substituted with a cyano group, a C1-C6 haloalkyl group {substituted with an N-carbamoyl group (that may be substituted with a C1-C6 alkyl group)}, a C1-C6 haloalkyl group {substituted with an N-arylcarbamoyl group (that may be substituted with a halogen atom or a C1-C6 alkyl group)}, a C1-C6 haloalkoxy group, a C1-C6 alkoxycarbonyl group, a C1-C6 alkylcarbonyl group, a pentafluorosulfanyl group, an N-(phenyl)carbamoyl group that may be substituted with a halogen atom or a C1-C6 alkyl group, a phenyl group that may be substituted with a halogen atom or a C1-C6 alkyl group, a phenoxy group that may be substituted with a halogen atom or a C1-C6 alkyl group, and a benzoyl group that may be substituted with a halogen atom, more preferably a phenyl group that may be substituted with one or more groups selected from the group consisting of a halogen atom, a cyano group, a C3-C6 cycloalkyl group that may be substituted with a cyano group, a C1-C6 haloalkyl group that may be substituted with a cyano group, a C1-C6 haloalkoxy group, a C1-C6 alkoxycarbonyl group, and a pentafluorosulfanyl group.

The pyridyl group that may be substituted with one or more groups selected from the group of substituents above is preferably a pyridyl group that may be substituted with one or more groups selected from the group consisting of a halogen atom, a cyano group, a C1-C6 alkyl group that may be substituted with a cyano group, a C3-C6 cycloalkyl group that may be substituted with a cyano group, a C1-C6 alkoxy group, a C1-C6 haloalkyl group that may be substituted with a cyano group, a C1-C6 haloalkoxy group, a C1-C6 alkylthio group, a C1-C6 haloalkylthio group, a C1-C6 alkylsulfinyl group, a C1-C6 alkylsulfonyl group, a C1-C6 alkylcarbonyl group, a C1-C6 haloalkylcarbonyl group, and a pentafluorosulfanyl group, more preferably a pyridyl group that may be substituted with one or more groups selected from the group consisting of a halogen atom, a cyano group, a C1-C6 alkoxy group, and a C1-C6 haloalkyl group that may be substituted with a cyano group, and most preferably a pyridyl group that may be substituted with one or more groups selected from the group consisting of a halogen atom, a cyano group, and a C1-C6 haloalkyl group that may be substituted with a cyano group.

Z in formula (1) is preferably a hydrogen atom, a halogen atom, a cyano group, an amino group, a carboxyl group, a carbamoyl group, a C1-C6 alkyl group, a C3-C6 cycloalkyl group, a (C1-C6 alkoxy)C1-C6 alkyl group, a C1-C6 haloalkyl group, a C1-C6 alkoxycarbonyl group, an N—(C1-C6 alkyl)carbamoyl group, an N-(phenyl)carbamoyl group that may be substituted with a halogen atom or a C1-C6 alkyl group, an N,N'-di(C1-C6 alkyl)carbamoyl group, a (C1-C6 haloalkyl)carbonylamino group, an N,N'-di(C1-C6 alkyl)carbonylamino group, or an arylcarbonylamino group that may be substituted with a halogen atom or a C1-C6 alkyl group, more preferably a hydrogen atom, a halogen atom, a cyano group, an amino group, a carboxyl group, a carbamoyl group, a C1-C6 alkyl group, a (C1-C6 alkoxy)C1-C6 alkyl group, a C1-C6 alkoxycarbonyl group, an N—(C1-C6 alkyl)carbamoyl group, an N-(phenyl)carbamoyl group that may be substituted with a halogen atom or a C1-C6 alkyl group, an N,N'-di(C1-C6 alkyl)carbamoyl group, a (C1-C6 haloalkyl)carbonylamino group, an N,N'-di(C1-C6 alkyl)carbonylamino group, or an arylcarbonylamino group that may be substituted with a halogen atom or a C1-C6 alkyl group, still more preferably a hydrogen atom, a halogen atom, a cyano group, an amino group, a C1-C6 alkyl group, a C1-C6 alkoxycarbonyl group, or an N,N'-di(C1-C6 alkyl)carbamoyl group, yet still more preferably a hydrogen atom, a halogen atom, a cyano group, an amino group, or a C1-C6 alkyl group.

Incidentally, in one preferred embodiment of the present application, the 1,2,3-triazole derivative represented by formula (1) is a 1,2,3-triazole derivative represented by the following formula (1A):

[Chem. 2]

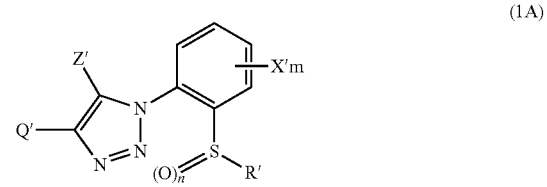

(1A)

In formula (1A):

R' represents a C1-C6 alkyl group or a C1-C6 haloalkyl group;

n represents an integer of 0 to 2;

X' represents a hydrogen atom, a halogen atom, a cyano group, a nitro group, an amino group, a C1-C6 alkyl group, a C3-C6 cycloalkyl group, a C1-C6 alkoxy group, a C1-C6 haloalkyl group, a C1-C6 haloalkoxy group, a C1-C6 alkylthio group, a C1-C6 alkylsulfinyl group, a C1-C6 alkylsulfonyl group, a C1-C6 alkylamino group, a (C1-C6 alkoxy)carbonyl group, a di(C1-C6 alkyl)amino group, a (C1-C6 alkyl)carbonylamino group, a (C1-C6 alkyl)carbonyl(C1-C6 alkyl)amino group, an N—(C1-C6 alkyl)carbamoyl group, or an N,N-di(C1-C6 alkyl)carbamoyl group;

m represents an integer of 1 to 4 and when m represents an integer of 2 or more, respective X may be the same or different;

Q' represents a phenyl group or a pyridyl group, each of which may be substituted with one or more groups selected from the group consisting of a hydrogen atom, a halogen atom, a cyano group, a nitro group, a C1-C6 alkyl group, a C3-C6 cycloalkyl group, a C1-C6 alkoxy group, a C1-C6 haloalkyl group, a C1-C6 haloalkoxy group, a C1-C6 alkylthio group, a C1-C6 haloalkylthio group, a C1-C6 alkoxycarbonyl group, a C1-C6 alkylsulfinyl group, a C1-C6 alkylsulfonyl group, an N—(C1-C6 alkyl)carbamoyl group, an N—(C1-C6 haloalkyl)carbamoyl group, an N-(phenyl) carbamoyl group that may be substituted with a halogen atom or a C1-C6 alkyl group, an N-(pyridyl)carbamoyl group that may be substituted with a halogen atom or a C1-C6 alkyl group, an N,N-di(C1-C6 alkyl)carbamoyl group, an N—(C1-C6 alkylcarbonyl)amino group, an N—(C1-C6 haloalkylcarbonyl)amino group, an N—(C1-C6 alkoxycarbonyl)amino group, an N—(C1-C6 haloalkoxycarbonyl)amino group, a C1-C6 alkylsulfonylamino group in which the nitrogen atom may be substituted with a C1-C6 alkyl group, a C1-C6 haloalkylsulfonylamino group in which the nitrogen atom may be substituted with a C1-C6 alkyl group, a phenylsulfonylamino group in which the nitrogen atom may be substituted with a C1-C6 alkyl group and the phenyl group may be substituted with a halogen atom or a C1-C6 alkyl group, a (C1-C6 alkyl)aminosulfonyl group in which the nitrogen atom may be substituted with a C1-C6 alkyl group, a phenyl group that may be substituted with a halogen atom or a C1-C6 alkyl group, and a phenoxy group that may be substituted with a halogen atom or a C1-C6 alkyl group;

Z' represents a hydrogen atom, a halogen atom, a cyano group, a C1-C6 alkyl group, a C3-C6 cycloalkyl group, a C1-C6 alkoxy group, a C1-C6 haloalkyl group, a C1-C6 alkylthio group, a C1-C6 haloalkylthio group, a C1-C6 alkoxycarbonyl group, an N—(C1-C6 alkyl)carbamoyl group, an N—(C1-C6 haloalkyl)carbamoyl group, an N-(phenyl)carbamoyl group that may be substituted with a halogen atom or a C1-C6 alkyl group, an N,N-di(C1-C6 alkyl)carbamoyl group, an amino group, a C1-C6 alkylamino group, a di(C1-C6 alkyl)amino group, a (C1-C6 alkyl)carbonylamino group, or a (C1-C6 haloalkyl)carbonylamino group.

Examples of each group of R' include those of the corresponding group described for R in formula (1).

Examples of each group of X' include those of the corresponding group described for X in formula (1).

Examples of each group of Q' include those of the corresponding group described for Q in formula (1).

Examples of each group of Z' include those of the corresponding group described for Z in formula (1).

Representative examples of the 1,2,3-triazole derivative represented by formula (1) are shown together in Tables 1 to 4 below, but the present invention is not limited to these compounds. These compounds include compounds encompassing an optical isomer, an E form, and a Z form.

Each of the following notations in the Tables as well as in the present description represents the corresponding group described below.

In addition, "Me" stands for a methyl group, "Et" stands for an ethyl group, "n-Pr" stands for a normal-propyl group, "i-Pr" stands for an isopropyl group, "c-Pr" stands for a cyclopropyl group, "n-Bu" stands for a normal-butyl group, "n-Pen" stands for a normal-pentyl group, "tert-Bu" stands for a tertiary-butyl group, "n-Pen" stands for a normal-pentyl group, "n-Hex" stands for a normal-hexyl group, "Ac" stands for an acetyl group, and "Ph" stands for a phenyl group.

TABLE 1-1

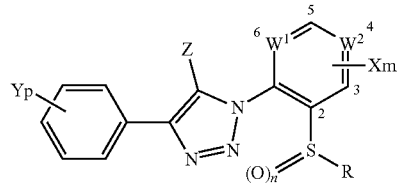

| Compound No. | R | n | Xm | Yp | Z | W¹ | W² | Profile | Melting Point (° C.) |
|---|---|---|---|---|---|---|---|---|---|
| 1-1 | Me | 0 | H | H | H | CH | CH | | |
| 1-2 | Me | 0 | H | 3-CF$_3$ | H | CH | CH | | |
| 1-3 | Me | 0 | H | 3-CF$_3$ | Me | CH | CH | | |
| 1-4 | Me | 0 | H | 4-CF$_3$ | H | CH | CH | | |
| 1-5 | Me | 0 | H | 4-CF$_3$ | Me | CH | CH | | |
| 1-6 | Me | 0 | H | 3,5-(CF$_3$)$_2$ | H | CH | CH | | |
| 1-7 | Me | 0 | H | 3,5-(CF$_3$)$_2$ | Me | CH | CH | | |
| 1-8 | Me | 0 | H | 3,5-(CF$_3$)$_2$ | F | CH | CH | | |
| 1-9 | Me | 0 | H | 3,5-(CF$_3$)$_2$ | Cl | CH | CH | | |
| 1-10 | Me | 0 | H | 3,5-(CF$_3$)$_2$ | Br | CH | CH | | |
| 1-11 | Me | 0 | H | 3,5-(CF$_3$)$_2$ | I | CH | CH | | |
| 1-12 | Me | 0 | 3-Cl | 3,5-(CF$_3$)$_2$ | H | CH | CH | | |
| 1-13 | Me | 0 | 6-Cl | 3,5-(CF$_3$)$_2$ | H | CH | CH | | |
| 1-14 | Me | 0 | 4-CF$_3$ | 3,5-(CF$_3$)$_2$ | H | CH | CH | | |
| 1-15 | Me | 0 | 5-CF$_3$ | 3,5-(CF$_3$)$_2$ | H | CH | CH | | |
| 1-16 | Et | 0 | H | H | H | CH | CH | pale yellow solid | 88-90 |
| 1-17 | Et | 0 | H | H | Me | CH | CH | | |
| 1-18 | Et | 0 | H | H | Cl | CH | CH | | |
| 1-19 | Et | 0 | H | H | Br | CH | CH | | |
| 1-20 | Et | 0 | H | H | I | CH | CH | | |
| 1-21 | Et | 0 | H | 3-Cl | H | CH | CH | red-tan oily | |
| 1-22 | Et | 0 | H | 4-Cl | H | CH | CH | colorless oily | |
| 1-23 | Et | 0 | H | 3-Br | H | CH | CH | red-tan oily | |
| 1-24 | Et | 0 | H | 3-OCF$_3$ | H | CH | CH | red-tan oily | |
| 1-25 | Et | 0 | H | 2-CF$_3$ | H | CH | CH | colorless oily | |
| 1-26 | Et | 0 | H | 3-CF$_3$ | H | CH | CH | tan oily | |
| 1-27 | Et | 0 | H | 3-CF$_3$ | Me | CH | CH | red-tan oily | |
| 1-28 | Et | 0 | H | 3-CF$_3$ | Et | CH | CH | red-tan oily | |
| 1-29 | Et | 0 | H | 3-CF$_3$ | Cl | CH | CH | yellow solid | 87-90 |
| 1-30 | Et | 0 | H | 3-CF$_3$ | Br | CH | CH | | |
| 1-31 | Et | 0 | H | 3-CF$_3$ | I | CH | CH | white solid | 136-139 |
| 1-32 | Et | 0 | 3-Cl | 3-CF$_3$ | H | CH | CH | | |
| 1-33 | Et | 0 | 4-Cl | 3-CF$_3$ | H | CH | CH | | |
| 1-34 | Et | 0 | 5-Cl | 3-CF$_3$ | H | CH | CH | | |
| 1-35 | Et | 0 | 6-Cl | 3-CF$_3$ | H | CH | CH | | |
| 1-36 | Et | 0 | 3-CF$_3$ | 3-CF$_3$ | H | CH | CH | | |
| 1-37 | Et | 0 | 4-CF$_3$ | 3-CF$_3$ | H | CH | CH | | |
| 1-38 | Et | 0 | 5-CF$_3$ | 3-CF$_3$ | H | CH | CH | yellow oily | |
| 1-39 | Et | 0 | 6-CF$_3$ | 3-CF$_3$ | H | CH | CH | | |
| 1-40 | Et | 0 | H | 4-CF$_3$ | H | CH | CH | white solid | 114-115 |
| 1-41 | Et | 0 | H | 4-CF$_3$ | Me | CH | CH | | |
| 1-42 | Et | 0 | H | 4-CF$_3$ | Cl | CH | CH | | |
| 1-43 | Et | 0 | H | 4-CF$_3$ | Br | CH | CH | | |
| 1-44 | Et | 0 | H | 4-CF$_3$ | I | CH | CH | | |
| 1-45 | Et | 0 | 3-Cl | 4-CF$_3$ | H | CH | CH | | |

TABLE 1-2

| Compound No. | R | n | Xm | Yp | Z | W¹ | W² | Profile | Melting Point (° C.) |
|---|---|---|---|---|---|---|---|---|---|
| 1-46 | Et | 0 | 4-Cl | 4-CF$_3$ | H | CH | CH | | |
| 1-47 | Et | 0 | 5-Cl | 4-CF$_3$ | H | CH | CH | | |
| 1-48 | Et | 0 | 6-Cl | 4-CF$_3$ | H | CH | CH | | |
| 1-49 | Et | 0 | 3-CF$_3$ | 4-CF$_3$ | H | CH | CH | | |
| 1-50 | Et | 0 | 4-CF$_3$ | 4-CF$_3$ | H | CH | CH | | |
| 1-51 | Et | 0 | 5-CF$_3$ | 4-CF$_3$ | H | CH | CH | | |
| 1-52 | Et | 0 | 6-CF$_3$ | 4-CF$_3$ | H | CH | CH | | |
| 1-53 | Et | 0 | H | 4-tert-Bu | H | CH | CH | colorless oily | |
| 1-54 | Et | 0 | H | 4-Ph | H | CH | CH | brown solid | 117-121 |

TABLE 1-2-continued

| Compound No. | R | n | Xm | Yp | Z | W¹ | W² | Profile | Melting Point (° C.) |
|---|---|---|---|---|---|---|---|---|---|
| 1-55 | Et | 0 | H | 4-OPh | H | CH | CH | tan oily | |
| 1-56 | Et | 0 | H | 4-CN | H | CH | CH | yellow solid | 72-76 |
| 1-57 | Et | 0 | H | 2-Cl-4-CF$_3$ | H | CH | CH | white solid | <60 |
| 1-58 | Et | 0 | H | 2-Cl-4-CF$_3$ | Me | CH | CH | | |
| 1-59 | Et | 0 | H | 2-Cl-4-CF$_3$ | Cl | CH | CH | | |
| 1-60 | Et | 0 | H | 2-Cl-4-CF$_3$ | Br | CH | CH | | |
| 1-61 | Et | 0 | H | 2-Cl-4-CF$_3$ | I | CH | CH | | |
| 1-62 | Et | 0 | H | 3-Me-5-CF$_3$ | H | CH | CH | | |
| 1-63 | Et | 0 | H | 3-Me-5-CF$_3$ | Me | CH | CH | | |
| 1-64 | Et | 0 | H | 3-Me-5-CF$_3$ | Cl | CH | CH | | |
| 1-65 | Et | 0 | H | 3-Me-5-CF$_3$ | Br | CH | CH | | |
| 1-66 | Et | 0 | H | 3-Me-5-CF$_3$ | I | CH | CH | | |
| 1-67 | Et | 0 | 3-Cl | 3-Me-5-CF$_3$ | H | CH | CH | | |
| 1-68 | Et | 0 | 4-Cl | 3-Me-5-CF$_3$ | H | CH | CH | | |
| 1-69 | Et | 0 | 5-Cl | 3-Me-5-CF$_3$ | H | CH | CH | | |
| 1-70 | Et | 0 | 6-Cl | 3-Me-5-CF$_3$ | H | CH | CH | | |
| 1-71 | Et | 0 | 3-CF$_3$ | 3-Me-5-CF$_3$ | H | CH | CH | | |
| 1-72 | Et | 0 | 4-CF$_3$ | 3-Me-5-CF$_3$ | H | CH | CH | | |
| 1-73 | Et | 0 | 5-CF$_3$ | 3-Me-5-CF$_3$ | H | CH | CH | | |
| 1-74 | Et | 0 | 6-CF$_3$ | 3-Me-5-CF$_3$ | H | CH | CH | | |
| 1-75 | Et | 0 | H | 3,5-(CF$_3$)$_2$ | H | CH | CH | yellow solid | 67 |
| 1-76 | Et | 0 | H | 3,5-(CF$_3$)$_2$ | Me | CH | CH | | |
| 1-77 | Et | 0 | H | 3,5-(CF$_3$)$_2$ | c-Pr | CH | CH | | |
| 1-78 | Et | 0 | H | 3,5-(CF$_3$)$_2$ | CF$_3$ | CH | CH | | |
| 1-79 | Et | 0 | H | 3,5-(CF$_3$)$_2$ | Cl | CH | CH | | |
| 1-80 | Et | 0 | H | 3,5-(CF$_3$)$_2$ | Br | CH | CH | | |
| 1-81 | Et | 0 | H | 3,5-(CF$_3$)$_2$ | I | CH | CH | white solid | 122-125 |
| 1-82 | Et | 0 | H | 3,5-(CF$_3$)$_2$ | NH$_2$ | CH | CH | red-tan oily | |
| 1-83 | Et | 0 | H | 3,5-(CF$_3$)$_2$ | CO$_2$Et | CH | CH | yellow oily | |
| 1-84 | Et | 0 | H | 3,5-(CF$_3$)$_2$ | CN | CH | CH | yellow solid | 119-121 |
| 1-85 | Et | 0 | 3-Cl | 3,5-(CF$_3$)$_2$ | H | CH | CH | white solid | 118-120 |
| 1-86 | Et | 0 | 4-Cl | 3,5-(CF$_3$)$_2$ | H | CH | CH | white solid | 115-118 |
| 1-87 | Et | 0 | 5-Cl | 3,5-(CF$_3$)$_2$ | H | CH | CH | white solid | 98-100 |
| 1-88 | Et | 0 | 6-Cl | 3,5-(CF$_3$)$_2$ | H | CH | CH | yellow solid | 119-124 |
| 1-89 | Et | 0 | 3-CF$_3$ | 3,5-(CF$_3$)$_2$ | H | CH | CH | | |
| 1-90 | Et | 0 | 4-CF$_3$ | 3,5-(CF$_3$)$_2$ | H | CH | CH | yellow solid | 125-127 |
| 1-91 | Et | 0 | 5-CF$_3$ | 3,5-(CF$_3$)$_2$ | H | CH | CH | colorless oily | 98-100 |
| 1-92 | Et | 0 | 6-CF$_3$ | 3,5-(CF$_3$)$_2$ | H | CH | CH | | |
| 1-93 | Et | 0 | H | 3,5-(CF$_3$)$_2$ | Me | CH | CH | | |
| 1-94 | Et | 0 | 3-Cl | 3,5-(CF$_3$)$_2$ | Me | CH | CH | | |
| 1-95 | Et | 0 | 4-Cl | 3,5-(CF$_3$)$_2$ | Me | CH | CH | | |
| 1-96 | Et | 0 | 5-Cl | 3,5-(CF$_3$)$_2$ | Me | CH | CH | | |
| 1-97 | Et | 0 | 6-Cl | 3,5-(CF$_3$)$_2$ | Me | CH | CH | | |
| 1-98 | Et | 0 | 3-CF$_3$ | 3,5-(CF$_3$)$_2$ | Me | CH | CH | | |
| 1-99 | Et | 0 | 4-CF$_3$ | 3,5-(CF$_3$)$_2$ | Me | CH | CH | | |
| 1-100 | Et | 0 | 5-CF$_3$ | 3,5-(CF$_3$)$_2$ | Me | CH | CH | | |

TABLE 1-3

| Compound No. | R | n | Xm | Yp | Z | W¹ | W² | Profile | Melting Point (° C.) |
|---|---|---|---|---|---|---|---|---|---|
| 1-101 | Et | 0 | 6-CF$_3$ | 3,5-(CF$_3$)$_2$ | Me | CH | CH | | |
| 1-102 | Et | 0 | 3-Cl | 3,5-(CF$_3$)$_2$ | Cl | CH | CH | | |
| 1-103 | Et | 0 | 4-Cl | 3,5-(CF$_3$)$_2$ | Cl | CH | CH | | |
| 1-104 | Et | 0 | 5-Cl | 3,5-(CF$_3$)$_2$ | Cl | CH | CH | | |
| 1-105 | Et | 0 | 6-Cl | 3,5-(CF$_3$)$_2$ | Cl | CH | CH | | |
| 1-106 | Et | 0 | 3-CF$_3$ | 3,5-(CF$_3$)$_2$ | Cl | CH | CH | | |
| 1-107 | Et | 0 | 4-CF$_3$ | 3,5-(CF$_3$)$_2$ | Cl | CH | CH | | |
| 1-108 | Et | 0 | 5-CF$_3$ | 3,5-(CF$_3$)$_2$ | Cl | CH | CH | | |
| 1-109 | Et | 0 | 6-CF$_3$ | 3,5-(CF$_3$)$_2$ | Cl | CH | CH | | |
| 1-110 | Et | 0 | 3-Cl | 3,5-(CF$_3$)$_2$ | Br | CH | CH | | |
| 1-111 | Et | 0 | 4-Cl | 3,5-(CF$_3$)$_2$ | Br | CH | CH | | |
| 1-112 | Et | 0 | 5-Cl | 3,5-(CF$_3$)$_2$ | Br | CH | CH | | |
| 1-113 | Et | 0 | 6-Cl | 3,5-(CF$_3$)$_2$ | Br | CH | CH | | |
| 1-114 | Et | 0 | 3-CF$_3$ | 3,5-(CF$_3$)$_2$ | Br | CH | CH | | |
| 1-115 | Et | 0 | 4-CF$_3$ | 3,5-(CF$_3$)$_2$ | Br | CH | CH | | |
| 1-116 | Et | 0 | 5-CF$_3$ | 3,5-(CF$_3$)$_2$ | Br | CH | CH | | |
| 1-117 | Et | 0 | 6-CF$_3$ | 3,5-(CF$_3$)$_2$ | Br | CH | CH | | |
| 1-118 | Et | 0 | 3-Cl | 3,5-(CF$_3$)$_2$ | I | CH | CH | | |
| 1-119 | Et | 0 | 4-Cl | 3,5-(CF$_3$)$_2$ | I | CH | CH | | |
| 1-120 | Et | 0 | 5-Cl | 3,5-(CF$_3$)$_2$ | I | CH | CH | | |
| 1-121 | Et | 0 | 6-Cl | 3,5-(CF$_3$)$_2$ | I | CH | CH | | |
| 1-122 | Et | 0 | 3-CF$_3$ | 3,5-(CF$_3$)$_2$ | I | CH | CH | | |

TABLE 1-3-continued

| Compound No. | R | n | Xm | Yp | Z | W¹ | W² | Profile | Melting Point (° C.) |
|---|---|---|---|---|---|---|---|---|---|
| 1-123 | Et | 0 | 4-CF₃ | 3,5-(CF₃)₂ | I | CH | CH | | |
| 1-124 | Et | 0 | 5-CF₃ | 3,5-(CF₃)₂ | I | CH | CH | | |
| 1-125 | Et | 0 | 6-CF₃ | 3,5-(CF₃)₂ | I | CH | CH | | |
| 1-126 | Et | 0 | H | 4-Cl-3,5-(CF₃)₂ | H | CH | CH | | |
| 1-127 | Et | 0 | H | 4-Cl-3,5-(CF₃)₂ | Me | CH | CH | | |
| 1-128 | Et | 0 | H | 4-Cl-3,5-(CF₃)₂ | Cl | CH | CH | | |
| 1-129 | Et | 0 | H | 4-Cl-3,5-(CF₃)₂ | Br | CH | CH | | |
| 1-130 | Et | 0 | H | 4-Cl-3,5-(CF₃)₂ | I | CH | CH | | |
| 1-131 | Et | 0 | 3-Cl | 4-Cl-3,5-(CF₃)₂ | H | CH | CH | | |
| 1-132 | Et | 0 | 4-Cl | 4-Cl-3,5-(CF₃)₂ | H | CH | CH | | |
| 1-133 | Et | 0 | 5-Cl | 4-Cl-3,5-(CF₃)₂ | H | CH | CH | | |
| 1-134 | Et | 0 | 6-Cl | 4-Cl-3,5-(CF₃)₂ | H | CH | CH | | |
| 1-135 | Et | 0 | 3-CF₃ | 4-Cl-3,5-(CF₃)₂ | H | CH | CH | | |
| 1-136 | Et | 0 | 4-CF₃ | 4-Cl-3,5-(CF₃)₂ | H | CH | CH | | |
| 1-137 | Et | 0 | 5-CF₃ | 4-Cl-3,5-(CF₃)₂ | H | CH | CH | | |
| 1-138 | Et | 0 | 6-CF₃ | 4-Cl-3,5-(CF₃)₂ | H | CH | CH | | |
| 1-139 | Et | 0 | 3-Cl | 4-Me-3,5-(CF₃)₂ | Me | CH | CH | | |
| 1-140 | Et | 0 | 4-Cl | 4-Me-3,5-(CF₃)₂ | Me | CH | CH | | |
| 1-141 | Et | 0 | 5-Cl | 4-Me-3,5-(CF₃)₂ | Me | CH | CH | | |
| 1-142 | Et | 0 | 6-Cl | 4-Me-3,5-(CF₃)₂ | Me | CH | CH | | |
| 1-143 | Et | 0 | 3-CF₃ | 4-Me-3,5-(CF₃)₂ | Me | CH | CH | | |
| 1-144 | Et | 0 | 4-CF₃ | 4-Me-3,5-(CF₃)₂ | Me | CH | CH | | |
| 1-145 | Et | 0 | 5-CF₃ | 4-Me-3,5-(CF₃)₂ | Me | CH | CH | | |
| 1-146 | Et | 0 | 6-CF₃ | 4-Me-3,5-(CF₃)₂ | Me | CH | CH | | |
| 1-147 | Et | 0 | 3-Cl | 4-Me-3,5-(CF₃)₂ | Cl | CH | CH | | |
| 1-148 | Et | 0 | 4-Cl | 4-Me-3,5-(CF₃)₂ | Cl | CH | CH | | |
| 1-149 | Et | 0 | 5-Cl | 4-Me-3,5-(CF₃)₂ | Cl | CH | CH | | |
| 1-150 | Et | 0 | 6-Cl | 4-Me-3,5-(CF₃)₂ | Cl | CH | CH | | |
| 1-151 | Et | 0 | 3-CF₃ | 4-Me-3,5-(CF₃)₂ | Cl | CH | CH | | |
| 1-152 | Et | 0 | 4-CF₃ | 4-Me-3,5-(CF₃)₂ | Cl | CH | CH | | |
| 1-153 | Et | 0 | 5-CF₃ | 4-Me-3,5-(CF₃)₂ | Cl | CH | CH | | |
| 1-154 | Et | 0 | 6-CF₃ | 4-Me-3,5-(CF₃)₂ | Cl | CH | CH | | |
| 1-155 | Et | 0 | 3-Cl | 4-Me-3,5-(CF₃)₂ | Br | CH | CH | | |

TABLE 1-4

| Compound No. | R | n | Xm | Yp | Z | W¹ | W² | Profile | Melting Point (° C.) |
|---|---|---|---|---|---|---|---|---|---|
| 1-156 | Et | 0 | 4-Cl | 4-Me-3,5-(CF₃)₂ | Br | CH | CH | | |
| 1-157 | Et | 0 | 5-Cl | 4-Me-3,5-(CF₃)₂ | Br | CH | CH | | |
| 1-158 | Et | 0 | 6-Cl | 4-Me-3,5-(CF₃)₂ | Br | CH | CH | | |
| 1-159 | Et | 0 | 3-CF₃ | 4-Me-3,5-(CF₃)₂ | Br | CH | CH | | |
| 1-160 | Et | 0 | 4-CF₃ | 4-Me-3,5-(CF₃)₂ | Br | CH | CH | | |
| 1-161 | Et | 0 | 5-CF₃ | 4-Me-3,5-(CF₃)₂ | Br | CH | CH | | |
| 1-162 | Et | 0 | 6-CF₃ | 4-Me-3,5-(CF₃)₂ | Br | CH | CH | | |
| 1-163 | Et | 0 | 3-Cl | 4-Me-3,5-(CF₃)₂ | I | CH | CH | | |
| 1-164 | Et | 0 | 4-Cl | 4-Me-3,5-(CF₃)₂ | I | CH | CH | | |
| 1-165 | Et | 0 | 5-Cl | 4-Me-3,5-(CF₃)₂ | I | CH | CH | | |
| 1-166 | Et | 0 | 6-Cl | 4-Me-3,5-(CF₃)₂ | I | CH | CH | | |
| 1-167 | Et | 0 | 3-CF₃ | 4-Me-3,5-(CF₃)₂ | I | CH | CH | | |
| 1-168 | Et | 0 | 4-CF₃ | 4-Me-3,5-(CF₃)₂ | I | CH | CH | | |
| 1-169 | Et | 0 | 5-CF₃ | 4-Me-3,5-(CF₃)₂ | I | CH | CH | | |
| 1-170 | Et | 0 | 6-CF₃ | 4-Me-3,5-(CF₃)₂ | I | CH | CH | | |
| 1-171 | Et | 0 | H | 3-F-5-CF₃ | H | CH | CH | | |
| 1-172 | Et | 0 | H | 3-F-5-CF₃ | Me | CH | CH | | |
| 1-173 | Et | 0 | H | 3-F-5-CF₃ | Cl | CH | CH | | |
| 1-174 | Et | 0 | H | 3-F-5-CF₃ | Br | CH | CH | | |
| 1-175 | Et | 0 | H | 3-F-5-CF₃ | I | CH | CH | | |
| 1-176 | Et | 0 | 3-Cl | 3-F-5-CF₃ | H | CH | CH | | |
| 1-177 | Et | 0 | 4-Cl | 3-F-5-CF₃ | H | CH | CH | | |
| 1-178 | Et | 0 | 5-Cl | 3-F-5-CF₃ | H | CH | CH | | |
| 1-179 | Et | 0 | 6-Cl | 3-F-5-CF₃ | H | CH | CH | | |
| 1-180 | Et | 0 | 3-CF₃ | 3-F-5-CF₃ | H | CH | CH | | |
| 1-181 | Et | 0 | 4-CF₃ | 3-F-5-CF₃ | H | CH | CH | | |
| 1-182 | Et | 0 | 5-CF₃ | 3-F-5-CF₃ | H | CH | CH | | |
| 1-183 | Et | 0 | 6-CF₃ | 3-F-5-CF₃ | H | CH | CH | | |
| 1-184 | Et | 0 | H | 3-Cl-5-CF₃ | H | CH | CH | | |
| 1-185 | Et | 0 | H | 3-Cl-5-CF₃ | Me | CH | CH | | |
| 1-186 | Et | 0 | H | 3-Cl-5-CF₃ | Cl | CH | CH | | |
| 1-187 | Et | 0 | H | 3-Cl-5-CF₃ | Br | CH | CH | | |
| 1-188 | Et | 0 | H | 3-Cl-5-CF₃ | I | CH | CH | | |
| 1-189 | Et | 0 | 3-Cl | 3-Cl-5-CF₃ | H | CH | CH | | |
| 1-190 | Et | 0 | 4-Cl | 3-Cl-5-CF₃ | H | CH | CH | | |

TABLE 1-4-continued

| Compound No. | R | n | Xm | Yp | Z | W$^1$ | W$^2$ | Profile | Melting Point (° C.) |
|---|---|---|---|---|---|---|---|---|---|
| 1-191 | Et | 0 | 5-Cl | 3-Cl-5-CF$_3$ | H | CH | CH | | |
| 1-192 | Et | 0 | 6-Cl | 3-Cl-5-CF$_3$ | H | CH | CH | | |
| 1-193 | Et | 0 | 3-CF$_3$ | 3-Cl-5-CF$_3$ | H | CH | CH | | |
| 1-194 | Et | 0 | 4-CF$_3$ | 3-Cl-5-CF$_3$ | H | CH | CH | | |
| 1-195 | Et | 0 | 5-CF$_3$ | 3-Cl-5-CF$_3$ | H | CH | CH | | |
| 1-196 | Et | 0 | 6-CF$_3$ | 3-Cl-5-CF$_3$ | H | CH | CH | | |
| 1-197 | Et | 0 | H | 3-Br-5-CF$_3$ | H | CH | CH | colorless oily | |
| 1-198 | Et | 0 | H | 3-Br-5-CF$_3$ | Me | CH | CH | | |
| 1-199 | Et | 0 | H | 3-Br-5-CF$_3$ | Cl | CH | CH | | |
| 1-200 | Et | 0 | H | 3-Br-5-CF$_3$ | Br | CH | CH | | |
| 1-201 | Et | 0 | H | 3-Br-5-CF$_3$ | I | CH | CH | | |
| 1-202 | Et | 0 | 3-Cl | 3-Br-5-CF$_3$ | H | CH | CH | | |
| 1-203 | Et | 0 | 4-Cl | 3-Br-5-CF$_3$ | H | CH | CH | | |
| 1-204 | Et | 0 | 5-Cl | 3-Br-5-CF$_3$ | H | CH | CH | | |
| 1-205 | Et | 0 | 6-Cl | 3-Br-5-CF$_3$ | H | CH | CH | | |
| 1-206 | Et | 0 | 3-CF$_3$ | 3-Br-5-CF$_3$ | H | CH | CH | | |
| 1-207 | Et | 0 | 4-CF$_3$ | 3-Br-5-CF$_3$ | H | CH | CH | | |
| 1-208 | Et | 0 | 5-CF$_3$ | 3-Br-5-CF$_3$ | H | CH | CH | | |
| 1-209 | Et | 0 | 6-CF$_3$ | 3-Br-5-CF$_3$ | H | CH | CH | | |
| 1-210 | Et | 0 | H | 3-CO$_2$Me-5-CF$_3$ | H | CH | CH | yellow solid | 97-100 |

TABLE 1-5

| Compound No. | R | n | Xm | Yp | Z | W$^1$ | W$^2$ | Profile | Melting Point (° C.) |
|---|---|---|---|---|---|---|---|---|---|
| 1-211 | Et | 0 | H | 3,4-(CF$_3$)$_2$ | H | CH | CH | | |
| 1-212 | Et | 0 | 4-Cl | 3,4-(CF$_3$)$_2$ | H | CH | CH | | |
| 1-213 | Et | 0 | 5-Cl | 3,4-(CF$_3$)$_2$ | H | CH | CH | | |
| 1-214 | Et | 0 | 6-Cl | 3,4-(CF$_3$)$_2$ | H | CH | CH | | |
| 1-215 | Et | 0 | 3-CF$_3$ | 3,4-(CF$_3$)$_2$ | H | CH | CH | | |
| 1-216 | Et | 0 | 4-CF$_3$ | 3,4-(CF$_3$)$_2$ | H | CH | CH | | |
| 1-217 | Et | 0 | 5-CF$_3$ | 3,4-(CF$_3$)$_2$ | H | CH | CH | | |
| 1-218 | Et | 0 | 6-CF$_3$ | 3,4-(CF$_3$)$_2$ | H | CH | CH | | |
| 1-219 | Et | 0 | H | 3,4-(CF$_3$)$_2$ | I | CH | CH | | |
| 1-220 | Et | 0 | 4-Cl | 3,4-(CF$_3$)$_2$ | I | CH | CH | | |
| 1-221 | Et | 0 | 5-Cl | 3,4-(CF$_3$)$_2$ | I | CH | CH | | |
| 1-222 | Et | 0 | 6-Cl | 3,4-(CF$_3$)$_2$ | I | CH | CH | | |
| 1-223 | Et | 0 | 3-CF$_3$ | 3,4-(CF$_3$)$_2$ | I | CH | CH | | |
| 1-224 | Et | 0 | 4-CF$_3$ | 3,4-(CF$_3$)$_2$ | I | CH | CH | | |
| 1-225 | Et | 0 | 5-CF$_3$ | 3,4-(CF$_3$)$_2$ | I | CH | CH | | |
| 1-226 | Et | 0 | 6-CF$_3$ | 3,4-(CF$_3$)$_2$ | I | CH | CH | | |
| 1-227 | Et | 0 | H | 3-CONHPh-5-CF$_3$ | H | CH | CH | white solid | 89-96 |
| 1-228 | Et | 0 | H | 3-CONH(4-ClC$_6$H$_4$)-5-CF$_3$ | H | CH | CH | white solid | 93-106 |
| 1-229 | Et | 0 | 5-F | 3,5-(CF$_3$)$_2$ | H | CH | CH | yellow solid | 72-77 |
| 1-230 | Et | 0 | 5-Me | 3,5-(CF$_3$)$_2$ | H | CH | CH | orange solid | 98-99 |
| 1-231 | Et | 0 | 5-OMe | 3,5-(CF$_3$)$_2$ | H | CH | CH | orange oily | |
| 1-232 | Et | 0 | 4-CF$_3$ | 3,5-(CF$_3$)$_2$ | H | N | CH | white solid | 136-138 |
| 1-233 | Et | 0 | H | 4-CF(CF$_3$)$_2$ | H | CH | CH | pale yellow solid | 134-138 |
| 1-234 | Et | 0 | H | 3-CF$_2$CONH$_2$-5-CF$_3$ | H | CH | CH | yellow solid | 82-84 |
| 1-235 | Et | 0 | H | 3,5-(CF$_3$)$_2$ | F | CH | CH | colorless oily | |
| 1-236 | Et | 0 | H | 3-SF$_5$ | H | CH | CH | white solid | 62-63 |
| 1-237 | Et | 0 | H | 3-Ac-5-CF$_3$ | H | CH | CH | yellow oily | |
| 1-238 | Et | 0 | H | 3-CF$_3$-5-CF$_2$CONHMe | H | CH | CH | yellow oily | |
| 1-239 | Et | 0 | H | 3,5-Cl$_2$ | H | CH | CH | white solid | 113-114 |
| 1-240 | Et | 0 | H | 3-CF$_2$CN-5-CF$_3$ | H | CH | CH | white solid | 66-68 |
| 1-241 | Et | 0 | H | 3-COPh-5-CF$_3$ | H | CH | CH | colorless oily | |
| 1-242 | Et | 0 | H | 3-CF$_3$-5-CF$_2$CONHPh | H | CH | CH | white solid | 125-127 |
| 1-243 | Et | 0 | H | 3-CF$_2$Me-5-CF$_3$ | H | CH | CH | colorless oily | |
| 1-244 | CHFCH$_3$ | 0 | H | 3-CF$_2$Me-5-CF$_3$ | H | CH | CH | pale yellow oily | |
| 1-245 | Et | 0 | H | 3-Ph-5-CF$_3$ | H | CH | CH | white solid | 130-131 |
| 1-246 | Et | 0 | H | 3-(c-Pr)-5-CF$_3$ | H | CH | CH | orange oily | |
| 1-247 | Et | 0 | 4-Ph | 3,5-(CF$_3$)$_2$ | H | CH | CH | white solid | 92-93 |
| 1-248 | Et | 0 | 4-(4-ClC$_6$H$_4$) | 3,5-(CF$_3$)$_2$ | H | CH | CH | white solid | 170-171 |
| 1-249 | Et | 0 | 4-OPh | 3,5-(CF$_3$)$_2$ | H | CH | CH | colorless oily | |
| 1-250 | Et | 0 | 4-CN | 3,5-(CF$_3$)$_2$ | H | CH | CH | yellow solid | 187-188 |
| 1-251 | Et | 0 | 4-Br | 3,5-(CF$_3$)$_2$ | H | CH | CH | white solid | 125-126 |

TABLE 1-5-continued

| Compound No. | R | n | Xm | Yp | Z | W¹ | W² | Profile | Melting Point (° C.) |
|---|---|---|---|---|---|---|---|---|---|
| 1-252 | Et | 0 | 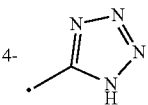 | 3,5-(CF₃)₂ | H | CH | CH | brown solid | 205-206 |
| 1-253 | Et | 0 | 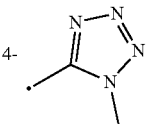 | 3,5-(CF₃)₂ | H | CH | CH | | |
| 1-254 | Et | 0 | 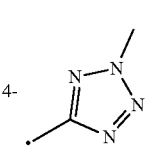 | 3,5-(CF₃)₂ | H | CH | CH | white solid | 162-164 |
| 1-255 | Et | 0 | 4-(c-Pr) | 3,5-(CF₃)₂ | H | CH | CH | white solid | 110-112 |
| 1-256 | Et | 0 | H | 3-CH₂CN-5-CF₃ | H | CH | CH | colorless oily | |
| 1-257 | Et | 0 | 4-COOH | 3,5-(CH₃)₂ | H | CH | CH | pale yellow solid | 248-250 |
| 1-258 | Et | 0 | 4-CH₂OH | 3,5-(CH₃)₂ | H | CH | CH | yellow solid | 122-126 |
| 1-259 | Et | 0 | H | 3-(1-cyanocyclopropyl)-5-CF₃ | H | CH | CH | colorless oily | |
| 1-260 | Et | 0 | 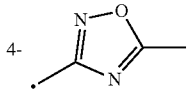 | 3,5-(CF₃)₂ | H | CH | CH | | |

TABLE 1-6

| Compound No. | R | n | Xm | Yp | Z | W¹ | W² | Profile | Melting Point (° C.) |
|---|---|---|---|---|---|---|---|---|---|
| 1-261 | Et | 0 | 4-NHPh | 3,5-(CF₃)₂ | H | CH | CH | colorless oily | |
| 1-262 | Et | 0 | 4-SOPh | 3,5-(CF₃)₂ | H | CH | CH | | |
| 1-263 | Et | 0 | 4-SPh | 3,5-(CF₃)₂ | H | CH | CH | | |
| 1-264 | Et | 0 | 4-SO₂Ph | 3,5-(CF₃)₂ | H | CH | CH | | |
| 1-265 | Et | 0 | 4-COOEt | 3,5-(CF₃)₂ | H | CH | CH | | 156-159 |
| 1-266 | Et | 0 | 4-CONHMe | 3,5-(CF₃)₂ | H | CH | CH | white solid | 209-211 |
| 1-267 | Et | 0 | 4-CH₂CN | 3,5-(CF₃)₂ | H | CH | CH | white solid | 146-149 |
| 1-268 | Et | 0 | 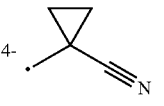 | 3,5-(CF₃)₂ | H | CH | CH | orange solid | 130-133 |
| 1-269 | Et | 0 | 6-COOEt | 3,5-(CF₃)₂ | H | CH | CH | white solid | 114-117 |
| 1-270 | Et | 0 | 6-CONHMe | 3,5-(CF₃)₂ | H | CH | CH | white solid | 218-219 |
| 1-271 | Et | 0 | 4-Cl-6-SEt | 3,5-(CF₃)₂ | H | CH | CH | yellow solid | 169-171 |
| 1-272 | Et | 0 | 4-Cl-6-SO₂Et | 3,5-(CF₃)₂ | H | CH | CH | | |
| 1-273 | Et | 0 | 4-Ac | 3,5-(CF₃)₂ | H | CH | CH | white solid | 163-165 |
| 1-274 | Et | 0 | 4-COPh | 3,5-(CF₃)₂ | H | CH | CH | white solid | 147-150 |
| 1-275 | Et | 0 | H | 2-F-5-CF₃ | H | CH | CH | white solid | 60> |
| 1-276 | Et | 0 | 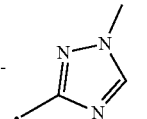 | 3,5-(CF₃)₂ | H | CH | CH | | |
| 1-277 | Et | 0 | 4-I | 3,5-(CF₃)₂ | H | CH | CH | orange solid | 113-118 |
| 1-278 | Et | 0 | 4-OCF₃ | 3,5-(CF₃)₂ | H | CH | CH | white solid | 91-94 |
| 1-279 | Et | 0 | 4-CF₃ | 4-CF₃ | H | N | CH | white solid | 101-103 |
| 1-280 | Et | 0 | H | 3,5-(CF₃)₂ | COOH | CH | CH | white solid | 158-161 |
| 1-281 | Et | 0 | H | 3,5-(CF₃)₂ | CONH₂ | CH | CH | white solid | 227-232 |

TABLE 1-6-continued

| Compound No. | R | n | Xm | Yp | Z | W¹ | W² | Profile | Melting Point (° C.) |
|---|---|---|---|---|---|---|---|---|---|
| 1-282 | Et | 0 | H | 3,5-(CF₃)₂ | CONHPh | CH | CH | white solid | 173-175 |
| 1-283 | Et | 0 | H | 3,5-(CF₃)₂ | CONH(4-ClC₆H₄) | CH | CH | white solid | 207-209 |
| 1-284 | Et | 0 | H | 3,5-(CF₃)₂ | CONHMe | CH | CH | white solid | 136-139 |
| 1-285 | Et | 0 | H | 3,5-(CF₃)₂ | CONMe₂ | CH | CH | yellow oily | |
| 1-286 | Et | 0 | H | 3,5-(CF₃)₂ | NHCOCF₃ | CH | CH | white solid | 166-169 |
| 1-287 | Et | 0 | H | 3,5-(CF₃)₂ | NHCOPh | CH | CH | orange solid | 160-164 |
| 1-288 | Et | 0 | H | 3,5-(CF₃)₂ | NHCO(3-ClC₆H₄) | CH | CH | orange solid | 138-140 |
| 1-289 | Et | 0 | H | 3,5-(CF₃)₂ | NHCO(4-ClC₆H₄) | CH | CH | white solid | 204-208 |
| 1-290 | Et | 0 | H | 3,5-(CF₃)₂ | NAc₂ | CH | CH | pale yellow oily | |
| 1-291 | Et | 0 | H | 3-COOH-5-CF₃ | H | CH | CH | pale yellow solid | 208-209 |
| 1-292 | Et | 0 | H | 3,5-(CF₃)₂ | NHCO(2-ClC₆H₄) | CH | CH | orange solid | 155-158 |
| 1-293 | Et | 0 | 4-CF(CF₃)₂ | 3,5-(CF₃)₂ | H | CH | CH | | |
| 1-294 | Et | 0 | 4-SF₅ | 3,5-(CF₃)₂ | H | CH | CH | | |
| 1-295 | Et | 1 | H | H | H | CH | CH | white solid | 161-165 |
| 1-296 | Et | 1 | H | H | Me | CH | CH | | |
| 1-297 | Et | 1 | H | H | Cl | CH | CH | | |
| 1-298 | Et | 1 | H | H | Br | CH | CH | | |
| 1-299 | Et | 1 | H | H | I | CH | CH | | |
| 1-300 | Et | 1 | H | 3-Cl | H | CH | CH | white solid | 134-136 |
| 1-301 | Et | 1 | H | 4-Cl | H | CH | CH | white solid | 180-181 |
| 1-302 | Et | 1 | H | 3-Br | H | CH | CH | white solid | 141-144 |
| 1-303 | Et | 1 | H | 3-OCF₃ | H | CH | CH | white solid | 109-112 |
| 1-304 | Et | 1 | H | 2-CF₃ | H | CH | CH | white solid | 131-133 |
| 1-305 | Et | 1 | H | 3-CF₃ | H | CH | CH | white solid | 144-147 |
| 1-306 | Et | 1 | H | 3-CF₃ | Me | CH | CH | red-tan oily | |
| 1-307 | Et | 1 | H | 3-CF₃ | Et | CH | CH | | |
| 1-308 | Et | 1 | H | 3-CF₃ | Cl | CH | CH | pale yellow oily | |
| 1-309 | Et | 1 | H | 3-CF₃ | Br | CH | CH | | |
| 1-310 | Et | 1 | H | 3-CF₃ | I | CH | CH | white solid | 122-125 |

TABLE 1-7

| Compound No. | R | n | Xm | Yp | Z | W¹ | W² | Profile | Melting Point (° C.) |
|---|---|---|---|---|---|---|---|---|---|
| 1-311 | Et | 1 | 3-Cl | 3-CF₃ | H | CH | CH | | |
| 1-312 | Et | 1 | 4-Cl | 3-CF₃ | H | CH | CH | | |
| 1-313 | Et | 1 | 5-Cl | 3-CF₃ | H | CH | CH | | |
| 1-314 | Et | 1 | 6-Cl | 3-CF₃ | H | CH | CH | | |
| 1-315 | Et | 1 | 3-CF₃ | 3-CF₃ | H | CH | CH | | |
| 1-316 | Et | 1 | 4-CF₃ | 3-CF₃ | H | CH | CH | | |
| 1-317 | Et | 1 | 5-CF₃ | 3-CF₃ | H | CH | CH | white solid | 140-145 |
| 1-318 | Et | 1 | 6-CF₃ | 3-CF₃ | H | CH | CH | | |
| 1-319 | Et | 1 | H | 4-CF₃ | H | CH | CH | white solid | 149-152 |
| 1-320 | Et | 1 | H | 4-CF₃ | Me | CH | CH | | |
| 1-321 | Et | 1 | H | 4-CF₃ | Cl | CH | CH | | |
| 1-322 | Et | 1 | H | 4-CF₃ | Br | CH | CH | | |
| 1-323 | Et | 1 | H | 4-CF₃ | I | CH | CH | | |
| 1-324 | Et | 1 | 3-Cl | 4-CF₃ | H | CH | CH | | |
| 1-325 | Et | 1 | 4-Cl | 4-CF₃ | H | CH | CH | | |
| 1-326 | Et | 1 | 5-Cl | 4-CF₃ | H | CH | CH | | |
| 1-327 | Et | 1 | 6-Cl | 4-CF₃ | H | CH | CH | | |
| 1-328 | Et | 1 | 3-CF₃ | 4-CF₃ | H | CH | CH | | |
| 1-329 | Et | 1 | 4-CF₃ | 4-CF₃ | H | CH | CH | | |
| 1-330 | Et | 1 | 5-CF₃ | 4-CF₃ | H | CH | CH | | |
| 1-331 | Et | 1 | 6-CF₃ | 4-CF₃ | H | CH | CH | | |
| 1-332 | Et | 1 | H | 4-tert-Bu | H | CH | CH | white solid | 162-167 |
| 1-333 | Et | 1 | H | 4-Ph | H | CH | CH | yellow solid | 157-160 |
| 1-334 | Et | 1 | H | 4-OPh | H | CH | CH | tan oily | |
| 1-335 | Et | 1 | H | 4-CN | H | CH | CH | white solid | 158-160 |
| 1-336 | Et | 1 | H | 2-Cl-4-CF₃ | H | CH | CH | white solid | 103-105 |
| 1-337 | Et | 1 | H | 2-Cl-4-CF₃ | Me | CH | CH | | |
| 1-338 | Et | 1 | H | 2-Cl-4-CF₃ | Cl | CH | CH | | |
| 1-339 | Et | 1 | H | 2-Cl-4-CF₃ | Br | CH | CH | | |
| 1-340 | Et | 1 | H | 2-Cl-4-CF₃ | I | CH | CH | | |
| 1-341 | Et | 1 | H | 3-Me-5-CF₃ | H | CH | CH | | |
| 1-342 | Et | 1 | H | 3-Me-5-CF₃ | Me | CH | CH | | |
| 1-343 | Et | 1 | H | 3-Me-5-CF₃ | Cl | CH | CH | | |
| 1-344 | Et | 1 | H | 3-Me-5-CF₃ | Br | CH | CH | | |

TABLE 1-7-continued

| Compound No. | R | n | Xm | Yp | Z | W¹ | W² | Profile | Melting Point (° C.) |
|---|---|---|---|---|---|---|---|---|---|
| 1-345 | Et | 1 | H | 3-Me-5-CF$_3$ | I | CH | CH | | |
| 1-346 | Et | 1 | 3-Cl | 3-Me-5-CF$_3$ | H | CH | CH | | |
| 1-347 | Et | 1 | 4-Cl | 3-Me-5-CF$_3$ | H | CH | CH | | |
| 1-348 | Et | 1 | 5-Cl | 3-Me-5-CF$_3$ | H | CH | CH | | |
| 1-349 | Et | 1 | 6-Cl | 3-Me-5-CF$_3$ | H | CH | CH | | |
| 1-350 | Et | 1 | 3-CF$_3$ | 3-Me-5-CF$_3$ | H | CH | CH | | |
| 1-351 | Et | 1 | 4-CF$_3$ | 3-Me-5-CF$_3$ | H | CH | CH | | |
| 1-352 | Et | 1 | 5-CF$_3$ | 3-Me-5-CF$_3$ | H | CH | CH | | |
| 1-353 | Et | 1 | 6-CF$_3$ | 3-Me-5-CF$_3$ | H | CH | CH | | |
| 1-354 | Et | 1 | H | 3,5-(CF$_3$)$_2$ | H | CH | CH | yellow solid | 169-171 |
| 1-355 | Et | 1 | H | 3,5-(CF$_3$)$_2$ | Me | CH | CH | | |
| 1-356 | Et | 1 | H | 3,5-(CF$_3$)$_2$ | c-Pr | CH | CH | | |
| 1-357 | Et | 1 | H | 3,5-(CF$_3$)$_2$ | CF3 | CH | CH | | |
| 1-358 | Et | 1 | H | 3,5-(CF$_3$)$_2$ | Cl | CH | CH | | |
| 1-359 | Et | 1 | H | 3,5-(CF$_3$)$_2$ | Br | CH | CH | | |
| 1-360 | Et | 1 | H | 3,5-(CF$_3$)$_2$ | I | CH | CH | white solid | 148-152 |
| 1-361 | Et | 1 | H | 3,5-(CF$_3$)$_2$ | NH$_2$ | CH | CH | white solid | 84-89 |
| 1-362 | Et | 1 | H | 3,5-(CF$_3$)$_2$ | CO$_2$Et | CH | CH | pale yellow oily | |
| 1-363 | Et | 1 | H | 3,5-(CF$_3$)$_2$ | CN | CH | CH | white solid | 134-137 |
| 1-364 | Et | 1 | 3-Cl | 3,5-(CF$_3$)$_2$ | H | CH | CH | | 79-82 |
| 1-365 | Et | 1 | 4-Cl | 3,5-(CF$_3$)$_2$ | H | CH | CH | | 186-187 |

TABLE 1-8

| Compound No. | R | n | Xm | Yp | Z | W¹ | W² | Profile | Melting Point (° C.) |
|---|---|---|---|---|---|---|---|---|---|
| 1-366 | Et | 1 | 5-Cl | 3,5-(CF$_3$)$_2$ | H | CH | CH | pale yellow solid | 78-82 |
| 1-367 | Et | 1 | 6-Cl | 3,5-(CF$_3$)$_2$ | H | CH | CH | | 64-68 |
| 1-368 | Et | 1 | 3-CF$_3$ | 3,5-(CF$_3$)$_2$ | H | CH | CH | | |
| 1-369 | Et | 1 | 4-CF$_3$ | 3,5-(CF$_3$)$_2$ | H | CH | CH | white solid | 136-137 |
| 1-370 | Et | 1 | 5-CF$_3$ | 3,5-(CF$_3$)$_2$ | H | CH | CH | white solid | 66-81 |
| 1-371 | Et | 1 | 6-CF$_3$ | 3,5-(CF$_3$)$_2$ | H | CH | CH | | |
| 1-372 | Et | 1 | 3-Cl | 3,5-(CF$_3$)$_2$ | Me | CH | CH | | |
| 1-373 | Et | 1 | 4-Cl | 3,5-(CF$_3$)$_2$ | Me | CH | CH | | |
| 1-374 | Et | 1 | 5-Cl | 3,5-(CF$_3$)$_2$ | Me | CH | CH | | |
| 1-375 | Et | 1 | 6-Cl | 3,5-(CF$_3$)$_2$ | Me | CH | CH | | |
| 1-376 | Et | 1 | 3-CF$_3$ | 3,5-(CF$_3$)$_2$ | Me | CH | CH | | |
| 1-377 | Et | 1 | 4-CF$_3$ | 3,5-(CF$_3$)$_2$ | Me | CH | CH | | |
| 1-378 | Et | 1 | 5-CF$_3$ | 3,5-(CF$_3$)$_2$ | Me | CH | CH | | |
| 1-379 | Et | 1 | 6-CF$_3$ | 3,5-(CF$_3$)$_2$ | Me | CH | CH | | |
| 1-380 | Et | 1 | 3-Cl | 3,5-(CF$_3$)$_2$ | Cl | CH | CH | | |
| 1-381 | Et | 1 | 4-Cl | 3,5-(CF$_3$)$_2$ | Cl | CH | CH | | |
| 1-382 | Et | 1 | 5-Cl | 3,5-(CF$_3$)$_2$ | Cl | CH | CH | | |
| 1-383 | Et | 1 | 6-Cl | 3,5-(CF$_3$)$_2$ | Cl | CH | CH | | |
| 1-384 | Et | 1 | 3-CF$_3$ | 3,5-(CF$_3$)$_2$ | Cl | CH | CH | | |
| 1-385 | Et | 1 | 4-CF$_3$ | 3,5-(CF$_3$)$_2$ | Cl | CH | CH | | |
| 1-386 | Et | 1 | 5-CF$_3$ | 3,5-(CF$_3$)$_2$ | Cl | CH | CH | | |
| 1-387 | Et | 1 | 6-CF$_3$ | 3,5-(CF$_3$)$_2$ | Cl | CH | CH | | |
| 1-388 | Et | 1 | 3-Cl | 3,5-(CF$_3$)$_2$ | Br | CH | CH | | |
| 1-389 | Et | 1 | 4-Cl | 3,5-(CF$_3$)$_2$ | Br | CH | CH | | |
| 1-390 | Et | 1 | 5-Cl | 3,5-(CF$_3$)$_2$ | Br | CH | CH | | |
| 1-391 | Et | 1 | 6-Cl | 3,5-(CF$_3$)$_2$ | Br | CH | CH | | |
| 1-392 | Et | 1 | 3-CF$_3$ | 3,5-(CF$_3$)$_2$ | Br | CH | CH | | |
| 1-393 | Et | 1 | 4-CF$_3$ | 3,5-(CF$_3$)$_2$ | Br | CH | CH | | |
| 1-394 | Et | 1 | 5-CF$_3$ | 3,5-(CF$_3$)$_2$ | Br | CH | CH | | |
| 1-395 | Et | 1 | 6-CF$_3$ | 3,5-(CF$_3$)$_2$ | Br | CH | CH | | |
| 1-396 | Et | 1 | 3-Cl | 3,5-(CF$_3$)$_2$ | I | CH | CH | | |
| 1-397 | Et | 1 | 4-Cl | 3,5-(CF$_3$)$_2$ | I | CH | CH | | |
| 1-398 | Et | 1 | 5-Cl | 3,5-(CF$_3$)$_2$ | I | CH | CH | | |
| 1-399 | Et | 1 | 6-Cl | 3,5-(CF$_3$)$_2$ | I | CH | CH | | |
| 1-400 | Et | 1 | 3-CF$_3$ | 3,5-(CF$_3$)$_2$ | I | CH | CH | | |
| 1-401 | Et | 1 | 4-CF$_3$ | 3,5-(CF$_3$)$_2$ | I | CH | CH | | |
| 1-402 | Et | 1 | 5-CF$_3$ | 3,5-(CF$_3$)$_2$ | I | CH | CH | | |
| 1-403 | Et | 1 | 6-CF$_3$ | 3,5-(CF$_3$)$_2$ | I | CH | CH | | |
| 1-404 | Et | 1 | H | 4-Cl-3,5-(CF$_3$)$_2$ | H | CH | CH | | |
| 1-405 | Et | 1 | H | 4-Cl-3,5-(CF$_3$)$_2$ | Me | CH | CH | | |
| 1-406 | Et | 1 | H | 4-Cl-3,5-(CF$_3$)$_2$ | Cl | CH | CH | | |
| 1-407 | Et | 1 | H | 4-Cl-3,5-(CF$_3$)$_2$ | Br | CH | CH | | |
| 1-408 | Et | 1 | H | 4-Cl-3,5-(CF$_3$)$_2$ | I | CH | CH | | |
| 1-409 | Et | 1 | 3-Cl | 4-Cl-3,5-(CF$_3$)$_2$ | H | CH | CH | | |
| 1-410 | Et | 1 | 4-Cl | 4-Cl-3,5-(CF$_3$)$_2$ | H | CH | CH | | |
| 1-411 | Et | 1 | 5-Cl | 4-Cl-3,5-(CF$_3$)$_2$ | H | CH | CH | | |
| 1-412 | Et | 1 | 6-Cl | 4-Cl-3,5-(CF$_3$)$_2$ | H | CH | CH | | |

TABLE 1-8-continued

| Compound No. | R | n | Xm | Yp | Z | W¹ | W² | Profile | Melting Point (° C.) |
|---|---|---|---|---|---|---|---|---|---|
| 1-413 | Et | 1 | 3-CF$_3$ | 4-Cl-3,5-(CF$_3$)$_2$ | H | CH | CH | | |
| 1-414 | Et | 1 | 4-CF$_3$ | 4-Cl-3,5-(CF$_3$)$_2$ | H | CH | CH | | |
| 1-415 | Et | 1 | 5-CF$_3$ | 4-Cl-3,5-(CF$_3$)$_2$ | H | CH | CH | | |
| 1-416 | Et | 1 | 6-CF$_3$ | 4-Cl-3,5-(CF$_3$)$_2$ | H | CH | CH | | |
| 1-417 | Et | 1 | 3-Cl | 4-Me-3,5-(CF$_3$)$_2$ | Me | CH | CH | | |
| 1-418 | Et | 1 | 4-Cl | 4-Me-3,5-(CF$_3$)$_2$ | Me | CH | CH | | |
| 1-419 | Et | 1 | 5-Cl | 4-Me-3,5-(CF$_3$)$_2$ | Me | CH | CH | | |
| 1-420 | Et | 1 | 6-Cl | 4-Me-3,5-(CF$_3$)$_2$ | Me | CH | CH | | |

TABLE 1-9

| Compound No. | R | n | Xm | Yp | Z | W¹ | W² | Profile | Melting Point (° C.) |
|---|---|---|---|---|---|---|---|---|---|
| 1-421 | Et | 1 | 3-CF$_3$ | 4-Me-3,5-(CF$_3$)$_2$ | Me | CH | CH | | |
| 1-422 | Et | 1 | 4-CF$_3$ | 4-Me-3,5-(CF$_3$)$_2$ | Me | CH | CH | | |
| 1-423 | Et | 1 | 5-CF$_3$ | 4-Me-3,5-(CF$_3$)$_2$ | Me | CH | CH | | |
| 1-424 | Et | 1 | 6-CF$_3$ | 4-Me-3,5-(CF$_3$)$_2$ | Me | CH | CH | | |
| 1-425 | Et | 1 | 3-Cl | 4-Me-3,5-(CF$_3$)$_2$ | Cl | CH | CH | | |
| 1-426 | Et | 1 | 4-Cl | 4-Me-3,5-(CF$_3$)$_2$ | Cl | CH | CH | | |
| 1-427 | Et | 1 | 5-Cl | 4-Me-3,5-(CF$_3$)$_2$ | Cl | CH | CH | | |
| 1-428 | Et | 1 | 6-Cl | 4-Me-3,5-(CF$_3$)$_2$ | Cl | CH | CH | | |
| 1-429 | Et | 1 | 3-CF$_3$ | 4-Me-3,5-(CF$_3$)$_2$ | Cl | CH | CH | | |
| 1-430 | Et | 1 | 4-CF$_3$ | 4-Me-3,5-(CF$_3$)$_2$ | Cl | CH | CH | | |
| 1-431 | Et | 1 | 5-CF$_3$ | 4-Me-3,5-(CF$_3$)$_2$ | Cl | CH | CH | | |
| 1-432 | Et | 1 | 6-CF$_3$ | 4-Me-3,5-(CF$_3$)$_2$ | Cl | CH | CH | | |
| 1-433 | Et | 1 | 3-Cl | 4-Me-3,5-(CF$_3$)$_2$ | Br | CH | CH | | |
| 1-434 | Et | 1 | 4-Cl | 4-Me-3,5-(CF$_3$)$_2$ | Br | CH | CH | | |
| 1-435 | Et | 1 | 5-Cl | 4-Me-3,5-(CF$_3$)$_2$ | Br | CH | CH | | |
| 1-436 | Et | 1 | 6-Cl | 4-Me-3,5-(CF$_3$)$_2$ | Br | CH | CH | | |
| 1-437 | Et | 1 | 3-CF$_3$ | 4-Me-3,5-(CF$_3$)$_2$ | Br | CH | CH | | |
| 1-438 | Et | 1 | 4-CF$_3$ | 4-Me-3,5-(CF$_3$)$_2$ | Br | CH | CH | | |
| 1-439 | Et | 1 | 5-CF$_3$ | 4-Me-3,5-(CF$_3$)$_2$ | Br | CH | CH | | |
| 1-440 | Et | 1 | 6-CF$_3$ | 4-Me-3,5-(CF$_3$)$_2$ | Br | CH | CH | | |
| 1-441 | Et | 1 | 3-Cl | 4-Me-3,5-(CF$_3$)$_2$ | I | CH | CH | | |
| 1-442 | Et | 1 | 4-Cl | 4-Me-3,5-(CF$_3$)$_2$ | I | CH | CH | | |
| 1-443 | Et | 1 | 5-Cl | 4-Me-3,5-(CF$_3$)$_2$ | I | CH | CH | | |
| 1-444 | Et | 1 | 6-Cl | 4-Me-3,5-(CF$_3$)$_2$ | I | CH | CH | | |
| 1-445 | Et | 1 | 3-CF$_3$ | 4-Me-3,5-(CF$_3$)$_2$ | I | CH | CH | | |
| 1-446 | Et | 1 | 4-CF$_3$ | 4-Me-3,5-(CF$_3$)$_2$ | I | CH | CH | | |
| 1-447 | Et | 1 | 5-CF$_3$ | 4-Me-3,5-(CF$_3$)$_2$ | I | CH | CH | | |
| 1-448 | Et | 1 | 6-CF$_3$ | 4-Me-3,5-(CF$_3$)$_2$ | I | CH | CH | | |
| 1-449 | Et | 1 | H | 3-F-5-CF$_3$ | H | CH | CH | | |
| 1-450 | Et | 1 | H | 3-F-5-CF$_3$ | Me | CH | CH | | |
| 1-451 | Et | 1 | H | 3-F-5-CF$_3$ | Cl | CH | CH | | |
| 1-452 | Et | 1 | H | 3-F-5-CF$_3$ | Br | CH | CH | | |
| 1-453 | Et | 1 | H | 3-F-5-CF$_3$ | I | CH | CH | | |
| 1-454 | Et | 1 | 3-Cl | 3-F-5-CF$_3$ | H | CH | CH | | |
| 1-455 | Et | 1 | 4-Cl | 3-F-5-CF$_3$ | H | CH | CH | | |
| 1-456 | Et | 1 | 5-Cl | 3-F-5-CF$_3$ | H | CH | CH | | |
| 1-457 | Et | 1 | 6-Cl | 3-F-5-CF$_3$ | H | CH | CH | | |
| 1-458 | Et | 1 | 3-CF$_3$ | 3-F-5-CF$_3$ | H | CH | CH | | |
| 1-459 | Et | 1 | 4-CF$_3$ | 3-F-5-CF$_3$ | H | CH | CH | | |
| 1-460 | Et | 1 | 5-CF$_3$ | 3-F-5-CF$_3$ | H | CH | CH | | |
| 1-461 | Et | 1 | 6-CF$_3$ | 3-F-5-CF$_3$ | H | CH | CH | | |
| 1-462 | Et | 1 | H | 3-Cl-5-CF$_3$ | H | CH | CH | | |
| 1-463 | Et | 1 | H | 3-Cl-5-CF$_3$ | Me | CH | CH | | |
| 1-464 | Et | 1 | H | 3-Cl-5-CF$_3$ | Cl | CH | CH | | |
| 1-465 | Et | 1 | H | 3-Cl-5-CF$_3$ | Br | CH | CH | | |
| 1-466 | Et | 1 | H | 3-Cl-5-CF$_3$ | I | CH | CH | | |
| 1-467 | Et | 1 | 3-Cl | 3-Cl-5-CF$_3$ | H | CH | CH | | |
| 1-468 | Et | 1 | 4-Cl | 3-Cl-5-CF$_3$ | H | CH | CH | | |
| 1-469 | Et | 1 | 5-Cl | 3-Cl-5-CF$_3$ | H | CH | CH | | |
| 1-470 | Et | 1 | 6-Cl | 3-Cl-5-CF$_3$ | H | CH | CH | | |
| 1-471 | Et | 1 | 3-CF$_3$ | 3-Cl-5-CF$_3$ | H | CH | CH | | |
| 1-472 | Et | 1 | 4-CF$_3$ | 3-Cl-5-CF$_3$ | H | CH | CH | | |
| 1-473 | Et | 1 | 5-CF$_3$ | 3-Cl-5-CF$_3$ | H | CH | CH | | |
| 1-474 | Et | 1 | 6-CF$_3$ | 3-Cl-5-CF$_3$ | H | CH | CH | | |
| 1-475 | Et | 1 | H | 3-Br-5-CF$_3$ | H | CH | CH | white solid | 172-173 |

TABLE 1-10

| Compound No. | R | n | Xm | Yp | Z | W¹ | W² | Profile | Melting Point (° C.) |
|---|---|---|---|---|---|---|---|---|---|
| 1-476 | Et | 1 | H | 3-Br-5-CF$_3$ | Me | CH | CH | | |
| 1-477 | Et | 1 | H | 3-Br-5-CF$_3$ | Cl | CH | CH | | |
| 1-478 | Et | 1 | H | 3-Br-5-CF$_3$ | Br | CH | CH | | |
| 1-479 | Et | 1 | H | 3-Br-5-CF$_3$ | I | CH | CH | | |
| 1-480 | Et | 1 | 3-Cl | 3-Br-5-CF$_3$ | H | CH | CH | | |
| 1-481 | Et | 1 | 4-Cl | 3-Br-5-CF$_3$ | H | CH | CH | | |
| 1-482 | Et | 1 | 5-Cl | 3-Br-5-CF$_3$ | H | CH | CH | | |
| 1-483 | Et | 1 | 6-Cl | 3-Br-5-CF$_3$ | H | CH | CH | | |
| 1-484 | Et | 1 | 3-CF$_3$ | 3-Br-5-CF$_3$ | H | CH | CH | | |
| 1-485 | Et | 1 | 4-CF$_3$ | 3-Br-5-CF$_3$ | H | CH | CH | | |
| 1-486 | Et | 1 | 5-CF$_3$ | 3-Br-5-CF$_3$ | H | CH | CH | | |
| 1-487 | Et | 1 | 6-CF$_3$ | 3-Br-5-CF$_3$ | H | CH | CH | | |
| 1-488 | Et | 1 | H | 3-CO$_2$Me-5-CF$_3$ | H | CH | CH | white solid | 71-82 |
| 1-489 | Et | 1 | H | 3,4-(CF$_3$)$_2$ | H | CH | CH | | |
| 1-490 | Et | 1 | 4-Cl | 3,4-(CF$_3$)$_2$ | H | CH | CH | | |
| 1-491 | Et | 1 | 5-Cl | 3,4-(CF$_3$)$_2$ | H | CH | CH | | |
| 1-492 | Et | 1 | 6-Cl | 3,4-(CF$_3$)$_2$ | H | CH | CH | | |
| 1-493 | Et | 1 | 3-CF$_3$ | 3,4-(CF$_3$)$_2$ | H | CH | CH | | |
| 1-494 | Et | 1 | 4-CF$_3$ | 3,4-(CF$_3$)$_2$ | H | CH | CH | | |
| 1-495 | Et | 1 | 5-CF$_3$ | 3,4-(CF$_3$)$_2$ | H | CH | CH | | |
| 1-496 | Et | 1 | 6-CF$_3$ | 3,4-(CF$_3$)$_2$ | H | CH | CH | | |
| 1-497 | Et | 1 | H | 3,4-(CF$_3$)$_2$ | I | CH | CH | | |
| 1-498 | Et | 1 | 4-Cl | 3,4-(CF$_3$)$_2$ | I | CH | CH | | |
| 1-499 | Et | 1 | 5-Cl | 3,4-(CF$_3$)$_2$ | I | CH | CH | | |
| 1-500 | Et | 1 | 6-Cl | 3,4-(CF$_3$)$_2$ | I | CH | CH | | |
| 1-501 | Et | 1 | 3-CF$_3$ | 3,4-(CF$_3$)$_2$ | I | CH | CH | | |
| 1-502 | Et | 1 | 4-CF$_3$ | 3,4-(CF$_3$)$_2$ | I | CH | CH | | |
| 1-503 | Et | 1 | 5-CF$_3$ | 3,4-(CF$_3$)$_2$ | I | CH | CH | | |
| 1-504 | Et | 1 | 6-CF$_3$ | 3,4-(CF$_3$)$_2$ | I | CH | CH | | |
| 1-505 | Et | 1 | H | 3-CONHPh-5-CF$_3$ | H | CH | CH | white solid | 227-230 |
| 1-506 | Et | 1 | H | 3-CONH(4-ClC$_6$H$_4$)-5-CF$_3$ | H | CH | CH | white solid | 206-211 |
| 1-507 | Et | 1 | 5-F | 3,5-(CF$_3$)$_2$ | H | CH | CH | white solid | 187-188 |
| 1-508 | Et | 1 | 5-Me | 3,5-(CF$_3$)$_2$ | H | CH | CH | white solid | 166-167 |
| 1-509 | Et | 1 | 5-OMe | 3,5-(CF$_3$)$_2$ | H | CH | CH | white solid | 65-70 |
| 1-510 | Et | 1 | 4-CF$_3$ | 3,5-(CF$_3$)$_2$ | H | N | CH | white solid | 250≤ |
| 1-511 | Et | 1 | H | 4-CF(CF$_3$)$_2$ | H | CH | CH | white solid | 174-179 |
| 1-512 | Et | 1 | H | 3,5-(CF$_3$)$_2$ | F | CH | CH | white solid | 120-122 |
| 1-513 | Et | 1 | H | 3-SF$_5$ | H | CH | CH | white solid | 153-154 |
| 1-514 | Et | 1 | H | 3-Ac-5-CF$_3$ | H | CH | CH | white solid | 154-156 |
| 1-515 | Et | 1 | H | 3-CF$_3$-5-CF$_2$CONHMe | H | CH | CH | white solid | 79-83 |
| 1-516 | Et | 1 | H | 3,5-Cl$_2$ | H | CH | CH | white solid | 196-199 |
| 1-517 | Et | 1 | H | 3-CF$_2$CN-5-CF$_3$ | H | CH | CH | white solid | 152-155 |
| 1-518 | Et | 1 | H | 3-COPh-5-CF$_3$ | H | CH | CH | white solid | 112-122 |
| 1-519 | Et | 1 | H | 3-CF$_3$-5-CF$_2$CONHPh | H | CH | CH | white solid | 90-97 |
| 1-520 | Et | 1 | H | 3-CF$_2$Me-5-CF$_3$ | H | CH | CH | white solid | 165-167 |
| 1-521 | CHFCH$_3$ | 1 | H | 3-CF$_2$Me-5-CF$_3$ | H | CH | CH | | |
| 1-522 | Et | 1 | H | 3-Ph-5-CF$_3$ | H | CH | CH | white solid | 158-159 |
| 1-523 | Et | 1 | H | 3-(c-Pr)-5-CF$_3$ | H | CH | CH | white solid | 159-160 |
| 1-524 | Et | 1 | 4-Ph | 3,5-(CF$_3$)$_2$ | H | CH | CH | white solid | 178-179 |
| 1-525 | Et | 1 | 4-(4-ClC$_6$H$_4$) | 3,5-(CF$_3$)$_2$ | H | CH | CH | white solid | 188-189 |
| 1-526 | Et | 1 | 4-OPh | 3,5-(CF$_3$)$_2$ | H | CH | CH | white solid | 142-144 |
| 1-527 | Et | 1 | 4-CN | 3,5-(CF$_3$)$_2$ | H | CH | CH | white solid | 203-206 |
| 1-528 | Et | 1 | 4-Br | 3,5-(CF$_3$)$_2$ | H | CH | CH | white solid | 187-189 |
| 1-529 | Et | 1 | 4-(1H-tetrazol-5-yl) | 3,5-(CF$_3$)$_2$ | H | CH | CH | white solid | 250≤ |
| 1-530 | Et | 1 | 4-(1-methyl-tetrazol-5-yl) | 3,5-(CF$_3$)$_2$ | H | CH | CH | | |

TABLE 1-11

| Compound No. | R | n | Xm | Yp | Z | W¹ | W² | Profile | Melting Point (° C.) |
|---|---|---|---|---|---|---|---|---|---|
| 1-531 | Et | 1 | 4-(2-methyl-2H-tetrazol-5-yl) | 3,5-(CF$_3$)$_2$ | H | CH | CH | white solid | 207-212 |
| 1-532 | Et | 1 | 4-(c-Pr) | 3,5-(CF$_3$)$_2$ | H | CH | CH | white solid | 180-181 |
| 1-533 | Et | 1 | H | 3-CH$_2$CN-5-CF$_3$ | H | CH | CH | | |
| 1-534 | Et | 1 | 4-COOH | 3,5-(CF$_3$)$_2$ | H | CH | CH | | |
| 1-535 | Et | 1 | 4-CH$_2$OH | 3,5-(CF$_3$)$_2$ | H | CH | CH | | |
| 1-536 | Et | 1 | H | 3-(1-cyanocyclopropyl)-5-CF$_3$ | H | CH | CH | white solid | 189-191 |
| 1-537 | Et | 1 | 4-(5-methyl-1,2,4-oxadiazol-3-yl) | 3,5-(CF$_3$)$_2$ | H | CH | CH | white solid | 176-178 |
| 1-538 | Et | 1 | 4-NHPh | 3,5-(CF$_3$)$_2$ | H | CH | CH | white solid | 163-164 |
| 1-539 | Et | 1 | 4-SPh | 3,5-(CF$_3$)$_2$ | H | CH | CH | | |
| 1-540 | Et | 1 | 4-SOPh | 3,5-(CF$_3$)$_2$ | H | CH | CH | | |
| 1-541 | Et | 1 | 4-SO$_2$Ph | 3,5-(CF$_3$)$_2$ | H | CH | CH | | |
| 1-542 | Et | 1 | 4-COOEt | 3,5-(CF$_3$)$_2$ | H | CH | CH | white solid | 166-169 |
| 1-543 | Et | 1 | 4-CONHMe | 3,5-(CF$_3$)$_2$ | H | CH | CH | white solid | 225-226 |
| 1-544 | Et | 1 | 4-CH$_2$CN | 3,5-(CF$_3$)$_2$ | H | CH | CH | | |
| 1-545 | Et | 1 | 4-(1-cyanocyclopropyl) | 3,5-(CF$_3$)$_2$ | H | CH | CH | white solid | 201-204 |
| 1-546 | Et | 1 | 6-COOEt | 3,5-(CF$_3$)$_2$ | H | CH | CH | | |
| 1-547 | Et | 1 | 6-CONHMe | 3,5-(CF$_3$)$_2$ | H | CH | CH | white solid | 101-112 |
| 1-548 | Et | 1 | 4-Cl-6-SEt | 3,5-(CF$_3$)$_2$ | H | CH | CH | | |
| 1-549 | Et | 1 | 4-Cl-6-SO$_2$Et | 3,5-(CF$_3$)$_2$ | H | CH | CH | | |
| 1-550 | Et | 1 | 4-Ac | 3,5-(CF$_3$)$_2$ | H | CH | CH | white solid | 163-165 |
| 1-551 | Et | 1 | 4-COPh | 3,5-(CF$_3$)$_2$ | H | CH | CH | white solid | 201-203 |
| 1-552 | Et | 1 | H | 2-F-5-CF$_3$ | H | CH | CH | white solid | 145-146 |
| 1-553 | Et | 1 | 4-(1-methyl-1H-1,2,4-triazol-3-yl) | 3,5-(CF$_3$)$_2$ | H | CH | CH | | |
| 1-554 | Et | 1 | 4-I | 3,5-(CF$_3$)$_2$ | H | CH | CH | white solid | 173-176 |
| 1-555 | Et | 1 | 4-OCF$_3$ | 3,5-(CF$_3$)$_2$ | H | CH | CH | white solid | 131-132 |
| 1-556 | Et | 1 | 4-CF$_3$ | 4-CF$_3$ | H | N | CH | white solid | 196-198 |
| 1-557 | Et | 1 | H | 3,5-(CF$_3$)$_2$ | COOH | CH | CH | | |
| 1-558 | Et | 1 | H | 3,5-(CF$_3$)$_2$ | CONH$_2$ | CH | CH | | |
| 1-559 | Et | 1 | H | 3,5-(CF$_3$)$_2$ | CONHPh | CH | CH | white solid | 184-186 |
| 1-560 | Et | 1 | H | 3,5-(CF$_3$)$_2$ | CONH(4-ClC$_6$H$_4$) | CH | CH | white solid | 102-106 |
| 1-561 | Et | 1 | H | 3,5-(CF$_3$)$_2$ | CONHMe | CH | CH | white solid | 209-211 |
| 1-562 | Et | 1 | H | 3,5-(CF$_3$)$_2$ | CONMe$_2$ | CH | CH | white solid | 140-142 |
| 1-563 | Et | 1 | H | 3,5-(CF$_3$)$_2$ | NHCOCF$_3$ | CH | CH | pale yellow solid | 97-99 |
| 1-564 | Et | 1 | H | 3,5-(CF$_3$)$_2$ | NHCOPh | CH | CH | white solid | 103-108 |
| 1-565 | Et | 1 | H | 3,5-(CF$_3$)$_2$ | NHCO(3-ClC$_6$H$_4$) | CH | CH | white solid | 96-103 |
| 1-566 | Et | 1 | H | 3,5-(CF$_3$)$_2$ | NHCO(4-ClC$_6$H$_4$) | CH | CH | white solid | 104-112 |
| 1-567 | Et | 1 | H | 3,5-(CF$_3$)$_2$ | NAc$_2$ | CH | CH | colorless oily | |
| 1-568 | Et | 1 | H | 3-COOH-5-CF$_3$ | H | CH | CH | | |
| 1-569 | Et | 1 | H | 3,5-(CF$_3$)$_2$ | NHCO(4-ClC$_6$H$_4$) | CH | CH | white solid | 173-177 |
| 1-570 | Et | 1 | 4-CF(CH$_3$)$_2$ | 3,5-(CF$_3$)$_2$ | H | CH | CH | | |
| 1-571 | Et | 1 | 4-SF$_5$ | 3,5-(CF$_3$)$_2$ | H | CH | CH | | |
| 1-572 | Et | 2 | H | H | H | CH | CH | white solid | 156-158 |
| 1-573 | Et | 2 | H | H | Me | CH | CH | | |
| 1-574 | Et | 2 | H | H | Cl | CH | CH | | |
| 1-575 | Et | 2 | H | H | Br | CH | CH | | |

TABLE 1-11-continued

| Compound No. | R | n | Xm | Yp | Z | W¹ | W² | Profile | Melting Point (° C.) |
|---|---|---|---|---|---|---|---|---|---|
| 1-576 | Et | 2 | H | H | I | CH | CH | | |
| 1-577 | Et | 2 | H | 3-Cl | H | CH | CH | colorless oily | |
| 1-578 | Et | 2 | H | 4-Cl | H | CH | CH | white solid | 150-151 |
| 1-579 | Et | 2 | H | 3-Br | H | CH | CH | white solid | 155-160 |
| 1-580 | Et | 2 | H | 3-OCF$_3$ | H | CH | CH | colorless oily | |

TABLE 1-12

| Compound No. | R | n | Xm | Yp | Z | W¹ | W² | Profile | Melting Point (° C.) |
|---|---|---|---|---|---|---|---|---|---|
| 1-581 | Et | 2 | H | 2-CF$_3$ | H | CH | CH | colorless oily | |
| 1-582 | Et | 2 | H | 3-CF$_3$ | H | CH | CH | yellow solid | 105-114 |
| 1-583 | Et | 2 | H | 3-CF$_3$ | Me | CH | CH | red-tan oily | |
| 1-584 | Et | 2 | H | 3-CF$_3$ | Et | CH | CH | pale yellow oily | |
| 1-585 | Et | 2 | H | 3-CF$_3$ | Cl | CH | CH | pale yellow oily | |
| 1-586 | Et | 2 | H | 3-CF$_3$ | Br | CH | CH | | |
| 1-587 | Et | 2 | H | 3-CF$_3$ | I | CH | CH | white solid | 163-165 |
| 1-588 | Et | 2 | 3-Cl | 3-CF$_3$ | H | CH | CH | | |
| 1-589 | Et | 2 | 4-Cl | 3-CF$_3$ | H | CH | CH | | |
| 1-590 | Et | 2 | 5-Cl | 3-CF$_3$ | H | CH | CH | | |
| 1-591 | Et | 2 | 6-Cl | 3-CF$_3$ | H | CH | CH | | |
| 1-592 | Et | 2 | 3-CF$_3$ | 3-CF$_3$ | H | CH | CH | | |
| 1-593 | Et | 2 | 4-CF$_3$ | 3-CF$_3$ | H | CH | CH | | |
| 1-594 | Et | 2 | 5-CF$_3$ | 3-CF$_3$ | H | CH | CH | colorless oily | |
| 1-595 | Et | 2 | 6-CF$_3$ | 3-CF$_3$ | H | CH | CH | | |
| 1-596 | Et | 2 | H | 4-CF$_3$ | H | CH | CH | white solid | 168-171 |
| 1-597 | Et | 2 | H | 4-CF$_3$ | Me | CH | CH | | |
| 1-598 | Et | 2 | H | 4-CF$_3$ | Cl | CH | CH | | |
| 1-599 | Et | 2 | H | 4-CF$_3$ | Br | CH | CH | | |
| 1-600 | Et | 2 | H | 4-CF$_3$ | I | CH | CH | | |
| 1-601 | Et | 2 | 3-Cl | 4-CF$_3$ | H | CH | CH | | |
| 1-602 | Et | 2 | 4-Cl | 4-CF$_3$ | H | CH | CH | | |
| 1-603 | Et | 2 | 5-Cl | 4-CF$_3$ | H | CH | CH | | |
| 1-604 | Et | 2 | 6-Cl | 4-CF$_3$ | H | CH | CH | | |
| 1-605 | Et | 2 | 3-CF$_3$ | 4-CF$_3$ | H | CH | CH | | |
| 1-606 | Et | 2 | 4-CF$_3$ | 4-CF$_3$ | H | CH | CH | | |
| 1-607 | Et | 2 | 5-CF$_3$ | 4-CF$_3$ | H | CH | CH | | |
| 1-608 | Et | 2 | 6-CF$_3$ | 4-CF$_3$ | H | CH | CH | | |
| 1-609 | Et | 2 | H | 4-tert-Bu | H | CH | CH | white solid | 127-131 |
| 1-610 | Et | 2 | H | 4-Ph | H | CH | CH | yellow solid | 178-181 |
| 1-611 | Et | 2 | H | 4-OPh | H | CH | CH | tan solid | 155-159 |
| 1-612 | Et | 2 | H | 4-CN | H | CH | CH | white solid | 165-167 |
| 1-613 | Et | 2 | H | 2-Cl-4-CF$_3$ | H | CH | CH | white solid | 137-139 |
| 1-614 | Et | 2 | H | 2-Cl-4-CF$_3$ | Me | CH | CH | | |
| 1-615 | Et | 2 | H | 2-Cl-4-CF$_3$ | Cl | CH | CH | | |
| 1-616 | Et | 2 | H | 2-Cl-4-CF$_3$ | Br | CH | CH | | |
| 1-617 | Et | 2 | H | 2-Cl-4-CF$_3$ | I | CH | CH | | |
| 1-618 | Et | 2 | H | 3-Me-5-CF$_3$ | H | CH | CH | | |
| 1-619 | Et | 2 | H | 3-Me-5-CF$_3$ | Me | CH | CH | | |
| 1-620 | Et | 2 | H | 3-Me-5-CF$_3$ | Cl | CH | CH | | |
| 1-621 | Et | 2 | H | 3-Me-5-CF$_3$ | Br | CH | CH | | |
| 1-622 | Et | 2 | H | 3-Me-5-CF$_3$ | I | CH | CH | | |
| 1-623 | Et | 2 | 3-Cl | 3-Me-5-CF$_3$ | H | CH | CH | | |
| 1-624 | Et | 2 | 4-Cl | 3-Me-5-CF$_3$ | H | CH | CH | | |
| 1-625 | Et | 2 | 5-Cl | 3-Me-5-CF$_3$ | H | CH | CH | | |
| 1-626 | Et | 2 | 6-Cl | 3-Me-5-CF$_3$ | H | CH | CH | | |
| 1-627 | Et | 2 | 3-CF$_3$ | 3-Me-5-CF$_3$ | H | CH | CH | | |
| 1-628 | Et | 2 | 4-CF$_3$ | 3-Me-5-CF$_3$ | H | CH | CH | | |
| 1-629 | Et | 2 | 5-CF$_3$ | 3-Me-5-CF$_3$ | H | CH | CH | | |
| 1-630 | Et | 2 | 6-CF$_3$ | 3-Me-5-CF$_3$ | H | CH | CH | | |
| 1-631 | Et | 2 | H | 3,5-(CF$_3$)$_2$ | H | CH | CH | white solid | 135-139 |
| 1-632 | Et | 2 | H | 3,5-(CF$_3$)$_2$ | Me | CH | CH | | |
| 1-633 | Et | 2 | H | 3,5-(CF$_3$)$_2$ | c-Pr | CH | CH | | |
| 1-634 | Et | 2 | H | 3,5-(CF$_3$)$_2$ | CF$_3$ | CH | CH | | |
| 1-635 | Et | 2 | H | 3,5-(CF$_3$)$_2$ | Cl | CH | CH | | |

TABLE 1-13

| Compound No. | R | n | Xm | Yp | Z | W¹ | W² | Profile | Melting Point (° C.) |
|---|---|---|---|---|---|---|---|---|---|
| 1-636 | Et | 2 | H | 3,5-(CF$_3$)$_2$ | Br | CH | CH | | |
| 1-637 | Et | 2 | H | 3,5-(CF$_3$)$_2$ | I | CH | CH | white solid | 182-185 |
| 1-638 | Et | 2 | H | 3,5-(CF$_3$)$_2$ | NH$_2$ | CH | CH | white solid | 83-90 |
| 1-639 | Et | 2 | H | 3,5-(CF$_3$)$_2$ | CO$_2$Et | CH | CH | pale yellow oily | |
| 1-640 | Et | 2 | H | 3,5-(CF$_3$)$_2$ | CN | CH | CH | white solid | 135-138 |
| 1-641 | Et | 2 | 3-Cl | 3,5-(CF$_3$)$_2$ | H | CH | CH | white solid | 170-172 |
| 1-642 | Et | 2 | 4-Cl | 3,5-(CF$_3$)$_2$ | H | CH | CH | white solid | 180-182 |
| 1-643 | Et | 2 | 5-Cl | 3,5-(CF$_3$)$_2$ | H | CH | CH | white solid | 72-75 |
| 1-644 | Et | 2 | 6-Cl | 3,5-(CF$_3$)$_2$ | H | CH | CH | white solid | 156-158 |
| 1-645 | Et | 2 | 3-CF$_3$ | 3,5-(CF$_3$)$_2$ | H | CH | CH | | |
| 1-646 | Et | 2 | 4-CF$_3$ | 3,5-(CF$_3$)$_2$ | H | CH | CH | white solid | 156-158 |
| 1-647 | Et | 2 | 5-CF$_3$ | 3,5-(CF$_3$)$_2$ | H | CH | CH | white solid | 171-173 |
| 1-648 | Et | 2 | 6-CF$_3$ | 3,5-(CF$_3$)$_2$ | H | CH | CH | | |
| 1-649 | Et | 2 | 3-Cl | 3,5-(CF$_3$)$_2$ | Me | CH | CH | | |
| 1-650 | Et | 2 | 4-Cl | 3,5-(CF$_3$)$_2$ | Me | CH | CH | | |
| 1-651 | Et | 2 | 5-Cl | 3,5-(CF$_3$)$_2$ | Me | CH | CH | | |
| 1-652 | Et | 2 | 6-Cl | 3,5-(CF$_3$)$_2$ | Me | CH | CH | | |
| 1-653 | Et | 2 | 3-CF$_3$ | 3,5-(CF$_3$)$_2$ | Me | CH | CH | | |
| 1-654 | Et | 2 | 4-CF$_3$ | 3,5-(CF$_3$)$_2$ | Me | CH | CH | | |
| 1-655 | Et | 2 | 5-CF$_3$ | 3,5-(CF$_3$)$_2$ | Me | CH | CH | | |
| 1-656 | Et | 2 | 6-CF$_3$ | 3,5-(CF$_3$)$_2$ | Me | CH | CH | | |
| 1-657 | Et | 2 | 3-Cl | 3,5-(CF$_3$)$_2$ | Cl | CH | CH | | |
| 1-658 | Et | 2 | 4-Cl | 3,5-(CF$_3$)$_2$ | Cl | CH | CH | | |
| 1-659 | Et | 2 | 5-Cl | 3,5-(CF$_3$)$_2$ | Cl | CH | CH | | |
| 1-660 | Et | 2 | 6-Cl | 3,5-(CF$_3$)$_2$ | Cl | CH | CH | | |
| 1-661 | Et | 2 | 3-CF$_3$ | 3,5-(CF$_3$)$_2$ | Cl | CH | CH | | |
| 1-662 | Et | 2 | 4-CF$_3$ | 3,5-(CF$_3$)$_2$ | Cl | CH | CH | | |
| 1-663 | Et | 2 | 5-CF$_3$ | 3,5-(CF$_3$)$_2$ | Cl | CH | CH | | |
| 1-664 | Et | 2 | 6-CF$_3$ | 3,5-(CF$_3$)$_2$ | Cl | CH | CH | | |
| 1-665 | Et | 2 | 3-Cl | 3,5-(CF$_3$)$_2$ | Br | CH | CH | | |
| 1-666 | Et | 2 | 4-Cl | 3,5-(CF$_3$)$_2$ | Br | CH | CH | | |
| 1-667 | Et | 2 | 5-Cl | 3,5-(CF$_3$)$_2$ | Br | CH | CH | | |
| 1-668 | Et | 2 | 6-Cl | 3,5-(CF$_3$)$_2$ | Br | CH | CH | | |
| 1-669 | Et | 2 | 3-CF$_3$ | 3,5-(CF$_3$)$_2$ | Br | CH | CH | | |
| 1-670 | Et | 2 | 4-CF$_3$ | 3,5-(CF$_3$)$_2$ | Br | CH | CH | | |
| 1-671 | Et | 2 | 5-CF$_3$ | 3,5-(CF$_3$)$_2$ | Br | CH | CH | | |
| 1-672 | Et | 2 | 6-CF$_3$ | 3,5-(CF$_3$)$_2$ | Br | CH | CH | | |
| 1-673 | Et | 2 | 3-Cl | 3,5-(CF$_3$)$_2$ | I | CH | CH | | |
| 1-674 | Et | 2 | 4-Cl | 3,5-(CF$_3$)$_2$ | I | CH | CH | | |
| 1-675 | Et | 2 | 5-Cl | 3,5-(CF$_3$)$_2$ | I | CH | CH | | |
| 1-676 | Et | 2 | 6-Cl | 3,5-(CF$_3$)$_2$ | I | CH | CH | | |
| 1-677 | Et | 2 | 3-CF$_3$ | 3,5-(CF$_3$)$_2$ | I | CH | CH | | |
| 1-678 | Et | 2 | 4-CF$_3$ | 3,5-(CF$_3$)$_2$ | I | CH | CH | | |
| 1-679 | Et | 2 | 5-CF$_3$ | 3,5-(CF$_3$)$_2$ | I | CH | CH | | |
| 1-680 | Et | 2 | 6-CF$_3$ | 3,5-(CF$_3$)$_2$ | I | CH | CH | | |
| 1-681 | Et | 2 | H | 4-Cl-3,5-(CF$_3$)$_2$ | H | CH | CH | | |
| 1-682 | Et | 2 | H | 4-Cl-3,5-(CF$_3$)$_2$ | Me | CH | CH | | |
| 1-683 | Et | 2 | H | 4-Cl-3,5-(CF$_3$)$_2$ | Cl | CH | CH | | |
| 1-684 | Et | 2 | H | 4-Cl-3,5-(CF$_3$)$_2$ | Br | CH | CH | | |
| 1-685 | Et | 2 | H | 4-Cl-3,5-(CF$_3$)$_2$ | I | CH | CH | | |
| 1-686 | Et | 2 | 3-Cl | 4-Cl-3,5-(CF$_3$)$_2$ | H | CH | CH | | |
| 1-687 | Et | 2 | 4-Cl | 4-Cl-3,5-(CF$_3$)$_2$ | H | CH | CH | | |
| 1-688 | Et | 2 | 5-Cl | 4-Cl-3,5-(CF$_3$)$_2$ | H | CH | CH | | |
| 1-689 | Et | 2 | 6-Cl | 4-Cl-3,5-(CF$_3$)$_2$ | H | CH | CH | | |
| 1-690 | Et | 2 | 3-CF$_3$ | 4-Cl-3,5-(CF$_3$)$_2$ | H | CH | CH | | |

TABLE 1-14

| Compound No. | R | n | Xm | Yp | Z | W¹ | W² | Profile | Melting Point (° C.) |
|---|---|---|---|---|---|---|---|---|---|
| 1-691 | Et | 2 | 4-CF$_3$ | 4-Cl-3,5-(CF$_3$)$_2$ | H | CH | CH | | |
| 1-692 | Et | 2 | 5-CF$_3$ | 4-Cl-3,5-(CF$_3$)$_2$ | H | CH | CH | | |
| 1-693 | Et | 2 | 6-CF$_3$ | 4-Cl-3,5-(CF$_3$)$_2$ | H | CH | CH | | |
| 1-694 | Et | 2 | 3-Cl | 4-Me-3,5-(CF$_3$)$_2$ | Me | CH | CH | | |
| 1-695 | Et | 2 | 4-Cl | 4-Me-3,5-(CF$_3$)$_2$ | Me | CH | CH | | |
| 1-696 | Et | 2 | 5-Cl | 4-Me-3,5-(CF$_3$)$_2$ | Me | CH | CH | | |
| 1-697 | Et | 2 | 6-Cl | 4-Me-3,5-(CF$_3$)$_2$ | Me | CH | CH | | |
| 1-698 | Et | 2 | 3-CF$_3$ | 4-Me-3,5-(CF$_3$)$_2$ | Me | CH | CH | | |
| 1-699 | Et | 2 | 4-CF$_3$ | 4-Me-3,5-(CF$_3$)$_2$ | Me | CH | CH | | |
| 1-700 | Et | 2 | 5-CF$_3$ | 4-Me-3,5-(CF$_3$)$_2$ | Me | CH | CH | | |
| 1-701 | Et | 2 | 6-CF$_3$ | 4-Me-3,5-(CF$_3$)$_2$ | Me | CH | CH | | |
| 1-702 | Et | 2 | 3-Cl | 4-Me-3,5-(CF$_3$)$_2$ | Cl | CH | CH | | |
| 1-703 | Et | 2 | 4-Cl | 4-Me-3,5-(CF$_3$)$_2$ | Cl | CH | CH | | |

TABLE 1-14-continued

| Compound No. | R | n | Xm | Yp | Z | $W^1$ | $W^2$ | Profile | Melting Point (° C.) |
|---|---|---|---|---|---|---|---|---|---|
| 1-704 | Et | 2 | 5-Cl | 4-Me-3,5-(CF$_3$)$_2$ | Cl | CH | CH | | |
| 1-705 | Et | 2 | 6-Cl | 4-Me-3,5-(CF$_3$)$_2$ | Cl | CH | CH | | |
| 1-706 | Et | 2 | 3-CF$_3$ | 4-Me-3,5-(CF$_3$)$_2$ | Cl | CH | CH | | |
| 1-707 | Et | 2 | 4-CF$_3$ | 4-Me-3,5-(CF$_3$)$_2$ | Cl | CH | CH | | |
| 1-708 | Et | 2 | 5-CF$_3$ | 4-Me-3,5-(CF$_3$)$_2$ | Cl | CH | CH | | |
| 1-709 | Et | 2 | 6-CF$_3$ | 4-Me-3,5-(CF$_3$)$_2$ | Cl | CH | CH | | |
| 1-710 | Et | 2 | 3-Cl | 4-Me-3,5-(CF$_3$)$_2$ | Br | CH | CH | | |
| 1-711 | Et | 2 | 4-Cl | 4-Me-3,5-(CF$_3$)$_2$ | Br | CH | CH | | |
| 1-712 | Et | 2 | 5-Cl | 4-Me-3,5-(CF$_3$)$_2$ | Br | CH | CH | | |
| 1-713 | Et | 2 | 6-Cl | 4-Me-3,5-(CF$_3$)$_2$ | Br | CH | CH | | |
| 1-714 | Et | 2 | 3-CF$_3$ | 4-Me-3,5-(CF$_3$)$_2$ | Br | CH | CH | | |
| 1-715 | Et | 2 | 4-CF$_3$ | 4-Me-3,5-(CF$_3$)$_2$ | Br | CH | CH | | |
| 1-716 | Et | 2 | 5-CF$_3$ | 4-Me-3,5-(CF$_3$)$_2$ | Br | CH | CH | | |
| 1-717 | Et | 2 | 6-CF$_3$ | 4-Me-3,5-(CF$_3$)$_2$ | Br | CH | CH | | |
| 1-718 | Et | 2 | 3-Cl | 4-Me-3,5-(CF$_3$)$_2$ | I | CH | CH | | |
| 1-719 | Et | 2 | 4-Cl | 4-Me-3,5-(CF$_3$)$_2$ | I | CH | CH | | |
| 1-720 | Et | 2 | 5-Cl | 4-Me-3,5-(CF$_3$)$_2$ | I | CH | CH | | |
| 1-721 | Et | 2 | 6-Cl | 4-Me-3,5-(CF$_3$)$_2$ | I | CH | CH | | |
| 1-722 | Et | 2 | 3-CF$_3$ | 4-Me-3,5-(CF$_3$)$_2$ | I | CH | CH | | |
| 1-723 | Et | 2 | 4-CF$_3$ | 4-Me-3,5-(CF$_3$)$_2$ | I | CH | CH | | |
| 1-724 | Et | 2 | 5-CF$_3$ | 4-Me-3,5-(CF$_3$)$_2$ | I | CH | CH | | |
| 1-725 | Et | 2 | 6-CF$_3$ | 4-Me-3,5-(CF$_3$)$_2$ | I | CH | CH | | |
| 1-726 | Et | 2 | H | 3-F-5-CF$_3$ | H | CH | CH | | |
| 1-727 | Et | 2 | H | 3-F-5-CF$_3$ | Me | CH | CH | | |
| 1-728 | Et | 2 | H | 3-F-5-CF$_3$ | Cl | CH | CH | | |
| 1-729 | Et | 2 | H | 3-F-5-CF$_3$ | Br | CH | CH | | |
| 1-730 | Et | 2 | H | 3-F-5-CF$_3$ | I | CH | CH | | |
| 1-731 | Et | 2 | 3-Cl | 3-F-5-CF$_3$ | H | CH | CH | | |
| 1-732 | Et | 2 | 4-Cl | 3-F-5-CF$_3$ | H | CH | CH | | |
| 1-733 | Et | 2 | 5-Cl | 3-F-5-CF$_3$ | H | CH | CH | | |
| 1-734 | Et | 2 | 6-Cl | 3-F-5-CF$_3$ | H | CH | CH | | |
| 1-735 | Et | 2 | 3-CF$_3$ | 3-F-5-CF$_3$ | H | CH | CH | | |
| 1-736 | Et | 2 | 4-CF$_3$ | 3-F-5-CF$_3$ | H | CH | CH | | |
| 1-737 | Et | 2 | 5-CF$_3$ | 3-F-5-CF$_3$ | H | CH | CH | | |
| 1-738 | Et | 2 | 6-CF$_3$ | 3-F-5-CF$_3$ | H | CH | CH | | |
| 1-739 | Et | 2 | H | 3-Cl-5-CF$_3$ | H | CH | CH | | |
| 1-740 | Et | 2 | H | 3-Cl-5-CF$_3$ | Me | CH | CH | | |
| 1-741 | Et | 2 | H | 3-Cl-5-CF$_3$ | Cl | CH | CH | | |
| 1-742 | Et | 2 | H | 3-Cl-5-CF$_3$ | Br | CH | CH | | |
| 1-743 | Et | 2 | H | 3-Cl-5-CF$_3$ | I | CH | CH | | |
| 1-744 | Et | 2 | 3-Cl | 3-Cl-5-CF$_3$ | H | CH | CH | | |
| 1-745 | Et | 2 | 4-Cl | 3-Cl-5-CF$_3$ | H | CH | CH | | |

TABLE 1-15

| Compound No. | R | n | Xm | Yp | Z | $W^1$ | $W^2$ | Profile | Melting Point (° C.) |
|---|---|---|---|---|---|---|---|---|---|
| 1-746 | Et | 2 | 5-Cl | 3-Cl-5-CF$_3$ | H | CH | CH | | |
| 1-747 | Et | 2 | 6-Cl | 3-Cl-5-CF$_3$ | H | CH | CH | | |
| 1-748 | Et | 2 | 3-CF$_3$ | 3-Cl-5-CF$_3$ | H | CH | CH | | |
| 1-749 | Et | 2 | 4-CF$_3$ | 3-Cl-5-CF$_3$ | H | CH | CH | | |
| 1-750 | Et | 2 | 5-CF$_3$ | 3-Cl-5-CF$_3$ | H | CH | CH | | |
| 1-751 | Et | 2 | 6-CF$_3$ | 3-Cl-5-CF$_3$ | H | CH | CH | | |
| 1-752 | Et | 2 | H | 3-Br-5-CF$_3$ | H | CH | CH | white solid | 161-164 |
| 1-753 | Et | 2 | H | 3-Br-5-CF$_3$ | Me | CH | CH | | |
| 1-754 | Et | 2 | H | 3-Br-5-CF$_3$ | Cl | CH | CH | | |
| 1-755 | Et | 2 | H | 3-Br-5-CF$_3$ | Br | CH | CH | | |
| 1-756 | Et | 2 | H | 3-Br-5-CF$_3$ | I | CH | CH | | |
| 1-757 | Et | 2 | 3-Cl | 3-Br-5-CF$_3$ | H | CH | CH | | |
| 1-758 | Et | 2 | 4-Cl | 3-Br-5-CF$_3$ | H | CH | CH | | |
| 1-759 | Et | 2 | 5-Cl | 3-Br-5-CF$_3$ | H | CH | CH | | |
| 1-760 | Et | 2 | 6-Cl | 3-Br-5-CF$_3$ | H | CH | CH | | |
| 1-761 | Et | 2 | 3-CF$_3$ | 3-Br-5-CF$_3$ | H | CH | CH | | |
| 1-762 | Et | 2 | 4-CF$_3$ | 3-Br-5-CF$_3$ | H | CH | CH | | |
| 1-763 | Et | 2 | 5-CF$_3$ | 3-Br-5-CF$_3$ | H | CH | CH | | |
| 1-764 | Et | 2 | 6-CF$_3$ | 3-Br-5-CF$_3$ | H | CH | CH | | |
| 1-765 | Et | 2 | H | 3-CO$_2$Me-5-CF$_3$ | H | CH | CH | white solid | 159-162 |
| 1-766 | Et | 2 | H | 3,4-(CF$_3$)$_2$ | H | CH | CH | | |
| 1-767 | Et | 2 | 4-Cl | 3,4-(CF$_3$)$_2$ | H | CH | CH | | |
| 1-768 | Et | 2 | 5-Cl | 3,4-(CF$_3$)$_2$ | H | CH | CH | | |
| 1-769 | Et | 2 | 6-Cl | 3,4-(CF$_3$)$_2$ | H | CH | CH | | |
| 1-770 | Et | 2 | 3-CF$_3$ | 3,4-(CF$_3$)$_2$ | H | CH | CH | | |
| 1-771 | Et | 2 | 4-CF$_3$ | 3,4-(CF$_3$)$_2$ | H | CH | CH | | |

TABLE 1-15-continued

| Compound No. | R | n | Xm | Yp | Z | W¹ | W² | Profile | Melting Point (° C.) |
|---|---|---|---|---|---|---|---|---|---|
| 1-772 | Et | 2 | 5-CF$_3$ | 3,4-(CF$_3$)$_2$ | H | CH | CH | | |
| 1-773 | Et | 2 | 6-CF$_3$ | 3,4-(CF$_3$)$_2$ | H | CH | CH | | |
| 1-774 | Et | 2 | H | 3,4-(CF$_3$)$_2$ | I | CH | CH | | |
| 1-775 | Et | 2 | 4-Cl | 3,4-(CF$_3$)$_2$ | I | CH | CH | | |
| 1-776 | Et | 2 | 5-Cl | 3,4-(CF$_3$)$_2$ | I | CH | CH | | |
| 1-777 | Et | 2 | 6-Cl | 3,4-(CF$_3$)$_2$ | I | CH | CH | | |
| 1-778 | Et | 2 | 3-CF$_3$ | 3,4-(CF$_3$)$_2$ | I | CH | CH | | |
| 1-779 | Et | 2 | 4-CF$_3$ | 3,4-(CF$_3$)$_2$ | I | CH | CH | | |
| 1-780 | Et | 2 | 5-CF$_3$ | 3,4-(CF$_3$)$_2$ | I | CH | CH | | |
| 1-781 | Et | 2 | 6-CF$_3$ | 3,4-(CF$_3$)$_2$ | I | CH | CH | | |
| 1-782 | Et | 2 | H | 3-CONHPh-5-CF$_3$ | H | CH | CH | white solid | 232-233 |
| 1-783 | Et | 2 | H | 3-CONH(4-ClC$_6$H$_4$)-5-CF$_3$ | H | CH | CH | white solid | 200-201 |
| 1-784 | Et | 2 | 5-F | 3,5-(CF$_3$)$_2$ | H | CH | CH | white solid | 132-133 |
| 1-785 | Et | 2 | 5-Me | 3,5-(CF$_3$)$_2$ | H | CH | CH | white solid | 137-140 |
| 1-786 | Et | 2 | 5-OMe | 3,5-(CF$_3$)$_2$ | H | CH | CH | white solid | 146-147 |
| 1-787 | Et | 2 | 4-CF$_3$ | 3,5-(CF$_3$)$_2$ | H | N | CH | white solid | 230-233 |
| 1-788 | Et | 2 | H | 4-CF(CF$_3$)$_2$ | H | CH | CH | white solid | 180-182 |
| 1-789 | Et | 2 | H | 3-CF$_2$CONH$_2$-5-CF$_3$ | H | CH | CH | | |
| 1-790 | Et | 2 | H | 3,5-(CF$_3$)$_2$ | F | CH | CH | white solid | 149-150 |
| 1-791 | Et | 2 | H | 3-SF$_5$ | H | CH | CH | white solid | 139-142 |
| 1-792 | Et | 2 | H | 3-Ac-5-CF$_3$ | H | CH | CH | white solid | 181-183 |
| 1-793 | Et | 2 | H | 3-CF$_3$-5-CF$_2$CONHMe | H | CH | CH | white solid | <60 |
| 1-794 | Et | 2 | H | 3,5-Cl$_2$ | H | CH | CH | white solid | 179-181 |
| 1-795 | Et | 2 | H | 3-CF$_2$CN-5-CF$_3$ | H | CH | CH | white solid | 104-108 |
| 1-796 | Et | 2 | H | 3-COPh-5-CF$_3$ | H | CH | CH | white solid | 201-202 |
| 1-797 | Et | 2 | H | 3-CF$_2$CONH$_2$-5-CF$_3$ | H | CH | CH | thin red solid | 174-177 |
| 1-798 | Et | 2 | H | 3-CF$_2$Me-5-CF$_3$ | H | CH | CH | white solid | 126-128 |
| 1-799 | CHFCH$_3$ | 2 | H | 3-CF$_2$Me-5-CF$_3$ | H | CH | CH | | |
| 1-800 | Et | 2 | H | 3-Ph-5-CF$_3$ | H | CH | CH | colorless oily | |

TABLE 1-16

| Compound No. | R | n | Xm | Yp | Z | W¹ | W² | Profile | Melting Point (° C.) |
|---|---|---|---|---|---|---|---|---|---|
| 1-801 | Et | 2 | H | 3-(c-Pr)-5-CF$_3$ | H | CH | CH | white solid | 63-68 |
| 1-802 | Et | 2 | 4-Ph | 3,5-(CF$_3$)$_2$ | H | CH | CH | white solid | 225-226 |
| 1-803 | Et | 2 | 4-(4-ClC$_6$H$_4$) | 3,5-(CF$_3$)$_2$ | H | CH | CH | white solid | 221-222 |
| 1-804 | Et | 2 | 4-OPh | 3,5-(CF$_3$)$_2$ | H | CH | CH | white solid | 183-184 |
| 1-805 | Et | 2 | 4-CN | 3,5-(CF$_3$)$_2$ | H | CH | CH | white solid | 210-211 |
| 1-806 | Et | 2 | 4-Br | 3,5-(CF$_3$)$_2$ | H | CH | CH | white solid | 181-182 |
| 1-807 | Et | 2 | 4-(1H-tetrazol-5-yl) | 3,5-(CF$_3$)$_2$ | H | CH | CH | | |
| 1-808 | Et | 2 | 4-(1-methyl-tetrazol-5-yl) | 3,5-(CF$_3$)$_2$ | H | CH | CH | white solid | 211-213 |
| 1-809 | Et | 2 | 4-(2-methyl-tetrazol-5-yl) | 3,5-(CF$_3$)$_2$ | H | CH | CH | white solid | 195-197 |
| 1-810 | Et | 2 | 4-(c-Pr) | 3,5-(CF$_3$)$_2$ | H | CH | CH | white solid | 118-120 |
| 1-811 | Et | 2 | H | 3-CH$_2$CN-5-CF$_3$ | H | CH | CH | | |
| 1-812 | Et | 2 | 4-COOH | 3,5-(CF$_3$)$_2$ | H | CH | CH | | |
| 1-813 | Et | 2 | 4-CH$_2$OH | 3,5-(CF$_3$)$_2$ | H | CH | CH | | |
| 1-814 | Et | 2 | H | 3-(1-cyanocyclopropyl)-5-CF$_3$ | H | CH | CH | colorless oily | |
| 1-815 | Et | 2 | 4-(1,3,4-oxadiazol-2-yl) | 3,5-(CF$_3$)$_2$ | H | CH | CH | white solid | 80-82 |

TABLE 1-16-continued

| Compound No. | R | n | Xm | Yp | Z | W¹ | W² | Profile | Melting Point (° C.) |
|---|---|---|---|---|---|---|---|---|---|
| 1-816 | Et | 2 | 4-NHPh | 3,5-(CF$_3$)$_2$ | H | CH | CH | colorless oily | |
| 1-817 | Et | 2 | 4-SPh | 3,5-(CF$_3$)$_2$ | H | CH | CH | white solid | 179-184 |
| 1-818 | Et | 2 | 4-SOPh | 3,5-(CF$_3$)$_2$ | H | CH | CH | white solid | 94-98 |
| 1-819 | Et | 2 | 4-SO$_2$Ph | 3,5-(CF$_3$)$_2$ | H | CH | CH | pale yellow solid | 207-209 |
| 1-820 | Et | 2 | 4-COOEt | 3,5-(CF$_3$)$_2$ | H | CH | CH | white solid | 162-164 |
| 1-821 | Et | 2 | 4-CONHMe | 3,5-(CF$_3$)$_2$ | H | CH | CH | white solid | ≥250 |
| 1-822 | Et | 2 | 4-CH$_2$CN | 3,5-(CF$_3$)$_2$ | H | CH | CH | | |
| 1-823 | Et | 2 |  | 3,5-(CF$_3$)$_2$ | H | CH | CH | white solid | 171-173 |
| 1-824 | Et | 2 | 6-COOEt | 3,5-(CF$_3$)$_2$ | H | CH | CH | | |
| 1-825 | Et | 2 | 6-CONHMe | 3,5-(CF$_3$)$_2$ | H | CH | CH | white solid | 211-214 |
| 1-826 | Et | 2 | 4-Cl-6-SEt | 3,5-(CF$_3$)$_2$ | H | CH | CH | | |
| 1-827 | Et | 2 | 4-Cl-6-SO$_2$Et | 3,5-(CF$_3$)$_2$ | H | CH | CH | white solid | 209-212 |
| 1-828 | Et | 2 | 4-Ac | 3,5-(CF$_3$)$_2$ | H | CH | CH | white solid | 211-212 |
| 1-829 | Et | 2 | 4-COPh | 3,5-(CF$_3$)$_2$ | H | CH | CH | white solid | 227-230 |
| 1-830 | Et | 2 | H | 2-F-5-CF$_3$ | H | CH | CH | colorless oily | |
| 1-831 | Et | 2 | 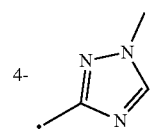 | 3,5-(CF$_3$)$_2$ | H | CH | CH | white solid | 80-83 |
| 1-832 | Et | 2 | 4-I | 3,5-(CF$_3$)$_2$ | H | CH | CH | white solid | 203-204 |
| 1-833 | Et | 2 | 4-OCF$_3$ | 3,5-(CF$_3$)$_2$ | H | CH | CH | white solid | 143-144 |
| 1-834 | Et | 2 | 4-CF$_3$ | 4-CF$_3$ | H | N | CH | white solid | 213-215 |
| 1-835 | Et | 2 | H | 3,5-(CF$_3$)$_2$ | COOH | CH | CH | white solid | |
| 1-836 | Et | 2 | H | 3,5-(CF$_3$)$_2$ | CONH$_2$ | CH | CH | white solid | |
| 1-837 | Et | 2 | H | 3,5-(CF$_3$)$_2$ | CONHPh | CH | CH | white solid | 74-85 |
| 1-838 | Et | 2 | H | 3,5-(CF$_3$)$_2$ | CONH(4-ClC$_6$H$_4$) | CH | CH | white solid | |
| 1-839 | Et | 2 | H | 3,5-(CF$_3$)$_2$ | CONHMe | CH | CH | white solid | 161-165 |
| 1-840 | Et | 2 | H | 3,5-(CF$_3$)$_2$ | CONMe$_2$ | CH | CH | colorless oily | |
| 1-841 | Et | 2 | H | 3,5-(CF$_3$)$_2$ | NHCOCF$_3$ | CH | CH | white solid | 198-200 |
| 1-842 | Et | 2 | H | 3,5-(CF$_3$)$_2$ | NHCOPh | CH | CH | white solid | 91-97 |
| 1-843 | Et | 2 | H | 3,5-(CF$_3$)$_2$ | NHCO(3-ClC$_6$H$_4$) | CH | CH | white solid | |
| 1-844 | Et | 2 | H | 3,5-(CF$_3$)$_2$ | NHCO(4-ClC$_6$H$_4$) | CH | CH | white solid | 96-102 |
| 1-845 | Et | 2 | H | 3,5-(CF$_3$)$_2$ | NAc$_2$ | CH | CH | white solid | 159-162 |

TABLE 1-17

| Compound No. | R | n | Xm | Yp | Z | W¹ | W² | Profile | Melting Point (° C.) |
|---|---|---|---|---|---|---|---|---|---|
| 1-846 | Et | 2 | H | 3-COOH-5-CF$_3$ | H | CH | CH | | |
| 1-847 | Et | 2 | H | 3,5-(CF$_3$)$_2$ | NHCO(2-ClC$_6$H$_4$) | CH | CH | white solid | 88-95 |
| 1-848 | Et | 2 | 4-CF(CF$_3$)$_2$ | 3,5-(CF$_3$)$_2$ | H | CH | CH | | |
| 1-849 | Et | 2 | 4-SF$_5$ | 3,5-(CF$_3$)$_2$ | H | CH | CH | | |
| 1-850 | Et | 0 | H | 3-CF$_3$-4-Cl | H | CH | CH | | |
| 1-851 | Et | 0 | 4-Cl | 3-CF$_3$-4-Cl | H | CH | CH | | |
| 1-852 | Et | 0 | 4-Br | 3-CF$_3$-4-Cl | H | CH | CH | | |
| 1-853 | Et | 0 | 4-I | 3-CF$_3$-4-Cl | H | CH | CH | yellow oily product | |
| 1-854 | Et | 0 | 4-CF$_3$ | 3-CF$_3$-4-Cl | H | CH | CH | | |
| 1-855 | Et | 0 | 4-OCF$_3$ | 3-CF$_3$-4-Cl | H | CH | CH | yellow oily product | |
| 1-856 | Et | 0 | 4-SF$_5$ | 3-CF$_3$-4-Cl | H | CH | CH | | |
| 1-857 | Et | 1 | H | 3-CF$_3$-4-Cl | H | CH | CH | | |
| 1-858 | Et | 1 | 4-Cl | 3-CF$_3$-4-Cl | H | CH | CH | | |
| 1-859 | Et | 1 | 4-Br | 3-CF$_3$-4-Cl | H | CH | CH | | |
| 1-860 | Et | 1 | 4-I | 3-CF$_3$-4-Cl | H | CH | CH | white solid | 135-140 |

TABLE 1-17-continued

| Compound No. | R | n | Xm | Yp | Z | W¹ | W² | Profile | Melting Point (° C.) |
|---|---|---|---|---|---|---|---|---|---|
| 1-861 | Et | 1 | 4-CF$_3$ | 3-CF$_3$-4-Cl | H | CH | CH | | |
| 1-862 | Et | 1 | 4-OCF$_3$ | 3-CF$_3$-4-Cl | H | CH | CH | white solid | 135-140 |
| 1-863 | Et | 1 | 4-SF$_5$ | 3-CF$_3$-4-Cl | H | CH | CH | | |
| 1-864 | Et | 2 | H | 3-CF$_3$-4-Cl | H | CH | CH | | |
| 1-865 | Et | 2 | 4-Cl | 3-CF$_3$-4-Cl | H | CH | CH | | |
| 1-866 | Et | 2 | 4-Br | 3-CF$_3$-4-Cl | H | CH | CH | | |
| 1-867 | Et | 2 | 4-I | 3-CF$_3$-4-Cl | H | CH | CH | white solid | 183-187 |
| 1-868 | Et | 2 | 4-CF$_3$ | 3-CF$_3$-4-Cl | H | CH | CH | | |
| 1-869 | Et | 2 | 4-OCF$_3$ | 3-CF$_3$-4-Cl | H | CH | CH | white solid | 114-117 |
| 1-870 | Et | 2 | 4-SF$_5$ | 3-CF$_3$-4-Cl | H | CH | CH | | |
| 1-871 | n-Pr | 0 | H | 3,5-(CF$_3$)$_2$ | H | CH | CH | | |
| 1-872 | n-Pr | 0 | H | 3,5-(CF$_3$)$_2$ | Me | CH | CH | | |
| 1-873 | n-Pr | 0 | H | 3,5-(CF$_3$)$_2$ | Cl | CH | CH | | |
| 1-874 | n-Pr | 0 | H | 3,5-(CF$_3$)$_2$ | Br | CH | CH | | |
| 1-875 | n-Pr | 0 | H | 3,5-(CF$_3$)$_2$ | I | CH | CH | | |
| 1-876 | n-Pr | 0 | 4-CF$_3$ | 3,5-(CF$_3$)$_2$ | H | CH | CH | | |
| 1-877 | n-Pr | 0 | 4-CF$_3$ | 3,5-(CF$_3$)$_2$ | Me | CH | CH | | |
| 1-878 | n-Pr | 0 | 4-CF$_3$ | 3,5-(CF$_3$)$_2$ | Cl | CH | CH | | |
| 1-879 | n-Pr | 0 | 4-CF$_3$ | 3,5-(CF$_3$)$_2$ | Br | CH | CH | | |
| 1-880 | n-Pr | 0 | 4-CF$_3$ | 3,5-(CF$_3$)$_2$ | I | CH | CH | | |
| 1-881 | i-Pr | 0 | H | 3,5-(CF$_3$)$_2$ | H | CH | CH | | |
| 1-882 | i-Pr | 0 | H | 3,5-(CF$_3$)$_2$ | Me | CH | CH | | |
| 1-883 | i-Pr | 0 | H | 3,5-(CF$_3$)$_2$ | Cl | CH | CH | | |
| 1-884 | i-Pr | 0 | H | 3,5-(CF$_3$)$_2$ | Br | CH | CH | | |
| 1-885 | i-Pr | 0 | H | 3,5-(CF$_3$)$_2$ | I | CH | CH | | |
| 1-886 | i-Pr | 0 | 4-CF$_3$ | 3,5-(CF$_3$)$_2$ | H | CH | CH | | |
| 1-887 | i-Pr | 0 | 4-CF$_3$ | 3,5-(CF$_3$)$_2$ | Me | CH | CH | | |
| 1-888 | i-Pr | 0 | 4-CF$_3$ | 3,5-(CF$_3$)$_2$ | Cl | CH | CH | | |
| 1-889 | i-Pr | 0 | 4-CF$_3$ | 3,5-(CF$_3$)$_2$ | Br | CH | CH | | |
| 1-890 | i-Pr | 0 | 4-CF$_3$ | 3,5-(CF$_3$)$_2$ | I | CH | CH | | |
| 1-891 | n-Bu | 0 | H | 3,5-(CF$_3$)$_2$ | H | CH | CH | | |
| 1-892 | n-Bu | 0 | H | 3,5-(CF$_3$)$_2$ | Me | CH | CH | | |
| 1-893 | n-Bu | 0 | H | 3,5-(CF$_3$)$_2$ | Cl | CH | CH | | |
| 1-894 | n-Bu | 0 | H | 3,5-(CF$_3$)$_2$ | Br | CH | CH | | |
| 1-895 | n-Bu | 0 | H | 3,5-(CF$_3$)$_2$ | I | CH | CH | | |
| 1-896 | n-Bu | 0 | 4-CF$_3$ | 3,5-(CF$_3$)$_2$ | H | CH | CH | | |
| 1-897 | n-Bu | 0 | 4-CF$_3$ | 3,5-(CF$_3$)$_2$ | Me | CH | CH | | |
| 1-898 | n-Bu | 0 | 4-CF$_3$ | 3,5-(CF$_3$)$_2$ | Cl | CH | CH | | |
| 1-899 | n-Bu | 0 | 4-CF$_3$ | 3,5-(CF$_3$)$_2$ | Br | CH | CH | | |
| 1-900 | n-Bu | 0 | 4-CF$_3$ | 3,5-(CF$_3$)$_2$ | I | CH | CH | | |

TABLE 1-18

| Compound No. | R | n | Xm | Yp | Z | W¹ | W² | Profile | Melting Point (° C.) |
|---|---|---|---|---|---|---|---|---|---|
| 1-901 | n-Pen | 0 | H | 3,5-(CF$_3$)$_2$ | H | CH | CH | | |
| 1-902 | n-Pen | 0 | H | 3,5-(CF$_3$)$_2$ | Me | CH | CH | | |
| 1-903 | n-Pen | 0 | H | 3,5-(CF$_3$)$_2$ | Cl | CH | CH | | |
| 1-904 | n-Pen | 0 | H | 3,5-(CF$_3$)$_2$ | Br | CH | CH | | |
| 1-905 | n-Pen | 0 | H | 3,5-(CF$_3$)$_2$ | I | CH | CH | | |
| 1-906 | n-Pen | 0 | 4-CF$_3$ | 3,5-(CF$_3$)$_2$ | H | CH | CH | | |
| 1-907 | n-Pen | 0 | 4-CF$_3$ | 3,5-(CF$_3$)$_2$ | Me | CH | CH | | |
| 1-908 | n-Pen | 0 | 4-CF$_3$ | 3,5-(CF$_3$)$_2$ | Cl | CH | CH | | |
| 1-909 | n-Pen | 0 | 4-CF$_3$ | 3,5-(CF$_3$)$_2$ | Br | CH | CH | | |
| 1-910 | n-Pen | 0 | 4-CF$_3$ | 3,5-(CF$_3$)$_2$ | I | CH | CH | | |
| 1-911 | n-Hex | 0 | H | 3,5-(CF$_3$)$_2$ | H | CH | CH | | |
| 1-912 | n-Hex | 0 | H | 3,5-(CF$_3$)$_2$ | Me | CH | CH | | |
| 1-913 | n-Hex | 0 | H | 3,5-(CF$_3$)$_2$ | Cl | CH | CH | | |
| 1-914 | n-Hex | 0 | H | 3,5-(CF$_3$)$_2$ | Br | CH | CH | | |
| 1-915 | n-Hex | 0 | H | 3,5-(CF$_3$)$_2$ | I | CH | CH | | |
| 1-916 | n-Hex | 0 | 4-CF$_3$ | 3,5-(CF$_3$)$_2$ | H | CH | CH | | |
| 1-917 | n-Hex | 0 | 4-CF$_3$ | 3,5-(CF$_3$)$_2$ | Me | CH | CH | | |
| 1-918 | n-Hex | 0 | 4-CF$_3$ | 3,5-(CF$_3$)$_2$ | Cl | CH | CH | | |
| 1-919 | n-Hex | 0 | 4-CF$_3$ | 3,5-(CF$_3$)$_2$ | Br | CH | CH | | |
| 1-920 | n-Hex | 0 | 4-CF$_3$ | 3,5-(CF$_3$)$_2$ | I | CH | CH | | |

TABLE 2-1

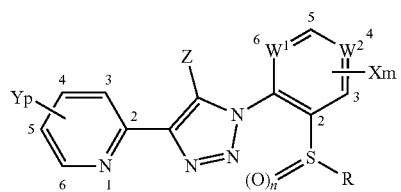

| Compound No. | R | n | Xm | Yp | Z | W¹ | W² | Profile | Melting Point (° C.) |
|---|---|---|---|---|---|---|---|---|---|
| 2-1 | Me | 0 | H | H | H | CH | CH | | |
| 2-2 | Me | 0 | H | 4-CF$_3$ | H | CH | CH | | |
| 2-3 | Me | 0 | H | 5-CF$_3$ | H | CH | CH | | |
| 2-4 | Me | 0 | H | 6-CF$_3$ | H | CH | CH | | |
| 2-5 | Me | 0 | H | 4-CF$_3$ | Br | CH | CH | | |
| 2-6 | Me | 0 | H | 5-CF$_3$ | Br | CH | CH | | |
| 2-7 | Me | 0 | H | 6-CF$_3$ | Br | CH | CH | | |
| 2-8 | Me | 0 | 4-CF$_3$ | 4-CF$_3$ | Br | CH | CH | | |
| 2-9 | Me | 0 | 4-CF$_3$ | 5-CF$_3$ | Br | CH | CH | | |
| 2-10 | Me | 0 | 4-CF$_3$ | 6-CF$_3$ | Br | CH | CH | | |
| 2-11 | Me | 0 | H | 4-CF$_3$ | I | CH | CH | | |
| 2-12 | Me | 0 | H | 5-CF$_3$ | I | CH | CH | | |
| 2-13 | Me | 0 | H | 6-CF$_3$ | I | CH | CH | | |
| 2-14 | Et | 0 | H | H | H | CH | CH | yellow oily | |
| 2-15 | Et | 0 | H | 4,6-(CF$_3$)$_2$ | H | CH | CH | red-tan oily | |
| 2-16 | Et | 0 | 4-Cl | 4,6-(CF$_3$)$_2$ | H | CH | CH | | |
| 2-17 | Et | 0 | 4-Br | 4,6-(CF$_3$)$_2$ | H | CH | CH | | |
| 2-18 | Et | 0 | 4-I | 4,6-(CF$_3$)$_2$ | H | CH | CH | | |
| 2-19 | Et | 0 | 4-CF$_3$ | 4,6-(CF$_3$)$_2$ | H | CH | CH | | |
| 2-20 | Et | 0 | 4-OCF$_3$ | 4,6-(CF$_3$)$_2$ | H | CH | CH | yellow solid | 82-84 |
| 2-21 | Et | 0 | 4-SF$_5$ | 4,6-(CF$_3$)$_2$ | H | CH | CH | | |
| 2-22 | Et | 0 | 5-CF$_3$ | 4,6-(CF$_3$)$_2$ | H | CH | CH | | |
| 2-23 | Et | 0 | H | 4,6-(CF$_3$)$_2$ | Me | CH | CH | | |
| 2-24 | Et | 0 | H | 4,6-(CF$_3$)$_2$ | Cl | CH | CH | | |
| 2-25 | Et | 0 | H | 4,6-(CF$_3$)$_2$ | Br | CH | CH | | |
| 2-26 | Et | 0 | H | 4,6-(CF$_3$)$_2$ | I | CH | CH | | |

TABLE 2-1-continued

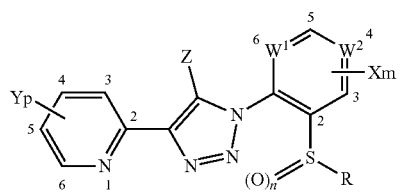

| Compound No. | R | n | Xm | Yp | Z | W¹ | W² | Profile | Melting Point (° C.) |
|---|---|---|---|---|---|---|---|---|---|
| 2-27 | Et | 0 | H | 3-CN-4,6-(CF$_3$)$_2$ | H | CH | CH | | |
| 2-28 | Et | 0 | 4-Cl | 3-CN-4,6-(CF$_3$)$_2$ | H | CH | CH | | |
| 2-29 | Et | 0 | 4-Br | 3-CN-4,6-(CF$_3$)$_2$ | H | CH | CH | | |
| 2-30 | Et | 0 | 4-I | 3-CN-4,6-(CF$_3$)$_2$ | H | CH | CH | yellow solid | 103-105 |
| 2-31 | Et | 0 | 4-CF$_3$ | 3-CN-4,6-(CF$_3$)$_2$ | H | CH | CH | | |
| 2-32 | Et | 0 | 4-OCF$_3$ | 3-CN-4,6-(CF$_3$)$_2$ | H | CH | CH | yellow solid | 86-87 |
| 2-33 | Et | 0 | 4-SF$_5$ | 3-CN-4,6-(CF$_3$)$_2$ | H | CH | CH | yellow solid | 84-87 |
| 2-34 | Et | 0 | H | 3-Cl-4-CF$_3$ | H | CH | CH | | |
| 2-35 | Et | 0 | 4-Cl | 3-Cl-4-CF$_3$ | H | CH | CH | | |
| 2-36 | Et | 0 | 4-Br | 3-Cl-4-CF$_3$ | H | CH | CH | | |
| 2-37 | Et | 0 | 4-I | 3-Cl-4-CF$_3$ | H | CH | CH | | |
| 2-38 | Et | 0 | 4-CF$_3$ | 3-Cl-4-CF$_3$ | H | CH | CH | | |
| 2-39 | Et | 0 | 4-OCF$_3$ | 3-Cl-4-CF$_3$ | H | CH | CH | | |
| 2-40 | Et | 0 | 4-SF$_5$ | 3-Cl-4-CF$_3$ | H | CH | CH | | |
| 2-41 | Et | 0 | H | 4-CF$_3$-5-Cl | H | CH | CH | | |
| 2-42 | Et | 0 | 4-Cl | 4-CF$_3$-5-Cl | H | CH | CH | | |
| 2-43 | Et | 0 | 4-Br | 4-CF$_3$-5-Cl | H | CH | CH | | |
| 2-44 | Et | 0 | 4-I | 4-CF$_3$-5-Cl | H | CH | CH | | |
| 2-45 | Et | 0 | 4-CF$_3$ | 4-CF$_3$-5-Cl | H | CH | CH | | |

TABLE 2-2

| Compound No. | R | n | Xm | Yp | Z | W¹ | W² | Profile | Melting Point (° C.) |
|---|---|---|---|---|---|---|---|---|---|
| 2-46 | Et | 0 | 4-OCF$_3$ | 4-CF$_3$-5-Cl | H | CH | CH | | |
| 2-47 | Et | 0 | 4-SF$_5$ | 4-CF$_3$-5-Cl | H | CH | CH | | |
| 2-48 | Et | 0 | H | 4-CF$_3$-6-Cl | H | CH | CH | | |
| 2-49 | Et | 0 | 4-Cl | 4-CF$_3$-6-Cl | H | CH | CH | | |
| 2-50 | Et | 0 | 4-Br | 4-CF$_3$-6-Cl | H | CH | CH | | |
| 2-51 | Et | 0 | 4-I | 4-CF$_3$-6-Cl | H | CH | CH | | |
| 2-52 | Et | 0 | 4-CF$_3$ | 4-CF$_3$-6-Cl | H | CH | CH | | |
| 2-53 | Et | 0 | 4-OCF$_3$ | 4-CF$_3$-6-Cl | H | CH | CH | | |
| 2-54 | Et | 0 | 4-SF$_5$ | 4-CF$_3$-6-Cl | H | CH | CH | | |
| 2-55 | Et | 0 | H | 4-CF$_3$-3-Br | H | CH | CH | | |
| 2-56 | Et | 0 | 4-Cl | 4-CF$_3$-3-Br | H | CH | CH | | |
| 2-57 | Et | 0 | 4-Br | 4-CF$_3$-3-Br | H | CH | CH | | |
| 2-58 | Et | 0 | 4-I | 4-CF$_3$-3-Br | H | CH | CH | | |
| 2-59 | Et | 0 | 4-CF$_3$ | 4-CF$_3$-3-Br | H | CH | CH | | |
| 2-60 | Et | 0 | 4-OCF$_3$ | 4-CF$_3$-3-Br | H | CH | CH | | |
| 2-61 | Et | 0 | 4-SF$_5$ | 4-CF$_3$-3-Br | H | CH | CH | | |
| 2-62 | Et | 0 | H | 4-CF$_3$-5-Br | H | CH | CH | | |
| 2-63 | Et | 0 | 4-Cl | 4-CF$_3$-5-Br | H | CH | CH | | |
| 2-64 | Et | 0 | 4-Br | 4-CF$_3$-5-Br | H | CH | CH | | |
| 2-65 | Et | 0 | 4-I | 4-CF$_3$-5-Br | H | CH | CH | white solid | 188-197 |
| 2-66 | Et | 0 | 4-CF$_3$ | 4-CF$_3$-5-Br | H | CH | CH | | |
| 2-67 | Et | 0 | 4-OCF$_3$ | 4-CF$_3$-5-Br | H | CH | CH | | |
| 2-68 | Et | 0 | 4-SF$_5$ | 4-CF$_3$-5-Br | H | CH | CH | | |
| 2-69 | Et | 0 | H | 4-CF$_3$-6-Br | H | CH | CH | | |
| 2-70 | Et | 0 | 4-Cl | 4-CF$_3$-6-Br | H | CH | CH | | |
| 2-71 | Et | 0 | 4-Br | 4-CF$_3$-6-Br | H | CH | CH | | |
| 2-72 | Et | 0 | 4-I | 4-CF$_3$-6-Br | H | CH | CH | | |
| 2-73 | Et | 0 | 4-CF$_3$ | 4-CF$_3$-6-Br | H | CH | CH | | |
| 2-74 | Et | 0 | 4-OCF$_3$ | 4-CF$_3$-6-Br | H | CH | CH | | |
| 2-75 | Et | 0 | 4-SF$_5$ | 4-CF$_3$-6-Br | H | CH | CH | | |
| 2-76 | Et | 0 | H | 4-CF$_3$-6-OMe | H | CH | CH | | |

TABLE 2-2-continued

| Compound No. | R | n | Xm | Yp | Z | W$^1$ | W$^2$ | Profile | Melting Point (° C.) |
|---|---|---|---|---|---|---|---|---|---|
| 2-77 | Et | 0 | 4-Cl | 4-CF$_3$-6-OMe | H | CH | CH | | |
| 2-78 | Et | 0 | 4-Br | 4-CF$_3$-6-OMe | H | CH | CH | | |
| 2-79 | Et | 0 | 4-I | 4-CF$_3$-6-OMe | H | CH | CH | | |
| 2-80 | Et | 0 | 4-CF$_3$ | 4-CF$_3$-6-OMe | H | CH | CH | | |
| 2-81 | Et | 0 | 4-OCF$_3$ | 4-CF$_3$-6-OMe | H | CH | CH | | |
| 2-82 | Et | 0 | 4-SF$_5$ | 4-CF$_3$-6-OMe | H | CH | CH | | |
| 2-83 | Et | 0 | H | 4-CF$_3$-6-CN | H | CH | CH | | |
| 2-84 | Et | 0 | 4-Cl | 4-CF$_3$-6-CN | H | CH | CH | | |
| 2-85 | Et | 0 | 4-Br | 4-CF$_3$-6-CN | H | CH | CH | | |
| 2-86 | Et | 0 | 4-I | 4-CF$_3$-6-CN | H | CH | CH | | |
| 2-87 | Et | 0 | 4-CF$_3$ | 4-CF$_3$-6-CN | H | CH | CH | | |
| 2-88 | Et | 0 | 4-OCF$_3$ | 4-CF$_3$-6-CN | H | CH | CH | white solid | 163 |
| 2-89 | Et | 0 | 4-SF$_5$ | 4-CF$_3$-6-CN | H | CH | CH | | |
| 2-90 | Et | 0 | H | 3-CF$_3$ | H | CH | CH | colorless oily | |
| 2-91 | Et | 0 | H | 4-CF$_3$ | H | CH | CH | tan oily | |
| 2-92 | Et | 0 | H | 4-CF$_3$ | H | N | CH | | |
| 2-93 | Et | 0 | H | 4-CF$_3$ | H | CH | N | | |
| 2-94 | Et | 0 | H | 4-CF$_3$ | H | N | N | | |
| 2-95 | Et | 0 | 3-Cl | 4-CF$_3$ | H | CH | CH | tan oily | |
| 2-96 | Et | 0 | 4-Cl | 4-CF$_3$ | H | CH | CH | white solid | 114-116 |
| 2-97 | Et | 0 | 5-Cl | 4-CF$_3$ | H | CH | CH | tan solid | 122-123 |
| 2-98 | Et | 0 | 6-Cl | 4-CF$_3$ | H | CH | CH | colorless oily | |
| 2-99 | Et | 0 | 4-F | 4-CF$_3$ | H | CH | CH | brown solid | 102 |
| 2-100 | Et | 0 | 4-Br | 4-CF$_3$ | H | CH | CH | tan solid | 97-98 |

TABLE 2-3

| Compound No. | R | n | Xm | Yp | Z | W$^1$ | W$^2$ | Profile | Melting Point (° C.) |
|---|---|---|---|---|---|---|---|---|---|
| 2-101 | Et | 0 | 4-Br | 4-CF$_3$ | H | N | CH | | |
| 2-102 | Et | 0 | 4-I | 4-CF$_3$ | H | CH | CH | red solid | 99-101 |
| 2-103 | Et | 0 | 4-Me | 4-CF$_3$ | H | CH | CH | white solid | 78-80 |
| 2-104 | Et | 0 | 4-CN | 4-CF$_3$ | H | CH | CH | red solid | 145-147 |
| 2-105 | Et | 0 | 4-OH | 4-CF$_3$ | H | CH | CH | | |
| 2-106 | Et | 0 | 4-COOEt | 4-CF$_3$ | H | CH | CH | | |
| 2-107 | Et | 0 | 4-CF$_3$ | 4-CF$_3$ | H | CH | CH | white solid | 143-145 |
| 2-108 | Et | 0 | 4-CF$_3$ | 4-CF$_3$ | H | N | CH | | |
| 2-109 | Et | 0 | 4-CF(CF$_3$)$_2$ | 4-CF$_3$ | H | CH | CH | yellow solid | 90-92 |
| 2-110 | Et | 0 | 4-CH(CF$_3$)$_2$ | 4-CF$_3$ | H | CH | CH | orange oily | |
| 2-111 | Et | 0 | 4-C(CF$_3$)$_2$OMe | 4-CF$_3$ | H | CH | CH | orange solid | 88-93 |
| 2-112 | Et | 0 | 4-OCF$_3$ | 4-CF$_3$ | H | CH | CH | white solid | 100-102 |
| 2-113 | Et | 0 | 4-SCF$_3$ | 4-CF$_3$ | H | CH | CH | yellow solid | 73-75 |
| 2-114 | Et | 0 | 4-SMe | 4-CF$_3$ | H | CH | CH | | |
| 2-115 | Et | 0 | 4-SOMe | 4-CF$_3$ | H | CH | CH | | |
| 2-116 | Et | 0 | 4-SO$_2$Me | 4-CF$_3$ | H | CH | CH | | |
| 2-117 | Et | 0 | 4-OSO$_2$CF$_3$ | 4-CF$_3$ | H | CH | CH | | |
| 2-118 | Et | 0 | 4-SF$_5$ | 4-CF$_3$ | H | CH | CH | red solid | 116-120 |
| 2-119 | Et | 0 | 4-OCH$_2$OCH$_3$ | 4-CF$_3$ | H | CH | CH | | |
| 2-120 | Et | 0 | 4-I-5-Cl | 4-CF$_3$ | H | CH | CH | pale yellow solid | 112-114 |
| 2-121 | Et | 0 | 3,4-Cl$_2$ | 4-CF$_3$ | H | CH | CH | tan solid | 82-84 |
| 2-122 | Et | 0 | 3-Cl-4-Br | 4-CF$_3$ | H | CH | CH | yellow oily | |
| 2-123 | Et | 0 | 4-CH$_2$CN | 4-CF$_3$ | H | CH | CH | white solid | 169 |
| 2-124 | Et | 0 | 4-CF$_2$CN | 4-CF$_3$ | H | CH | CH | | |
| 2-125 | Et | 0 | 4-CH$_2$Cl | 4-CF$_3$ | H | CH | CH | pale yellow solid | 122-124 |
| 2-126 | Et | 0 | 4-CH$_2$OH | 4-CF$_3$ | H | CH | CH | red-tan oily | |
| 2-127 | Et | 0 | 4-(c-Pr) | 4-CF$_3$ | H | CH | CH | white solid | 84-87 |
| 2-128 | Et | 0 | 4-[cyclopropyl-CN] | 4-CF$_3$ | H | CH | CH | white solid | 128-130 |
| 2-129 | Et | 0 | 4-[triazolyl] | 4-CF$_3$ | H | CH | CH | colorless oily | |

TABLE 2-3-continued

| Compound No. | R | n | Xm | Yp | Z | W¹ | W² | Profile | Melting Point (° C.) |
|---|---|---|---|---|---|---|---|---|---|
| 2-130 | Et | 0 | 4-(1-methyl-1H-tetrazol-5-yl) | 4-CF₃ | H | CH | CH | | |
| 2-131 | Et | 0 | 4-(5-methyl-1,2,4-oxadiazol-3-yl) | 4-CF₃ | H | CH | CH | white solid | 126-127 |
| 2-132 | Et | 0 | 4-((4-(trifluoromethyl)-1H-1,2,3-triazol-1-yl)methyl) | 4-CF₃ | H | CH | CH | white solid | 110-111 |
| 2-133 | Et | 0 | H | 4-CF₃ | Me | CH | CH | | |
| 2-134 | Et | 0 | 4-CF₃ | 4-CF₃ | Me | CH | CH | tan solid | 89-98 |
| 2-135 | Et | 0 | 4-OCF₃ | 4-CF₃ | Me | CH | CH | tan oily | |
| 2-136 | Et | 0 | 4-OCF₃ | 4-CF₃ | CH₂OMe | CH | CH | | |
| 2-137 | Et | 0 | H | 4-CF₃ | Cl | CH | CH | | |
| 2-138 | Et | 0 | H | 4-CF₃ | Br | CH | CH | | |
| 2-139 | Et | 0 | H | 4-CF₃ | I | CH | CH | | |
| 2-140 | Et | 0 | H | 4-CF₂CF₃ | H | CH | CH | yellow oily | |
| 2-141 | Et | 0 | 4-Cl | 4-CF₂CF₃ | H | CH | CH | | |
| 2-142 | Et | 0 | 4-Br | 4-CF₂CF₃ | H | CH | CH | | |
| 2-143 | Et | 0 | 4-I | 4-CF₂CF₃ | H | CH | CH | red oily | |
| 2-144 | Et | 0 | 4-CF₃ | 4-CF₂CF₃ | H | CH | CH | | |
| 2-145 | Et | 0 | 4-OCF₃ | 4-CF₂CF₃ | H | CH | CH | orange solid | 113-115 |

TABLE 2-4

| Compound No. | R | n | Xm | Yp | Z | W¹ | W² | Profile | Melting Point (° C.) |
|---|---|---|---|---|---|---|---|---|---|
| 2-146 | Et | 0 | 4-SF₅ | 4-CF₂CF₃ | H | CH | CH | | |
| 2-147 | Et | 0 | H | 5-CF₃ | H | CH | CH | white solid | 103-104 |
| 2-148 | Et | 0 | H | 6-CF₃ | H | CH | CH | colorless oily | |
| 2-149 | Et | 0 | H | 6-CF₃ | Me | CH | CH | | |
| 2-150 | Et | 0 | H | 6-CF₃ | Cl | CH | CH | | |
| 2-151 | Et | 0 | H | 6-CF₃ | Br | CH | CH | | |
| 2-152 | Et | 0 | H | 6-CF₃ | I | CH | CH | | |
| 2-153 | Et | 1 | H | H | H | CH | CH | white solid | 170-172 |
| 2-154 | Et | 1 | H | 4,6-(CF₃)₂ | H | CH | CH | | |
| 2-155 | Et | 1 | 4-Cl | 4,6-(CF₃)₂ | H | CH | CH | | |
| 2-156 | Et | 1 | 4-Br | 4,6-(CF₃)₂ | H | CH | CH | | |
| 2-157 | Et | 1 | 4-I | 4,6-(CF₃)₂ | H | CH | CH | | |
| 2-158 | Et | 1 | 4-CF₃ | 4,6-(CF₃)₂ | H | CH | CH | | |
| 2-159 | Et | 1 | 4-OCF₃ | 4,6-(CF₃)₂ | H | CH | CH | | |
| 2-160 | Et | 1 | 4-SF₅ | 4,6-(CF₃)₂ | H | CH | CH | | |
| 2-161 | Et | 1 | 5-CF₃ | 4,6-(CF₃)₂ | H | CH | CH | | |
| 2-162 | Et | 1 | H | 4,6-(CF₃)₂ | Me | CH | CH | | |
| 2-163 | Et | 1 | H | 4,6-(CF₃)₂ | Cl | CH | CH | | |
| 2-164 | Et | 1 | H | 4,6-(CF₃)₂ | Br | CH | CH | | |
| 2-165 | Et | 1 | H | 4,6-(CF₃)₂ | I | CH | CH | | |
| 2-166 | Et | 1 | H | 3-CN-4,6-(CF₃)₂ | H | CH | CH | | |
| 2-167 | Et | 1 | 4-Cl | 3-CN-4,6-(CF₃)₂ | H | CH | CH | | |
| 2-168 | Et | 1 | 4-Br | 3-CN-4,6-(CF₃)₂ | H | CH | CH | | |
| 2-169 | Et | 1 | 4-I | 3-CN-4,6-(CF₃)₂ | H | CH | CH | white solid | 167-170 |
| 2-170 | Et | 1 | 4-CF₃ | 3-CN-4,6-(CF₃)₂ | H | CH | CH | | |
| 2-171 | Et | 1 | 4-OCF₃ | 3-CN-4,6-(CF₃)₂ | H | CH | CH | white solid | 150-152 |
| 2-172 | Et | 1 | 4-SF₅ | 3-CN-4,6-(CF₃)₂ | H | CH | CH | white solid | 79-84 |
| 2-173 | Et | 1 | H | 3-Cl-4-CF₃ | H | CH | CH | | |
| 2-174 | Et | 1 | 4-Cl | 3-Cl-4-CF₃ | H | CH | CH | | |
| 2-175 | Et | 1 | 4-Br | 3-Cl-4-CF₃ | H | CH | CH | | |
| 2-176 | Et | 1 | 4-I | 3-Cl-4-CF₃ | H | CH | CH | | |
| 2-177 | Et | 1 | 4-CF₃ | 3-Cl-4-CF₃ | H | CH | CH | | |
| 2-178 | Et | 1 | 4-OCF₃ | 3-Cl-4-CF₃ | H | CH | CH | | |
| 2-179 | Et | 1 | 4-SF₅ | 3-Cl-4-CF₃ | H | CH | CH | | |
| 2-180 | Et | 1 | H | 4-CF₃-5-Cl | H | CH | CH | | |
| 2-181 | Et | 1 | 4-Cl | 4-CF₃-5-Cl | H | CH | CH | | |
| 2-182 | Et | 1 | 4-Br | 4-CF₃-5-Cl | H | CH | CH | | |

TABLE 2-4-continued

| Compound No. | R | n | Xm | Yp | Z | W¹ | W² | Profile | Melting Point (° C.) |
|---|---|---|---|---|---|---|---|---|---|
| 2-183 | Et | 1 | 4-I | 4-CF₃-5-Cl | H | CH | CH | | |
| 2-184 | Et | 1 | 4-CF₃ | 4-CF₃-5-Cl | H | CH | CH | | |
| 2-185 | Et | 1 | 4-OCF₃ | 4-CF₃-5-Cl | H | CH | CH | | |
| 2-186 | Et | 1 | 4-SF₅ | 4-CF₃-5-Cl | H | CH | CH | | |
| 2-187 | Et | 1 | H | 4-CF₃-6-Cl | H | CH | CH | | |
| 2-188 | Et | 1 | 4-Cl | 4-CF₃-6-Cl | H | CH | CH | | |
| 2-189 | Et | 1 | 4-Br | 4-CF₃-6-Cl | H | CH | CH | | |
| 2-190 | Et | 1 | 4-I | 4-CF₃-6-Cl | H | CH | CH | | |
| 2-191 | Et | 1 | 4-CF₃ | 4-CF₃-6-Cl | H | CH | CH | | |
| 2-192 | Et | 1 | 4-OCF₃ | 4-CF₃-6-Cl | H | CH | CH | | |
| 2-193 | Et | 1 | 4-SF₅ | 4-CF₃-6-Cl | H | CH | CH | | |
| 2-194 | Et | 1 | H | 4-CF₃-3-Br | H | CH | CH | | |
| 2-195 | Et | 1 | 4-Cl | 4-CF₃-3-Br | H | CH | CH | | |
| 2-196 | Et | 1 | 4-Br | 4-CF₃-3-Br | H | CH | CH | | |
| 2-197 | Et | 1 | 4-I | 4-CF₃-3-Br | H | CH | CH | | |
| 2-198 | Et | 1 | 4-CF₃ | 4-CF₃-3-Br | H | CH | CH | | |
| 2-199 | Et | 1 | 4-OCF₃ | 4-CF₃-3-Br | H | CH | CH | | |
| 2-200 | Et | 1 | 4-SF₅ | 4-CF₃-3-Br | H | CH | CH | | |

TABLE 2-5

| Compound No. | R | n | Xm | Yp | Z | W¹ | W² | Profile | Melting Point (° C.) |
|---|---|---|---|---|---|---|---|---|---|
| 2-201 | Et | 1 | H | 4-CF₃-5-Br | H | CH | CH | | |
| 2-202 | Et | 1 | 4-Cl | 4-CF₃-5-Br | H | CH | CH | | |
| 2-203 | Et | 1 | 4-Br | 4-CF₃-5-Br | H | CH | CH | | |
| 2-204 | Et | 1 | 4-I | 4-CF₃-5-Br | H | CH | CH | white solid | 188-197 |
| 2-205 | Et | 1 | 4-CF₃ | 4-CF₃-5-Br | H | CH | CH | | |
| 2-206 | Et | 1 | 4-OCF₃ | 4-CF₃-5-Br | H | CH | CH | | |
| 2-207 | Et | 1 | 4-SF₅ | 4-CF₃-5-Br | H | CH | CH | | |
| 2-208 | Et | 1 | H | 4-CF₃-6-Br | H | CH | CH | | |
| 2-209 | Et | 1 | 4-Cl | 4-CF₃-6-Br | H | CH | CH | | |
| 2-210 | Et | 1 | 4-Br | 4-CF₃-6-Br | H | CH | CH | | |
| 2-211 | Et | 1 | 4-I | 4-CF₃-6-Br | H | CH | CH | | |
| 2-212 | Et | 1 | 4-CF₃ | 4-CF₃-6-Br | H | CH | CH | | |
| 2-213 | Et | 1 | 4-OCF₃ | 4-CF₃-6-Br | H | CH | CH | | |
| 2-214 | Et | 1 | 4-SF₅ | 4-CF₃-6-Br | H | CH | CH | | |
| 2-215 | Et | 1 | H | 4-CF₃-6-OMe | H | CH | CH | | |
| 2-216 | Et | 1 | 4-Cl | 4-CF₃-6-OMe | H | CH | CH | | |
| 2-217 | Et | 1 | 4-Br | 4-CF₃-6-OMe | H | CH | CH | | |
| 2-218 | Et | 1 | 4-I | 4-CF₃-6-OMe | H | CH | CH | | |
| 2-219 | Et | 1 | 4-CF₃ | 4-CF₃-6-OMe | H | CH | CH | | |
| 2-220 | Et | 1 | 4-OCF₃ | 4-CF₃-6-OMe | H | CH | CH | | |
| 2-221 | Et | 1 | 4-SF₅ | 4-CF₃-6-OMe | H | CH | CH | | |
| 2-222 | Et | 1 | H | 4-CF₃-6-CN | H | CH | CH | | |
| 2-223 | Et | 1 | 4-Cl | 4-CF₃-6-CN | H | CH | CH | | |
| 2-224 | Et | 1 | 4-Br | 4-CF₃-6-CN | H | CH | CH | | |
| 2-225 | Et | 1 | 4-I | 4-CF₃-6-CN | H | CH | CH | | |
| 2-226 | Et | 1 | 4-CF₃ | 4-CF₃-6-CN | H | CH | CH | | |
| 2-227 | Et | 1 | 4-OCF₃ | 4-CF₃-6-CN | H | CH | CH | white solid | 163 |
| 2-228 | Et | 1 | 4-SF₅ | 4-CF₃-6-CN | H | CH | CH | | |
| 2-229 | Et | 1 | H | 3-CF₃ | H | CH | CH | white solid | 175-177 |
| 2-230 | Et | 1 | H | 4-CF₃ | H | CH | CH | white solid | 165-166 |
| 2-231 | Et | 1 | H | 4-CF₃ | H | N | CH | | |
| 2-232 | Et | 1 | H | 4-CF₃ | H | CH | N | | |
| 2-233 | Et | 1 | H | 4-CF₃ | H | N | N | | |
| 2-234 | Et | 1 | 3-Cl | 4-CF₃ | H | CH | CH | colorless oily | |
| 2-235 | Et | 1 | 4-Cl | 4-CF₃ | H | CH | CH | white solid | 175-177 |
| 2-236 | Et | 1 | 5-Cl | 4-CF₃ | H | CH | CH | white solid | 158-162 |
| 2-237 | Et | 1 | 6-Cl | 4-CF₃ | H | CH | CH | colorless oily | |
| 2-238 | Et | 1 | 4-F | 4-CF₃ | H | CH | CH | white solid | 183-185 |
| 2-239 | Et | 1 | 4-Br | 4-CF₃ | H | CH | CH | white solid | 186-193 |
| 2-240 | Et | 1 | 4-Br | 4-CF₃ | H | N | CH | white solid | 182-186 |
| 2-241 | Et | 1 | 4-I | 4-CF₃ | H | CH | CH | white solid | 182-186 |
| 2-242 | Et | 1 | 4-Me | 4-CF₃ | H | CH | CH | white solid | 153-156 |
| 2-243 | Et | 1 | 4-CN | 4-CF₃ | H | CH | CH | white solid | 213-215 |
| 2-244 | Et | 1 | 4-OH | 4-CF₃ | H | CH | CH | | |
| 2-245 | Et | 1 | 4-COOEt | 4-CF₃ | H | CH | CH | white solid | 162-165 |
| 2-246 | Et | 1 | 4-CF₃ | 4-CF₃ | H | CH | CH | white solid | 186-187 |
| 2-247 | Et | 1 | 4-CF₃ | 4-CF₃ | H | N | CH | | |
| 2-248 | Et | 1 | 4-CF(CF₃)₂ | 4-CF₃ | H | CH | CH | white solid | 190-192 |
| 2-249 | Et | 1 | 4-CH(CF₃)₂ | 4-CF₃ | H | CH | CH | white solid | 154-156 |
| 2-250 | Et | 1 | 4-C(CF₃)₂OMe | 4-CF₃ | H | CH | CH | white solid | 167-169 |

TABLE 2-5-continued

| Compound No. | R | n | Xm | Yp | Z | W¹ | W² | Profile | Melting Point (° C.) |
|---|---|---|---|---|---|---|---|---|---|
| 2-251 | Et | 1 | 4-OMe | 4-CF$_3$ | H | CH | CH | white solid | 134-144 |
| 2-252 | Et | 1 | 4-OCF$_3$ | 4-CF$_3$ | H | CH | CH | white solid | 161-165 |
| 2-253 | Et | 1 | 4-SCF$_3$ | 4-CF$_3$ | H | CH | CH | white solid | 166-168 |
| 2-254 | Et | 1 | 4-SMe | 4-CF$_3$ | H | CH | CH | | |
| 2-255 | Et | 1 | 4-SOMe | 4-CF$_3$ | H | CH | CH | | |

TABLE 2-6

| Compound No. | R | n | Xm | Yp | Z | W¹ | W² | Profile | Melting Point (° C.) |
|---|---|---|---|---|---|---|---|---|---|
| 2-256 | Et | 1 | 4-SO$_2$Me | 4-CF$_3$ | H | CH | CH | | |
| 2-257 | Et | 1 | 4-OSO$_2$CF$_3$ | 4-CF$_3$ | H | CH | CH | | |
| 2-258 | Et | 1 | 4-SF$_5$ | 4-CF$_3$ | H | CH | CH | white solid | 199-201 |
| 2-259 | Et | 1 | 4-OCH$_2$OCH$_3$ | 4-CF$_3$ | H | CH | CH | | |
| 2-260 | Et | 1 | 4-I-5-Cl | 4-CF$_3$ | H | CH | CH | white solid | 208-214 |
| 2-261 | Et | 1 | 3,4-Cl$_2$ | 4-CF$_3$ | H | CH | CH | white solid | 144-146 |
| 2-262 | Et | 1 | 3-Cl-4-Br | 4-CF$_3$ | H | CH | CH | white solid | 161-165 |
| 2-263 | Et | 1 | 4-CH$_2$CN | 4-CF$_3$ | H | CH | CH | white solid | 200-204 |
| 2-264 | Et | 1 | 4-CF$_2$CN | 4-CF$_3$ | H | CH | CH | | |
| 2-265 | Et | 1 | 4-CH$_2$Cl | 4-CF$_3$ | H | CH | CH | | |
| 2-266 | Et | 1 | 4-CH$_2$OH | 4-CF$_3$ | H | CH | CH | | |
| 2-267 | Et | 1 | 4-(c-Pr) | 4-CF$_3$ | H | CH | CH | white solid | 117-121 |
| 2-268 | Et | 1 |  | 4-CF$_3$ | H | CH | CH | white solid | 157-159 |
| 2-269 | Et | 1 | 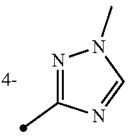 | 4-CF$_3$ | H | CH | CH | | |
| 2-270 | Et | 1 | 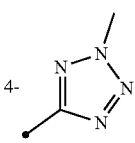 | 4-CF$_3$ | H | CH | CH | | |
| 2-271 | Et | 1 | 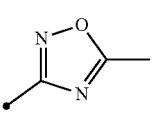 | 4-CF$_3$ | H | CH | CH | white solid | 186-187 |
| 2-272 | Et | 1 |  | 4-CF$_3$ | H | CH | CH | white solid | 123-126 |
| 2-273 | Et | 1 | H | 4-CF$_3$ | Me | CH | CH | | |
| 2-274 | Et | 1 | 4-CF$_3$ | 4-CF$_3$ | Me | CH | CH | tan oily | |
| 2-275 | Et | 1 | 4-OCF$_3$ | 4-CF$_3$ | Me | CH | CH | pale yellow solid | 96-97 |
| 2-276 | Et | 1 | 4-OCF$_3$ | 4-CF$_3$ | CH$_2$OMe | CH | CH | | |
| 2-277 | Et | 1 | H | 4-CF$_3$ | Cl | CH | CH | | |
| 2-278 | Et | 1 | H | 4-CF$_3$ | Br | CH | CH | | |
| 2-279 | Et | 1 | H | 4-CF$_3$ | I | CH | CH | | |
| 2-280 | Et | 1 | H | 4-CF$_2$CF$_3$ | H | CH | CH | | |
| 2-281 | Et | 1 | 4-Cl | 4-CF$_2$CF$_3$ | H | CH | CH | | |
| 2-282 | Et | 1 | 4-Br | 4-CF$_2$CF$_3$ | H | CH | CH | | |
| 2-283 | Et | 1 | 4-I | 4-CF$_2$CF$_3$ | H | CH | CH | white solid | 157-162 |
| 2-284 | Et | 1 | 4-CF$_3$ | 4-CF$_2$CF$_3$ | H | CH | CH | | |
| 2-285 | Et | 1 | 4-OCF$_3$ | 4-CF$_2$CF$_3$ | H | CH | CH | white solid | 165-167 |
| 2-286 | Et | 1 | 4-SF$_5$ | 4-CF$_2$CF$_3$ | H | CH | CH | | |
| 2-287 | Et | 1 | H | 5-CF$_3$ | H | CH | CH | | |
| 2-288 | Et | 1 | H | 6-CF$_3$ | H | CH | CH | white solid | 172-175 |
| 2-289 | Et | 1 | H | 6-CF$_3$ | Me | CH | CH | | |

TABLE 2-6-continued

| Compound No. | R | n | Xm | Yp | Z | W¹ | W² | Profile | Melting Point (° C.) |
|---|---|---|---|---|---|---|---|---|---|
| 2-290 | Et | 1 | H | 6-CF$_3$ | Cl | CH | CH | | |
| 2-291 | Et | 1 | H | 6-CF$_3$ | Br | CH | CH | | |
| 2-292 | Et | 1 | H | 6-CF$_3$ | I | CH | CH | | |
| 2-293 | Et | 2 | H | H | H | CH | CH | | |
| 2-294 | Et | 2 | H | 4,6-(CF$_3$)$_2$ | H | CH | CH | white solid | |
| 2-295 | Et | 2 | 4-Cl | 4,6-(CF$_3$)$_2$ | H | CH | CH | | |

TABLE 2-7

| Compound No. | R | n | Xm | Yp | Z | W¹ | W² | Profile | Melting Point (° C.) |
|---|---|---|---|---|---|---|---|---|---|
| 2-296 | Et | 2 | 4-Br | 4,6-(CF$_3$)$_2$ | H | CH | CH | | |
| 2-297 | Et | 2 | 4-I | 4,6-(CF$_3$)$_2$ | H | CH | CH | white solid | 154-155 |
| 2-298 | Et | 2 | 4-CF$_3$ | 4,6-(CF$_3$)$_2$ | H | CH | CH | | |
| 2-299 | Et | 2 | 4-OCF$_3$ | 4,6-(CF$_3$)$_2$ | H | CH | CH | white solid | 179-180 |
| 2-300 | Et | 2 | 4-SF$_5$ | 4,6-(CF$_3$)$_2$ | H | CH | CH | | |
| 2-301 | Et | 2 | 5-CF$_3$ | 4,6-(CF$_3$)$_2$ | H | CH | CH | | |
| 2-302 | Et | 2 | H | 4,6-(CF$_3$)$_2$ | Me | CH | CH | | |
| 2-303 | Et | 2 | H | 4,6-(CF$_3$)$_2$ | Cl | CH | CH | | |
| 2-304 | Et | 2 | H | 4,6-(CF$_3$)$_2$ | Br | CH | CH | | |
| 2-305 | Et | 2 | H | 4,6-(CF$_3$)$_2$ | I | CH | CH | | |
| 2-306 | Et | 2 | H | 3-CN-4,6-(CF$_3$)$_2$ | H | CH | CH | | |
| 2-307 | Et | 2 | 4-Cl | 3-CN-4,6-(CF$_3$)$_2$ | H | CH | CH | | |
| 2-308 | Et | 2 | 4-Br | 3-CN-4,6-(CF$_3$)$_2$ | H | CH | CH | | |
| 2-309 | Et | 2 | 4-I | 3-CN-4,6-(CF$_3$)$_2$ | H | CH | CH | white solid | 186-188 |
| 2-310 | Et | 2 | 4-CF$_3$ | 3-CN-4,6-(CF$_3$)$_2$ | H | CH | CH | | |
| 2-311 | Et | 2 | 4-OCF$_3$ | 3-CN-4,6-(CF$_3$)$_2$ | H | CH | CH | white solid | 163-164 |
| 2-312 | Et | 2 | 4-SF$_5$ | 3-CN-4,6-(CF$_3$)$_2$ | H | CH | CH | white solid | 208-209 |
| 2-313 | Et | 2 | H | 3-Cl-4-CF$_3$ | H | CH | CH | | |
| 2-314 | Et | 2 | 4-Cl | 3-Cl-4-CF$_3$ | H | CH | CH | | |
| 2-315 | Et | 2 | 4-Br | 3-Cl-4-CF$_3$ | H | CH | CH | | |
| 2-316 | Et | 2 | 4-I | 3-Cl-4-CF$_3$ | H | CH | CH | | |
| 2-317 | Et | 2 | 4-CF$_3$ | 3-Cl-4-CF$_3$ | H | CH | CH | | |
| 2-318 | Et | 2 | 4-OCF$_3$ | 3-Cl-4-CF$_3$ | H | CH | CH | | |
| 2-319 | Et | 2 | 4-SF$_5$ | 3-Cl-4-CF$_3$ | H | CH | CH | | |
| 2-320 | Et | 2 | H | 4-CF$_3$-5-Cl | H | CH | CH | | |
| 2-321 | Et | 2 | 4-Cl | 4-CF$_3$-5-Cl | H | CH | CH | | |
| 2-322 | Et | 2 | 4-Br | 4-CF$_3$-5-Cl | H | CH | CH | white solid | 195-198 |
| 2-323 | Et | 2 | 4-I | 4-CF$_3$-5-Cl | H | CH | CH | white solid | 190-194 |
| 2-324 | Et | 2 | 4-CF$_3$ | 4-CF$_3$-5-Cl | H | CH | CH | | |
| 2-325 | Et | 2 | 4-OCF$_3$ | 4-CF$_3$-5-Cl | H | CH | CH | white solid | 149-151 |
| 2-326 | Et | 2 | 4-SF$_5$ | 4-CF$_3$-5-Cl | H | CH | CH | | |
| 2-327 | Et | 2 | H | 4-CF$_3$-6-Cl | H | CH | CH | | |
| 2-328 | Et | 2 | 4-Cl | 4-CF$_3$-6-Cl | H | CH | CH | | |
| 2-329 | Et | 2 | 4-Br | 4-CF$_3$-6-Cl | H | CH | CH | white solid | 179-180 |
| 2-330 | Et | 2 | 4-I | 4-CF$_3$-6-Cl | H | CH | CH | white solid | 187-188 |
| 2-331 | Et | 2 | 4-CF$_3$ | 4-CF$_3$-6-Cl | H | CH | CH | | |
| 2-332 | Et | 2 | 4-OCF$_3$ | 4-CF$_3$-6-Cl | H | CH | CH | white solid | 179-180 |
| 2-333 | Et | 2 | 4-SF$_5$ | 4-CF$_3$-6-Cl | H | CH | CH | | |
| 2-334 | Et | 2 | H | 4-CF$_3$-3-Br | H | CH | CH | | |
| 2-335 | Et | 2 | 4-Cl | 4-CF$_3$-3-Br | H | CH | CH | | |
| 2-336 | Et | 2 | 4-Br | 4-CF$_3$-3-Br | H | CH | CH | | |
| 2-337 | Et | 2 | 4-I | 4-CF$_3$-3-Br | H | CH | CH | | |
| 2-338 | Et | 2 | 4-CF$_3$ | 4-CF$_3$-3-Br | H | CH | CH | | |
| 2-339 | Et | 2 | 4-OCF$_3$ | 4-CF$_3$-3-Br | H | CH | CH | | |
| 2-340 | Et | 2 | 4-SF$_5$ | 4-CF$_3$-3-Br | H | CH | CH | | |
| 2-341 | Et | 2 | H | 4-CF$_3$-5-Br | H | CH | CH | | |
| 2-342 | Et | 2 | 4-Cl | 4-CF$_3$-5-Br | H | CH | CH | | |
| 2-343 | Et | 2 | 4-Br | 4-CF$_3$-5-Br | H | CH | CH | | |
| 2-344 | Et | 2 | 4-I | 4-CF$_3$-5-Br | H | CH | CH | white solid | 188-197 |
| 2-345 | Et | 2 | 4-CF$_3$ | 4-CF$_3$-5-Br | H | CH | CH | | |
| 2-346 | Et | 2 | 4-OCF$_3$ | 4-CF$_3$-5-Br | H | CH | CH | | |
| 2-347 | Et | 2 | 4-SF$_5$ | 4-CF$_3$-5-Br | H | CH | CH | | |
| 2-348 | Et | 2 | H | 4-CF$_3$-6-Br | H | CH | CH | | |
| 2-349 | Et | 2 | 4-Cl | 4-CF$_3$-6-Br | H | CH | CH | | |
| 2-350 | Et | 2 | 4-Br | 4-CF$_3$-6-Br | H | CH | CH | | |

TABLE 2-8

| Compound No. | R | n | Xm | Yp | Z | W¹ | W² | Profile | Melting Point (° C.) |
|---|---|---|---|---|---|---|---|---|---|
| 2-351 | Et | 2 | 4-I | 4-CF₃-6-Br | H | CH | CH | white solid | 180-181 |
| 2-352 | Et | 2 | 4-CF₃ | 4-CF₃-6-Br | H | CH | CH | | |
| 2-353 | Et | 2 | 4-OCF₃ | 4-CF₃-6-Br | H | CH | CH | white solid | 182-183 |
| 2-354 | Et | 2 | 4-SF₅ | 4-CF₃-6-Br | H | CH | CH | | |
| 2-355 | Et | 2 | H | 4-CF₃-6-OMe | H | CH | CH | | |
| 2-356 | Et | 2 | 4-Cl | 4-CF₃-6-OMe | H | CH | CH | | |
| 2-357 | Et | 2 | 4-Br | 4-CF₃-6-OMe | H | CH | CH | white solid | 112-115 |
| 2-358 | Et | 2 | 4-I | 4-CF₃-6-OMe | H | CH | CH | | |
| 2-359 | Et | 2 | 4-CF₃ | 4-CF₃-6-OMe | H | CH | CH | | |
| 2-360 | Et | 2 | 4-OCF₃ | 4-CF₃-6-OMe | H | CH | CH | | |
| 2-361 | Et | 2 | 4-SF₅ | 4-CF₃-6-OMe | H | CH | CH | | |
| 2-362 | Et | 2 | H | 4-CF₃-6-CN | H | CH | CH | | |
| 2-363 | Et | 2 | 4-Cl | 4-CF₃-6-CN | H | CH | CH | | |
| 2-364 | Et | 2 | 4-Br | 4-CF₃-6-CN | H | CH | CH | | |
| 2-365 | Et | 2 | 4-I | 4-CF₃-6-CN | H | CH | CH | | |
| 2-366 | Et | 2 | 4-CF₃ | 4-CF₃-6-CN | H | CH | CH | | |
| 2-367 | Et | 2 | 4-OCF₃ | 4-CF₃-6-CN | H | CH | CH | white solid | 163 |
| 2-368 | Et | 2 | 4-SF₅ | 4-CF₃-6-CN | H | CH | CH | | |
| 2-369 | Et | 2 | H | 3-CF₃ | H | CH | CH | colorless oily | |
| 2-370 | Et | 2 | H | 4-CF₃ | H | CH | CH | white solid | 162-165 |
| 2-371 | Et | 2 | H | 4-CF₃ | H | N | CH | | |
| 2-372 | Et | 2 | H | 4-CF₃ | H | CH | N | | |
| 2-373 | Et | 2 | H | 4-CF₃ | H | N | N | | |
| 2-374 | Et | 2 | 3-Cl | 4-CF₃ | H | CH | CH | white solid | 175-179 |
| 2-375 | Et | 2 | 4-Cl | 4-CF₃ | H | CH | CH | white solid | 166-168 |
| 2-376 | Et | 2 | 5-Cl | 4-CF₃ | H | CH | CH | white solid | 115-118 |
| 2-377 | Et | 2 | 6-Cl | 4-CF₃ | H | CH | CH | colorless oily | |
| 2-378 | Et | 2 | 4-F | 4-CF₃ | H | CH | CH | white solid | 160-162 |
| 2-379 | Et | 2 | 4-Br | 4-CF₃ | H | CH | CH | white solid | 157-158 |
| 2-380 | Et | 2 | 4-Br | 4-CF₃ | H | N | CH | | |
| 2-381 | Et | 2 | 4-I | 4-CF₃ | H | CH | CH | white solid | 144-147 |
| 2-382 | Et | 2 | 4-Me | 4-CF₃ | H | CH | CH | white solid | 147-148 |
| 2-383 | Et | 2 | 4-CN | 4-CF₃ | H | CH | CH | white solid | 193-196 |
| 2-384 | Et | 2 | 4-OH | 4-CF₃ | H | CH | CH | white solid | 128-133 |
| 2-385 | Et | 2 | 4-COOEt | 4-CF₃ | H | CH | CH | white solid | 153-156 |
| 2-386 | Et | 2 | 4-CF₃ | 4-CF₃ | H | CH | CH | white solid | 168-170 |
| 2-387 | Et | 2 | 4-CF₃ | 4-CF₃ | H | N | CH | white solid | 145-149 |
| 2-388 | Et | 2 | 4-CF(CF₃)₂ | 4-CF₃ | H | CH | CH | colorless oily | |
| 2-389 | Et | 2 | 4-CH(CF₃)₂ | 4-CF₃ | H | CH | CH | white solid | 145-147 |
| 2-390 | Et | 2 | 4-C(CF₃)₂OMe | 4-CF₃ | H | CH | CH | white solid | 169-171 |
| 2-391 | Et | 2 | 4-OMe | 4-CF₃ | H | CH | CH | white solid | 108-115 |
| 2-392 | Et | 2 | 4-OCF₃ | 4-CF₃ | H | CH | CH | white solid | 126-129 |
| 2-393 | Et | 2 | 4-SCF₃ | 4-CF₃ | H | CH | CH | white solid | 124-126 |
| 2-394 | Et | 2 | 4-SMe | 4-CF₃ | H | CH | CH | white solid | 125-126 |
| 2-395 | Et | 2 | 4-SOMe | 4-CF₃ | H | CH | CH | white solid | 178-180 |
| 2-396 | Et | 2 | 4-SO₂Me | 4-CF₃ | H | CH | CH | white solid | 147-151 |
| 2-397 | Et | 2 | 4-OSO₂CF₃ | 4-CF₃ | H | CH | CH | white solid | 120-124 |
| 2-398 | Et | 2 | 4-SF₅ | 4-CF₃ | H | CH | CH | white solid | 173-175 |
| 2-399 | Et | 2 | 4-OCH₂OCH₃ | 4-CF₃ | H | CH | CH | white solid | 99-101 |
| 2-400 | Et | 2 | 4-I-5-Cl | 4-CF₃ | H | CH | CH | white solid | 200-202 |
| 2-401 | Et | 2 | 3,4-Cl₂ | 4-CF₃ | H | CH | CH | white solid | 212-214 |
| 2-402 | Et | 2 | 3-Cl-4-Br | 4-CF₃ | H | CH | CH | white solid | 203-207 |
| 2-403 | Et | 2 | 4-CH₂CN | 4-CF₃ | H | CH | CH | white solid | 103-106 |
| 2-404 | Et | 2 | 4-CF₂CN | 4-CF₃ | H | CH | CH | tan oily | |
| 2-405 | Et | 2 | 4-CH₂Cl | 4-CF₃ | H | CH | CH | | |

TABLE 2-9

| Compound No. | R | n | Xm | Yp | Z | W¹ | W² | Profile | Melting Point (° C.) |
|---|---|---|---|---|---|---|---|---|---|
| 2-406 | Et | 2 | 4-CH₂OH | 4-CF₃ | H | CH | CH | | |
| 2-407 | Et | 2 | 4-(c-Pr) | 4-CF₃ | H | CH | CH | white solid | 61-64 |
| 2-408 | Et | 2 |  | 4-CF₃ | H | CH | CH | white solid | 118-121 |

TABLE 2-9-continued

| Compound No. | R | n | Xm | Yp | Z | W¹ | W² | Profile | Melting Point (° C.) |
|---|---|---|---|---|---|---|---|---|---|
| 2-409 | Et | 2 | 4-(1-methyl-1,2,4-triazol-3-yl) | 4-$CF_3$ | H | CH | CH | white solid | 176-177 |
| 2-410 | Et | 2 | 4-(2-methyl-2H-tetrazol-5-yl) | 4-$CF_3$ | H | CH | CH | pale yellow | 190-191 |
| 2-411 | Et | 2 | 4-(5-methyl-1,2,4-oxadiazol-3-yl) | 4-$CF_3$ | H | CH | CH | white solid | 171-174 |
| 2-412 | Et | 2 | 4-((5-$CF_3$-tetrazol-2-yl)methyl) | 4-$CF_3$ | H | CH | CH | white solid | 128-130 |
| 2-413 | Et | 2 | H | 4-$CF_3$ | Me | CH | CH | | |
| 2-414 | Et | 2 | 4-$CF_3$ | 4-$CF_3$ | Me | CH | CH | yellow solid | 118-123 |
| 2-415 | Et | 2 | 4-$OCF_3$ | 4-$CF_3$ | Me | CH | CH | white solid | 127-130 |
| 2-416 | Et | 2 | 4-$OCF_3$ | 4-$CF_3$ | $CH_2OMe$ | CH | CH | pale yellow oily | |
| 2-417 | Et | 2 | H | 4-$CF_3$ | Cl | CH | CH | | |
| 2-418 | Et | 2 | H | 4-$CF_3$ | Br | CH | CH | | |
| 2-419 | Et | 2 | H | 4-$CF_3$ | I | CH | CH | | |
| 2-420 | Et | 2 | H | 4-$CF_2CF_3$ | H | CH | CH | white solid | 111-115 |
| 2-421 | Et | 2 | 4-Cl | 4-$CF_2CF_3$ | H | CH | CH | | |
| 2-422 | Et | 2 | 4-Br | 4-$CF_2CF_3$ | H | CH | CH | | |
| 2-423 | Et | 2 | 4-I | 4-CF | H | CH | CH | white solid | 71-76 |
| 2-424 | Et | 2 | 4-$CF_3$ | 4-$CF_2CF_3$ | H | CH | CH | | |
| 2-425 | Et | 2 | 4-$OCF_3$ | 4-$CF_2CF_3$ | H | CH | CH | white solid | 144-146 |
| 2-426 | Et | 2 | 4-$SF_5$ | 4-$CF_2CF_3$ | H | CH | CH | colorless oily | |
| 2-427 | Et | 2 | H | 5-$CF_3$ | H | CH | CH | | |
| 2-428 | Et | 2 | H | 6-$CF_3$ | H | CH | CH | white solid | 141-143 |
| 2-429 | Et | 2 | H | 6-$CF_3$ | Me | CH | CH | | |
| 2-430 | Et | 2 | H | 6-$CF_3$ | Cl | CH | CH | | |
| 2-431 | Et | 2 | H | 6-$CF_3$ | Br | CH | CH | | |
| 2-432 | Et | 2 | H | 6-$CF_3$ | I | CH | CH | | |
| 2-433 | n-Pr | 0 | H | 4-$CF_3$ | H | CH | CH | white solid | 66-67 |
| 2-434 | n-Pr | 0 | H | 5-$CF_3$ | H | CH | CH | pale yellow solid | 93-95 |
| 2-435 | n-Pr | 0 | H | 4,6-$(CF_3)_2$ | H | CH | CH | | |
| 2-436 | n-Pr | 0 | 4-Cl | 4,6-$(CF_3)_2$ | H | CH | CH | | |
| 2-437 | n-Pr | 0 | 4-Br | 4,6-$(CF_3)_2$ | H | CH | CH | | |
| 2-438 | n-Pr | 0 | 4-$CF_3$ | 4,6-$(CF_3)_2$ | H | CH | CH | | |
| 2-439 | n-Pr | 0 | 5-$CF_3$ | 4,6-$(CF_3)_2$ | H | CH | CH | | |
| 2-440 | n-Pr | 0 | H | 4,6-$(CF_3)_2$ | Me | CH | CH | | |
| 2-441 | n-Pr | 0 | H | 4,6-$(CF_3)_2$ | Cl | CH | CH | | |
| 2-442 | n-Pr | 0 | H | 4,6-$(CF_3)_2$ | Br | CH | CH | | |
| 2-443 | n-Pr | 0 | H | 4,6-$(CF_3)_2$ | I | CH | CH | | |
| 2-444 | n-Pr | 1 | H | 4-$CF_3$ | H | CH | CH | white solid | 193-194 |
| 2-445 | n-Pr | 1 | H | 5-$CF_3$ | H | CH | CH | white solid | 179-180 |

TABLE 2-10

| Compound No. | R | n | Xm | Yp | Z | W¹ | W² | Profile | Melting Point (° C.) |
|---|---|---|---|---|---|---|---|---|---|
| 2-446 | n-Pr | 2 | H | 4-$CF_3$ | H | CH | CH | white solid | 120-123 |
| 2-447 | n-Pr | 2 | H | 5-$CF_3$ | H | CH | CH | white solid | 109-111 |
| 2-448 | i-Pr | 0 | H | 4,6-$(CF_3)_2$ | H | CH | CH | | |
| 2-449 | i-Pr | 0 | 4-Cl | 4,6-$(CF_3)_2$ | H | CH | CH | | |
| 2-450 | i-Pr | 0 | 4-Br | 4,6-$(CF_3)_2$ | H | CH | CH | | |
| 2-451 | i-Pr | 0 | 4-$CF_3$ | 4,6-$(CF_3)_2$ | H | CH | CH | | |

TABLE 2-10-continued

| Compound No. | R | n | Xm | Yp | Z | W¹ | W² | Profile | Melting Point (° C.) |
|---|---|---|---|---|---|---|---|---|---|
| 2-452 | i-Pr | 0 | 5-CF₃ | 4,6-(CF₃)₂ | H | CH | CH | | |
| 2-453 | i-Pr | 0 | H | 4,6-(CF₃)₂ | Me | CH | CH | | |
| 2-454 | i-Pr | 0 | H | 4,6-(CF₃)₂ | Cl | CH | CH | | |
| 2-455 | i-Pr | 0 | H | 4,6-(CF₃)₂ | Br | CH | CH | | |
| 2-456 | i-Pr | 0 | H | 4,6-(CF₃)₂ | I | CH | CH | | |
| 2-457 | n-Bu | 0 | H | 4,6-(CF₃)₂ | H | CH | CH | | |
| 2-458 | n-Bu | 0 | 4-Cl | 4,6-(CF₃)₂ | H | CH | CH | | |
| 2-459 | n-Bu | 0 | 4-Br | 4,6-(CF₃)₂ | H | CH | CH | | |
| 2-460 | n-Bu | 0 | 4-CF₃ | 4,6-(CF₃)₂ | H | CH | CH | | |
| 2-461 | n-Bu | 0 | 5-CF₃ | 4,6-(CF₃)₂ | H | CH | CH | | |
| 2-462 | n-Bu | 0 | H | 4,6-(CF₃)₂ | Me | CH | CH | | |
| 2-463 | n-Bu | 0 | H | 4,6-(CF₃)₂ | Cl | CH | CH | | |
| 2-464 | n-Bu | 0 | H | 4,6-(CF₃)₂ | Br | CH | CH | | |
| 2-465 | n-Bu | 0 | H | 4,6-(CF₃)₂ | I | CH | CH | | |
| 2-466 | n-Pen | 0 | H | 4,6-(CF₃)₂ | H | CH | CH | | |
| 2-467 | n-Pen | 0 | 4-Cl | 4,6-(CF₃)₂ | H | CH | CH | | |
| 2-468 | n-Pen | 0 | 4-Br | 4,6-(CF₃)₂ | H | CH | CH | | |
| 2-469 | n-Pen | 0 | 4-CF₃ | 4,6-(CF₃)₂ | H | CH | CH | | |
| 2-470 | n-Pen | 0 | 5-CF₃ | 4,6-(CF₃)₂ | H | CH | CH | | |
| 2-471 | n-Pen | 0 | H | 4,6-(CF₃)₂ | Me | CH | CH | | |
| 2-472 | n-Pen | 0 | H | 4,6-(CF₃)₂ | Cl | CH | CH | | |
| 2-473 | n-Pen | 0 | H | 4,6-(CF₃)₂ | Br | CH | CH | | |
| 2-474 | n-Pen | 0 | H | 4,6-(CF₃)₂ | I | CH | CH | | |
| 2-475 | n-Hex | 0 | H | 4,6-(CF₃)₂ | H | CH | CH | | |
| 2-476 | n-Hex | 0 | 4-Cl | 4,6-(CF₃)₂ | H | CH | CH | | |
| 2-477 | n-Hex | 0 | 4-Br | 4,6-(CF₃)₂ | H | CH | CH | | |
| 2-478 | n-Hex | 0 | 4-CF₃ | 4,6-(CF₃)₂ | H | CH | CH | | |
| 2-479 | n-Hex | 0 | 5-CF₃ | 4,6-(CF₃)₂ | H | CH | CH | | |
| 2-480 | n-Hex | 0 | H | 4,6-(CF₃)₂ | Me | CH | CH | | |
| 2-481 | n-Hex | 0 | H | 4,6-(CF₃)₂ | Cl | CH | CH | | |
| 2-482 | n-Hex | 0 | H | 4,6-(CF₃)₂ | Br | CH | CH | | |
| 2-483 | n-Hex | 0 | H | 4,6-(CF₃)₂ | I | CH | CH | | |
| 2-484 | CF₃CH₂ | 0 | H | 5-CF₃ | H | CH | CH | yellow oily | |
| 2-485 | CF₃CH₂ | 1 | H | 5-CF₃ | H | CH | CH | white solid | 198-199 |
| 2-486 | CF₃CH₂ | 2 | H | 5-CF₃ | H | CH | CH | | |

TABLE 3-1

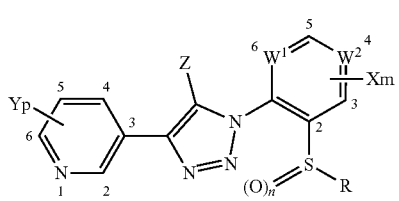

| Compound No. | R | n | Xm | Yp | Z | W¹ | W² | Profile | Melting Point (° C.) |
|---|---|---|---|---|---|---|---|---|---|
| 3-1 | Me | 0 | H | H | H | CH | CH | | |
| 3-2 | Me | 0 | H | 4-CF₃ | H | CH | CH | | |
| 3-3 | Me | 0 | H | 5-CF₃ | H | CH | CH | | |
| 3-4 | Me | 0 | H | 6-CF₃ | H | CH | CH | | |
| 3-5 | Me | 0 | H | 4-CF₃ | Br | CH | CH | | |
| 3-6 | Me | 0 | H | 5-CF₃ | Br | CH | CH | | |
| 3-7 | Me | 0 | H | 6-CF₃ | Br | CH | CH | | |
| 3-8 | Me | 0 | 4-CF₃ | 4-CF₃ | Br | CH | CH | | |
| 3-9 | Me | 0 | 4-CF₃ | 5-CF₃ | Br | CH | CH | | |
| 3-10 | Me | 0 | 4-CF₃ | 6-CF₃ | Br | CH | CH | | |
| 3-11 | Me | 0 | H | 4-CF₃ | I | CH | CH | | |
| 3-12 | Me | 0 | H | 5-CF₃ | I | CH | CH | | |
| 3-13 | Me | 0 | H | 6-CF₃ | I | CH | CH | | |
| 3-14 | Et | 0 | H | H | H | CH | CH | white solid | 83-84 |
| 3-15 | Et | 0 | H | 5-CF₃ | H | CH | CH | pale yellow solid | 79-81 |
| 3-16 | Et | 0 | 4-Cl | 5-CF₃ | H | CH | CH | | |
| 3-17 | Et | 0 | 4-Br | 5-CF₃ | H | CH | CH | | |
| 3-18 | Et | 0 | 4-CF₃ | 5-CF₃ | H | CH | CH | | |
| 3-19 | Et | 0 | 5-CF₃ | 5-CF₃ | H | CH | CH | | |
| 3-20 | Et | 0 | H | 5-CF₃ | Me | CH | CH | | |
| 3-21 | Et | 0 | H | 5-CF₃ | Cl | CH | CH | | |
| 3-22 | Et | 0 | H | 5-CF₃ | Br | CH | CH | | |

TABLE 3-1-continued

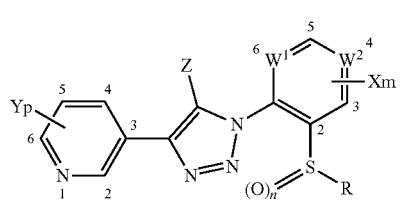

| Compound No. | R | n | Xm | Yp | Z | W¹ | W² | Profile | Melting Point (° C.) |
|---|---|---|---|---|---|---|---|---|---|
| 3-23 | Et | 0 | H | 5-CF₃ | I | CH | CH | | |
| 3-24 | Et | 0 | H | 6-CF₃ | H | CH | CH | | |
| 3-25 | Et | 0 | H | 6-CF₃ | Me | CH | CH | | |
| 3-26 | Et | 0 | H | 6-CF₃ | Cl | CH | CH | | |
| 3-27 | Et | 0 | H | 6-CF₃ | Br | CH | CH | | |
| 3-28 | Et | 0 | H | 6-CF₃ | I | CH | CH | | |
| 3-29 | Et | 1 | H | H | H | CH | CH | white solid | 132-133 |
| 3-30 | Et | 1 | H | 5-CF₃ | H | CH | CH | white solid | 186-187 |
| 3-31 | Et | 1 | 4-Cl | 5-CF₃ | H | CH | CH | | |
| 3-32 | Et | 1 | 4-Br | 5-CF₃ | H | CH | CH | | |
| 3-33 | Et | 1 | 4-CF₃ | 5-CF₃ | H | CH | CH | | |
| 3-34 | Et | 1 | 5-CF₃ | 5-CF₃ | H | CH | CH | | |
| 3-35 | Et | 1 | H | 5-CF₃ | Me | CH | CH | | |
| 3-36 | Et | 1 | H | 5-CF₃ | Cl | CH | CH | | |
| 3-37 | Et | 1 | H | 5-CF₃ | Br | CH | CH | | |
| 3-38 | Et | 1 | H | 5-CF₃ | I | CH | CH | | |
| 3-39 | Et | 1 | H | 6-CF₃ | H | CH | CH | | |
| 3-40 | Et | 1 | H | 6-CF₃ | Me | CH | CH | | |
| 3-41 | Et | 1 | H | 6-CF₃ | Cl | CH | CH | | |
| 3-42 | Et | 1 | H | 6-CF₃ | Br | CH | CH | | |

TABLE 3-1-continued

| Compound No. | R | n | Xm | Yp | Z | W¹ | W² | Profile | Melting Point (° C.) |
|---|---|---|---|---|---|---|---|---|---|
| 3-43 | Et | 1 | H | 6-CF$_3$ | I | CH | CH | | |
| 3-44 | Et | 2 | H | H | H | CH | CH | | |
| 3-45 | Et | 2 | H | 5-CF$_3$ | H | CH | CH | white solid | 124-126 |

TABLE 3-2

| Compound No. | R | n | Xm | Yp | Z | W¹ | W² | Profile | Melting Point (° C.) |
|---|---|---|---|---|---|---|---|---|---|
| 3-46 | Et | 2 | 4-Cl | 5-CF$_3$ | H | CH | CH | | |
| 3-47 | Et | 2 | 4-Br | 5-CF$_3$ | H | CH | CH | | |
| 3-48 | Et | 2 | 4-CF$_3$ | 5-CF$_3$ | H | CH | CH | | |
| 3-49 | Et | 2 | 5-CF$_3$ | 5-CF$_3$ | H | CH | CH | | |
| 3-50 | Et | 2 | H | 5-CF$_3$ | Me | CH | CH | | |
| 3-51 | Et | 2 | H | 5-CF$_3$ | Cl | CH | CH | | |
| 3-52 | Et | 2 | H | 5-CF$_3$ | Br | CH | CH | | |
| 3-53 | Et | 2 | H | 5-CF$_3$ | I | CH | CH | | |
| 3-54 | Et | 2 | H | 6-CF$_3$ | H | CH | CH | | |
| 3-55 | Et | 2 | H | 6-CF$_3$ | Me | CH | CH | | |
| 3-56 | Et | 2 | H | 6-CF$_3$ | Cl | CH | CH | | |
| 3-57 | Et | 2 | H | 6-CF$_3$ | Br | CH | CH | | |
| 3-58 | Et | 2 | H | 6-CF$_3$ | I | CH | CH | | |
| 3-59 | n-Hex | 0 | H | H | H | CH | CH | | |
| 3-60 | n-Hex | 0 | H | 5-CF$_3$ | H | CH | CH | | |
| 3-61 | n-Hex | 0 | 4-Cl | 5-CF$_3$ | H | CH | CH | | |
| 3-62 | n-Hex | 0 | 4-Br | 5-CF$_3$ | H | CH | CH | | |
| 3-63 | n-Hex | 0 | 4-CF$_3$ | 5-CF$_3$ | H | CH | CH | | |
| 3-64 | n-Hex | 0 | 5-CF$_3$ | 5-CF$_3$ | H | CH | CH | | |
| 3-65 | n-Hex | 0 | H | 5-CF$_3$ | Me | CH | CH | | |
| 3-66 | n-Hex | 0 | H | 5-CF$_3$ | Cl | CH | CH | | |
| 3-67 | n-Hex | 0 | H | 5-CF$_3$ | Br | CH | CH | | |
| 3-68 | n-Hex | 0 | H | 5-CF$_3$ | I | CH | CH | | |
| 3-69 | n-Hex | 0 | H | 6-CF$_3$ | H | CH | CH | | |
| 3-70 | n-Hex | 0 | H | 6-CF$_3$ | Me | CH | CH | | |
| 3-71 | n-Hex | 0 | H | 6-CF$_3$ | Cl | CH | CH | | |
| 3-72 | n-Hex | 0 | H | 6-CF$_3$ | Br | CH | CH | | |
| 3-73 | n-Hex | 0 | H | 6-CF$_3$ | I | CH | CH | | |

TABLE 4-1

| Compound No. | R | n | Xm | Yp | Z | W¹ | W² | Profile | Melting Point (° C.) |
|---|---|---|---|---|---|---|---|---|---|
| 4-1 | Me | 0 | H | H | H | CH | CH | | |
| 4-2 | Me | 0 | H | 2-CF$_3$ | H | CH | CH | | |
| 4-3 | Me | 0 | H | 3-CF$_3$ | H | CH | CH | | |
| 4-4 | Me | 0 | H | 2-CF$_3$ | Br | CH | CH | | |
| 4-5 | Me | 0 | H | 3-CF$_3$ | Br | CH | CH | | |
| 4-6 | Me | 0 | 4-CF$_3$ | 2-CF$_3$ | Br | CH | CH | | |
| 4-7 | Me | 0 | 4-CF$_3$ | 3-CF$_3$ | Br | CH | CH | | |
| 4-8 | Me | 0 | H | 2-CF$_3$ | I | CH | CH | | |
| 4-9 | Me | 0 | H | 3-CF$_3$ | I | CH | CH | | |
| 4-10 | Et | 0 | H | H | H | CH | CH | light brown solid | 103-105 |
| 4-11 | Et | 0 | H | 2-CF$_3$ | H | CH | CH | | |
| 4-12 | Et | 0 | 4-Cl | 2-CF$_3$ | H | CH | CH | | |
| 4-13 | Et | 0 | 4-Br | 2-CF$_3$ | H | CH | CH | | |
| 4-14 | Et | 0 | 4-CF$_3$ | 2-CF$_3$ | H | CH | CH | | |
| 4-15 | Et | 0 | 5-CF$_3$ | 2-CF$_3$ | H | CH | CH | | |
| 4-16 | Et | 0 | H | 2-CF$_3$ | Me | CH | CH | | |
| 4-17 | Et | 0 | H | 2-CF$_3$ | Cl | CH | CH | | |

TABLE 4-1-continued

| Compound No. | R | n | Xm | Yp | Z | W¹ | W² | Profile | Melting Point (° C.) |
|---|---|---|---|---|---|---|---|---|---|
| 4-18 | Et | 0 | H | 2-CF$_3$ | Br | CH | CH | | |
| 4-19 | Et | 0 | H | 2-CF$_3$ | I | CH | CH | | |
| 4-20 | Et | 0 | H | 2,5-(CF$_3$)$_2$ | H | CH | CH | | |
| 4-21 | Et | 0 | H | 2,5-(CF$_3$)$_2$ | Me | CH | CH | | |
| 4-22 | Et | 0 | H | 2,5-(CF$_3$)$_2$ | Cl | CH | CH | | |
| 4-23 | Et | 0 | H | 2,5-(CF$_3$)$_2$ | Br | CH | CH | | |
| 4-24 | Et | 0 | H | 2,5-(CF$_3$)$_2$ | I | CH | CH | | |
| 4-25 | Et | 1 | H | H | H | CH | CH | white solid | 160-164 |
| 4-26 | Et | 1 | H | 2-CF$_3$ | H | CH | CH | | |
| 4-27 | Et | 1 | 4-Cl | 2-CF$_3$ | H | CH | CH | | |
| 4-28 | Et | 1 | 4-Br | 2-CF$_3$ | H | CH | CH | | |
| 4-29 | Et | 1 | 4-CF$_3$ | 2-CF$_3$ | H | CH | CH | | |
| 4-30 | Et | 1 | 5-CF$_3$ | 2-CF$_3$ | H | CH | CH | | |
| 4-31 | Et | 1 | H | 2-CF$_3$ | Me | CH | CH | | |
| 4-32 | Et | 1 | H | 2-CF$_3$ | Cl | CH | CH | | |
| 4-33 | Et | 1 | H | 2-CF$_3$ | Br | CH | CH | | |
| 4-34 | Et | 1 | H | 2-CF$_3$ | I | CH | CH | | |
| 4-35 | Et | 1 | H | 2,5-(CF$_3$)$_2$ | H | CH | CH | | |
| 4-36 | Et | 1 | H | 2,5-(CF$_3$)$_2$ | Me | CH | CH | | |
| 4-37 | Et | 1 | H | 2,5-(CF$_3$)$_2$ | Cl | CH | CH | | |
| 4-38 | Et | 1 | H | 2,5-(CF$_3$)$_2$ | Br | CH | CH | | |
| 4-39 | Et | 1 | H | 2,5-(CF$_3$)$_2$ | I | CH | CH | | |
| 4-40 | Et | 2 | H | H | H | CH | CH | | |
| 4-41 | Et | 2 | H | 2-CF$_3$ | H | CH | CH | | |
| 4-42 | Et | 2 | 4-Cl | 2-CF$_3$ | H | CH | CH | | |
| 4-43 | Et | 2 | 4-Br | 2-CF$_3$ | H | CH | CH | | |
| 4-44 | Et | 2 | 4-CF$_3$ | 2-CF$_3$ | H | CH | CH | | |
| 4-45 | Et | 2 | 5-CF$_3$ | 2-CF$_3$ | H | CH | CH | | |

TABLE 4-2

| Compound No. | R | n | Xm | Yp | Z | W¹ | W² | Profile | Melting Point (° C.) |
|---|---|---|---|---|---|---|---|---|---|
| 4-46 | Et | 2 | H | 2-CF$_3$ | Me | CH | CH | | |
| 4-47 | Et | 2 | H | 2-CF$_3$ | Cl | CH | CH | | |
| 4-48 | Et | 2 | H | 2-CF$_3$ | Br | CH | CH | | |
| 4-49 | Et | 2 | H | 2-CF$_3$ | I | CH | CH | | |
| 4-50 | Et | 2 | H | 2,5-(CF$_3$)$_2$ | H | CH | CH | | |
| 4-51 | Et | 2 | H | 2,5-(CF$_3$)$_2$ | Me | CH | CH | | |
| 4-52 | Et | 2 | H | 2,5-(CF$_3$)$_2$ | Cl | CH | CH | | |
| 4-53 | Et | 2 | H | 2,5-(CF$_3$)$_2$ | Br | CH | CH | | |
| 4-54 | Et | 2 | H | 2,5-(CF$_3$)$_2$ | I | CH | CH | | |
| 4-55 | n-Hex | 0 | H | H | H | CH | CH | | |
| 4-56 | n-Hex | 0 | H | 2-CF$_3$ | H | CH | CH | | |
| 4-57 | n-Hex | 0 | 4-Cl | 2-CF$_3$ | H | CH | CH | | |
| 4-58 | n-Hex | 0 | 4-Br | 2-CF$_3$ | H | CH | CH | | |
| 4-59 | n-Hex | 0 | 4-CF$_3$ | 2-CF$_3$ | H | CH | CH | | |
| 4-60 | n-Hex | 0 | 5-CF$_3$ | 2-CF$_3$ | H | CH | CH | | |
| 4-61 | n-Hex | 0 | H | 2-CF$_3$ | Me | CH | CH | | |
| 4-62 | n-Hex | 0 | H | 2-CF$_3$ | Cl | CH | CH | | |
| 4-63 | n-Hex | 0 | H | 2-CF$_3$ | Br | CH | CH | | |
| 4-64 | n-Hex | 0 | H | 2-CF$_3$ | I | CH | CH | | |
| 4-65 | n-Hex | 0 | H | 2,5-(CF$_3$)$_2$ | H | CH | CH | | |
| 4-66 | n-Hex | 0 | H | 2,5-(CF$_3$)$_2$ | Me | CH | CH | | |
| 4-67 | n-Hex | 0 | H | 2,5-(CF$_3$)$_2$ | Cl | CH | CH | | |
| 4-68 | n-Hex | 0 | H | 2,5-(CF$_3$)$_2$ | Br | CH | CH | | |
| 4-69 | n-Hex | 0 | H | 2,5-(CF$_3$)$_2$ | I | CH | CH | | |

Next, the production method of the 1,2,3-triazole derivative (1) of the present invention is described in detail below. Incidentally, as for the reaction apparatus, a reaction using a microwave synthesis apparatus may also be possible, in addition to using a magnetic stirrer or a mechanical stirrer.

[Production Method 1]

[Chem. 3]

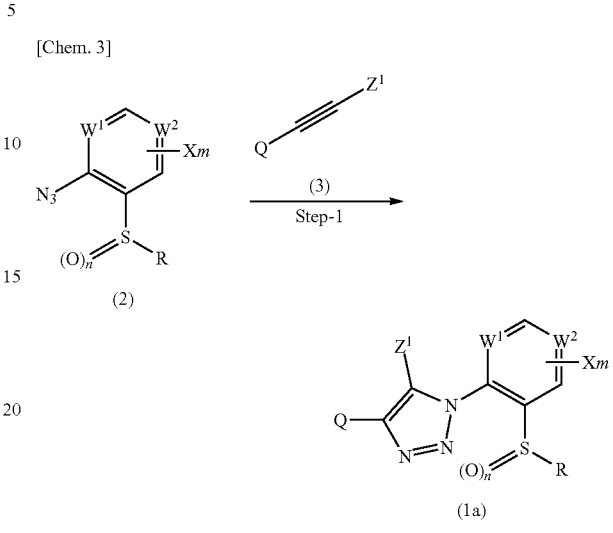

(R, n, X, m, W¹, W² and Q have the same meanings as R, n, X, m, W¹, W² and Q in formula (1), and Z¹ represents a hydrogen atom or a halogen atom).

The step-1 is a step of reacting an azide derivative represented by formula (2) and an acetylene derivative represented by formula (3) to produce a 1,2,3-triazole derivative (1a). The azide derivative represented by formula (2) and the acetylene derivative represented by formula (3) are known depending on the case and are available, for example, from Tokyo Chemical Industry Co., Ltd. Alternatively, these derivatives may also be easily produced from an available reagent in conformity with a known method described in *Experimental Chemistry Course, Organic Syntheses*, etc.

In this reaction, the derivatives must be reacted in the presence of a monovalent or divalent copper reagent, and specific examples of the copper reagent include copper(I) chloride, copper(II) chloride, copper(I) bromide, copper(II) bromide, copper(I) iodide, copper(I) acetate, copper(II) acetate, copper(II) hydroxide, copper(I) triflate, copper(I) 2-thiophenecarboxylate, and copper(II) sulfate. Depending on the case, a combination with a reducing agent such as sodium ascorbate may be required. The derivatives are reacted using such a copper reagent in an amount of 0.01 to 1 equivalent relative to the substrate (2), and the target compound can thereby be efficiently obtained. The reactant (3) is usually used in an amount of 1 to 5 equivalents relative to the substrate (2).

The reaction above can be performed either in the absence of a solvent or in the presence of a solvent. As the solvent used, a solvent not adversely affecting the reaction may be used, and an aromatic hydrocarbon-based solvent such as benzene, toluene, xylene and chlorobenzene, an aliphatic hydrocarbon-based solvent such as pentane, hexane and octane, an ether-based solvent such as diethyl ether, diisopropyl ether, cyclopentylmethyl ether, tetrahydrofuran, dimethoxyethane and 1,4-dioxane, ketones such as acetone, methyl ethyl ketone and cyclohexanone, a halogen-based solvent such as chloroform and dichloromethane, a nitrile-based solvent such as acetonitrile and propionitrile, an ester-based solvent such as ethyl acetate, n-propyl acetate, n-butyl acetate and methyl propionate, an amide-based solvent such as N,N'-dimethylformamide, N,N'-dimethylacetamide and N-methylpyrrolidone, an alcohol-based solvent such as methanol, ethanol, 1-propanol, 2-propanol and tert-butanol, dimethyl sulfoxide, water, or a mixed solvent thereof may be used.

The reaction may be performed at a temperature appropriately selected in the range from −78° C. to 200° C., though this may vary depending on the reaction conditions. After the completion of reaction, the target compound can be obtained by performing a normal post-treatment operation but, if desired, the obtained compound may be purified by column chromatography, recrystallization, etc.

In addition, when $Z^1$ is H, the obtained 1,2,3-triazole derivative may be reacted with an electrophile in the presence of a base such as butyllithium or lithium diisopropylamide and thereby be led to a desired 5-substituted-1,2,3-triazole derivative.

[Production Method 2]

[Chem. 4]

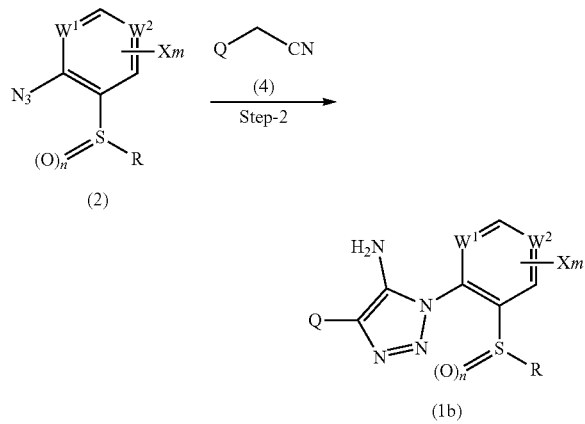

($R$, $n$, $X$, $m$, $W^1$, $W^2$ and $Q$ have the same meanings as R, n, X, m, $W^1$, $W^2$ and Q in formula (1)).

The step-2 is a step of reacting an azide derivative represented by formula (2) and a substituted acetonitrile derivative represented by formula (4) to produce a 5-amino-1,2,3-triazole derivative (1b). The substituted acetonitrile derivative represented by formula (4) is known depending on the case and is available from Tokyo Chemical Industry Co., Ltd., etc. Alternatively, this derivative may also be easily produced from an available reagent in conformity with a known method described, for example, in *Experimental Chemistry Course* and *Organic Syntheses*.

This reaction must be performed in the presence of a base, and the base that can be used includes, for example, an organic base such as triethylamine, diisopropylethylamine, tri(n-butyl)amine, N-methylmorpholine, N,N'-dimethylaniline, N,N'-diethylaniline, 4-tert-butyl-N,N'-dimethylaniline, pyridine, picoline and lutidine, and an alkali metal salt such as sodium carbonate, potassium carbonate, sodium hydrogencarbonate, potassium hydrogencarbonate, sodium acetate, potassium acetate, sodium methoxide, sodium ethoxide, potassium-tert-butoxide, sodium hydride, potassium hydride, sodium amide, n-butyllithium, tert-butyllithium, lithium diisopropylamide, trimethylsilyl lithium and lithium hexamethyldisilazide. Among these bases, a metal base such as sodium methoxide and sodium ethoxide is preferred in view of good yield. The derivatives above are reacted using the base in an amount of 0.1 to 5 equivalents relative to the substrate, and the target compound can thereby be efficiently obtained. The reactant (4) is used usually in an amount of 1 to 5 equivalents relative to the substrate (2).

The reaction above can be performed either in the absence of a solvent or in the presence of a solvent. As the solvent used, a solvent not adversely affecting the reaction may be used, and an aromatic hydrocarbon-based solvent such as benzene, toluene, xylene and chlorobenzene, an aliphatic hydrocarbon-based solvent such as pentane, hexane and octane, an ether-based solvent such as diethyl ether, diisopropyl ether, cyclopentylmethyl ether, tetrahydrofuran, dimethoxyethane and 1,4-dioxane, ketones such as acetone, methyl ethyl ketone and cyclohexanone, a halogen-based solvent such as chloroform and dichloromethane, a nitrile-based solvent such as acetonitrile and propionitrile, an ester-based solvent such as ethyl acetate, n-propyl acetate, n-butyl acetate and methyl propionate, an amide-based solvent such as N,N'-dimethylformamide, N,N'-dimethylacetamide and N-methylpyrrolidone, an alcohol-based solvent such as methanol, ethanol, 1-propanol, 2-propanol and tert-butanol, dimethyl sulfoxide, water, or a mixed solvent thereof may be used.

The reaction may be performed at a temperature appropriately selected in the range from −78° C. to 200° C., though this may vary depending on the base used or the reaction conditions. After the completion of reaction, the target compound can be obtained by performing a normal post-treatment operation but, if desired, the obtained compound may be purified by column chromatography, recrystallization, etc.

In addition, the obtained 5-amino-1,2,3-triazole derivative may be reacted with an electrophile and thereby be led to a 5-substituted amino-1,2,3-triazole derivative.

[Production Method 3]

[Chem. 5]

(R, n, X, m, $W^1$, $W^2$ and Q have the same meanings as R, n, X, m, $W^1$, $W^2$ and Q in formula (1), and $R^2$ represents a phenyl group that may be substituted, or a C1-C6 alkyl group).

The step-3 is a step of reacting an aniline derivative represented by formula (5), an acetyl derivative represented by formula (6), and a substituted sulfonyl hydrazide derivative represented by formula (7) in the presence of iodine to produce a 1,2,3-triazole derivative (1c). The aniline derivative represented by formula (5), the acetyl derivative represented by formula (6), and the substituted sulfonyl hydrazide derivative represented by formula (7) are known depending on the case and are available, for example, from Tokyo Chemical Industry Co., Ltd. Alternatively, these derivatives may also be easily produced from an available reagent in conformity with a known method described in *Experimental Chemistry Course, Organic Syntheses*, etc. In this step, the synthesis may be performed in conformity with the method described in the document (*Chemistry A European Journal*, (2014), 20, 17635-17639).

In addition, the obtained 1,2,3-triazole derivative may be reacted with an electrophile in the presence of a base such as butyllithium or lithium diisopropylamide and thereby be led to a desired 5-substituted-1,2,3-triazole derivative.

[Production Method 4]

[Chem. 6]

(R, n, X, m, $W^1$, $W^2$ and Q have the same meanings as R, n, X, m, $W^1$, $W^2$ and Q in formula (1), $R^2$ represents a phenyl group that may be substituted, or a C1-C6 alkyl group, and $R^{11}$ represents a hydrogen atom, a C1-C6 alkyl group, or a C1-C6 cycloalkyl group).

The step-4 is a step of reacting a ketone derivative represented by formula (8) and a substituted sulfonyl hydrazide derivative represented by formula (7), and then reacting an aniline derivative represented by formula (5) in the presence of copper acetate to produce a 1,2,3-triazine derivative (1d). In this step, the synthesis may also be performed in conformity with the method described in the document (*Chemistry A European Journal*, (2014), 20, 13692-13697).

[Production Method 5]

[Chem. 7]

(R, n, X, m, $W^1$, $W^2$ and Q have the same meanings as R, n, X, m, $W^1$, $W^2$ and Q in formula (1), and M represents a halogen atom or an alkylsulfonyl group).

The step-5 is a step of reacting a triazole derivative represented by formula (1e) with formula (5a) to produce a 1,2,3-triazole derivative (1c).

This reaction is preferably performed in the presence of a base, and the base that can be used includes, for example, an organic base such as triethylamine, diisopropylethylamine, tributylamine, N-methylmorpholine, N,N'-dimethyl aniline, N,N'-diethylaniline, 4-tert-butyl-N,N'-dimethylaniline, pyridine, picoline and lutidine, and an alkali metal salt such as sodium carbonate, potassium carbonate, sodium hydrogencarbonate, potassium hydrogencarbonate, sodium acetate, potassium acetate, sodium methoxide, sodium ethoxide, potassium-tert-butoxide, sodium hydride, potassium hydride, sodium amide, butyllithium, tert-butyllithium, lithium diisopropylamide, trimethylsilyl lithium and lithium hexamethyldisilazide. Among these bases, a metal base such as sodium methoxide and sodium ethoxide is preferred in view of good yield. The reaction is performed using the base in an amount of 1 to 5 equivalents relative to the substrate, and the target compound can thereby be efficiently obtained.

The reaction above can be performed either in the absence of a solvent or in the presence of a solvent. As the solvent, a solvent not adversely affecting the reaction may be used, and an aromatic hydrocarbon-based solvent such as benzene, toluene, xylene and chlorobenzene, an aliphatic hydrocarbon-based solvent such as pentane, hexane and octane, an ether-based solvent such as diethyl ether, diisopropyl ether, cyclopentylmethyl ether, tetrahydrofuran, dimethoxyethane and 1,4-dioxane, ketones such as acetone, methyl ethyl ketone and cyclohexanone, a halogen-based solvent such as chloroform and dichloromethane, a nitrile-based solvent such as acetonitrile and propionitrile, an ester-based solvent such as ethyl acetate, n-propyl acetate, n-butyl acetate and methyl propionate, an amide-based solvent such as N,N'-dimethylformamide, N,N'-dimethylacetamide and N-methylpyrrolidone, an alcohol-based solvent such as methanol, ethanol, 1-propanol, 2-propanol and tert-butanol, dimethyl sulfoxide, water, or a mixed solvent thereof may be used.

The reaction may be performed at a temperature appropriately selected in the range from −78° C. to 200° C., though this may vary depending on the base used or the reaction conditions. After the completion of reaction, the target compound can be obtained by performing a normal post-treatment operation but, if desired, the obtained compound may be purified by column chromatography, recrystallization, etc.

[Production Method 6]

[Chem. 8]

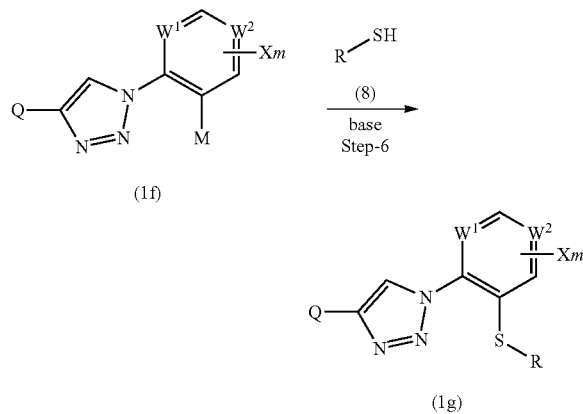

(R, X, m, $W^1$, $W^2$ and Q have the same meanings as R, X, m, W', $W^2$ and Q in formula (1), and M has the same meaning as M in formula (5a)).

The step-6 is a step of reacting a triazole derivative represented by formula (1f) with thiols represented by formula (8) to produce a 1,2,3-triazole derivative (1g).

This reaction must be performed in the presence of a base, and the base that can be used includes, for example, an organic base such as triethylamine, diisopropylethylamine, tributylamine, N-methylmorpholine, N,N'-dimethyl aniline, N,N'-diethylaniline, 4-tert-butyl-N,N'-dimethylaniline, pyridine, picoline and lutidine, and an alkali metal salt such as sodium carbonate, potassium carbonate, sodium hydrogencarbonate, potassium hydrogencarbonate, sodium acetate, potassium acetate, sodium methoxide, sodium ethoxide, potassium-tert-butoxide, sodium hydride, potassium hydride, sodium amide, butyllithium, tert-butyllithium, lithium diisopropylamide, trimethylsilyl lithium and lithium hexamethyldisilazide. Among these bases, a metal base such as sodium methoxide and sodium ethoxide is preferred in view of good yield. The reaction is performed using the base in an amount of 1 to 5 equivalents relative to the substrate, and the target compound can thereby be efficiently obtained. Depending on the case, a thiol salt of compound (8) may be prepared and then reacted.

In addition, this reaction may also be performed in the presence of a transition metal catalyst such as copper, palladium, rhodium and ruthenium to obtain a compound (1g). As the transition metal catalyst, specifically, copper(I) iodide or tris(dibenzylideneacetone)dipalladium(0) may be used.

The reaction above can be performed either in the absence of a solvent or in the presence of a solvent. As the solvent, a solvent not adversely affecting the reaction may be used, and an aromatic hydrocarbon-based solvent such as benzene, toluene, xylene and chlorobenzene, an aliphatic hydrocarbon-based solvent such as pentane, hexane and octane, an ether-based solvent such as diethyl ether, diisopropyl ether, cyclopentylmethyl ether, tetrahydrofuran, dimethoxyethane and 1,4-dioxane, ketones such as acetone, methyl ethyl ketone and cyclohexanone, a halogen-based solvent such as chloroform and dichloromethane, a nitrile-based solvent such as acetonitrile and propionitrile, an ester-based solvent such as ethyl acetate, propyl acetate, butyl acetate and methyl propionate, an amide-based solvent such as N,N'-dimethylformamide, N,N'-dimethylacetamide and N-methylpyrrolidone, an alcohol-based solvent such as methanol, ethanol, 1-propanol, 2-propanol and tert-butanol, dimethyl sulfoxide, water, or a mixed solvent thereof may be used.

The reaction may be performed at a temperature appropriately selected in the range from −78° C. to 200° C., though this may vary depending on the base used or the reaction conditions. After the completion of reaction, the target compound can be obtained by performing a normal post-treatment operation but, if desired, the obtained compound may be purified by column chromatography, recrystallization, etc.

[Production Method 7]

[Chem. 9]

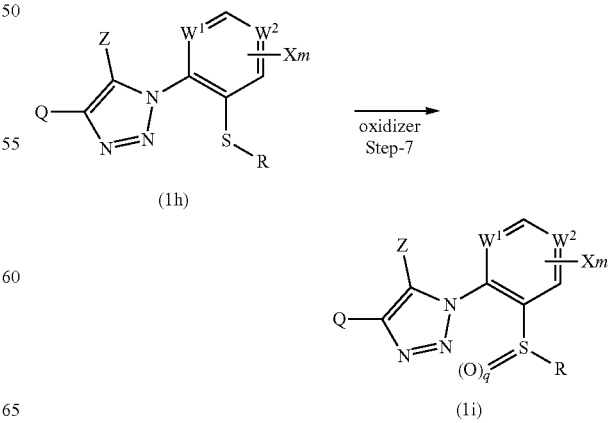

(R, X, m, Z, $W^1$, $W^2$ and Q have the same meanings as R, X, m, Z, W', $W^2$ and Q in formula (1), and q represents an integer of 1 to 2).

A compound represented by formula (1i) according to the present invention can be produced, for example, by reacting a compound represented by formula (1h) with an oxidizer.

As the oxidizer for use in this reaction, hydrogen peroxide, m-chloroperbenzoic acid, sodium periodate, OXONE (trade name of E.I. DuPont, an oxidizer containing potassium hydrogenperoxosulfate), N-chlorosuccinimide, N-bromosuccinimide, tert-butyl hypochlorite, sodium hypochlorite, oxygen, etc. can be used. Among these oxidizers, m-chloroperbenzoic acid, hydrogen peroxide, etc. are preferred in view of good yield. Such an oxidizer is preferably used in the range of 0.01 to 10 equivalents relative to the substrate so as not to adversely affect the progress of reaction, and use in the range of 1 to 3 equivalents is preferred, because the target compound can be obtained with good yield.

As the catalyst for use in this reaction, for example, molybdenum oxide, boric acid, tris(acetylacetone) iron and sodium tungstate may be used, and molybdenum oxide, etc. are preferred. The reaction is performed using such a catalyst in an amount of 0.01 to 1 equivalent relative to the substrate (1h), and the target compound can thereby be efficiently obtained.

This reaction is preferably conducted in a solvent. As for the solvent, a solvent not adversely affecting the reaction may be used, and an ether-based solvent such as diethyl ether, tetrahydrofuran and dioxane, an aromatic hydrocarbon-based solvent such as benzene, toluene, xylene and chlorobenzene, a nitrile-based solvent such as acetonitrile and propionitrile, an amide-based solvent such as N,N'-dimethylformamide, N,N'-dimethylacetamide and N-methylpyrrolidone, an alcohol-based solvent such as methanol, ethanol and isopropyl alcohol, a halogen-based solvent such as dichloromethane, chloroform and 1,2-dichloroethane, an aliphatic hydrocarbon-based solvent such as pentane, hexane, cyclohexane and cycloheptane, ketones such as acetone, methyl ethyl ketone and cyclohexanone, an alcohol-based solvent such as methanol, ethanol, 1-propanol, 2-propanol and tert-butanol, acetic acid, water, or a mixed solvent thereof may be used.

The reaction may be performed at a temperature appropriately selected in the range from −78° C. to the solvent reflux temperature, though this may vary depending on the reaction conditions. After the completion of reaction, the target compound can be obtained by performing a normal post-treatment operation but, if desired, the obtained compound may be purified by column chromatography, recrystallization, etc.

The compound of the present invention may be, if desired, analyzed, confirmed or identified by the melting point, infrared absorption spectrum, $^1$H-NMR, $^{13}$C-NMR, mass spectrometry, X-ray structural analysis, etc.

The compound of the present invention is useful as an active ingredient of agricultural/horticultural pest control agents, among others, insecticides or acaricides.

The compound of the present invention can also exert an excellent activity in controlling a wide range of insects, mites, crustaceans, mollusks, and nematodes. Specific examples of the agricultural/horticultural pests include the followings:

for example, insects from the order Thysanura, for example, *Ctenolepisma villosa, Lepisma saccharina*, and *Thermobia domestica*, from the order Blattodea, for example, *Periplaneta americana, Periplaneta fuliginosa, Periplaneta japonica, Blattella germanica*, and *Blattella lituricollis*, from the order Isoptera, for example, *Incisitermes minor, Coptotermes formosanus, Reticulitermes speratus*, and *Odontotermes formosanus*, from the order Orthoptera, for example, *Ruspolia lineosa, Teleogryllus emma, Gryllotalpa orientalis, Locusta migratoria*, and *Oxya yezoensis*, from the order Psocoptera, for example, *Trogium pulsatorium, Liposcelis bostrychophila*, and *Liposcelis corrodens*, from the order Mallophaga, for example, *Lipeurus caponis, Menacanthus stramineus, Damalinia bovis*, and *Damalinia caprae*, from the order Anoplura, for example, *Haematopinus eurysternus, Haematopinus suis, Pediculus humanus capitis, Pediculus humanus humanus*, and *Pthirus pubis*, from the order Thysanoptera, for example, *Frankliniella intonsa, Frankliniella occidentalis, Heliothrips haemorrhoidalis, Mycterothrips glycines, Scirtothrips dorsalis, Stenchaetothrips biformis, Thrips palmi, Thrips tabaci, Haplothrips aculeatus*, and *Ponticulothrips diospyrosi*, from the order Hemiptera, for example, *Arboridia apicalis, Empoasca onukii, Nephotettix cincticeps, Laodelphax striatella, Nilaparvata lugens, Sogatella furcifera, Geisha distinctissima, Diaphorina citri, Viteus vitifoliae, Acyrthosiphon pisum, Aphis craccivora, Aphis gossypii, Aphis pomi, Aphis spiraecola, Aulacorthum solani, Eriosoma lanigerum, Hyalopterus pruni, Lipaphis erysimi, Myzus persicae, Rhopalosiphum padi, Schizaphis graminum, Schizaphis piricola, Toxoptera aurantii, Toxoptera citricida, Aleurocanthus spiniferus, Bemisia argentifolii, Bemisia tabaci, Dialeurodes citri, Trialeurodes vaporariorum, Drosicha corpulenta, Icerya purchasi, Planococcus citri, Planococcus kraunhiae, Pseudococcus comstocki, Ceroplastes ceriferus, Ceroplastes rubens, Aonidiella aurantii, Diaspidiotus perniciosus, Pseudaulacaspis pentagona, Unaspis yanonensis, Creontiades coloripes, Trigonotylus caelestialium, Stephanitis nashi, Stephanitis pyrioides, Eysarcoris aeneus, Eysarcoris lewisi, Glaucias subpunctatus, Graphosoma rubrolineatum, Halyomorpha halys, Nezara antennata, Nezara viridula, Plautia crossota stali, Cavelerius saccharivorus, Togo hemipterus, Leptocorisa chinensis, Riptortus clavatus, Cletus punctiger, Rhopalus maculatus*, and *Cimex lectularis*, from the order Coleoptera, for example, *Anomala albopilosa, Anomala cuprea, Anomala rufocuprea, Eucetonia pilifera, Gametis jucunda, Heptophylla picea, Popillia japonica, Agriotes ogurae fuscicollis, Ectinus sericeus sericeus, Melanotus fortnumi fortnumi, Anthrenus verbasci, Lasioderma serricorne, Tenebroides mauritanicus, Epuraea domina, Epilachna varivestis, Henosepilachna vigintioctopunctata, Tenebrio molitor, Tribolium castaneum, Anoplophora malasiaca, Monochamus alternatus endai, Xylotrechus pyrrhoderus, Callosobruchus chinensis, Aulacophora femoralis, Cassida nebulosa, Chaetocnema concinna, Diabrotica virgifera virgifera, Diabrotica undecimpunctata howardi, Diabrotica spp., Leptinotarsa decemlineata, Oulema oryzae, Phyllotreta striolata, Cylas formicarius, Anthonomus grandis, Euscepes postfasciatus, Hypera postica, Listroderes costirostris, Echinocnemus bipunctatus, Lissorhoptrus oryzophilus, Sitophilus zeamais, Sphenophrus venatus vestitus, Tomicus piniperda*, and *Lyctus brunneus*, from the order Siphonaptera, for example, *Ceratophyllus gallinae, Ctenocephalides canis, Ctenocephalides felis, Echidnophaga gallinacea, Pulex irritans*, and *Xenopsylla cheopis*, from the order Diptera, for example, *Asphondylia yushimai, Aedes aegypti, Anopheles sinensis, Culex pipines pallens, Culex quinquefasciatus, Culex tritaeniorhynchus, Bactrocera cucurbitae, Bactrocera dorsalis, Agromyza oryzae, Chromatomyia horticola, Liriomyza huidobrensis, Liriomyza sativae, Liriomyza trifolii, Delia antiqua, Delia platura, Musca domestica*, and *Stomoxys calcitrans*, from the order Lepidoptera, for example, *Adoxophyes honmai, Adoxophyes orana fasciata, Archips fuscocupreanus, Cydia pomonella, Grapholita molesta, Homona magnanima, Leguminivora glycinivorella, Pandemis heparana, Tinea translucens, Lyonetia clerkella, Lyonetia prunifoliella malinella, Caloptilia theivora, Phyllonorycter ringoniella, Phyllocnistis citrella, Plutella xylostella, Nokona regalis, Synanthedon hector, Stathmopoda masinissa, Helcystogramma triannulellum, Pectinophora gossypiella, Carposina sasakii, Chilo suppressalis, Cnaphalocrocis medinalis, Conogethes punctiferalis, Hellula undalis, Ostrinia furnacalis, Ostrinia nubilalis, Etiella zinckenella, Papilio xuthus, Pieris rapae crucivora, Parnara guttata guttata, Ascotis selenaria, Arna pseudoconspersa, Lymantria dispar, Hyphantria cunea, Agrotis ipsilon, Agrotis segetum, Autographa nigrisigna, Helicoverpa armigera, Heliothis* spp., *Mamestra brassicae, Mythimna separata, Naranga aenescens, Spodoptera exigua*, and *Spodoptera litura*, and from the order Hymenoptera, for example, *Arge pagana, Athalia rosae ruficornis, Dryocosmus kuriphilus, Vespa simillima xanthoptera, Formica japonica, Monomorium pharaonis*, and *Solenopsis invicta*;

mites, for example, *Varroa jacobsoni, Dermanyssus gallinae, Ornithonyssus bacoti, Ornithonyssus sylvialum, Amblyomma* spp., *Boophilus microplus, Dermacentor* spp., *Haemaphysalis flava, Haemophysalis campanulata, Haemaphysalis longicornis, Ixodes ovatus, Ixodes persulcatus, Rhipicephalus sanguineus, Penthaleus erythrocephalus, Penthaleus major, Phytonemus pallidus, Polyphagotarsonemus latus, Tarsonemus bilobatus, Demodex canis, Demodex cati, Oligonychus shinkajii, Panonychus citri, Panonychus mori, Panonychus ulmi, Tetranychus cinnabarinus, Tetranychus kanzawai, Tetranychus urticae, Acaphylla theavagrans, Aceria tulipae, Aculops lycopersici, Aculops pelekassi, Aculus schlechtendali, Calacarus carinatus, Epitrimerus pyri, Eriophyes chibaensis, Phyllocoptruta oleivora, Rhizoglyphus robini, Tyrophagus putrescentiae, Tyrophagus similis, Knemidokoptes* spp., *Psoroptes ovis, Notoedres cati, Sarcoptes scabiei, Leptotrombidium akamushi, Cheyletiella blakei, Cheyletiella yasguri, Dermatophagoides farinae*, and *Latrodectus hasseltii*;

crustaceans from the order Polydesmida, for example, *Oxidus gracilis*, from the order Isopoda, for example, *Armadillidium vulgare*, from the order Decapoda, for example, *Procambarus clarkia*, and from the order Collembola, for example, *Bourletiella hortensis*;

mollusks from the order Architaenioglossa, for example, *Pomacea canaliculata*, and from the order Pulmonata, for example, *Achatina fulica, Meghimatium bilineatum, Lehmannina valentiana*, and *Acusta despecta sieboldiana*; and nematodes from the order Tylenchida, for example, *Nothotylenchus acris, Meloidogyne incognita, Globodera rostochiensis, Heterodera glycines, Tylenchulus semipenetrans, Pratylenchus coffeae, Pratylenchus penetrans, Pratylenchus yamagutii, Aphelenchus avenae, Aphelenchoides besseyi*, and *Bursaphelenchus xylophilus*.

In addition, the pests include endoparasites in animals, such as roundworms, pinworms, filarial worms, *distoma hepaticum*, pulmonary distomiasis, *metagonimus yuokogawa, Schistosoma japonicum, Taenia solium, Taenia saginata, Echinococcus multilocularis*, and *diphyllobothrium latum*.

The compound of the present invention can be used as an agricultural/horticultural pest controlling ingredient. At the time of formulation, an appropriate carrier, adjuvant, surfactant, binder, stabilizer, etc. described in *Pesticide Formulation Guide* (edited by: Pesticide Science Society of Japan, Agricultural Formulation and Application Committee, issued by: Japan Plant Protection Association) may also be blended.

The agricultural/horticultural pest control agent containing the compound of the present invention can be formulated into an arbitrary form that is generally employed as a form of the agricultural/horticultural pest control agent. For example, the pest control agent may be formulated into a generally employed form such as dust, coarse dust, DL (driftless type) dust, flow dust, microgranule, fine granule, granule, wettable powder, granular wettable powder, liquid formulation, sol (flowable formulation), emulsifiable concentrate, and oil solution, but the formulation is not limited thereto.

The content of the compound of the present invention may be appropriately selected according to the formulation form and use method. In general, the content is preferably from 0.0001 to 90 wt % relative to the total amount of the formulation.

In the case of using the compound of the present invention as an agricultural/horticultural pest control agent, one or more optional ingredients selected from fungicides (mildewcide, bactericide, antiviral agent, plant resistance inducing agent), insecticides, acaricides, nematicides, herbicides, bird repellents, growth regulators, fertilizers, soil conditioners, etc. may be mixed, if desired, at the time of formulation or spraying to provide a mixed formulaion or may be mixed and applied as a tankmix at the time of spraying.

Out of the above-described optional ingredients, representative examples of fungicides and insecticides or acaricides are described below, but the present invention is not limited thereto.

Fungicides:
(1) Copper Agents
  Basic copper chloride (copper oxychloride), basic copper sulfate (copper sulfate), cupric hydroxide (copper hydroxide), copper sulfate, oxine-copper, copper nonylphenyl sulfonate, DBEDC, etc.
(2) Inorganic Fungicides
  Sulfur, lime-sulfur mixture (calcium polysulfide), sodium hydrogen carbonate, potassium hydrogen carbonate, metallic silver (silver), etc.
(3) Organosulfur Fungicides
  Ziram, maneb, mancozeb, ambam, polycarbamate, propineb, thiuram, thiadiazin, zineb, etc.
(4) Organophosphorus Fungicides
  IBP, EDDP, tolclofos-methyl, pyrazophos, fosetyl (fosetyl-alminium), etc.
(5) Benzimidazole Fungicides
  Carbendazim, thiabendazole, thiophanate-methyl, benomyl, etc.
(6) Dicarboxamide Fungicides
  Iprodione, procymidone, vinclozolin, etc.

(7) Carboxamide Fungicides

Oxycarboxin, carboxin, mepronil, flutolanil, boscalid, fluopyram, furametpyr, thifluzamide, penthiopyrad, bixafen, penflufen, fluxapyroxad, isopyrazam, tolfenpyrad, sedaxane, etc.

(8) Phenylamide Fungicides

Metalaxyl, metalaxyl-M, oxadixyl, furalaxyl, ofurace, benalaxyl, benalaxyl-M, etc.

(9) Carboxylic Acid Amide Fungicides

Dimethomorph, flumorph, iprovalicarb, benthiavalicarb-isopropyl, mandipropamid, valifenalate, etc.

(10) SBI Agents

Triflumizole, prochloraz, oxpoconazole fumarate, triadimefon, bitertanol, myclobutanil, fenbuconazole, hexaconazole, tebuconazole, propiconazole, prothioconazole, difenoconazole, ipconazole, imibenconazole, cyproconazole, tetraconazole, simeconazole, metconazole, epoxiconazole, flusilazole, imazalil, fenarimol, triforine, triadimenol, flutriafol, pyrifenox, tridemorph, dodemorph, fenpropimorph, fenpropidin, spiroxamine, pyrisoxazole, fenhexamid, pyributicarb, etc.

(11) Strobilurin Fungicides

Azoxystrobin, kresoxim-methyl, trifloxystrobin, metominostrobin, orysastrobin, pyraclostrobin, enestroburin, dimoxystrobin, picoxystrobin, pyribencarb, fluoxastrobin, etc.

(12) Anilinopyrimidine Fungicides

Cyprodinil, mepanipyrim, pyrimethanil, etc.

(13) Phenylpyrrole Fungicides

Fludioxonil, fenpiclonil, etc.

(14) Antibiotic Fungicides

Kasugamycin, polyoxin, validamycin, streptomycin, oxytetracycline, blasticidin-S, etc.

(15) Other Fungicides

DKF-1001 (code No.), IKF-5411 (code No.), MIF-1002 (code No.), NC-233 (code No.), S-2200 (code No.), SB-4303 (code No.), acibenzolar-S-methyl, amisulbrom, ametoctradin, isotianil, isoprothiolane, iminoctadine-albesilate (iminoctadine tris(albesilate)), iminoctadine acetate (iminoctadine triacetate), echlomezol, ethaboxam, oxolinic acid, captafol, carpropamid, quinoxyfen, chinomethionat, captan, chloroneb, chlorothalonil, cyazofamid, diethofencarb, diclocymet, diclomezine, dithianon, cyflufenamid, diflumetorim, cymoxanil, silthiofam, zoxamide, dazomet, tiadinil, teclofthalam, tebufloquin, dodine, triazoxide, tricyclazole, tolnifanide, hydroxyisoxazole, pyriofenone, pyroquilon, fenoxanil, ferimzone, fenpyrazamine, phthalide, bupirimate, famoxadone, fenamidone, fluazinam, fluopicolide, fluoroimide, flusulfamide, flutianil, proquinazid, propamocarb hydrochloride, probenazole, pencycuron, folpet, methasulfocarb, metrafenone, laminarin, etc.

Insecticides:

(1) Organophosphorus Insecticides

Acephate, azinphos-methyl, chlorfenvinphos, chlorpyrifos, chlorpyrifos-methyl, cyanophos, diazinon, dichlofenthion, dichlorvos, dimethoate, dimethylvinphos, disulfoton, EPN, ethion, ethoprophos, fenamiphos, fenitrothion, fenthion, isofenphos, isoxathion, malathion, methidathion, mevinphos, monocrotophos, naled, oxydemeton-methyl, parathion, parathion-methyl, phenthoate, phorate, phosalone, phosmet, phosphamidon, phoxim, pirimiphos-methyl, profenofos, propaphos, prothiofos, pyraclofos, pyridaphenthion, quinalphos, tebupirimfos, temephos, terbufos, tetrachlorvinphos, thiometon, trichlorfon, vamidothion, etc.

(2) Carbamate Insecticides

Aldicarb, alanycarb, bendiocarb, benfuracarb, carbaryl, carbofuran, carbosulfan, ethiofencarb, fenobucarb, fenoxycarb, furathiocarb, isoprocarb, methiocarb, methomyl, metolcarb, oxamyl, pirimicarb, propoxur, thiodicarb, triazamate, XMC, xylylcarb, etc.

(3) Pyrethroid Insecticides

Acrinathrin, allethrin, bifenthrin, cycloprothrin, cyfluthrin, beta-cyfluthrin, cyhalothrin, lambda-cyhalothrin, gamma-cyhalothrin, cypermethrin, alpha-cypermethrin, theta-cypermethrin, deltamethrin, esfenvalerate, etofenprox, fenpropathrin, fenvalerate, flucythrinate, fluvalinate, tau-fluvalinate, halfenprox, metofluthrin, permethrin, phenothrin (phenothrin[(1R)-trans-isomer]), pyrethrins, resmethrin, silafluofen, tefluthrin, tetramethrin, tralomethrin, etc.

(4) Nereistoxin Insecticides

Bensultap, cartap, thiocyclam, etc.

(5) Neonicotinoid Insecticides

Acetamiprid, clothianidin, dinotefuran, imidacloprid, nitenpyram, thiacloprid, thiamethoxam, etc.

(6) Diamide Insecticides

Chlorantraniliprole, cyantraniliprole, flubendiamide, cyclaniliprole, etc.

(7) Phenylpyrazole Insecticides

Acetoprole, ethiprole, fipronil, flufiprole, pyrafluprole, pyriprole, etc.

(8) Macrolide Insecticides

Abamectin, avermectin, emamectin benzoate, lepimectin, milbemectin, spinetoram, spinosad, etc.

(9) Benzoylurea Insecticides

Bistrifluron, chlorfluazuron, diflubenzuron, fluazuron, flucycloxuron, flufenoxuron, hexaflumuron, lufenuron, novaluron, noviflumuron, teflubenzuron, triflumuron, etc.

(10) Diacylhydrazine Insecticides

Chromafenozide, halofenozide, methoxyfenozide, tebufenozide, etc.

(11) Other Insecticide Active Ingredients

Azadiractin, buprofezin, chinomethionat, chlorfenapyr, cyromazine, diafenthiuron, dicofol, dienochlor, endosulfan, flometquin, flonicamid, flufenerim, flupyradifurone, hydramethylnon, hydroprene, indoxacarb, metaflumizone, metaldehyde, methoprene, methoxychlor, pymetrozine, pyridalyl, pyrifluquinazone, pyriproxyfen, rotenone, spirotetramat, sulfoxaflor, tolfenpyrad, triflumezopyrim, AKD-1193 (code No.), MIE-1209 (code No.), NA-89 (code No.), NC-515 (code No.), ME5382 (code No.), ZDI-2501 (code No.), sodium oleate, diatomaceous earth, fatty acid glyceride, starch, rapeseed oil, sticker (polybutene), propylene glycol monofatty acid ester, machine oil (petroleum oil), nicotine-sulfate, ferric phosphate, etc.

(12) Acaricides

Acequinocyl, amidoflumet, amitraz, bifenazate, bromopropylate, clofentezine, cyenopyrafen, cyflumetofen, cyhexatin, etoxazole, fenazaquin, fenbutatin oxide, fenothiocarb, fenpyroximate, fluacrypyrim, hexythiazox, propargite, pyrimidifen, pyridaben, spirodiclofen, spiromesifen, tebufenpyrad, tetradifon, etc.

(13) Nematicides

Aldoxycarb, cadusafos, carbam sodium, 1,3-dichloropropene, DCIP, fluensulfone, fosthiazate, imicyafos, levamisol hydrochloride, mesulfenfos, methyl isothiocyanate, morantel tartrate, nemadectin, etc.

(14) Others

Viral agents such as nuclear polyhedrosis virus (NPV), granulosis virus (GV), cytoplasmic polyhedrosis virus (CPV) and entomopoxvirus (EPV); live spores derived from and crystal toxins produced from *Bacillus* thuringiesis, and a mixture thereof; microbial pesticides, insect pheromones, and insect attractants, which are utilized as insecticides or nematicides, such as *Steinernema carpocapsae* and *Pasteuria penetrans*; etc.

The agricultural/horticultural pest control agent containing the compound of the present invention as an active ingredient can be used by a method usually employed for pest control agents. Specifically, in the case of wettable powder, liquid formulation, emulsifiable concentrate, sol (flowable formulation), granular wettable powder or oil solution, a liquid is prepared by diluting the pest control agent from 50 to 10,000 times with water to afford an active ingredient concentration of generally from 1 to 10,000 ppm, preferably from 1 to 1,000 ppm, and the resulting dilute solution may be sprayed on the foliage in the diseased region of the plant in the range of 50 to 1,000 L, usually from 100 to 600 L, per 10a of cropland, though this may vary depending on the crop shape such as paddy rice or fruit tree.

Alternatively, the pest control agent may be applied to agricultural/horticultural pests by aerial spraying in which a chemical solution after dilution with water to afford a predetermined active ingredient concentration is sprayed from a helicopter (including an RC helicopter).

In the case of dust, coarse particle, DL dust, flow dust, microgranule, fine granule or granule, from 0.3 to 50 kg/10a (active ingredient content: approximately from 5 to 500 g) of the pest control agent may be applied to foliage in the region where pests appeared, soil surface, under soil surface or water surface.

In growing seedlings of, for example, paddy rice in a nursery box, a granule, etc. may be applied to soil surface or under soil surface before sowing or between after sowing and on the day of transplanting, in an amount of 10 to 100 g and in the case of a flowable formulation, etc., directly without dilution or after dilution, in an amount of 30 to 1,000 mL, per the nursery box (standard size: 30 cm×60 cm×5 cm).

EXAMPLES

The present invention is described more specifically below by referring to Synthesis Examples, Formulation Examples and Test Examples of the 1,2,3-triazole derivative, but the present invention is not limited thereto.

Synthesis Example 1

(1) Synthesis of 2-[3,5-bis(trifluoromethyl)phenyl]ethynyltrimethylsilane

In a nitrogen atmosphere, palladium(II) chloride (2.4 g, 13.7 mmol), triphenylphosphine (7.2 g, 27.3 mmol) and copper(I) iodide (4.2 g, 21.8 mmol) were sequentially added to a triethylamine (270 mL) solution of 3,5-bis(trifluoromethyl)bromobenzene (80.0 g, 273.0 mmol), and trimethylsilylacetylene (32.2 g, 327.6 mmol) was added dropwise under ice cooling. After the completion of dropwise addition, the solution was stirred at room temperature overnight and filtered through Celite, and the filtrate was concentrated under reduced pressure. Subsequently, aqueous ammonia (30 mL) and water were added, and the resulting solution was extracted with hexane. The organic layer was washed with saturated brine, dried over sodium sulfate, filtered to remove the white precipitate, and concentrated under reduced pressure, and the obtained crude product was purified by silica gel column chromatography (eluting solvent: hexane) to afford the title compound (83.1 g, yield: 98%) as an orange oily product.

$^1$HNMR Spectrum (CDCl$_3$) σ: 7.88 (2H, s), 7.79 (1H, s), 0.27 (9H, s).

(2) Synthesis of 1-ethynyl-3,5-bis(trifluoromethyl)benzene

To a methanol (70 mL) and chloroform (70 mL) solution of 2-[3,5-bis(trifluoromethyl)phenyl]ethynyltrimethylsilane (83.1 g, 267.7 mmol), potassium carbonate (7.4 g, 53.5 mmol) was added, followed by stirring at room temperature overnight. After distilling off the solvent under reduced pressure, water was added to the solution, and the resulting solution was extracted with diethyl ether. The organic layer was washed with saturated brine, dried over sodium sulfate, filtered to remove the white precipitate, and concentrated under reduced pressure, and the crude product was purified by distillation under reduced pressure (82° C., 100 mbar) to afford the title compound (48.7 g, yield: 76%) as a colorless oily product.

$^1$HNMR Spectrum (CDCl$_3$) σ: 7.92 (2H, s), 7.84 (1H, s), 3.26 (1H, s).

(3) Synthesis of 2-ethylsulfanylaniline

To a methanol (25 mL) solution of 2-aminothiophenol (15.0 g, 119.8 mmol), a 28% sodium methoxide-methanol solution (27.7 g, 143.8 mmol) was added, and a methanol (15 mL) solution of iodoethane (18.7 g, 119.8 mmol) was added dropwise under heating at reflux. After the completion of dropwise addition, the solution was heated at reflux for 6 hours and allowed to cool to room temperature, and the solvent was then distilled off. Water was added to the obtained reaction solution, and the resulting solution was extracted with ethyl acetate. The organic layer was washed with saturated brine, dried over sodium sulfate, filtered to remove the white precipitate, and concentrated under reduced pressure, and the obtained crude product was purified by silica gel column chromatography (eluting solvent: ethyl acetate/hexane=1:20) to afford the title compound (yielded 17.8 g, yield: 97%) as an orange-tan oily product.

$^1$HNMR Spectrum (CDCl$_3$) σ: 7.37 (1H, dd, J1=7.6 Hz, J2=1.6 Hz), 7.11 (1H, td, J1=7.7 Hz, J2=1.8 Hz), 6.73 (1H, dd, J1=8.0 Hz, J2=1.1 Hz), 6.69 (1H, td, J1=7.6 Hz, J2=1.4 Hz), 4.34 (2H, br), 2.76 (2H, q, J=7.3 Hz), 1.23 (3H, t, J=7.3 Hz).

(4) Synthesis of 1-azido-2-ethyl Sulfanylbenzene

A 35% hydrochloric acid (30 mL) and water (30 mL) mixed solution of 2-ethylsulfanylaniline (17.8 g, 115.8 mmol) was cooled to −5° C., and an aqueous sodium nitrite (9.6 g, 139.0 mmol) solution (35 mL) was added dropwise. After the completion of dropwise addition, the resulting solution was stirred at −5° C. for 30 minutes and subsequently, an aqueous sodium azide (11.3 g, 173.7 mmol) solution (40 mL) was added dropwise. The resulting solution was stirred at −5° C. for 60 minutes and at room temperature for 4 hours. The reaction solution was extracted by adding ethyl acetate, and the organic layer was washed with saturated brine, dried over sodium sulfate, filtered to remove the white precipitate, and concentrated under reduced pressure. The obtained crude product was purified by silica gel column chromatography (eluting solvent: ethyl acetate/hexane=1:20) to afford the title compound (19.3 g, yield: 93%) as a yellow oily product.

$^1$HNMR Spectrum (CDCl$_3$) σ: 7.30 (1H, dd, J1=7.8 Hz, J2=1.4 Hz), 7.24-7.22 (1H, m), 7.14 (1H, dd, J1=7.8 Hz, J2=0.9 Hz), 7.10 (1H, td, J1=7.6 Hz, J2=1.4 Hz), 2.94 (2H, q, J=7.3 Hz), 1.32 (3H, t, J=7.3 Hz).

(5) Synthesis of 4-[3,5-bis(trifluoromethyl)phenyl]-1-(2-ethylsulfanylphenyl)triazole (1-75)

To a tert-butanol (36 mL) and water (18 mL) mixed solution of 1-azido-2-ethylsulfanylbenzene (4.5 g, 25.2 mmol), 1-ethynyl-3,5-bis(trifluoromethyl)benzene (6.0 g, 25.2 mmol), anhydrous copper(II) sulfate (603 mg, 3.8 mmol), and sodium L-ascorbate (2.0 g, 10.1 mmol) were sequentially added, followed by stirring at room temperature overnight. Water was added to the obtained reaction solution, and the resulting solution was extracted with ethyl acetate. The organic layer was washed with saturated brine, dried over sodium sulfate, filtered to remove the white precipitate, and concentrated under reduced pressure, and the obtained crude product was purified by silica gel column chromatography (eluting solvent: ethyl acetate/hexane=1:4) to afford the title compound (yielded 10.1 g, yield: 96%) as a yellow solid.
$^1$HNMR Spectrum (CDCl$_3$) σ: 8.39 (2H, s), 8.31 (1H, s), 7.86 (1H, s), 7.57-7.49 (3H, m), 7.40 (1H, td, J1=7.6 Hz, J2=1.7 Hz), 2.84 (2H, q, J=7.5 Hz), 1.25 (3H, t, J=7.3 Hz).

(6) Synthesis of 4-[3,5-bis(trifluoromethyl)phenyl]-1-(2-ethylsulfinylphenyl)triazole (1-354)

To a chloroform (3 mL) solution of 4-[3,5-bis(trifluoromethyl)phenyl]-1-(2-ethylsulfanylphenyl)triazole (350.0 mg, 0.84 mmol), 77% metachloroperbenzoic acid (188.0 mg, 0.84 mmol) was added under ice cooling, followed by stirring under ice cooling for 2 hours. An aqueous saturated sodium hydrogencarbonate solution was poured in the reaction solution, and the resulting solution was extracted with ethyl acetate. The organic layer was washed with saturated brine, dried over sodium sulfate, filtered to remove the white precipitate, and concentrated under reduced pressure, and the obtained crude product was purified by silica gel column chromatography (eluting solvent: ethyl acetate/hexane=1:1) to afford the title compound (yielded 350.2 mg, yield: 96%) as a white solid.
$^1$HNMR Spectrum (CDCl$_3$) σ: 8.38 (2H, br), 8.34 (1H, s), 8.27 (1H, dd, J1=8.0 Hz, J2=1.6 Hz), 7.91 (1H, br), 7.80 (1H, td, J1=7.7 Hz, J2=1.2 Hz), 7.71 (1H, td, J1=7.7 Hz, J2=1.5 Hz), 7.56 (1H, dd, J1=7.8 Hz, J2=0.9 Hz), 3.36-3.28 (1H, m), 2.97-2.88 (1H, m), 1.37 (3H, t, J=7.3 Hz).

(7) Synthesis of 4-[3,5-bis(trifluoromethyl)phenyl]-1-(2-ethylsulfonylphenyl)triazole (1-631)

To a chloroform (3 mL) solution of 4-[3,5-bis(trifluoromethyl)phenyl]-1-(2-ethylsulfanylphenyl)triazole (350.0 mg, 0.84 mmol), 77% metachloroperbenzoic acid (385.3 mg, 1.7 mmol) was added under ice cooling, followed by stirring under ice cooling for 2 hours. An aqueous saturated sodium hydrogencarbonate solution was poured in the reaction solution, and the resulting solution was extracted with ethyl acetate. The organic layer was washed with saturated brine, dried over sodium sulfate, filtered to remove the white precipitate, and concentrated under reduced pressure, and the obtained crude product was purified by silica gel column chromatography (eluting solvent: ethyl acetate/hexane=1:1) to afford the title compound (yielded 363.1 mg, yield: 96%) as a white solid.
$^1$HNMR Spectrum (CDCl$_3$) σ: 8.37 (2H, s), 8.34 (1H, s), 8.29 (1H, dd, J1=7.6 Hz, J2=1.6 Hz), 7.88-7.83 (3H, m), 7.58 (1H, dd, J1=7.3 Hz, J2=1.8 Hz), 3.21 (2H, q, J=7.5 Hz), 1.26 (3H, t, J=7.3 Hz).

Synthesis Example 2

(1) Synthesis of trimethyl-[2-[4-(trifluoromethyl)-2-pyridyl]ethynyl]silane

In a nitrogen atmosphere, palladium(II) chloride (3.17 g, 17.9 mmol), triphenylphosphine (9.4 g, 35.8 mmol) and copper(I) iodide (5.5 g, 28.6 mmol) were sequentially added to a triethylamine (320 mL) solution of 2-chloro-4-(trifluoromethyl)pyridine (65.0 g, 358.0 mmol), and trimethylsilylacetylene (42.2 g, 429.7 mmol) was added dropwise under ice cooling. After the completion of dropwise addition, the solution was stirred at 80° C. for 8 hours and filtered through Celite, and the filtrate was concentrated under reduced pressure. Subsequently, aqueous ammonia (30 mL) and water were added, and the resulting solution was extracted with ethyl acetate. The organic layer was washed with saturated brine, dried over sodium sulfate, filtered to remove the white precipitate, and concentrated under reduced pressure, and the obtained crude product was purified by silica gel column chromatography (eluting solvent: ethyl acetate/hexane=1:20) to afford the title compound (82.2 g, yield: 94.4%) as an orange oily product.
$^1$HNMR Spectrum (CDCl$_3$) σ: 8.75 (1H, d, J=5.0 Hz), 7.67 (1H, s), 7.44 (1H, dd, J1=5.0 Hz, J2=0.9 Hz), 0.29 (9H, s).

(2) Synthesis of 2-ethynyl-4-(trifluoromethyl)pyridine

To a methanol (200 mL) and chloroform (200 mL) solution of trimethyl-[2-[4-(trifluoromethyl)-2-pyridyl]ethynyl]silane (82.2 g, 337.9 mmol), potassium carbonate (2.3 g, 16.9 mmol) was added, followed by stirring at room temperature for 1 hour. After distilling off the solvent under reduced pressure, water was added to the solution, and the resulting solution was extracted with diethyl ether. The organic layer was washed with saturated brine, dried over sodium sulfate, filtered to remove the white precipitate, and concentrated under reduced pressure, and the crude product was purified by silica gel column chromatography (eluting solvent: ethyl acetate/hexane=1:10) to afford the title compound (45.8 g, yield: 79%) as a colorless oily product.
$^1$HNMR Spectrum (CDCl$_3$) σ: 8.79 (1H, d, J=5.0 Hz), 7.70 (1H, s), 7.49 (1H, dd, J1=5.0 Hz, J2=0.9 Hz), 3.27 (1H, s).

(3) Synthesis of 2-chloro-4-(pentafluoro-$\lambda^6$-sulfanyl)aniline

An acetonitrile solution (24 mL) of 4-aminophenylsulfur pentafluoride (6.00 g, 27.4 mmol) was heated at 60° C., and N-chlorosuccinimide (4.02 g, 30.1 mmol) was added, followed by stirring under heating at reflux for 3 hours. The resulting solution was allowed to cool to room temperature, and the solvent was then distilled off under reduced pressure. To the obtained residue, 30 mL of an aqueous 5% sodium hydroxide solution was added, and the resulting solution was extracted with ethyl acetate. The organic layer was washed with saturated brine, dried over sodium sulfate, filtered to remove the white precipitate, and concentrated under reduced pressure, and the obtained crude product was purified by silica gel column chromatography (eluting solvent: ethyl acetate/hexane=1:7) to afford the title compound (yielded 6.40 g, yield: 92%) as a red-tan oily product.

$^1$HNMR Spectrum (CDCl$_3$) σ: 7.66 (1H, d, J=2.7 Hz), 7.45 (1H, dd, J1=8.9 Hz, J2=2.5 Hz), 6.72 (1H, d, J=9.2 Hz), 4.42 (2H, br).

(4) Synthesis of (4-azido-3-chloro-phenyl)-pentafluoro-λ$^6$-sulfane

A 35% hydrochloric acid (30 mL) and water (30 mL) mixed solution of 2-chloro-4-(pentafluoro-λ$^6$-sulfanyl)aniline (6.40 g, 25.2 mmol) was cooled to −5° C., and an aqueous sodium nitrite (2.09 g, 30.3 mmol) solution (15 mL) was added dropwise. After the completion of dropwise addition, the resulting solution was stirred at −5° C. for 30 minutes and subsequently, an aqueous sodium azide (2.13 g, 32.8 mmol) solution (15 mL) was added dropwise. The resulting solution was stirred at −5° C. for 60 minutes and at room temperature for 4 hours. The reaction solution was extracted by adding ethyl acetate, and the organic layer was washed with saturated brine, dried over sodium sulfate, filtered to remove the white precipitate, and concentrated under reduced pressure. The obtained crude product was purified by silica gel column chromatography (eluting solvent: ethyl acetate/hexane=1:20) to afford the title compound (4.50 g, yield: 64%) as an orange oily product.

$^1$HNMR Spectrum (CDCl$_3$) σ: 7.80 (1H, d, J=2.3 Hz), 7.68 (1H, dd, J1=8.9 Hz, J2=2.5 Hz), 7.23 (1H, d, J=8.7 Hz).

(5) Synthesis of [3-chloro-4-[4-[4-(trifluoromethyl)-2-pyridyl]triazol-1-yl]phenyl]-pentafluoro-λ$^6$-sulfane To an N,N'-dimethylformamide (4 mL) and water (1 mL) mixed solution of (4-azido-3-chloro-phenyl)-pentafluoro-λ$^6$-sulfane (490.2 mg, 1.8 mmol), 2-ethynyl-4-(trifluoromethyl)pyridine (300.0 mg, 1.8 mmol), anhydrous copper(II) sulfate (42.0 mg, 0.3 mmol), and sodium L-ascorbate (138.9 g, 0.70 mmol) were sequentially added, followed by stirring at room temperature overnight. Water was added to the obtained reaction solution, and the resulting solution was extracted with ethyl acetate. The organic layer was washed with saturated brine, dried over sodium sulfate, filtered to remove the white precipitate, and concentrated under reduced pressure, and the obtained crude product was purified by silica gel column chromatography (eluting solvent: ethyl acetate/hexane=1:6) to afford the title compound (yielded 690.1 mg, yield: 87%) as a yellow solid.

$^1$HNMR Spectrum (CDCl$_3$) σ: 8.81 (1H, d, J=5.0 Hz), 8.74 (1H, s), 8.51 (1H, s), 8.06 (1H, s), 7.91 (2H, s), 7.51 (1H, d, J=5.0 Hz).

(6) Synthesis of 3-ethynylsulfanyl-4-[4-[4-(trifluoromethyl)-2-pyridyl]triazol-1-yl]phenyl]-pentafluoro-λ$^6$-sulfane (2-118)

An N,N'-dimethylformamide solution (5 mL) of 60% sodium hydride (71.4 mg, 1.8 mmol) was cooled on ice, and ethanethiol (110.8 mg, 1.8 mmol) was added dropwise thereto, followed by stirring for 10 minutes. Subsequently, [3-chloro-4-[4-[4-(trifluoromethyl)-2-pyridyl]triazol-1-yl]phenyl]-pentafluoro-λ$^6$-sulfane (618.5 mg, 1.4 mmol) was added under ice cooling, followed by stirring at room temperature for 2 hours. Water was added to the reaction solution, and the resulting solution was extracted with ethyl acetate. The organic layer was washed with saturated brine, dried over sodium sulfate, filtered to remove the white precipitate, and concentrated under reduced pressure, and the obtained crude product was purified by silica gel column chromatography (eluting solvent: ethyl acetate/hexane=1:6) to afford the title compound (419.1 mg, yield: 64%) as a red solid.

$^1$HNMR Spectrum (CDCl$_3$) σ: 8.81 (1H, d, J=5.0 Hz), 8.63 (1H, s), 8.51 (1H, s), 7.87 (1H, d, J=2.3 Hz), 7.76 (1H, dd, J1=8.7 Hz, J2=2.3 Hz), 7.67 (1H, d, J=8.7 Hz), 7.49 (1H, d, J=4.1 Hz), 2.93 (2H, q, J=7.3 Hz), 1.29 (3H, t, J=7.3 Hz).

(7) Synthesis of [3-ethylsulfonyl-4-[4-[4-(trifluoromethyl)-2-pyridyl]triazol-1-yl]phenyl]-pentafluoro-λ$^6$-sulfane (2-398)

To a chloroform (3 mL) solution of [3-ethylsulfanyl-4-[4-[4-(trifluoromethyl)-2-pyridyl]triazol-1-yl]phenyl]-pentafluoro-λ$^6$-sulfane (974.0 mg, 2.0 mmol), 77% metachloroperbenzoic acid (939.3 mg, 4.2 mmol) was added under ice cooling, followed by stirring under ice cooling overnight. An aqueous saturated sodium hydrogencarbonate solution was poured in the reaction solution, and the resulting solution was extracted with chloroform. The organic layer was washed with saturated brine, dried over sodium sulfate, filtered to remove the white precipitate, and concentrated under reduced pressure, and the obtained crude product was purified by silica gel column chromatography (eluting solvent: ethyl acetate/hexane=1:1) to afford the title compound (yielded 490.0 mg, yield: 47%) as a white solid.

$^1$HNMR Spectrum (CDCl$_3$) σ: 8.81 (1H, d, J=5.0 Hz), 8.66 (1H, d, J=2.7 Hz), 8.60 (1H, s), 8.48 (1H, s), 8.24 (1H, dd, J1=8.7 Hz, J2=2.7 Hz), 7.72 (1H, d, J=8.7 Hz), 7.51 (1H, d, J=6.0 Hz), 3.39 (2H, q, J=7.5 Hz), 1.33 (3H, t, J=7.3 Hz).

Synthesis Example 3

(1) Synthesis of 2-(1H-triazol-4-yl)-4-(trifluoromethyl)pyridine

In a nitrogen atmosphere, copper(I) iodide (223.0 mg, 1.2 mmol) and azidotrimethylsilane (4.0 g, 35.1 mmol) were sequentially added to an N,N'-dimethylformamide (9 mL) and methanol (1 mL) mixed solution of 2-ethynyl-4-(trifluoromethyl)pyridine (4.0 g, 23.4 mmol), followed by stirring at 100° C. for 7 hours. The resulting solution was allowed to cool to room temperature and filtered through Celite, and the filtrate was concentrated under reduced pressure. Subsequently, the obtained crude product was purified by silica gel column chromatography (eluting solvent: ethyl acetate/hexane=2:1) to afford the title compound (yielded 2.0 g, yield: 40%) as a brown solid.

$^1$HNMR Spectrum (CDCl$_3$) σ: 8.83 (1H, d, J=5.0 Hz), 8.36 (1H, s), 8.27 (1H, br), 7.50 (1H, d, J=4.6 Hz).

(2) Synthesis of 3-ethynylsulfonyl-5-(trifluoromethyl)-2-[4-[4-(trifluoromethyl)-2-pyridyl]triazol-1-yl]pyridine (2-387)

To an N,N'-dimethylformamide (3 mL) solution of 2-(1H-triazol-4-yl)-4-(trifluoromethyl)pyridine (200.0 mg, 0.9 mmol), potassium carbonate (193.6 mg, 1.4 mmol) and 2,3-bis(ethylsulfonyl)-5-(trifluoromethyl)pyridine (464.1 mg, 1.4 mmol, synthesized by reference to International Publication No. 2016/020286) were sequentially added, followed by stirring at room temperature overnight. Water was added to the solution, and the resulting solution was extracted with ethyl acetate. The organic layer was washed with saturated brine, dried over sodium sulfate, filtered to remove the white precipitate, and concentrated under reduced pressure, and the crude product was purified by silica gel column chromatography (eluting solvent: ethyl acetate/hexane=1:6) to afford the title compound (105.0 mg, yield: 25%) as a white solid.

¹HNMR Spectrum (CDCl₃) σ: 9.14 (1H, m), 8.90-8.87 (2H, m), 8.62 (1H, s), 8.32 (1H, s), 7.57 (1H, dd, J1=5.0 Hz, J2=0.9 Hz), 3.99 (2H, q, J=7.5 Hz), 1.50 (3H, t, J=7.6 Hz).

Synthesis Example 4

Synthesis of 1-(2-ethylsulfanylphenyl)-4-[3-(trifluoromethyl)phenyl]triazole (1-26)

To a dimethylsulfoxide (4 mL) solution of 3'-(trifluoromethyl)acetophenone (400 mg, 2.1 mmol), 2-ethylsulfanylaniline (390.9 mg, 2.6 mmol), 4-methylbenzene sulfonhydrazide (593.9 mg, 3.2 mmol), and iodine (809.4 mg, 3.2 mmol) were sequentially added, followed by stirring at 100° C. for 6 hours. Water was poured in the reaction solution, and the resulting solution was extracted with ethyl acetate. The organic layer was washed with an aqueous 10% sodium thiosulfate solution and then with saturated brine, dried over sodium sulfate, filtered to remove the white precipitate, and concentrated under reduced pressure, and the obtained crude product was purified by silica gel column chromatography (eluting solvent: ethyl acetate/hexane=1:6) to afford the title compound (yielded 315.5 mg, yield: 42%) as a tan oily product.

¹HNMR Spectrum (CDCl₃) σ: 8.24 (1H, s), 8.18 (1H, s), 8.14 (1H, d, J=7.3 Hz), 7.64-7.59 (2H, m), 7.55-7.47 (3H, m), 7.39 (1H, td, J1=7.4 Hz, J2=1.5 Hz), 2.83 (2H, q, J=7.3 Hz), 1.24 (3H, t, J=7.3 Hz).

Synthesis Example 5

Synthesis of 1-(2-ethylsulfanylphenyl)-5-methyl-4-[3-(trifluoromethyl)phenyl]triazole (1-27)

To a methanol (3 mL) solution of 4-methylbenzene sulfonhydrazide (460.6 mg, 2.5 mmol), 3'-(trifluoromethyl)propiophenone (500 mg, 2.5 mmol) was sequentially added, followed by stirring at room temperature for 10 minutes. The solvent was distilled off under reduced pressure, and to the obtained white solid, toluene (5 mL), copper(II) acetate (449.2 mg, 2.5 mmol), pivalic acid (505.2 mg, 4.9 mmol), and 2-ethylsulfanylaniline (758.0 mg, 4.9 mmol) were sequentially added, followed by stirring at 110° C. for 8 hours. The solvent was concentrated under reduced pressure, and the obtained crude product was purified by silica gel column chromatography (eluting solvent: ethyl acetate/hexane=1:6) to afford the title compound (yielded 383.5 mg, yield: 43%) as a red-tan oily product.

¹HNMR Spectrum (CDCl₃) σ: 8.11 (1H, s), 8.05 (1H, dt, J1=4.5 Hz, J2=2.4 Hz), 7.65-7.61 (2H, m), 7.54-7.51 (2H, m), 7.41-7.35 (1H, m), 2.85 (2H, q, J=7.3 Hz), 1.25 (3H, t, J=7.6 Hz).

Synthesis Example 6

Synthesis of 5-[3,5-bis(trifluoromethyl)phenyl]-3-(2-ethylsulfanylphenyl)triazole-4-amine (1-82)

An ethanol (10 mL) solution of 3,5-bis(trifluoromethyl)phenylacetonitrile (3.59 g, 14.2 mmol) and 2-ethylsulfanylaniline (2.54 g, 14.2 mmol) was cooled on ice, and an ethanol (10 mL) solution of sodium methoxide (1.2 g, 21.3 mmol) was sequentially added dropwise, followed by stirring under ice cooling for 72 hours. Water was poured in the reaction solution, and the resulting solution was extracted with ethyl acetate. The organic layer was washed with saturated brine, dried over sodium sulfate, filtered to remove the white precipitate, and concentrated under reduced pressure, and the obtained crude product was purified by silica gel column chromatography (eluting solvent: ethyl acetate/hexane=1:6) to afford the title compound (yielded 5.3 g, yield: 87%) as a red-tan oily product.

¹HNMR Spectrum (CDCl₃) σ: 8.29 (2H, s), 7.79 (1H, s), 7.58-7.52 (2H, m), 7.44-7.39 (2H, m), 4.00 (2H, br), 2.87 (2H, q, J=7.3 Hz), 1.27 (3H, t, J=7.3 Hz).

The values of ¹HNMR spectrum (CDCl₃) and σ (ppm) of each of the compounds according to the present invention synthesized based on the synthesis examples and production examples above are shown in Table 5. The ¹HNMR data was measured by JNM-ECS400 Spectrometer (manufactured by JEOL Ltd.).

TABLE 5

| Compound No. | ¹H-NMR Spectrum (CDCl₃) σ ppm: |
|---|---|
| 1-16 | 8.18 (1H, s), 7.95-7.93 (2H, m), 7.54 (2H, dd, J1 = 7.8 Hz, J2 = 1.4 Hz), 7.50-7.45 (3H, m), 7.40-7.35 (2H, m), 2.81 (2H, q, J = 7.3 Hz), 1.23 (3H, t, J = 7.3 Hz). |
| 1-21 | 8.18 (1H, s), 7.93 (1H, t, J = 1.8 Hz), 7.82 (1H, dt, J1 = 7.3 Hz, J2 = 1.4 Hz), 7.55-7.52 (2H, m), 7.48 (1H, td, J1 = 7.7 Hz, J2 = 1.5 Hz), 7.42-7.32 (3H, m), 2.81 (2H, q, J = 7.3 Hz), 1.23 (3H, t, J = 7.3 Hz). |
| 1-22 | 8.16 (1H, s), 7.87 (2H, d, J = 7.3 Hz), 7.54-7.36 (6H, m), 2.82 (2H, q, J = 7.3 Hz), 1.23 (3H, t, J = 7.3 Hz). |
| 1-23 | 8.18 (1H, s), 8.08 (1H, t, J = 1.8 Hz), 7.87 (1H, dt, J1 = 7.8 Hz, J2 = 1.4 Hz), 7.55-7.51 (2H, m), 7.50-7.46 (2H, m), 7.38 (1H, td, J1 = 7.6 Hz, J2 = 1.7 Hz), 7.35 (2H, m), 2.81 (2H, q, J = 7.3 Hz), 1.23 (3H, t, J = 7.3 Hz). |
| 1-24 | 8.20 (1H, s), 7.86 (1H, dt, J1 = 7.8 Hz, J2 = 1.4 Hz), 7.81 (1H, s), 7.53 (2H, td, J1 = 7.3 Hz, J2 = 1.4 Hz), 7.49 (2H, t, J = 8.2 Hz), 7.38 (1H, td, J1 = 7.6 Hz, J2 = 1.7 Hz), 7.22 (1H, dt, J1 = 8.2 Hz, J2 = 1.1 Hz), 2.82 (2H, q, J = 7.3 Hz), 1.23 (3H, t, J = 7.3 Hz). |
| 1-25 | 8.23 (1H, s), 8.12 (1H, d, J = 7.3 Hz), 7.80 (1H, d, J = 7.8 Hz), 7.69 (1H, t, J = 7.6 Hz), 7.57-7.47 (4H, m), 7.39 (1H, d, J = 7.6 Hz), 2.79 (2H, q, J = 7.2 Hz), 1.23 (3H, t, J = 7.3 Hz). |
| 1-26 | 8.24 (1H, s), 8.18 (1H, s), 8.14 (1H, d, J = 7.3 Hz), 7.64-7.59 (2H, m), 7.55-7.47 (3H, m), 7.39 (1H, td, J1 = 7.4 Hz, J2 = 1.5 Hz), 2.83 (2H, q, J = 7.3 Hz), 1.24 (3H, t, J = 7.3 Hz). |
| 1-27 | 8.11 (1H, s), 8.05 (1H, dt, J1 = 4.5 Hz, J2 = 2.4 Hz), 7.65-7.61 (2H, m), 7.54-7.51 (2H, m), 7.41-7.35 (1H, m), 2.85 (2H, q, J = 7.3 Hz), 1.25 (3H, t, J = 7.6 Hz). |
| 1-28 | 8.11 (1H, s), 8.02 (1H, dt, J1 = 7.3 Hz, J2 = 1.6 Hz), 7.63-7.60 (2H, m), 7.54-7.50 (2H, m), 7.38-7.37 (2H, m), 2.87 (2H, q, J = 7.3 Hz), 2.78 (2H, q, J = 7.8 Hz), 1.26 (3H, t, J = 7.3 Hz), 1.08 (3H, t, J = 7.8 Hz). |

TABLE 5-continued

| Compound No. | $^1$H-NMR Spectrum (CDCl$_3$) σ ppm: |
|---|---|
| 1-29 | 8.39 (1H, s), 8.30 (1H, d, J = 7.3 Hz), 7.68-7.61 (2H, m), 7.58-7.57 (2H, m), 7.42-7.39 (2H, m), 2.89 (2H, q, J = 7.3 Hz), 1.25 (3H, t, J = 7.3 Hz). |
| 1-31 | 8.41 (1H, s), 8.31 (1H, d, J = 7.8 Hz), 7.69-7.61 (2H, m), 7.57 (2H, d, J = 3.7 Hz), 7.43-7.39 (1H, m), 7.35 (1H, d, J = 8.2 Hz), 2.90 (2H, q, J = 7.3 Hz), 1.27 (3H, t, J = 7.3 Hz). |
| 1-38 | 8.24 (1H, s), 8.17-8.13 (2H, m), 7.78 (1H, d, J = 1.8 Hz), 7.75-7.72 (1H, m), 7.65-7.56 (3H, m), 2.96 (2H, q, J = 7.5 Hz), 1.33 (3H, t, J = 7.3 Hz). |
| 1-40 | 8.25 (1H, s), 8.05 (2H, d, J = 8.2 Hz), 7.72 (2H, d, J = 8.2 Hz), 7.56-7.48 (3H, m), 7.39 (1H, t, J = 7.6 Hz), 2.82 (2H, q, J = 7.2 Hz), 1.23 (3H, t, J = 7.3 Hz). |
| 1-53 | 8.16 (1H, s), 7.87 (1H, d, J = 8.2 Hz), 7.55-7.45 (5H, m), 7.37 (1H, td, J1 = 7.6 Hz, J2 = 1.4 Hz), 2.78 (2H, q, J = 7.3 Hz), 1.22 (3H, t, J = 7.3 Hz). |
| 1-54 | 8.22 (1H, s), 8.01 (2H, dt, J1 = 8.4 Hz, J2 = 1.9 Hz), 7.71 (2H, dt, J1 = 8.5 Hz, J2 = 1.9 Hz), 7.67-7.65 (2H, m), 7.50-7.45 (3H, m), 7.41-7.35 (2H, m), 2.81 (2H, q, J = 7.3 Hz), 1.24 (3H, t, J = 7.3 Hz). |
| 1-55 | 8.13 (1H, s), 7.90 (2H, dt, J1 = 9.5 Hz, J2 = 2.5 Hz), 7.53 (2H, d, J = 2.5 Hz), 7.47 (1H, td, J1 = 7.6 Hz, J2 = 1.7 Hz), 7.40-7.34 (3H, m), 7.16-7.05 (5H, m), 2.81 (2H, q, J = 7.3 Hz), 1.23 (3H, t, J = 7.6 Hz). |
| 1-56 | 8.27 (1H, s), 8.05 (2H, dt, J1 = 8.4 Hz, J2 = 1.6 Hz), 7.76 (2H, dt, J1 = 8.4 Hz, J2 = 1.8 Hz), 7.56-7.48 (3H, m), 7.39 (1H, td, J1 = 7.3 Hz, J2 = 1.7 Hz), 2.83 (2H, q, J = 7.5 Hz), 1.24 (3H, t, J = 7.6 Hz). |
| 1-57 | 8.69 (1H, s), 8.55 (1H, d, J = 8.2 Hz), 7.76 (1H, s), 7.67 (1H, dd, J1 = 8.2 Hz, J2 = 1.8 Hz), 7.56 (2H, d, J = 7.8 Hz), 7.50 (1H, td, J1 = 7.3 Hz, J2 = 1.2 Hz), 7.40 (1H, td, J1 = 7.6 Hz, J2 = 1.1 Hz), 2.83 (2H, q, J = 7.5 Hz), 1.24 (3H, t, J = 7.8 Hz). |
| 1-75 | 8.39 (2H, s), 8.31 (1H, s), 7.86 (1H, s), 7.57-7.49 (3H, m), 7.40 (1H, td, J1 = 7.6 Hz, J2 = 1.7 Hz), 2.84 (2H, q, J = 7.5 Hz), 1.25 (3H, t, J = 7.3 Hz). |
| 1-81 | 8.64 (2H, s), 7.93 (1H, s), 7.59-7.56 (2H, m), 7.44-7.40 (1H, m), 7.36-7.34 (1H, m), 2.91 (2H, q, J = 7.3 Hz), 1.27 (3H, t, J = 7.3 Hz). |
| 1-82 | 8.29 (2H, s), 7.79 (1H, s), 7.58-7.52 (2H, m), 7.44-7.39 (2H, m), 4.00 (2H, br), 2.87 (2H, q, J = 7.3 Hz), 1.27 (3H, t, J = 7.3 Hz). |
| 1-83 | 8.52 (1H, s), 7.96 (1H, s), 7.56-7.54 (2H, m), 7.44-7.42 (2H, m), 4.19 (2H, q, J = 7.2 Hz), 2.80 (2H, q, J = 7.3 Hz), 1.21 (3H, t, J = 7.3 Hz), 1.05 (3H, t, J = 7.1 Hz). |
| 1-84 | 8.63 (1H, s), 8.01 (1H, s), 7.64-7.63 (2H, m), 7.49-7.46 (2H, m), 2.93 (2H, q, J = 7.3 Hz), 1.28 (3H, t, J = 7.3 Hz). |
| 1-85 | 8.38 (2H, s), 8.34 (1H, s), 7.87 (1H, s), 7.70 (1H, dd, J1 = 7.8 Hz, J2 = 0.9 Hz), 7.53 (1H, dd, J1 = 7.8 Hz, J2 = 1.4 Hz), 7.50-7.46 (1H, m), 2.67 (2H, q, J = 7.3 Hz), 1.05 (3H, t, J = 7.3 Hz). |
| 1-86 | 8.37 (2H, s), 8.28 (1H, s), 7.87 (1H, s), 7.47-7.45 (2H, m), 7.35 (1H, dd, J = 8.7 Hz, J2 = 2.3 Hz), 2.89 (2H, q, J = 7.3 Hz), 1.29 (3H, t, J = 7.6 Hz). |
| 1-87 | 8.38 (2H, s), 8.33 (1H, s), 7.88 (1H, s), 7.58 (1H, t, J = 1.1 Hz), 7.49 (2H, d, J = 1.4 Hz), 2.82 (2H, q, J = 7.3 Hz), 1.24 (3H, t, J = 7.3 Hz). |
| 1-88 | 8.41 (2H, s), 8.09 (1H, s), 7.87 (1H, s), 7.49-7.42 (2H, m), 7.39 (1H, td, J1 = 8.5 Hz, J2 = 3.1 Hz), 2.90 (2H, q, J = 7.3 Hz), 1.28 (3H, t, J = 7.3 Hz). |
| 1-90 | 8.38 (2H, s), 8.36 (1H, s), 7.88 (1H, s), 7.75 (1H, s), 7.68 (1H, d, J = 8.2 Hz), 7.64 (1H, dd, J1 = 8.2 Hz, J = 1.8 Hz), 2.94 (2H, q, J = 7.5 Hz), 1.30 (3H, t, J = 7.6 Hz). |
| 1-91 | 8.38 (1H, br), 8.32 (1H, s), 7.88 (1H, br), 7.77 (1H, s), 7.75 (1H, d, J = 8.7 Hz), 7.58 (1H, d, J = 8.2 Hz), 2.98 (2H, q, J = 7.5 Hz), 1.33 (3H, t, J = 7.6 Hz). |
| 1-197 | 8.27 (1H, s), 8.24 (1H, s), 8.11 (1H, s), 7.74 (1H, s), 7.55-7.46 (3H, m), 7.40-7.35 (1H, m), 2.82 (2H, q, J = 7, 3 Hz), 1.23 (3H, t, J = 7.3 Hz). |
| 1-210 | 8.70 (1H, s), 8.47 (1H, s), 8.32 (1H, s), 8.28 (1H, s), 7.56-7.48 (3H, m), 7.39 (1H, td, J1 = 7.6 Hz, J2 = 1.5 Hz), 4.00 (3H, s), 2.84 (2H, q, J = 7.3 Hz), 1.24 (3H, t, J = 7.3 Hz). |
| 1-227 | 8.63 (1H, s), 8.33 (2H, s), 8.15 (1H, s), 8.00 (1H, br), 7.70 (2H, d, J = 7.8 Hz), 7.57-7.49 (3H, m), 7.44-7.38 (3H, m), 7.23-7.19 (1H, m), 2.85 (2H, q, J = 7.3 Hz), 1.25 (3H, t, J = 7.6 Hz). |
| 1-228 | 8.62 (1H, s), 8.32 (1H, s), 8.29 (1H, s), 8.14 (1H, s), 8.12 (1H, br), 7.69-7.65 (2H, m), 7.57-7.50 (3H, m), 7.42-7.36 (3H, m), 2.86 (2H, q, J = 7.5 Hz), 1.25 (3H, t, J = 7.3 Hz). |
| 1-229 | 8.40 (1H, s), 8.38 (2H, s), 7.88 (1H, s), 7.61 (1H, dd, J = 8.7, 5.5 Hz), 7.38 (1H, dd, J = 8.2, 2.7 Hz), 2.74 (2H, q, J = 7.3 Hz), 1.18 (3H, t, J = 7.3 Hz). |
| 1-230 | 8.38 (2H, s), 8.32 (1H, s), 7.86 (1H, s), 7.48 (1H, d, J = 8.2 Hz), 7.38 (1H, d, J = 1.8 Hz), 7.32 (1H, dd, J = 8.5, 1.6 Hz), 2.75 (2H, q, J = 7.3 Hz), 1.19 (3H, t, J = 7.3 Hz). |
| 1-231 | 8.40 (1H, s), 8.38 (2H, s), 7.87 (1H, s), 7.59 (1H, d, J = 8.7 Hz), 7.15 (1H, d, J = 2.7 Hz), 7.06 (1H, dd, J = 8.7, 2.7 Hz), 3.88 (3H, s), 2.63 (2H, q, J = 7.3 Hz), 1.12 (3H, t, J = 7.6 Hz). |
| 1-232 | 8.42 (2H, s), 8.31 (1H, s), 8.05 (1H, s), 7.84 (1H, s), 7.08 (1H, d, J = 0.9 Hz), 3.23 (2H, q, J = 7.3 Hz), 1.49 (3H, t, J = 7.6 Hz). |
| 1-233 | 8.25 (1H, s), 8.07 (1H, d, J = 8.7 Hz), 7.71 (1H, d, J = 8.2 Hz), 7.54 (1H, dt, J1 = 8.1 Hz, J2 = 1.7 Hz), 7.49 (1H, td, J1 = 7.6 Hz, J2 = 1.5 Hz), 7.39 (1H, td, J1 = 7.6 Hz, J2 = 1.4 Hz), 2.81 (2H, q, J = 7.3 Hz), 1.23 (3H, t, J = 7.3 Hz). |
| 1-234 | 8.37 (1H, s), 8.34 (1H, s), 8.29 (1H, s), 7.88 (1H, s), 7.56-7.49 (3H, m), 7.39 (1H, td, J1 = 7.4 Hz, J2 = 1.5 Hz), 6.48 (1H, br), 5.68 (1H, br), 2.84 (2H, q, J = 7.3 Hz), 1.24 (3H, t, J = 7.3 Hz). |
| 1-235 | 8.39 (2H, s), 7.87 (1H, s), 7.62-7.56 (2H, m), 7.49-7.42 (2H, m), 2.89 (2H, d, J = 7.3 Hz), 1.25 (3H, t, J = 7.3 Hz). |
| 1-236 | 8.33 (1H, s), 8.24 (1H, d, J = 7.8 Hz), 8.08 (1H, d, J = 8.2 Hz), 7.75 (1H, d, J = 8.2 Hz), 7.59-7.48 (4H, m), 7.39 (1H, t, J = 7.6 Hz), 2.83 (2H, q, J = 7.5 Hz), 1.24 (3H, t, J = 7.3 Hz). |
| 1-237 | 8.67 (1H, s), 8.41 (1H, s), 8.32 (1H, s), 8.19 (1H, s), 7.57-7.49 (3H, m), 7.40 (1H, td, J1 = 7.4 Hz, J2 = 1.7 Hz), 2.85 (2H, q, J = 7.3 Hz), 2.73 (3H, s), 1.25 (3H, t, J = 7.6 Hz). |
| 1-238 | 8.35 (1H, s), 8.33 (1H, s), 8.29 (1H, s), 7.86 (1H, s), 7.56-7.49 (3H, m), 7.39 (1H, td, J1 = 7.6 Hz, J2 = 1.5 Hz), 6.58 (1H, br), 2.96 (3H, d, J = 5.0 Hz), 2.84 (2H, q, J = 7.3 Hz), 1.24 (3H, t, J = 7.3 Hz). |

TABLE 5-continued

| Compound No. | $^1$H-NMR Spectrum (CDCl$_3$) σ ppm: |
|---|---|
| 1-239 | 8.18 (1H, s), 7.82 (2H, d, J = 1.8 Hz), 7.55-7.46 (3H, m), 7.40-7.33 (2H, m), 2.81 (2H, q, J = 7.3 Hz), 1.22 (3H, t, J = 7.3 Hz). |
| 1-240 | 8.43 (2H, s), 8.34 (1H, s), 7.89 (1H, s), 7.57-7.51 (3H, m), 7.42-7.39 (1H, m), 2.85 (2H, q, J = 7.3 Hz), 1.25 (3H, t, J = 7.3 Hz). |
| 1-241 | 8.49 (2H, d, J = 6.9 Hz), 8.37 (1H, s), 8.01 (1H, s), 7.83 (2H, dd, J = 5.0, 3.2 Hz), 7.62 (1H, tt, J1 = 7.3, J2 = 1.5 Hz), 7.53-7.44 (5H, m), 7.33 (1H, td, J1 = 7.6, J2 = 1.7 Hz), 2.83 (2H, q, J = 7.5 Hz), 1.22 (3H, t, J = 7.3 Hz). |
| 1-242 | 8.41 (1H, s), 8.33-8.29 (3H, m), 7.93 (1H, s), 7.59 (2H, d, J = 7.8 Hz), 7.52-7.50 (3H, m), 7.39-7.33 (3H, m), 7.19 (1H, td, J1 = 7.3 Hz, J2 = 1.1 Hz), 2.83 (2H, q, J = 7.5 Hz), 1.23 (3H, t, J = 7.3 Hz). |
| 1-243 | 8.29 (1H, s), 8.27 (1H, s), 8.25 (1H, s), 7.75 (1H, s), 7.53-7.50 (3H, m), 7.38 (1H, td, J1 = 7.4 Hz, J2 = 1.5 Hz), 2.84 (2H, q, J = 7.5 Hz), 2.01 (3H, t, J = 18.3 Hz), 1.24 (3H, t, J = 7.3 Hz). |
| 1-244 | 8.66 (1H, s), 8.40 (1H, s), 8.28 (1H, s), 8.19 (1H, s), 7.88-7.85 (1H, m), 7.60-7.52 (3H, m), 5.92 (1H, dq, J1 = 55.3 Hz, J2 = 6.3 Hz), 2.73 (3H, s), 1.63 (3H, dd, J1 = 20.1 Hz, J2 = 6.4 Hz). |
| 1-245 | 8.36 (1H, s), 8.28 (1H, s), 8.12 (1H, s), 7.82 (1H, s), 7.69-7.66 (2H, m), 7.56-7.46 (5H, m), 7.44-7.36 (2H, m), 2.82 (2H, q, J = 7.5 Hz), 1.23 (3H, t, J = 7.3 Hz). |
| 1-246 | 8.21 (1H, s), 7.88 (2H, s), 7.55-7.47 (3H, m), 7.40-7.36 (1H, m), 7.31 (1H, s), 2.82 (2H, q, J = 7.3 Hz), 1.23 (3H, t, J = 7.3 Hz). |
| 1-247 | 8.39 (2H, s), 8.35 (1H, s), 7.86 (1H, s), 7.73 (1H, d, J = 1.4 Hz), 7.64-7.56 (4H, m), 7.53-7.42 (3H, m), 2.88 (2H, q, J = 7.3 Hz), 1.26 (3H, t, J = 7.3 Hz). |
| 1-248 | 8.38 (2H, s), 8.35 (1H, s), 7.86 (1H, s), 7.68 (1H, d, J = 1.8 Hz), 7.60 (1H, d, J = 8.2 Hz), 7.56-7.52 (3H, m), 7.49-7.45 (2H, m), 2.86 (2H, q, J = 7.3 Hz), 1.26 (3H, t, J = 7.3 Hz). |
| 1-249 | 8.37 (2H, s), 8.24 (1H, s), 7.85 (1H, s), 7.44-7.39 (3H, m), 7.23-7.18 (1H, m), 7.11-7.08 (3H, m), 6.90 (1H, dd, J1 = 8.7 Hz, J2 = 2.7 Hz), 2.79 (2H, q, J = 7.3 Hz), 1.23 (3H, t, J = 7.6 Hz). |
| 1-250 | 8.39 (1H, s), 8.38 (2H, s), 7.89 (1H, s), 7.75 (1H, d, J = 0.9 Hz), 7.70-7.65 (2H, m), 2.96 (2H, q, J = 7.3 Hz), 1.33 (3H, t, J = 7.6 Hz). |
| 1-251 | 8.36 (2H, s), 8.27 (1H, s), 7.86 (1H, s), 7.61 (1H, d, J = 1.8 Hz), 7.49 (1H, dd, J1 = 8.2 Hz, J2 = 1.8 Hz), 7.38 (1H, d, J = 8.2 Hz), 2.88 (2H, q, J = 7.3 Hz), 1.27 (3H, t, J = 7.6 Hz). |
| 1-252 | 1H-NMR (DMSO-D6) δ: 12.82 (1H, br), 9.41 (1H, s), 8.62 (2H, s), 8.22 (1H, s), 8.13 (1H, s), 8.07 (1H, d, J = 8.2 Hz), 7.85 (1H, d, J = 8.2 Hz), 3.09 (2H, q, J = 7.3 Hz), 1.23 (3H, t, J = 7.1 Hz). |
| 1-254 | 8.40 (2H, s), 8.38 (1H, s), 8.32 (1H, d, J = 1.4 Hz), 8.13 (1H, dd, J = 8.2, 1.8 Hz), 7.88 (1H, s), 7.66 (1H, d, J = 8.2 Hz), 4.46 (3H, s), 2.99 (2H, q, J = 7.3 Hz), 1.32 (3H, t, J = 7.6 Hz). |
| 1-255 | 8.36 (2H, s), 8.25 (1H, s), 7.84 (1H, s), 7.38 (1H, d, J = 8.2 Hz), 7.24 (1H, s), 7.02 (1H, dd, J1 = 8.2 Hz, J2 = 1.8 Hz), 2.79 (2H, q, J = 7.3 Hz), 2.01-1.93 (1H, m), 1.21 (3H, t, J = 7.3 Hz), 1.11-1.05 (2H, m), 0.80-0.75 (2H, m). |
| 1-256 | 8.26 (1H, s), 8.12 (2H, s), 7.58 (1H, s), 7.55-7.46 (3H, m), 7.37 (1H, td, J1 = 7.6 Hz, J2 = 1.7 Hz), 3.89 (2H, s), 2.82 (2H, q, J = 7.3 Hz), 1.23 (3H, t, J = 7.3 Hz). |
| 1-257 | 8.40-8.39 (1H, m), 8.24 (1H, d, J = 1.4 Hz), 8.08 (1H, dd, J1 = 8.2 Hz, J2 = 1.8 Hz), 7.88 (1H, s), 7.68 (1H, d, J = 7.8 Hz), 2.97 (1H, q, J = 7.5 Hz), 1.31 (3H, t, J = 7.6 Hz). |
| 1-258 | 8.38 (1H, s), 8.30 (1H, s), 7.86 (1H, s), 7.57 (1H, d, J = 1.4 Hz), 7.51 (1H, d, J = 8.2 Hz), 7.36 (1H, dd, J1 = 8.0 Hz, J2 = 1.6 Hz), 4.83 (2H, d, J = 5.5 Hz), 2.86 (2H, q, J = 7.3 Hz), 1.88 (1H, t, J = 6.0 Hz), 1.25 (3H, t, J = 7.3 Hz). |
| 1-259 | 8.25 (1H, s), 8.04 (2H, s), 7.55-7.46 (4H, m), 7.37 (1H, td, J1 = 7.4 Hz, J2 = 1.7 Hz), 2.82 (2H, q, J = 7.5 Hz), 1.84 (2H, dd, J1 = 8.0 Hz, J2 = 5.3 Hz), 1.56 (2H, dd, J1 = 8.0 Hz, J2 = 5.3 Hz), 1.23 (3H, t, J = 7.3 Hz). |
| 1-261 | 8.36 (2H, s), 8.22 (1H, s), 7.84 (1H, s), 7.37-7.32 (3H, m), 7.18-7.04 (3H, m), 6.95 (1H, dd, J1 = 8.7 Hz, J2 = 2.3 Hz), 6.77-6.67 (2H, m), 5.99 (1H, s), 2.75 (2H, q, J = 7.3 Hz), 1.22 (3H, t, J = 7.3 Hz). |
| 1-265 | 8.38-8.35 (3H, m), 8.20 (1H, s), 8.04-8.01 (1H, m), 7.88 (1H, s), 7.63 (1H, d, J = 8.2 Hz), 4.45 (2H, q, J = 7.2 Hz), 2.94 (2H, q, J = 7.3 Hz), 1.45 (3H, t, J = 7.1 Hz), 1.29 (3H, t, J = 7.3 Hz). |
| 1-266 | 8.38 (2H, s), 8.37 (1H, s), 7.99 (1H, d, J = 1.8 Hz), 7.88 (1H, s), 7.65 (1H, dd, J1 = 8.2 Hz, J2 = 1.8 Hz), 7.60 (1H, d, J = 8.2 Hz), 6.24 (1H, br), 3.08 (3H, d, J = 5.0 Hz), 2.93 (2H, q, J = 7.3 Hz), 1.28 (3H, t, J = 7.3 Hz). |
| 1-267 | 8.38 (2H, s), 8.31 (1H, s), 7.87 (1H, s), 7.56 (1H, d, J = 7.8 Hz), 7.50 (1H, d, J = 1.4 Hz), 7.34 (1H, dd, J1 = 8.2 Hz, J2 = 1.4 Hz), 3.88 (2H, s), 2.89 (2H, q, J = 7.3 Hz), 1.28 (3H, t, J = 7.3 Hz). |
| 1-268 | 8.38 (2H, s), 8.31 (1H, s), 7.87 (1H, s), 7.55-7.51 (2H, m), 7.18 (1H, d, J = 8.2 Hz), 2.89 (2H, q, J = 7.3 Hz), 1.90-1.86 (2H, m), 1.54-1.52 (2H, m), 1.28 (3H, t, J = 7.6 Hz). |
| 1-269 | 8.40 (2H, s), 8.19 (1H, s), 7.90 (1H, dd, J1 = 7.6 Hz, J2 = 1.6 Hz), 7.86 (1H, s), 7.66-7.59 (2H, m), 4.13 (2H, q, J = 7.0 Hz), 2.88 (2H, q, J = 7.3 Hz), 1.27 (3H, t, J = 7.3 Hz), 1.10 (3H, t, J = 7.1 Hz). |
| 1-270 | 8.38 (2H, s), 8.19 (1H, s), 7.86 (1H, s), 7.60-7.53 (2H, m), 7.49 (1H, dd, J1 = 6.9 Hz, J2 = 1.8 Hz), 5.89 (1H, br), 2.90 (2H, q, J = 7.3 Hz), 2.75 (3H, d, J = 4.6 Hz), 1.27 (3H, t, J = 7.3 Hz). |
| 1-271 | 8.40 (2H, s), 8.03 (1H, s), 7.86 (1H, s), 7.18 (2H, s), 2.88 (4H, q, J = 7.3 Hz), 1.29 (6H, t, J = 7.3 Hz). |
| 1-273 | 8.40 (2H, s), 8.39 (2H, s), 8.12 (1H, d, J = 1.4 Hz), 7.92 (1H, dd, J1 = 8.0 Hz, J2 = 1.1 Hz), 7.88 (1H, s), 7.68 (1H, d, J = 8.3 Hz), 2.95 (2H, q, J = 7.3 Hz), 2.69 (3H, s), 1.29 (3H, t, J = 7.3 Hz). |
| 1-274 | 8.41 (1H, s), 8.40 (2H, s), 7.95 (1H, d, J = 1.4 Hz), 7.89-7.85 (3H, m), 7.73 (1H, dd, J1 = 8.2 Hz, J2 = 1.4 Hz), 7.69-7.65 (2H, m), 7.55 (2H, t, J = 7.6 Hz), 2.93 (2H, q, J = 7.3 Hz), 1.29 (3H, t, J = 7.3 Hz). |

TABLE 5-continued

| Compound No. | $^1$H-NMR Spectrum (CDCl$_3$) σ ppm: |
|---|---|
| 1-275 | 8.74 (1H, dd, J1 = 6.9 Hz, J2 = 2.3 Hz), 8.37 (1H, d, J = 3.7 Hz), 7.63-7.59 (1H, m), 7.56-7.47 (3H, m), 7.39 (1H, td, J1 = 7.6 Hz, J2 = 1.5 Hz), 7.30 (1H, d, J = 9.6 Hz), 2.83 (2H, q, J = 7.3 Hz), 1.24 (3H, t, J = 7.3 Hz). |
| 1-277 | 8.37 (2H, s), 8.28 (1H, s), 7.87 (1H, s), 7.82 (1H, d, J = 1.8 Hz), 7.71 (1H, dd, J1 = 8.2 Hz, J2 = 1.8 Hz), 7.24 (1H, d, J = 8.7 Hz), 2.87 (2H, q, J = 7.3 Hz), 1.27 (3H, t, J = 7.3 Hz). |
| 1-278 | 8.38 (2H, s), 8.29 (1H, s), 7.88 (1H, s), 7.56 (1H, d, J = 8.7 Hz), 7.32 (1H, d, J = 2.3 Hz), 7.24-7.21 (1H, m), 2.91 (2H, q, J = 7.3 Hz), 1.30 (3H, t, J = 7.3 Hz). |
| 1-279 | 8.30 (1H, t, J = 1.4 Hz), 8.11 (2H, d, J = 8.2 Hz), 7.99 (1H, s), 7.69 (2H, d, J = 8.2 Hz), 7.06 (1H, d, J = 1.8 Hz), 3.23 (2H, q, J = 7.3 Hz), 1.48 (3H, t, J = 7.3 Hz). |
| 1-280 | 8.61 (1H, s), 8.23 (1H, s), 7.66-7.58 (2H, m), 7.54 (1H, d, J = 8.0 Hz, J2 = 1.1 Hz), 7.44 (1H, td, J1 = 7.4 Hz, J2 = 1.7 Hz), 2.90 (2H, q, J = 7.3 Hz), 1.12 (3H, t, J = 7.3 Hz). |
| 1-281 | 8.42 (2H, s), 8.27 (1H, s), 8.25-8.23 (1H, m), 8.19-8.17 (2H, m), 7.92 (2H, br), 7.43-7.39 (1H, m), 2.91 (2H, q, J = 7.3 Hz), 1.11 (3H, t, J = 7.3 Hz). |
| 1-282 | 8.54 (2H, s), 7.92 (1H, s), 7.86 (1H, br), 7.60-7.53 (2H, m), 7.50-7.48 (1H, m), 7.41 (1H, td, J1 = 7.3 Hz, J2 = 1.8 Hz), 7.31-7.24 (4H, m), 7.16-7.12 (1H, m), 2.93 (2H, q, J = 7.3 Hz), 1.28 (3H, t, J = 7.6 Hz). |
| 1-283 | 8.54 (2H, s), 7.94 (1H, s), 7.79 (1H, br), 7.61-7.54 (2H, m), 7.51-7.42 (2H, m), 7.27-7.20 (4H, m), 2.93 (2H, q, J = 7.3 Hz), 1.28 (3H, t, J = 7.6 Hz). |
| 1-284 | 8.46 (2H, s), 7.91 (1H, s), 7.59-7.51 (2H, m), 7.46-7.39 (2H, m), 6.13 (1H, br), 2.90 (2H, q, J = 7.3 Hz), 2.81 (3H, d, J = 5.0 Hz), 1.26 (3H, t, J = 7.3 Hz). |
| 1-285 | 8.32 (2H, s), 7.90 (1H, s)7.53 (2H, dd, J1 = 4.8 Hz, J2 = 1.1 Hz), 7.49 (1H, dd, J1 = 7.8 Hz, J2 = 0.9 Hz), 7.41-7.36 (1H, m), 3.00 (3H, s), 2.91 (2H, q, J = 7.5 Hz), 1.25 (3H, t, J = 7.3 Hz). |
| 1-286 | 8.34 (1H, br), 8.28 (2H, s), 7.91 (1H, s), 7.62-7.56 (2H, m), 7.54-7.45 (2H, m), 2.82 (2H, q, J = 7.3 Hz), 1.27 (3H, t, J = 7.3 Hz). |
| 1-287 | 8.39 (2H, s), 8.03 (1H, br), 7.85 (1H, s), 7.69 (2H, d, J = 7.3 Hz), 7.60-7.41 (7H, m), 2.80 (2H, q, J = 7.3 Hz), 1.25 (3H, t, J = 7.3 Hz). |
| 1-288 | 8.37 (2H, s), 8.03 (1H, s), 7.86 (1H, s), 7.66 (1H, br), 7.59-7.52 (5H, m), 7.46-7.39 (2H, m), 2.82 (2H, q, J = 7.3 Hz), 1.27 (3H, t, J = 7.3 Hz). |
| 1-289 | 8.37 (2H, s), 8.01 (1H, br), 7.85 (1H, s), 7.64 (2H, d, J = 8.2 Hz), 7.58-7.51 (3H, m), 7.46-7.42 (3H, m), 2.79 (2H, q, J = 7.5 Hz), 1.29 (3H, t, J = 7.3 Hz). |
| 1-290 | 8.22 (2H, s), 7.92 (1H, s), 7.55-7.53 (2H, m), 7.34-7.30 (1H, m), 7.27-7.25 (1H, m), 3.00 (2H, q, J = 7.3 Hz), 2.31 (6H, s), 1.30 (3H, t, J = 7.3 Hz). |
| 1-291 | 9.29 (1H, s), 8.80 (1H, s), 8.52 (1H, s), 8.16 (1H, s), 7.69-7.59 (3H, m), 7.45 (1H, td, J1 = 7.4 Hz, J2 = 1.5 Hz), 2.96 (2H, q, J = 7.2 Hz), 1.17 (3H, t, J = 7.3 Hz). |
| 1-292 | 8.45 (2H, s), 8.03 (1H, br), 7.88 (1H, s), 7.58-7.49 (4H, m), 7.45-7.33 (4H, m), 2.79 (2H, q, J = 7.3 Hz), 1.23 (3H, t, J = 7.3 Hz). |
| 1-295 | 8.25 (1H, dd, J1 = 7.8 Hz, J2 = 1.4 Hz), 8.17 (1H, s), 7.93-7.91 (2H, m), 7.76 (1H, td, J1 = 7.6 Hz, J2 = 1.4 Hz), 7.69 (1H, td, J1 = 7.6 Hz, J2 = 1.7 Hz), 7.55 (1H, dd, J1 = 7.8 Hz, J2 = 1.4 Hz), 7.51-7.47 (2H, m), 7.43-7.39 (1H, m), 3.36-3.27 (1H, m), 2.94-2.85 (1H, m), 1.35 (3H, t, J = 7.3 Hz). |
| 1-300 | 8.25 (1H, dd, J1 = 8.0 Hz, J2 = 1.6 Hz), 8.18 (1H, s), 7.92 (1H, t, J = 1.8 Hz), 7.81-7.75 (2H, m), 7.69 (1H, td, J1 = 7.6 Hz, J2 = 1.4 Hz), 7.54 (1H, dd, J1 = 8.0 Hz, J2 = 1.1 Hz), 7.42 (1H, t, J = 7.6 Hz), 7.38 (1H, dt, J1 = 7.9 Hz, J2 = 1.7 Hz), 3.34-3.25 (1H, m), 2.94-2.85 (1H, m), 1.35 (3H, t, J = 7.6 Hz). |
| 1-301 | 8.25 (1H, dd, J1 = 8.0 Hz, J2 = 1.6 Hz), 8.16 (1H, s), 7.87-7.83 (1H, m), 7.77 (1H, td, J1 = 7.7 Hz, J2 = 1.2 Hz), 7.69 (1H, td, J1 = 7.7 Hz, J2 = 1.5 Hz), 7.54 (1H, dd, J1 = 7.8 Hz, J2 = 0.9 Hz), 7.48-7.45 (1H, m), 3.36-3.27 (1H, m), 2.95-2.86 (1H, m), 1.36 (3H, t, J = 7.3 Hz). |
| 1-302 | 8.25 (1H, dd, J1 = 7.8 Hz, J2 = 1.4 Hz), 8.17 (1H, s), 8.08 (1H, t, J = 1.6 Hz), 7.84 (1H, dt, J1 = 7.8 Hz, J2 = 1.4 Hz), 7.77 (1H, td, J1 = 7.6 Hz, J2 = 1.4 Hz), 7.69 (1H, td, J1 = 7.7 Hz, J2 = 1.5 Hz), 7.55-7.52 (2H, m), 7.36 (1H, t, J = 7.8 Hz), 3.34-3.25 (1H, m), 2.94-2.85 (1H, m), 1.35 (3H, t, J = 7.6 Hz). |
| 1-303 | 8.26 (1H, dd, J1 = 7.8 Hz, J2 = 1.4 Hz), 8.20 (1H, s), 7.84 (1H, d, J = 7.8 Hz), 7.80-7.76 (2H, m), 7.69 (1H, td, J1 = 7.8 Hz, J2 = 1.4 Hz), 7.56-7.50 (2H, m), 3.36-3.27 (1H, m), 2.96-2.87 (1H, m), 1.36 (3H, t, J = 7.3 Hz). |
| 1-304 | 8.25 (1H, dd, J1 = 7.8 Hz, J2 = 1.4 Hz), 8.17 (1H, s), 8.04 (1H, d, J = 7.8 Hz), 7.82 (1H, d, J = 8.2 Hz), 7.78 (1H, td, J1 = 7.7 Hz, J2 = 1.2 Hz), 7.70 (1H, td, J1 = 7.7 Hz, J2 = 1.7 Hz), 7.58-7.54 (2H, m), 3.27-3.18 (1H, m), 2.87-2.78 (1H, m), 1.33 (3H, t, J = 7.3 Hz). |
| 1-305 | 8.27-8.25 (2H, m), 8.18 (1H, s), 8.11 (1H, d, J = 7.3 Hz), 7.78 (1H, td, J1 = 7.7 Hz, J2 = 1.1 Hz), 7.70 (1H, td, J1 = 7.7 Hz, J2 = 1.5 Hz), 7.66-7.60 (2H, m), 7.56 (1H, dd, J1 = 7.8 Hz, J2 = 0.9 Hz), 3.37-3.28 (1H, m), 2.96-2.87 (1H, m), 1.37 (3H, t, J = 7.3 Hz). |
| 1-306 | 8.22 (1H, dd, J1 = 7.8 Hz, J2 = 1.4 Hz), 8.10 (1H, s), 7.99 (1H, d, J = 7.3 Hz), 7.84 (1H, td, J1 = 7.7 Hz, J2 = 1.2 Hz), 7.74 (1H, td, J1 = 7.7 Hz, J2 = 1.5Z Hz), 7.68-7.61 (2H, m), 7.42 (1H, dd, J1 = 7.8 Hz, J2 = 0.9 Hz), 3.21-3.12 (1H, m), 2.87 (1H, m), 2.47 (3H, s), 1.27 (3H, t, J = 7.3 Hz). |
| 1-308 | 8.36 (1H, s), 8.27-8.22 (2H, m), 7.87 (1H, td, J1 = 7.8 Hz, J2 = 1.4 Hz), 7.75 (1H, td, J1 = 7.7 Hz, J2 = 1.7 Hz), 7.72-7.63 (2H, m), 7.51 (1H, dd, J1 = 8.0 Hz, J2 = 1.1 Hz), 3.20-3.11 (1H, m), 2.88-2.79 (1H, m), 1.29 (3H, t, J = 7.3 Hz). |
| 1-310 | 8.36 (1H, s), 8.27 (1H, d, J = 7.8 Hz), 8.22 (1H, dd, J1 = 7.8 Hz, J2 = 1.4 Hz), 7.87 (1H, td, J1 = 7.8 Hz, J2 = 1.4 Hz), 7.77-7.71 (2H, m), 7.65 (1H, t, H = 7.8 Hz), 7.47 (1H, dd, J1 = 7.8 Hz, J2 = 1.4 Hz), 3.13-3.04 (1H, m), 2.83-2.75 (1H, m), 1.25 (3H, t, J = 7.3 Hz). |
| 1-317 | 8.43 (1H, d, J = 8.2 Hz), 8.33 (1H, s), 8.19 (1H, s), 8.12 (1H, d, J = 7.8 Hz), 8.02 (1H, dd, J1 = 8.5 Hz, J2 = 1.1 Hz), 7.83 (1H, s), 7.70-7.62 (2H, m), 3.44-3.35 (1H, m)3.00-2.91 (1H, m), 1.40 (3H, t, J = 7.3 Hz). |
| 1-319 | 8.26 (1H, dd, J1 = 7.8 Hz, J2 = 1.8 Hz), 8.25 (1H, s), 8.04 (2H, d, J = 8.2 Hz), 7.80-7.68 (4H, m), 7.56 (1H, dd, J1 = 7.8 Hz, J2 = 1.4 Hz), 3.36-3.27 (1H, m), 2.96-2.87 (1H, m), 1.36 (3H, t, J = 7.6 Hz). |

TABLE 5-continued

| Compound No. | $^1$H-NMR Spectrum (CDCl$_3$) σ ppm: |
|---|---|
| 1-332 | 8.24 (1H, dd, J1 = 7.8 Hz, J2 = 1.4 Hz), 8.14 (1H, s), 7.84 (2H, dt, J1 = 8.9 Hz, J2 = 2.2 Hz), 7.75 (1H, td, J1 = 7.6 Hz, J2 = 1.4 Hz), 7.68 (1H, td, J1 = 7.6 Hz, J2 = 1.7 Hz), 7.55 (1H, dd, J1 = 7.8 Hz, J2 = 0.9 Hz), 7.51 (2H, dt, J1 = 8.7 Hz, J2 = 2.1 Hz), 3.34-3.25 (1H, m), 2.93-2.84 (1H, m), 1.37 (9H, s), 1.34 (3H, t, J = 7.3 Hz). |
| 1-333 | 8.26 (1H, dd, J1 = 8.0 Hz, J2 = 1.6 Hz), 8.21 (1H, s), 7.99 (2H, dt, J1 = 8.7 Hz, J2 = 1.8 Hz), 7.79-7.65 (6H, m), 7.57 (1H, dd, J1 = 8.0 Hz, J2 = 1.1 Hz), 7.50-7.46 (2H, m), 7.41-7.36 (1H, m), 3.36-3.28 (1H, m), 2.95-2.86 (1H, m), 1.36 (3H, t, J = 7.3 Hz). |
| 1-334 | 8.25 (1H, d, J = 7.8 Hz), 8.12 (1H, s), 7.87 (2H, d, J = 7.8 Hz), 7.76 (1H, t, J = 7.6 Hz), 7.68 (1H, t, J = 7.8 Hz), 7.55 (1H, d, J = 7.8 Hz), 7.38 (2H, t, J = 7.6 Hz), 7.18-7.07 (5H, m), 3.36-3.27 (1H, m), 2.95-2.86 (1H, m), 1.36 (3H, t, J = 7.1 Hz). |
| 1-335 | 8.26 (1H, dd, J1 = 7.8 Hz, J2 = 1.4 Hz), 8.26 (1H, s), 8.03 (1H, dt, J1 = 8.7 Hz, J2 = 1.8 Hz), 7.81-7.77 (3H, m), 7.70 (1H, td, J1 = 7.7 Hz, J2 = 1.5 Hz), 7.54 (1H, dd, J1 = 7.8 Hz, J2 = 0.9 Hz), 3.35-3.26 (1H, m), 2.96-2.87 (1H, m), 1.36 (3H, t, J = 7.6 Hz). |
| 1-336 | 8.69 (1H, s), 8.50 (1H, d, J = 7.8 Hz), 8.26 (1H, dd, J1 = 7.8 Hz, J2 = 1.4 Hz), 7.81-7.77 (2H, m), 7.73-7.68 (2H, m), 7.59 (1H, dd, J1 = 7.8 Hz, J2 = 0.9 Hz), 3.33-3.24 (1H, m), 2.94-2.85 (1H, m), 1.36 (3H, t, J = 7.6 Hz). |
| 1-354 | 8.38 (2H, s), 8.34 (1H, s), 8.27 (1H, dd, J1 = 8.0 Hz, J2 = 1.6 Hz), 7.91 (1H, s), 7.80 (1H, td, J1 = 7.7 Hz, J2 = 1.2 Hz), 7.71 (1H, td, J1 = 7.7 Hz, J2 = 1.5 Hz), 7.56 (1H, dd, J1 = 7.8 Hz, J2 = 0.9 Hz), 3.36-3.28 (1H, m), 2.97-2.88 (1H, m), 1.37 (3H, t, J = 7.3 Hz). |
| 1-360 | 8.59 (2H, s), 8.23 (1H, dd, J1 = 8.0 Hz, J2 = 1.6 Hz), 7.96 (1H, s), 7.89 (1H, td, J1 = 7.7 Hz, J2 = 1.2 Hz), 7.77 (1H, td, J1 = 7.7 Hz, J2 = 1.5 Hz), 7.47 (1H, dd, J1 = 8.0 Hz, J2 = 1.1 Hz), 3.14-3.05 (1H, m), 2.85-2.76 (1H, m), 1.26 (3H, t, J = 7.3 Hz). |
| 1-361 | 8.25 (2H, s), 8.22 (1H, dd, J1 = 7.8 Hz, J2 = 1.4 Hz), 7.87-7.83 (2H, m), 7.76 (1H, td, J1 = 7.7 Hz, J2 = 1.5 Hz), 7.52 (1H, td, J1 = 7.8 Hz, J2 = 0.9 Hz), 4.20 (2H, s), 3.25-3.16 (1H, m), 2.95-2.86 (1H, m), 1.29 (3H, t, J = 7.3 Hz). |
| 1-362 | 8.50 (2H, s), 8.16 (1H, dd, J1 = 8.2 Hz, J2 = 1.4 Hz), 7.99 (1H, s), 7.85 (1H, td, J1 = 7.7 Hz, J2 = 1.2 Hz), 7.71 (1H, td, J1 = 7.7 Hz, J2 = 1.7 Hz), 7.45 (1H, dd, J1 = 7.8 Hz, J2 = 1.4 Hz), 4.22 (2H, q, J = 7.2 Hz), 3.05-2.96 (1H, m), 2.78-2.69 (1H, m), 1.24 (3H, t, J = 7.6 Hz), 1.06 (3H, t, J = 7.1 Hz). |
| 1-363 | 8.62 (2H, s), 8.30 (1H, dd, J1 = 7.8 Hz, J2 = 1.4 Hz), 8.05 (1H, s), 7.93 (1H, td, J1 = 7.7 Hz, J2 = 1.1 Hz), 7.82 (1H, td, J1 = 7.7 Hz, J2 = 1.7 Hz), 7.67 (1H, dd, J1 = 8.0 Hz, J2 = 1.1 Hz), 3.32-3.23 (1H, m), 3.00-2.91 (1H, m), 1.38 (3H, t, J = 7.3 Hz). |
| 1-364 | 8.36 (2H, s), 8.28 (1H, s), 7.87 (1H, s), 7.68 (1H, d, J = 8.2 Hz), 7.61 (1H, t, J = 8.0 Hz), 7.41 (1H, d, J = 7.8 Hz), 3.71-3.62 (1H, m), 3.29-3.20 (1H, m), 1.41 (3H, t, J = 7.6 Hz). |
| 1-365 | 8.37 (2H, s), 8.32 (1H, s), 8.23 (1H, d, J = 2.3 Hz), 7.91 (1H, s), 7.67 (1H, dd, J1 = 8.2 Hz, J2 = 2.3 Hz), 7.51 (1H, d, J = 8.7 Hz), 3.39-3.30 (1H, m), 2.98-2.89 (1H, m), 1.39 (3H, t, J = 7.6 Hz). |
| 1-366 | 8.36 (2H, s), 8.34 (1H, s), 8.21 (1H, d, J = 8.7 Hz), 7.89 (1H, s), 7.80 (1H, dd, J1 = 8.5 Hz, J2 = 2.1 Hz), 7.60 (1H, d, J = 2.3 Hz), 3.21 (2H, q, J = 7.5 Hz), 1.27 (3H, t, J = 7.6 Hz). |
| 1-367 | 8.39 (2H, s), 8.29 (1H, s), 8.10 (1H, dd, J1 = 5.7 Hz, J2 = 3.4 Hz), 7.91 (1H, s), 7.79 (1H, d, J = 2.3 Hz), 3.27-3.18 (1H, m), 2.94-2.85 (1H, m), 1.32 (3H, t, J = 7.6 Hz). |
| 1-369 | 8.58 (1H, d, J = 1.8 Hz), 8.41 (1H, s), 8.39 (1H, s), 7.97 (1H, dd, J1 = 8.2 Hz, J2 = 1.4 Hz), 7.93 (1H, s), 7.72 (1H, d, J = 8.2 Hz), 3.45-3.36 (1H, m), 3.01-2.92 (1H, m), 1.42 (3H, t, J = 7.6 Hz). |
| 1-370 | 8.45-8.43 (2H, m), 8.39 (1H, s), 8.04 (1H, d, J = 8.2 Hz), 7.93 (1H, s), 7.83 (1H, s), 3.44-3.35 (1H, m), 3.01-2.92 (1H, m), 1.41 (3H, t, J = 7.3 Hz). |
| 1-475 | 8.29 (1H, s), 8.26-8.21 (2H, m), 8.09 (1H, s), 7.78-7.73 (2H, m), 7.68 (1H, td, J1 = 7.6 Hz, J2 = 1.4 Hz), 7.53 (1H, dd, J1 = 7.8 Hz, J2 = 1.4 Hz), 3.34-3.25 (1H, m), 2.94-2.84 (1H, m), 1.34 (3H, t, J1 = 7.6 Hz). |
| 1-488 | 8.70 (1H, s), 8.45 (1H, s), 8.34 (1H, s), 8.32 (1H, s), 8.27 (1H, dd, J1 = 8.0 Hz, J2 = 1.6 Hz), 7.79 (1H, td, J1 = 7.6 Hz, J2 = 1.4 Hz), 7.71 (1H, td, J1 = 7.7 Hz, J2 = 1.5 Hz), 7.56 (1H, dd, J1 = 7.8 Hz, J2 = 1.4 Hz), 4.01 (3H, s), 3.37-3.28 (1H, m), 2.97-2.88 (1H, m), 1.37 (3H, t, J = 7.3 Hz). |
| 1-505 | 8.62 (1H, s), 8.36 (1H, s), 8.35 (1H, s), 8.27 (1H, dd, J1 = 7.8 Hz, J2 = 1.4 Hz), 8.17 (1H, s), 7.98 (1H, br), 7.80 (1H, t, J = 7.6 Hz), 7.74-7.68 (3H, m), 7.57 (1H, d, J = 7.8 Hz), 7.43 (1H, t, J = 8.0 Hz), 3.38-3.29 (1H, m), 2.98-2.89 (1H, m), 1.38 (3H, t, J = 7.3 Hz). |
| 1-506 | 8.60 (1H, s), 8.34 (1H, s), 8.32 (1H, s), 8.24 (1H, dd, J1 = 7.8 Hz, J2 = 1.4 Hz), 8.16 (1H, br), 7.77 (1H, td, J1 = 7.6 Hz, J2 = 1.2 Hz), 7.72 (1H, dd, J1 = 7.8 Hz, J2 = 1.8 Hz), 7.70-7.65 (2H, m), 7.55 (1H, dd, J1 = 7.8 Hz, J2 = 1.4 Hz), 7.40-7.36 (2H, m), 3.37-3.28 (1H, m), 2.98-2.89 (1H, m), 1.37 (3H, t, J = 7.3 Hz). |
| 1-507 | 8.38 (2H, s), 8.35 (1H, s), 8.27 (1H, dd, J1 = 8.9 Hz, J2 = 5.7 Hz), 7.92 (1H, s), 7.50 (1H, ddd, J1 = 9.3 Hz, J2 = 7.0 Hz, J3 = 1.9 Hz), 7.33 (1H, dd, J1 = 8.2 Hz, J2 = 2.3 Hz), 3.37-3.28 (1H, m), 2.98-2.89 (1H, m), 1.38 (3H, t, J = 7.3 Hz). |
| 1-508 | 8.38 (2H, s), 8.33 (1H, s), 8.12 (1H, d, J = 8.2 Hz), 7.90 (1H, s), 7.59 (1H, dd, J1 = 7.8 Hz, J2 = 0.9 Hz), 7.37 (1H, d, J = 0.9 Hz), 3.32-3.23 (1H, m), 2.95-2.86 (1H, m), 2.54 (3H, s), 1.35 (3H, t, J = 7.6 Hz). |
| 1-509 | 8.38 (2H, s), 8.33 (1H, s), 8.14 (1H, d, J = 9.2 Hz), 7.90 (1H, s), 7.28 (2H, dd, J1 = 8.9 Hz, J2 = 2.5 Hz), 7.05 (1H, d, J = 2.3 Hz), 3.95 (3H, s), 3.27-3.20 (1H, m), 2.95-2.86 (1H, m), 1.34 (3H, t, J = 7.3 Hz). |
| 1-510 | 8.61 (1H, s), 8.38 (2H, s), 8.19 (1H, s), 7.92 (1H, d, J = 1.8 Hz), 7.89 (1H, s), 3.62-3.53 (1H, m), 3.39-3.30 (1H, m), 1.31 (3H, t, J = 7.3 Hz). |
| 1-511 | 8.25 (1H, s), 8.24 (1H, d, J = 9.6 Hz), 8.04 (2H, d, J = 7.3 Hz), 7.78-7.69 (4H, m), 3.34-3.25 (1H, m), 2.94-2.86 (1H, m), 1.34 (3H, t, J = 7.3 Hz). |
| 1-512 | 8.38 (2H, s), 8.27 (1H, dd, J1 = 8.2 Hz, J2 = 1.4 Hz), 7.91 (1H, s), 7.86 (1H, td, J1 = 7.7 Hz, J2 = 1.1 Hz), 7.76 (1H, td, J1 = 7.7 Hz, J2 = 1.5 Hz), 7.55 (1H, d, J = 7.8 Hz), 3.31-3.22 (1H, m), 2.98-2.89 (1H, m), 1.36 (3H, t, J = 7.6 Hz). |

TABLE 5-continued

| Compound No. | $^1$H-NMR Spectrum (CDCl$_3$) σ ppm: |
|---|---|
| 1-513 | 8.32 (1H, t, J = 1.8 Hz), 8.26 (1H, s), 8.26 (1H, dd, J1 = 7.8 Hz, J2 = 1.4 Hz), 8.06 (1H, d, J = 7.8 Hz), 7.79-7.77 (2H, m), 7.70 (1H, td, J1 = 7.7 Hz, J2 = 1.7 Hz), 7.60 (1H, t, J = 8.0 Hz), 7.56 (1H, dd, J1 = 7.8 Hz, J2 = 1.4 Hz), 3.32 (1H, td, J1 = 7.6 Hz, J2 = 5.8 Hz), 2.92 (1H, td, J1 = 7.3 Hz, J2 = 6.0 Hz), 1.36 (3H, t, J = 7.3 Hz). |
| 1-514 | 8.58 (1H, s), 8.33 (2H, s), 8.18 (1H, dd, J1 = 8.2 Hz, J2 = 1.4 Hz), 8.13 (1H, s), 7.70 (1H, td, J1 = 7.6 Hz, J2 = 1.2 Hz), 7.63 (1H, td, J1 = 7.6 Hz, J2 = 1.4 Hz), 7.50 (1H, dd, J1 = 7.8 Hz, J2 = 0.9 Hz), 3.26-3.22 (1H, m), 2.90-2.80 (1H, m), 2.65 (3H, s), 1.29 (3H, t, J = 7.3 Hz). |
| 1-515 | 8.35 (2H, s), 8.33 (1H, s), 8.26 (1H, dd, J1 = 7.8 Hz, J2 = 1.4 Hz), 7.89 (1H, s), 7.79 (1H, td, J1 = 7.7 Hz, J2 = 1.2 Hz), 7.71 (1H, td, J1 = 7.7 Hz, J2 = 1.5 Hz), 7.56 (1H, dd, J1 = 7.8 Hz, J2 = 1.4 Hz), 6.60 (1H, br), 3.36-3.28 (1H, m), 2.97 (3H, d, J = 5.0 Hz), 2.96-2.87 (1H, m), 1.37 (3H, t, J = 7.3 Hz). |
| 1-516 | 8.24-8.21 (1H, m), 8.20 (1H, s), 7.80-7.65 (4H, m), 7.56-7.51 (1H, m), 7.37 (1H, t, J = 1.8 Hz), 3.33-3.23 (1H, m), 2.94-2.83 (1H, m), 1.34 (3H, t, J = 7.3 Hz). |
| 1-517 | 8.42 (2H, s), 8.38 (1H, s), 8.27 (1H, dd, J1 = 7.8 Hz, J2 = 1.4 Hz), 7.93 (1H, s), 7.81 (1H, td, J1 = 7.7 Hz, J2 = 1.1 Hz), 7.72 (1H, td, J1 = 7.6 Hz, J2 = 1.4 Hz), 7.57 (1H, dd, J1 = 8.0 Hz, J2 = 1.1 Hz), 3.37-3.28 (1H, m), 2.98-2.89 (1H, m), 1.38 (3H, t, J = 7.6 Hz). |
| 1-518 | 8.46 (2H, s), 8.36 (1H, s), 8.25 (1H, dd, J1 = 7.8 Hz, J2 = 1.4 Hz), 8.05 (1H, s), 7.86-7.83 (2H, m), 7.78 (1H, td, J1 = 7.7 Hz, J2 = 1.2 Hz), 7.72-7.65 (2H, m), 7.56-7.54 (3H, m), 3.35-3.30 (1H, m), 2.95-2.90 (1H, m), 1.36 (3H, t, J = 7.3 Hz). |
| 1-519 | 8.41 (1H, s), 8.35 (3H, s), 8.25 (1H, dd, J1 = 7.8 Hz, J2 = 1.4 Hz), 7.96 (1H, s), 7.77 (1H, td, J1 = 7.6 Hz, J2 = 1.2 Hz), 7.70 (1H, td, J1 = 7.7 Hz, J2 = 1.5 Hz), 7.60 (2H, dd, J1 = 8.9 Hz, J2 = 1.1 Hz), 7.55 (1H, dd, J1 = 8.0 Hz, J2 = 1.1 Hz), 7.37 (2H, t, J = 8.0 Hz), 7.21 (1H, tt, J1 = 7.6 Hz, J2 = 1.3 Hz), 3.32 (1H, dq, J1 = 17.9 Hz, J2 = 5.0 Hz), 2.92 (1H, dq, J1 = 17.7 Hz, J2 = 5.0 Hz), 1.36 (3H, t, J = 7.3 Hz). |
| 1-520 | 8.42 (1H, s), 8.25-8.23 (3H, m), 7.76-7.75 (2H, m), 7.69 (1H, t, J = 7.8 Hz), 7.58 (1H, d, J = 7.8 Hz), 3.35-3.30 (1H, m), 2.94-2.90 (1H, m), 2.01 (3H, t, J = 18.3 Hz), 1.36 (3H, t, J = 7.6 Hz). |
| 1-522 | 8.34 (1H, s), 8.30 (1H, s), 8.25 (1H, dd, J1 = 7.8 Hz, J2 = 1.4 Hz), 8.11 (1H, s), 7.85 (1H, s), 7.79-7.74 (1H, m), 7.71-7.65 (3H, m), 7.56 (1H, dd, J1 = 7.8, J2 = 1.4 Hz), 7.52-7.40 (3H, m), 3.37-3.27 (1H, m), 2.96-2.86 (1H, m), 1.36 (3H, t, J = 7.3 Hz). |
| 1-523 | 8.27-8.23 (2H, m), 7.88 (1H, s), 7.84 (1H, s), 7.77 (1H, t, J = 7.6 Hz), 7.69 (1H, t, J = 7.6 Hz), 7.55 (1H, d, J = 7.8 Hz), 7.35 (1H, s), 3.37-3.28 (1H, m), 2.96-2.87 (1H, m), 2.07-2.01 (1H, m), 1.36 (3H, t, J = 7.6 Hz), 1.12-1.07 (2H, m), 0.86-0.82 (2H, m). |
| 1-524 | 8.43 (1H, s), 8.41 (1H, d, J = 1.8 Hz), 8.36 (2H, s), 7.88-7.82 (2H, m), 7.66-7.59 (3H, m), 7.48-7.38 (3H, m), 3.41-3.31 (1H, m), 3.00-2.91 (1H, m), 1.39 (3H, t, J = 7.3 Hz). |
| 1-525 | 8.41 (1H, d, J = 1.8 Hz), 8.37 (3H, s), 7.90 (1H, s), 7.85 (1H, dd, J1 = 8.2 Hz, 1.8 Hz), 7.65-7.61 (3H, m), 7.48 (2H, d, J = 8.2 Hz), 3.37 (1H, m), 2.96 (1H, m), 1.40 (3H, t, J = 7.3 Hz). |
| 1-526 | 8.35 (2H, s), 8.31 (1H, s), 7.87 (1H, s), 7.78 (1H, d, J = 2.7 Hz), 7.48-7.38 (3H, m), 7.25-7.18 (2H, m), 7.09 (2H, d, J = 7.8 Hz), 3.29-3.21 (1H, m), 2.90-2.82 (1H, m), 1.31 (3H, t, J = 7.6 Hz). |
| 1-527 | 8.61 (1H, s), 8.43 (1H, s), 8.38 (2H, s), 7.99 (1H, d, J = 8.2 Hz), 7.94 (1H, s), 7.72 (1H, d, J = 8.2 Hz). 3.48-3.39 (1H, m), 3.03-2.94 (1H, m), 1.43 (3H, t, J = 7.6 Hz). |
| 1-528 | 8.37-8.35 (3H, m), 8.33 (1H, s), 7.90 (1H, s), 7.81 (1H, dd, J1 = 8.5 Hz, J2 = 2.1 Hz), 7.43 (1H, d, J = 8.7 Hz), 3.39-3.29 (1H, m), 2.97-2.88 (1H, m), 1.38 (3H, t, J = 7.6 Hz). |
| 1-529 | 1H-NMR (DMSO-D6) δ: 12.55 (1H, br), 9.76 (1H, s), 8.76 (1H, d, J = 1.8 Hz), 8.62 (2H, s), 8.49 (1H, dd, J1 = 8.2 Hz, J2 = 1.4 Hz), 8.17 (1H, s), 8.13 (1H, d, J = 8.7 Hz), 3.30-3.26 (1H, m), 2.85-2.81 (1H, m), 1.20 (3H, t, J = 7.3 Hz). |
| 1-531 | 9.01 (1H, d, J = 1.4 Hz), 8.50 (1H, dd, J1 = 8.2 Hz, J2 = 0.9 Hz), 8.42 (1H, s), 8.40 (2H, s), 7.92 (1H, s), 7.70 (1H, d, J = 8.2 Hz), 4.47 (3H, s), 3.41 (1H, td, J1 = 14.1 Hz, J2 = 6.7 Hz), 3.02 (1H, td, J1 = 13.7 Hz, J2 = 7.2 Hz), 1.43 (3H, t, J = 7.3 Hz). |
| 1-532 | 8.35 (2H, s), 8.32 (1H, s), 7.86 (2H, s), 7.41-7.28 (2H, m), 3.30-3.20 (1H, m), 2.90-2.80 (1H, m), 2.09-2.01 (1H, m), 1.32 (3H, t, J = 7.6 Hz), 1.16-1.10 (1H, m), 0.88-0.79 (1H, m). |
| 1-536 | 8.31 (1H, s), 8.24 (1H, dd, J1 = 7.8 Hz, J2 = 1.4 Hz), 8.06 (2H, s), 7.79-7.74 (1H, m), 7.71-7.66 (1H, m), 7.56-7.53 (2H, m), 3.36-3.26 (1H, m), 2.96-2.86 (1H, m), 1.87-1.84 (2H, m), 1.58-1.54 (2H, m), 1.35 (3H, t, J = 7.3 Hz). |
| 1-537 | 8.97 (1H, d, J = 1.8 Hz), 8.42 (1H, s), 8.40-8.38 (3H, m), 7.92 (1H, s), 7.69 (1H, d, J = 8.2 Hz), 3.45-3.36 (1H, m), 3.06-2.97 (1H, m), 1.43 (3H, t, J = 7.3 Hz). |
| 1-538 | 8.35 (2H, s), 8.21 (1H, s), 7.87 (1H, s), 7.71 (1H, d, J = 2.3 Hz), 7.39-7.32 (3H, m), 7.26-7.18 (3H, m), 7.10 (1H, t, J = 7.6 Hz), 6.53 (1H, s), 3.29-3.21 (1H, m), 2.92-2.84 (1H, m), 1.34 (3H, t, J = 7.6 Hz). |
| 1-542 | 8.91 (1H, d, J = 1.4 Hz), 8.41 (1H, s), 8.39-8.36 (3H, m), 7.92 (1H, s), 7.66 (1H, d, J = 8.2 Hz), 4.48 (2H, q, J = 7.0 Hz), 3.45-3.36 (1H, m), 3.03-2.94 (1H, m), 1.48-1.42 (6H, s). |
| 1-543 | 1H-NMR (DMSO-D6) δ: 9.70 (1H, s), 8.86 (1H, d, J = 4.6 Hz), 8.61 (2H, s), 8.55 (1H, d, J = 1.8 Hz), 8.24 (1H, dd, J1 = 8.2 Hz, J2 = 1.8 Hz), 8.17 (1H, s), 7.99 (1H, d, J = 8.2 Hz), 3.27-3.18 (1H, m), 2.85 (3H, d, J = 4.6 Hz), 2.83-2.76 (1H, m), 1.18 (3H, t, J = 7.3 Hz). |
| 1-545 | 8.38 (2H, s), 8.34 (1H, s), 7.91-7.86 (3H, m), 7.58 (1H, d, J = 7.8 Hz), 3.39-3.30 (1H, m), 2.93-2.84 (1H, m), 1.95-1.91 (2H, m), 1.66-1.62 (2H, m), 1.37 (3H, t, J = 7.6 Hz). |
| 1-547 | 8.36 (2H, s), 8.34 (1H, s), 8.25 (1H, dd, J1 = 7.8 Hz, J2 = 1.4 Hz), 7.89-7.83 (3H, m), 5.83 (1H, s), 3.09 (1H, td, J1 = 14.2 Hz, J2 = 6.9 Hz), 2.80 (3H, d, J = 5.0 Hz), 2.79-2.72 (1H, m), 1.26 (3H, t, J = 7.6 Hz). |
| 1-550 | 8.81 (1H, s), 8.43 (1H, s), 8.39 (2H, s), 8.30 (1H, d, J = 8.2 Hz), 7.93 (1H, s), 7.70 (1H, d, J = 8.2 Hz), 3.47-3.39 (1H, m), 3.03-2.94 (1H, m), 2.77 (3H, s), 1.44 (3H, t, J = 7.6 Hz). |
| 1-551 | 8.64 (1H, s), 8.45 (1H, s), 8.40 (2H, s), 8.17 (1H, d, J = 8.2 Hz), 7.93 (1H, s), 7.85 (2H, d, J = 7.8 Hz), 7.73 (1H, d, J = 8.2 Hz), 7.68 (1H, t, J = 8.0 Hz), 7.56 (2H, t, J = 7.3 Hz), 3.46-3.38 (1H, m), 3.05-2.96 (1H, m), 1.42 (3H, t, J = 7.6 Hz). |
| 1-552 | 8.71 (1H, dd, J1 = 6.9 Hz, J2 = 2.3 Hz), 8.39 (1H, d, J = 3.2 Hz), 8.26 (1H, dd, J1 = 7.8 Hz, J2 = 1.4 Hz), 7.78 (1H, td, J1 = 7.7 Hz, J2 = 1.2 Hz), 7.70 (1H, dd, J1 = 7.6 Hz, J2 = 1.4 Hz), |

TABLE 5-continued

| Compound No. | $^1$H-NMR Spectrum (CDCl$_3$) σ ppm: |
|---|---|
| | 7.68-7.64 (1H, m), 7, 57 (1H, dd, J1 = 8.0 Hz, J2 = 1.1 Hz), 7.33 (1H, t, J = 9.4 Hz), 3.36-3.28 (1H, m), 2.96-2.87 (1H, m), 1.37 (3H, t, J = 7.3 Hz). |
| 1-554 | 8.54 (1H, d, J = 1.8 Hz), 8.37 (2H, s), 8.32 (1H, s), 8.03 (1H, dd, J1 = 8.5 Hz, J2 = 2.1 Hz), 7.91 (1H, s), 7.28 (1H, d, J = 8.2 Hz), 3.40-3.31 (1H, m), 2.98-2.89 (1H, m), 1.40 (3H, t, J = 7.3 Hz). |
| 1-555 | 8.38 (2H, s), 8.34 (1H, s), 8.12 (1H, d, J = 2.3 Hz), 7.92 (1H, s), 7.63 (1H, d, J = 8.7 Hz), 7.54 (1H, dd, J1 = 8.7 Hz, J2 = 2.7 Hz), 3.40-3.31 (1H, m), 2.98-2.90 (1H, m), 1.38 (3H, t, J = 7.3 Hz). |
| 1-556 | 8.60 (1H, t, J = 1.4 Hz), 8.12 (1H, s), 8.08 (2H, d, J = 7.8 Hz), 7.88 (1H, d, J = 1.8 Hz), 7.72 (2H, d, J = 8.2 Hz), 3.62-3.53 (1H, m), 3.40-3.41 (1H, m), 1.30 (3H, t, J = 7.6 Hz). |
| 1-559 | 9.83 (1H, s), 8.55 (2H, s), 7.90 (1H, s), 7.81 (1H, dd, J1 = 5.7 Hz, J2 = 3.4 Hz), 7.72 (2H, dd, J1 = 5.7 Hz, J2 = 3.4 Hz), 7.56 (1H, dd, J1 = 6.0 Hz, J2 = 3.2 Hz), 7.45-7.42 (2H, m), 7.30-7.26 (2H, m), 7.14-7.10 (1H, m), 3.42-3.26 (2H, m), 1.30 (3H, t, J = 7.6 Hz). |
| 1-560 | 10.31 (1H, s), 8.47 (2H, s), 7.91 (1H, s), 7.84-7.82 (1H, m), 7.72-7.68 (2H, m), 7.60-7.58 (1H, m), 7.41-7.38 (2H, m), 7.23-7.20 (2H, m), 3.28-3.18 (1H, m), 3.15-3.07 (1H, m), 1.17 (3H, t, J = 7.6 Hz). |
| 1-561 | 8.46 (2H, s), 7.96 (1H, dd, J1 = 7.6 Hz, J2 = 1.6 Hz), 7.91 (1H, s), 7.79 (1H, td, J1 = 7.7 Hz, J2 = 1.5 Hz), 7.73 (1H, td, J1 = 7.7 Hz, J2 = 1.5 Hz), 7.54 (1H, dd, J1 = 7.8 Hz, J2 = 1.4 Hz), 7.04 (1H, br), 3.30 (2H, m), 2.79 (3H, d, J = 5.0 Hz), 1.31 (3H, t, J = 7.6 Hz). |
| 1-562 | 8.35 (2H, s), 8.22 (1H, d, J = 8.7 Hz), 7.92 (1H, s), 7.82 (1H, td, J1 = 7.7 Hz, J2 = 1.1 Hz), 7.69 (1H, td, J1 = 7.8 Hz, J2 = 1.4 Hz), 7.61 (1H, br), 3.41 (1H, dd, J1 = 14.2 Hz, J2 = 7.8 Hz), 3.08 (1H, dd, J1 = 13.5 Hz, J2 = 7.6 Hz), 3.02 (3H, s), 2.67 (3H, s), 1.41 (3H, t, J = 7.3 Hz). |
| 1-563 | 8.31-8.28 (3H, m), 7.95-7.92 (3H, m), 7.62-7.60 (1H, m), 3.07-3.00 (1H, m), 2.93-2.87 (1H, m), 1.23 (3H, t, J = 7.3 Hz). |
| 1-564 | 8.44 (2H, s), 7.86-7.83 (4H, m), 7.72-7.69 (2H, m), 7.64-7.61 (2H, m), 7.57-7.53 (1H, m), 7.44-7.40 (2H, m), 2.97-2.80 (2H, m), 1.13 (3H, t, J = 7.6 Hz). |
| 1-565 | 8.43 (2H, s), 7.89-7.84 (3H, m), 7.76 (1H, d, J = 7.3 Hz), 7.72-7.69 (2H, m), 7.62-7.60 (1H, m), 7.54-7.51 (1H, m), 7.36 (1H, t, J = 8.0 Hz), 2.93-2.81 (2H, m), 1.09 (3H, t, J = 7.3 Hz). |
| 1-566 | 9.96 (1H, br), 8.42 (2H, s), 7.86-7.84 (2H, m), 7.70 (2H, d, J = 8.7 Hz), 7.74-7.71 (2H, m), 7.64-7.62 (1H, m), 7.36 (1H, d, J = 8.7 Hz), 2.89-2.80 (2H, m), 1.11 (3H, t, J = 7.6 Hz). |
| 1-567 | 8.27 (1H, dd, J1 = 7.8 Hz, J2 = 1.4 Hz), 8.20 (2H, s), 7.96 (1H, s), 7.86 (1H, td, J1 = 7.7 Hz, J2 = 1.1 Hz), 7.69 (1H, td, J1 = 7.7 Hz, J2 = 1.5 Hz), 7.35 (1H, dd, J1 = 7.8 Hz, J2 = 0.9 Hz), 3.51-3.42 (1H, m), 3.17-3.08 (1H, m), 2.61 (3H, s), 1.95 (3H, s), 1.43 (3H, t, J = 7.3 Hz). |
| 1-569 | 9.21 (1H, br), 8.49 (1H, s), 7.91 (1H, s), 7.81 (1H, s), 7.75-7.73 (2H, m), 7.69-7.66 (1H, m), 7.45-7.38 (2H, m), 7.36-7.32 (1H, m), 2.88-2.81 (1H, m), 2.79-2.71 (1H, m), 1.06 (3H, t, J = 6.9 Hz). |
| 1-572 | 8.27 (1H, dd, J1 = 7.8 Hz, J2 = 1.8 Hz), 8.22 (1H, s), 7.93-7.90 (2H, m), 7.85 (1H, td, J1 = 7.6 Hz, J2 = 1.7 Hz), 7.79 (1H, td, J1 = 7.6 Hz, J2 = 1.4 Hz), 7.58 (1H, dd, J1 = 7.8 Hz, J2 = 1.4 Hz), 7.49-7.45 (2H, m), 7.41-7.36 (1H, m), 3.16 (2H, q, J = 7.3 Hz), 1.24 (3H, t, J = 7.3 Hz). |
| 1-577 | 8.28 (1H, dd, J1 = 7.8 Hz, J2 = 1.8 Hz), 8.21 (1H, s), 7.93 (1H, t, J = 1.6 Hz), 7.85 (1H, td, J1 = 7.7 Hz, J2 = 1.7 Hz), 7.82-7.77 (2H, m), 7.57 (1H, dd, J1 = 7.8 Hz, J2 = 1.4 Hz), 7.40 (1H, t, J = 7.6 Hz), 7.35 (1H, dt, J1 = 8.4 Hz, J2 = 1.6 Hz), 3.16 (2H, q, J = 7.5 Hz), 1.24 (3H, t, J = 7.6 Hz). |
| 1-578 | 8.27 (1H, dd, J1 = 7.6 Hz, J2 = 1.6 Hz), 8.20 (1H, s), 7.88-7.78 (4H, m), 7.57 (1H, dd, J1 = 7.3 Hz, J = 1.4 Hz), 7.46-7.43 (2H, m), 3.17 (2H, q, J = 7.5 Hz), 1.24 (1H, t, J = 7.6 Hz). |
| 1-579 | 8.27 (1H, dd, J1 = 7.8 Hz, J2 = 1.8 Hz), 8.21 (1H, s), 8.09 (1H, t, J = 1.8 Hz), 7.87-7.78 (3H, m), 7.56 (1H, dd, J1 = 7.8 Hz, J2 = 1.4 Hz), 7.51 (1H, dq, J1 = 7.9 Hz, J2 = 1.0 Hz), 7.33 (1H, t, J = 7.8 Hz), 3.16 (2H, q, J = 7.5 Hz), 1.24 (3H, t, J = 7.3 Hz). |
| 1-580 | 8.28 (1H, dd, J1 = 7.8 Hz, J2 = 1.4 Hz), 8.23 (1H, s), 7.88-7.79 (4H, m), 7.57 (1H, dd, J1 = 7.3 Hz, J2 = 1.4 Hz), 7.49 (1H, t, J = 8.2 Hz), 7.25-7.22 (1H, m), 3.18 (2H, q, J = 7.5 Hz), 1.25 (3H, t, J = 7.3 Hz). |
| 1-581 | 8.28 (1H, dd, J1 = 7.8 Hz, J2 = 1.8 Hz), 8.22 (1H, s), 8.02 (1H, d, J = 7.8 Hz), 7.86 (1H, td, J1 = 7.6 Hz, J2 = 1.7 Hz), 7.83-7.78 (2H, m), 7.68 (1H, d, J = 7.3 Hz), 7.60 (1H, td, J1 = 7.8 Hz, J2 = 1.4 Hz), 7.54 (1H, t, J = 7.6 Hz), 3.18 (2H, q, J = 7.5 Hz), 1.26 (3H, t, J = 7.6 Hz). |
| 1-582 | 8.29-8.27 (2H, m), 8.20 (1H, s), 8.10 (1H, d, J = 7.3 Hz), 7.89-7.80 (2H, m), 7.65-7.57 (3H, m), 3.19 (2H, q, J = 7.3 Hz), 1.25 (3H, t, J = 7.1 Hz). |
| 1-583 | 8.29 (1H, dd, J1 = 7.6 Hz, J2 = 1.6 Hz), 8.11 (1H, s), 8.00 (1H, d, J = 7.3 Hz), 7.89 (1H, td, J1 = 7.6 Hz, J2 = 1.8 Hz), 7.84 (1H, td, J1 = 7.6 Hz, J2 = 1.5 Hz), 7.66-7.59 (2H, m), 7.47 (1H, dd, J1 = 7.6 Hz, J2 = 1.6 Hz), 3.27 (2H, q, J = 7.5 Hz), 2.39 (3H, s), 1.26 (3H, t, J = 7.3 Hz). |
| 1-584 | 8.29 (1H, dd, J1 = 7.6 Hz, J2 = 1.6 Hz), 8.12 (1H, s), 7.99 (1H, d, J = 7.3 Hz), 7.91-7.82 (1H, m), 7.66-7.59 (2H, m), 7.50 (1H, dd, J1 = 7.3 Hz, J2 = 1.4 Hz), 3.32 (2H, br), 2.83 (2H, br), 1.26 (3H, t, J = 7.3 Hz), 1.11 (3H, t, J = 7.6 Hz). |
| 1-585 | 8.37 (1H, s), 8.29-8.25 (2H, m), 7.94-7.85 (2H, m), 7.69-7.61 (2H, m), 7.54 (1H, dd, J1 = 7.8 Hz, J2 = 1.4 Hz), 3.37 (2H, q, J = 7.5 Hz), 1.30 (3H, t, J = 7.3 Hz). |
| 1-587 | 8.38 (1H, s), 8.28 (2H, d, J = 7.6 Hz, J2 = 1.6 Hz), 7.91 (1H, td, J1 = 7.6 Hz, J2 = 1.7 Hz), 7.86 (1H, td, J1 = 7.7 Hz, J2 = 1.7 Hz), 7.69 (1H, d, J = 7.8 Hz), 7.63 (1H, t, J = 7.8 Hz), 7.51 (1H, dd, J1 = 7.6 Hz, J2 = 1.6 Hz), 3.36 (2H, br), 1.29 (3H, t, J = 7.6 Hz). |
| 1-594 | 8.43 (1H, d, J = 8.2 Hz), 8.31 (1H, s), 8.20 (1H, s), 8.10-8.06 (2H, m), 7.85 (1H, d, J = 1.4 Hz), 7.67-7.59 (2H, m), 3.24 (2H, q, J = 7.5 Hz), 1.28 (3H, t, J = 7.6 Hz). |
| 1-596 | 8.28 (1H, dd, J1 = 7.3 Hz, J2 = 1.8 Hz), 8.28 (1H, s), 8.04 (2H, d, J = 8.2 Hz), 7.87 (1H, td, J1 = 7.6 Hz, J2 = 1.8 Hz), 7.82 (1H, td, J1 = 7.6 Hz, J2 = 1.4 Hz), 7.73 (2H, d, J = 7.8 Hz), 7.58 (1H, dd, J1 = 7.8 Hz, J2 = 1.4 Hz), 3.17 (2H, q, J = 7.3 Hz), 1.28 (3H, t, J = 7.3 Hz). |
| 1-609 | 8.27 (1H, dd, J1 = 7.8 Hz, J2 = 1.4 Hz), 8.20 (1H, s), 7.87-7.82 (3H, m), 7.79 (1H, td, J1 = 7.8 Hz, J2 = 1.4 Hz), 7.58 (1H, dd, J1 = 7.8 Hz, J2 = 1.4 Hz), 7.49 (2H, dt, J1 = 8.5 Hz, J2 = 2.1 Hz), 3.13 (2H, q, J = 7.5 Hz), 1.36 (9H, s), 1.26 (3H, t, J = 7.1 Hz). |
| 1-610 | 8.28 (1H, dd, J1 = 7.8 Hz, J2 = 1.4 Hz), 8.26 (1H, s), 8.00 (2H, dt, J1 = 8.7 Hz, J2 = 1.8 Hz), 7.86 (1H, td, J1 = 7.6 Hz, J2 = 1.7 Hz), 7.80 (1H, td, J1 = 7.6 Hz, J2 = 1.4 Hz), 7.71 (2H, dt, |

TABLE 5-continued

| Compound No. | $^1$H-NMR Spectrum (CDCl$_3$) σ ppm: |
|---|---|
|  | J1 = 8.4 Hz, J2 = 1.9 Hz), 7.67-7.65 (2H, m), 7.59 (1H, dd, J1 = 7.8 Hz, J2 = 1.4 Hz), 7.49-7.45 (2H, m), 7.40-7.36 (1H, m), 3.17 (2H, q, J = 7.5 Hz), 1.25 (3H, t, J = 7.3 Hz). |
| 1-611 | 8.27 (1H, dd, J1 = 7.6 Hz, J2 = 1.6 Hz), 8.17 (1H, s), 7.90-7.86 (2H, m), 7.85-7.83 (1H, m), 7.79 (1H, td, J1 = 7.6 Hz, J2 = 1.4 Hz), 7.57 (1H, dd, J1 = 7.8 Hz, J2 = 1.4 Hz), 7.39-7.35 (2H, m), 7.16-7.06 (5H, m), 3.17 (2H, q, J = 7.5 Hz), 1.24 (3H, t, J = 7.3 Hz). |
| 1-612 | 8.29-8.27 (2H, m), 8.03 (2H, d, J = 8.7 Hz), 7.87 (1H, td, J1 = 7.6 Hz, J2 = 1.7 Hz), 7.83 (1H, td, J1 = 7.7 Hz, J2 = 1.5 Hz), 7.76 (2H, d, J = 8.7 Hz), 7.57 (1H, dd, J1 = 7.3 Hz, J2 = 1.8 Hz). 3.17 (2H, q, J = 7.5 Hz), 1.25 (3H, t, J = 7.5 Hz). |
| 1-613 | 8.71 (1H, s), 8.51 (1H, d, J = 8.2 Hz), 8.28 (1H, dd, J1 = 7.8 Hz, J2 = 1.8 Hz), 7.88 (1H, td, J1 = 7.6 Hz, J2 = 1.7 Hz), 7.82 (1H, td, J1 = 7.6 Hz, J2 = 1.4 Hz), 7.77 (1H, s), 7.67 (1H, dd, J1 = 8.2 Hz, J2 = 1.4 Hz), 7.61 (1H, dd, J1 = 7.3 Hz, J2 = 1.4 Hz), 3.23 (2H, q, J = 7.3 Hz), 1.27 (3H, t, J = 7.3 Hz). |
| 1-631 | 8.37 (2H, s), 8.34 (1H, s), 8.29 (1H, dd, J1 = 7.6 Hz, J2 = 1.6 Hz), 7.88-7.83 (3H, m), 7.58 (1H, dd, J1 = 7.3 Hz, J2 = 1.8 Hz), 3.21 (2H, q, J = 7.5 Hz), 1.26 (3H, t, J = 7.6 Hz). |
| 1-637 | 8.60 (2H, s), 8.29 (1H, dd, J1 = 7.6 Hz, J2 = 1.6 Hz), 7.95-7.86 (3H, m), 7.51 (1H, dd, J1 = 7.6 Hz, J2 = 1.6 Hz), 3.35 (2H, dd, J1 = 20.4 Hz, J2 = 7.1 Hz), 1.29 (3H, t, J = 7.6 Hz). |
| 1-638 | 8.30 (1H, dd, J1 = 7.6 Hz, J2 = 1.6 Hz), 8.25 (2H, s), 7.93 (1H, td, J1 = 7.6 Hz, J2 = 1.7 Hz), 7.87 (1H, td, J1 = 7.8 Hz, J2 = 1.4 Hz), 7.82 (1H, s), 7.55 (1H, dd, J1 = 7; .8 Hz, J2 = 1.4 Hz), 4.08 (2H, br), 3.20 (2H, q, J = 7.5 Hz), 1.27 (3H, t, J = 7.6 Hz). |
| 1-639 | 8.50 (2H, s), 8.23 (1H, dd, J1 = 7.6 Hz, J2 = 1.6 Hz), 7.97 (1H, s), 7.89-7.85 (2H, m), 7.57 (1H, dd, J1 = 7.6 Hz, J2 = 1.6 Hz), 4.19 (2H, q, J = 7.8 Hz), 3.10 (2H, q, J = 7.3 Hz), 1.24 (3H, t, J = 7.8 Hz), 1.04 (3H, t, J = 7.3 Hz). |
| 1-640 | 8.61 (2H, s), 8.32-8.30 (1H, m), 8.02 (1H, s), 8.00-7.93 (2H, m), 7.66-7.64 (1H, m), 3.35 (2H, q, J = 7.5 Hz), 1.33 (3H, t, J = 7.6 Hz). |
| 1-641 | 8.37 (2H, s), 8.24 (1H, s), 7.87 (1H, s), 7.85 (1H, dd, J1 = 8.2 Hz, J2 = 1.4 Hz), 7.72 (1H, t, J = 8.0 Hz), 7.43 (1H, dd, J1 = 8.0 Hz, J2 = 1.1 Hz), 3.57 (2H, q, J = 7.5 Hz), 1.41 (3H, t, J = 7.6 Hz). |
| 1-642 | 8.36 (2H, s), 8.32 (1H, s), 8.26 (1H, d, J = 2.7 Hz), 7.89 (1H, s), 7.83 (1H, dd, J1 = 8.5 Hz, J2 = 2.5 Hz), 7.52 (1H, d, J = 8.2 Hz), 3.21 (2H, q, J = 7.5 Hz), 1.29 (3H, t, J = 7.6 Hz). |
| 1-643 | 8.38 (2H, s), 8.36 (1H, s), 8.21 (1H, d, J = 8.2 Hz), 7.91 (1H, s), 7.75 (1H, dd, J1 = 8.5 Hz, J2 = 2.1 Hz), 7.60 (1H, d, J = 1.8 Hz), 3.38-3.29 (1H, m), 2.98-2.89 (1H, m), 1.38 (3H, t, J = 7.3 Hz). |
| 1-644 | 8.39 (2H, s), 8.24 (1H, s), 8.19 (1H, dd, J1 = 7.8 Hz, J2 = 1.4 Hz), 7.94 (1H, dd, J1 = 8.2 Hz, J2 = 1.4 Hz), 7.89 (1H, s), 7.79 (1H, t, J = 8.0 Hz), 3.21 (2H, q, J = 7.5 Hz), 1.28 (3H, t, J = 7.3 Hz). |
| 1-646 | 8.55 (1H, d, J = 1.8 Hz), 8.37 (3H, s), 8.14 (1H, dd, J1 = 8.0 Hz, J2 = 2.1 Hz), 7.90 (1H, s), 7.74 (1H, d, J = 8.2 Hz), 3.27 (2H, q, J = 7.5 Hz), 1.30 (3H, t, J = 7.3 Hz). |
| 1-647 | 8.44 (1H, d, J = 8.2 Hz), 8.39 (1H, s), 8.38 (2H, br), 8.10 (1H, d, J = 8.2 Hz), 7.90 (1H, s), 7.85 (1H, s), 3.27 (2H, q, J = 7.5 Hz), 1.29 (3H, t, J = 7.6 Hz). |
| 1-752 | 8.27-8.24 (3H, m), 8.09 (1H, s), 7.88-7.78 (2H, m), 7.75 (1H, s), 7.55 (1H, dd, J1 = 7.3 Hz, J2 = 1.4 Hz), 3.18 (2H, q, J = 7.3 Hz), 1.24 (3H, t, J = 7.6 Hz). |
| 1-765 | 8.70 (1H, s), 8.45 (1H, s), 8.34 (1H, s), 8.30 (1H, s), 8.28 (1H, dd, J1 = 8.0 Hz, J2 = 1.6 Hz), 7.88 (1H, td, J1 = 7.6 Hz, J2 = 1.8 Hz), 7.83 (1H, td, J1 = 7.7 Hz, J2 = 1.5 Hz), 7.58 (1H, dd, J1 = 7.3 Hz, J2 = 1.4 Hz), 3.21 (2H, q, J = 7.5 Hz), 1.26 (3H, t, J = 7.6 Hz). |
| 1-782 | 8.54 (1H, s), 8.33 (1H, s), 8.31 (1H, s), 8.26 (1H, dd, J1 = 8.0 Hz, J2 = 1.6 Hz), 8.15 (1H, s), 8.09 (1H, br), 7.87 (1H, td, J1 = 7.6 Hz, J2 = 1.8 Hz), 7.82 (1H, td, J1 = 7.6 Hz, J2 = 1.4 Hz), 7.70 (2H, d, J = 7.8 Hz), 7.57 (1H, dd, J1 = 7.3 Hz, J2 = 1.4 Hz), 7.40 (2H, t, J = 7.8 Hz), 7.19 (1H, t, J = 7.1 Hz), 3.26 (2H, q, J = 7.3 Hz), 1.27 (3H, t, J = 7.6 Hz). |
| 1-783 | 8.49 (1H, s), 8.32 (1H, s), 8.28 (1H, s), 8.25 (1H, dd, J1 = 7.8 Hz, J2 = 1.8 Hz), 8.17 (1H, br), 8.13 (1H, s), 7.87 (1H, td, J1 = 7.4 Hz, J2 = 1.7 Hz), 7.82 (1H, td, J1 = 7.7 Hz, J2 = 1.2 Hz), 7.69-7.65 (2H, m), 7.56 (1H, dd, J1 = 7.8 Hz, J2 = 1.4 Hz), 7.38-7.35 (2H, m), 3.27 (2H, q, J = 7.5 Hz), 1.26 (3H, t, J = 7.3 Hz). |
| 1-784 | 8.37 (2H, s), 8.36 (1H, s), 8.31 (1H, dd, J1 = 8.7 Hz, J2 = 5.5 Hz), 7.89 (1H, s), 7.53 (1H, ddd, J1 = 9.4 Hz, J2 = 6.9 Hz, J3 = 2.1 Hz), 7.34 (1H, dd, J1 = 7.8 Hz, J2 = 2.7 Hz), 3.20 (2H, q, J = 7.5 Hz), 1.27 (3H, t, J = 7.3 Hz). |
| 1-785 | 8.37 (2H, s), 8.32 (1H, s), 8.14 (1H, d, J = 7.8 Hz), 7.87 (1H, s), 7.61 (1H, dd, J1 = 8.2 Hz, J2 = 1.4 Hz), 7.38 (1H, d, J = 1.4 Hz), 3.16 (2H, q, J = 7.5 Hz), 2.56 (3H, s), 1.24 (3H, t, J = 7.5 Hz). |
| 1-786 | 8.37 (2H, s), 8.34 (1H, s), 8.17 (1H, d, J = 8.7 Hz), 7.88 (1H, s), 7.25 (1H, dd, J1 = 9.2 Hz, J2 = 2.7 Hz), 7.04 (1H, d, J = 2.3 Hz), 3.97 (3H, s), 3.15 (2H, q, J = 7.5 Hz), 1.24 (3H, t, J = 7.3 Hz). |
| 1-787 | 8.75 (1H, s), 8.42 (1H, s), 8.24 (1H, s), 8.19 (1H, s), 7.91 (1H, s), 3.92 (2H, q, J = 7.5 Hz), 1.38 (3H, t, J = 7.6 Hz). |
| 1-788 | 8.29 (1H, s), 8.28 (1H, d, J = 6.4 Hz), 8.06 (2H, d, J = 6.9 Hz), 7.87 (1H, t, J = 7.3 Hz), 7.82 (1H, t, J = 7.6 Hz), 7.72 (2H, d, J = 8.2 Hz), 7.58 (1H, t, J = 7.8 Hz), 3.15 |
| 1-790 | 8.37 (2H, s), 8.29 (1H, dd, J1 = 7.3 Hz, J2 = 1.8 Hz), 7.96-7.90 (2H, m), 7.88 (1H, s), 7.61 (1H, dd, J1 = 7.3 Hz, J2 = 1.8 Hz), 3.32 (2H, q, J = 7.5 Hz), 1.29 (3H, t, J = 7.6 Hz). |
| 1-791 | 8.34 (1H, t, J = 1.8 Hz), 8.29 (1H, s), 8.23 (1H, dd, J1 = 7.8 Hz, J2 = 1.8 Hz), 7.99 (1H, d, J = 7.8 Hz), 7.86-7.72 (3H, m), 7.57-7.52 (2H, m), 3.24 (2H, q, J = 7.5 Hz), 1.25 (3H, t, J = 7.3 Hz). |
| 1-792 | 8.63 (1H, s), 8.38 (1H, s), 8.36 (1H, s), 8.26 (1H, dd, J1 = 7.8, J2 = 1.8 Hz), 8.19 (1H, s), 7.87 (1H, td, J1 = 7.7 Hz, J2 = 1.7 Hz), 7.82 (1H, td, J1 = 7.6 Hz, J2 = 1.4 Hz), 7.58 (1H, dd, J1 = 7.3 Hz, J2 = 1.4 Hz), 3.25 (2H, q, J = 7.5 Hz), 2.72 (3H, s), 1.27 (3H, t, J = 7.3 Hz). |
| 1-793 | 8.33 (2H, s), 8.32 (1H, s), 8.28 (1H, dd, J1 = 7.8 Hz, J2 = 1.8 Hz), 7.90-7.85 (2H, m), 7.83 (1H, td, J1 = 7.7 Hz, J2 = 1.5 Hz), 7.57 (1H, dd, J1 = 7.6 Hz, J2 = 1.6 Hz), 6.57 (1H, br), 3.22 (2H, q, J = 7.5 Hz), 2.96 (3H, d, J = 5.0 Hz), 1.27 (3H, t, J = 7.6 Hz). |

TABLE 5-continued

| Compound No. | $^1$H-NMR Spectrum (CDCl$_3$) σ ppm: |
|---|---|
| 1-794 | 8.24-8.21 (1H, m), 8.20 (1H, s), 7.86-7.76 (4H, m), 7.53 (1H, dd, J1 = 7.8 Hz, J2 = 1.4 Hz), 7.33 (1H, t, J = 2.1 Hz), 3.16 (2H, qJ = 7.3 Hz), 1.22 (3H, t, J = 7.3 Hz) |
| 1-795 | 8.42 (2H, d, J = 8.7 Hz), 8.36 (1H, s), 8.29 (1H, dd, J1 = 7.6 Hz, J2 = 1.6 Hz), 7.91-7.83 (3H, m), 7.58 (1H, dd, J1 = 7.3 Hz, J2 = 1.8 Hz), 3.22 (2H, q, J = 7.5 Hz), 1.27 (3H, t, J = 7.3 Hz). |
| 1-796 | 8.45 (2H, d, J = 6.4 Hz), 8.32 (1H, s), 8.26 (1H, dd, J1 = 7.6 Hz, J2 = 1.6 Hz), 8.03 (1H, s), 7.89-7.80 (4H, m), 7.65 (1H, tt, J1 = 7.3 Hz, J2 = 1.5 Hz), 7.58-7.52 (3H, m), 3.24 (2H, q, J = 7.5 Hz), 1.26 (3H, t, J = 7.6 Hz). |
| 1-797 | 8.37-8.25 (5H, m), 7.93 (1H, s), 7.86-7.81 (2H, m), 7.60 (2H, d, J = 7.8 Hz), 7.56 (1H, d, J = 7.8 Hz), 7.36 (2H, q, J = 7.6 Hz), 7.19 (1H, q, J = 6.9 Hz), 3.27-3.20 (2H, m), 1.26 (3H, t, J = 7.3 Hz). |
| 1-798 | 8.32 (1H, s), 8.26 (1H, dd, J1 = 7.8 Hz, J2 = 1.8 Hz), 8.23 (2H, s), 7.86 (1H, td, J1 = 7.6 Hz, J2 = 1.7 Hz), 7.81 (1H, td, J1 = 7.6 Hz, J2 = 1.5 Hz), 7.75 (1H, s), 7.57 (1H, dd, J1 = 7.3 Hz, J2 = 1.4 Hz), 3.24 (2H, q, J = 7.3 Hz), 2.00 (3H, t, J = 18.3 Hz), 1.26 (3H, t, J = 7.6 Hz). |
| 1-800 | 8.32 (1H, s), 8.31 (1H, s), 8.27 (1H, dd, J1 = 7.6 Hz, J2 = 1.6 Hz), 8.13 (1H, s), 7.88-7.78 (3H, m), 7.68-7.65 (2H, m), 7.58 (1H, dd, J1 = 7.8 Hz, J2 = 1.4 Hz), 7.51-7.47 (2H, m), 7.43-7.40 (1H, m), 3.20 (2H, q, J = 7.5 Hz), 1.25 (3H, t, J = 7.3 Hz). |
| 1-801 | 8.29-8.23 (2H, m), 7.91-7.81 (4H, m), 7.58-7.54 (1H, m), 7.32-7.30 (1H, m), 3.19 (2H, q, J = 7.5 Hz), 2.05-1.98 (1H, m), 1.25 (3H, t, J = 7.3 Hz), 1.08-1.03 (2H, m), 0.84-0.79 (2H, m). |
| 1-802 | 8.45 (1H, d, J = 2.3 Hz), 8.37 (3H, s), 8.03 (1H, dd, J1 = 8.2 Hz, J2 = 2.3 Hz), 7.86 (1H, s), 7.70-7.67 (2H, m), 7.62 (1H, d, J = 8.2 Hz), 7.56-7.46 (3H, m), 3.25 (2H, q, J = 7.5 Hz), 1.29 (3H, t, J = 7.3 Hz). |
| 1-803 | 8.38 (1H, s), 8.36 (1H, d, J = 2.3 Hz), 8.32 (2H, s), 7.98 (1H, dd, J1 = 8.0 Hz, J2 = 2.1 Hz), 7.83 (1H, s), 7.62-7.56 (3H, m), 7.47 (2H, d, J = 8.2 Hz), 3.29 (2H, q, J = 7.5 Hz), 1.29 (3H, t, J = 7.3 Hz). |
| 1-804 | 8.35 (2H, s), 8.28 (1H, s), 7.86 (1H, s), 7.81 (1H, d, J = 2.7 Hz), 7.48-7.44 (3H, m), 7.34-7.24 (2H, m), 7.12 (2H, d, J = 7.8 Hz), 3.16 (2H, q, J = 7.5 Hz), 1.24 (3H, t, J = 7.6 Hz). |
| 1-805 | 8.58 (1H, s), 8.38 (1H, s), 8.37 (2H, s), 8.15 (1H, d, J = 8.2 Hz), 7.91 (1H, s), 7.74 (1H, d, J = 8.2 Hz), 3.29 (2H, q, J = 7.5 Hz), 1.31 (3H, t, J = 7.3 Hz). |
| 1-806 | 8.35 (1H, d, J = 1.8 Hz), 8.32 (3H, br), 7.96 (1H, dd, J1 = 8.2 Hz, J2 = 2.3 Hz), 7.84 (1H, s), 7.42 (1H, d, J = 8.2 Hz), 3.23 (2H, q, J = 7.5 Hz), 1.27 (3H, t, J = 7.6 Hz). |
| 1-808 | 8.63 (1H, d, J = 1.8 Hz), 8.43 (1H, s), 8.39-8.38 (3H, m), 7.91 (1H, s), 7.83 (1H, d, J = 8.2 Hz), 4.34 (3H, s), 3.33 (2H, q, J = 7.5 Hz), 1.32 (3H, t, J = 7.6 Hz). |
| 1-809 | 9.02 (1H, d, J = 1.8 Hz), 8.64 (1H, dd, J1 = 8.2 Hz, J2 = 1.8 Hz), 8.39 (3H, s), 7.89 (1H, s), 7.71 (1H, d, J = 8.2 Hz), 4.49 (3H, s), 3.28 (2H, q, J = 7.5 Hz), 1.32 (3H, t, J = 7.6 Hz). |
| 1-810 | 8.35 (2H, s), 8.27 (1H, s), 7.89 (1H, d, J = 1.8 Hz), 7.85 (1H, s), 7.48-7.39 (2H, m), 3.15 (2H, q, J = 7.5 Hz), 2.14-2.06 (1H, m), 1.24 (3H, t, J = 7.3 Hz), 1.23-1.17 (2H, m), 0.90-0.85 (2H, m). |
| 1-814 | 8.29 (1H, s), 8.13 (1H, dd, J = 7.8, 1.4 Hz), 7.97 (1H, s), 7.90 (1H, s), 7.78 (1H, td, J1 = 7.7 Hz, J2 = 1.5 Hz), 7.71 (1H, td, J1 = 7.6 Hz, J2 = 1.2 Hz), 7.51-7.48 (2H, m), 3.25 (2H, q, J = 7.3 Hz), 1.77 (2H, dd, J1 = 7.8 Hz, J2 = 5.5 Hz), 1.50 (2H, dd, J1 = 7.8 Hz, J2 = 5.5 Hz), 1.20 (3H, t, J = 7.3 Hz). |
| 1-815 | 8.96 (1H, s), 8.54 (1H, d, J = 8.2 Hz), 8.40 (1H, s), 8.38 (2H, s), 7.88 (1H, s), 7.69 (1H, d, J = 8.2 Hz), 3.30 (2H, q, J = 7.5 Hz), 2.73 (3H, s), 1.31 (3H, t, J = 7.6 Hz). |
| 1-816 | 8.33 (2H, s), 8.21 (1H, s), 7.83 (1H, s), 7.70 (1H, d, J = 2.3 Hz), 7.39-7.32 (2H, m), 7.30 (1H, s), 7.20-7.10 (3H, m), 6.62 (1H, s), 3.18 (2H, q, J = 7.5 Hz), 1.25 (3H, t, J = 7.6 Hz). |
| 1-817 | 8.35 (2H, s), 8.27 (1H, s), 8.00 (1H, d, J = 1.8 Hz), 7.87 (1H, s), 7.59-7.58 (2H, m), 7.49-7.48 (3H, m), 7.45 (1H, dd, J1 = 8.2 Hz, J2 = 2.3 Hz), 7.36 (1H, d, J = 8.2 Hz), 3.15 (2H, q, J = 7.5 Hz), 1.23 (3H, t, J = 7.3 Hz). |
| 1-818 | 8.42 (1H, d, J = 1.8 Hz), 8.34 (2H, s), 8.31 (1H, s), 8.23 (1H, dd, J1 = 8.0 Hz, J2 = 2.1 Hz), 7.88 (1H, s), 7.75-7.74 (2H, m), 7.69 (1H, d, J = 8.2 Hz), 7.56-7.56 (3H, m), 3.21 (2H, q, J = 7.5 Hz), 1.21 (3H, t, J = 7.3 Hz). |
| 1-819 | 8.78 (1H, d, J = 2.3 Hz), 8.42 (1H, dd, J1 = 8.2 Hz, J2 = 1.8 Hz), 8.34 (2H, s), 8.32 (1H, s), 8.04 (2H, d, J = 7.8 Hz), 7.89 (1H, s), 7.72-7.69 (2H, m), 7.62 (2H, t, J = 7.6 Hz), 3.25 (2H, q, J = 7.5 Hz), 1.27 (3H, t, J = 7.3 Hz). |
| 1-820 | 8.89 (1H, d, J = 1.8 Hz), 8.52 (1H, dd, J1 = 8.5 Hz, J2 = 1.6 Hz), 8.37 (3H, s), 7.89 (1H, s), 7.67 (1H, d, J = 7.8 Hz), 4.51 (2H, d, J = 7.2 Hz), 3.27 (2H, q, J = 7.5 Hz), 1.47 (3H, t, J = 6.9 Hz), 1.30 (3H, t, J = 7.6 Hz). |
| 1-821 | 1H-NMR (DMSO-D6) δ: 9.45 (1H, s), 8.97 (1H, d, J = 5.0 Hz), 8.61 (2H, s), 8.58 (1H, d, J = 1.8 Hz), 8.41 (1H, dd, J1 = 8.0 Hz, J2 = 2.1 Hz), 8.15 (1H, s), 8.00 (1H, d, J = 8.2 Hz), 3.51 (2H, q, J = 7.5 Hz), 2.86 (3H, d, J = 4.6 Hz), 1.18 (3H, t, J = 7.3 Hz). |
| 1-823 | 8.37 (2H, s), 8.31 (1H, s), 7.96-7.94 (2H, m), 7.89 (1H, s), 7.59 (1H, d, J = 7.8 Hz), 3.20 (2H, q, J = 7.5 Hz), 2.01-1.98 (2H, m), 1.65-1.62 (2H, m), 1.27 (3H, t, J = 7.3 Hz). |
| 1-825 | 8.36-8.33 (4H, m), 8.00 (1H, dd, J = 7.8 Hz, J2 = 1.8 Hz), 7.89 (1H, t, J = 7.8 Hz), 7.88 (1H, s), 5.77 (1H, s), 3.13 (2H, q, J = 7.5 Hz), 2.75 (3H, d, J = 4.6 Hz), 1.26 (3H, t, J = 7.6 Hz). |
| 1-827 | 8.52 (2H, s), 8.39 (1H, s), 8.37 (2H, s), 7.90 (1H, s), 3.16-3.07 (2H, m), 3.03-2.94 (2H, m), 1.28 (3H, t, J = 7.3 Hz). |
| 1-828 | 8.79 (1H, s), 8.43 (1H, d, J = 8.2 Hz), 8.38 (3H, s), 7.90 (1H, s), 7.70 (1H, d, J = 7.8 Hz), 3.28 (2H, q, J = 7.5 Hz), 2.77 (3H, s), 1.30 (3H, t, J = 7.3 Hz). |
| 1-829 | 8.64 (1H, s), 8.40-8.39 (3H, m), 8.28 (1H, d, J = 7.8 Hz), 7.91 (1H, s), 7.85 (1H, d, J = 8.2 Hz), 7.71 (1H, t, J = 7.8 Hz), 7.58 (1H, t, J = 7.6 Hz), 3.29 (2, q, J = 7.2 Hz), 1.31 (3H, t, J = 7.3 Hz). |
| 1-830 | 8.71 (1H, dd, J1 = 6.6 Hz, J2 = 2.1 Hz), 8.39 (1H, d, J = 3.7 Hz), 8.28 (1H, dd, J1 = 7.6 Hz, J2 = 1.6 Hz), 7.87 (1H, td, J1 = 7.7 Hz, J2 = 1.7 Hz), 7.82 (1H, td, J1 = 7.6 Hz, J2 = 1.4 Hz), 7.65-7.61 (1H, m), 7.58 (1H, dd, J1 = 7.6 Hz, J2 = 1.6 Hz), 7.30 (1H, t, J = 9.4 Hz), 3.27 (2H, q, J = 7.3 Hz), 1.28 (3H, t, J = 7.6 Hz). |

TABLE 5-continued

| Compound No. | $^1$H-NMR Spectrum (CDCl$_3$) σ ppm: |
|---|---|
| 1-831 | 8.99 (1H, d, J = 1.8 Hz), 8.55 (1H, dd, J1 = 8.0 Hz, J2 = 2.1 Hz), 8.38 (2H, s), 8.36 (1H, s), 8.15 (1H, s), 7.88 (1H, s), 7.63 (1H, d, J = 8.2 Hz), 4.04 (3H, s), 3.26 (2H, q, J = 7.3 Hz), 1.30 (3H, t, J = 7.3 Hz). |
| 1-832 | 8.58 (1H, d, J = 1.8 Hz), 8.36 (2H, s), 8.31 (1H, s), 8.20 (1H, dd, J1 = 8.2 Hz, J2 = 2.3 Hz), 7.88 (1H, s), 7.28 (1H, d, J = 7.8 Hz), 3.21 (2H, q, J = 7.3 Hz), 1.28 (3H, t, J = 7.6 Hz). |
| 1-833 | 8.37 (2H, s), 8.34 (1H, s), 8.12 (1H, d, J = 2.3 Hz), 7.90 (1H, s), 7.72-7.69 (1H, m), 7.65 (1H, d, J = 8.2 Hz), 3.23 (2H, q, J = 7.5 Hz), 1.29 (3H, t, J = 7.3 Hz). |
| 1-834 | 8.74 (1H, s), 8.17 (1H, s), 8.14 (1H, s), 8.13 (2H, d, J = 7.8 Hz), 7.73 (2H, d, J = 8.2 Hz), 3.93 (2H, q, J = 7.5 Hz), 1.37 (3H, t, J = 7.6 Hz). |
| 1-837 | 9.05 (2H, s), 8.59 (1H, s), 8.27 (1H, dd, J1 = 7.3 Hz, J2 = 2.3 Hz), 7.92 (1H, s), 7.90-7.82 (2H, m), 7.58 (1H, dd, J1 = 7.1 Hz, J2 = 1.6 Hz), 7.37 (2H, d, J = 7.8 Hz), 7.29-7.25 (2H, m), 7.11 (1H, d, J = 7.3 Hz), 3.54 (2H, dd, J1 = 27.2 Hz, J2 = 6.2 Hz), 1.39 (3H, t, J = 7.6 Hz). |
| 1-838 | 9.15 (1H, s), 8.58 (2H, s), 8.28-8.26 (1H, m), 7.93 (1H, s), 7.91-7.83 (2H, m), 7.58-7.56 (1H, m), 7.36-7.32 (2H, m), 7.24-7.21 (2H, m), 3.54 (2H, dd, J1 = 26.3 Hz, J2 = 7.1 Hz), 1.39 (3H, t, J = 7.6 Hz). |
| 1-839 | 8.50 (2H, s), 8.27-8.24 (1H, m), 7.92-7.85 (3H, m), 7.59-7.56 (1H, m), 7.00 (1H, br), 3.47 (2H, br), 2.74 (3H, d, J = 4.6 Hz), 1.35 (3H, t, J = 7.6 Hz). |
| 1-840 | 8.29 (2H, s), 8.20 (1H, dd, J1 = 7.8 Hz, J2 = 1.4 Hz), 7.92 (1H, s), 7.90-7.79 (3H, m), 3.56 (2H, br), 2.99 (3H, s), 2.75 (3H, s), 1.36 (3H, t, J = 7.3 Hz). |
| 1-841 | 8.37 (2H, s), 7.93 (1H, s), 7.82-7.74 (3H, m), 7.53-7.49 (1H, m), 2.92-2.80 (2H, m), 1.12 (3H, t, J = 7.3 Hz). |
| 1-842 | 8.39 (2H, s), 8.31 (1H, s), 8.26 (1H, dd, J1 = 7.3 Hz, J2 = 1.8 Hz), 7.90-7.82 (3H, m), 7.72-7.67 (3H, m), 7.57 (1H, t, J = 7.3 Hz), 7.45 (2H, t, J = 7.8 Hz), 3.06 (1H, br), 2.95 (1H, br), 1.25 (3H, t, J = 7.3 Hz). |
| 1-843 | 8.36 (2H, s), 8.29-8.26 (2H, m), 7.91-7.83 (3H, m), 7.72 (1H, t, J = 1.8 Hz), 7.68-7.66 (1H, m), 7.56-7.53 (2H, m), 7.39 (1H, t, J = 7.8 Hz), 3.05 (1H, br), 2.91 (1H, br), 1.25 (3H, t, J = 7.6 Hz). |
| 1-844 | 8.36 (2H, s), 8.33 (1H, s), 8.28-8.25 (1H, dd, J1 = 7.6 Hz, J2 = 2.1 Hz), 7.90-7.82 (3H, m), 7.67-7.65 (3H, m), 7.44-7.41 (2H, m), 3.05 (1H, br), 2.91 (1H, br), 1.25 (3H, t, J = 7.3 Hz). |
| 1-845 | 8.32-8.27 (1H, m), 8.21 (2H, s), 7.94 (1H, m), 7.86-7.82 (1H, m), 7.55-7.51 (1H, m), 3.70 (2H, q, J = 7.3 Hz), 2.36 (6H, br), 1.39 (3H, t, J = 7.6 Hz). |
| 1-847 | 8.45 (2H, s), 8.27 (1H, d, J = 7.3 Hz), 8.10 (1H, s), 7.94-7.86 (3H, m), 7.73 (1H, d, J = 6.9 Hz), 7.47-7.39 (2H, m), 7.36-7.31 (2H, m), 3.09-2.98 (2H, m), 1.24 (3H, t, J = 6.9 Hz). |
| 1-853 | 8.21 (1H, d, J = 1.8 Hz), 8.20 (1H, s), 8.04 (1H, dd, J1 = 8.2 Hz, J2 = 1.8 Hz), 7.81 (1H, d, J = 1.8 Hz), 7.70 (1H, dd, J1 = 8.2 Hz, J2 = 1.8 Hz), 7.60 (1H, d, J = 8.2 Hz), 7.23 (1H, d, J = 8.2 Hz), 2.85 (2H, q, J = 7.3 Hz), 1.26 (3H, t, J = 7.3 Hz). |
| 1-855 | 8.22 (1H, d, J = 2.3 Hz), 8.20 (1H, s), 8.05 (1H, dd, J1 = 8.5 Hz, J2 = 2.1 Hz), 7.61 (1H, d, J = 8.7 Hz), 7.55 (1H, d, J = 8.7 Hz), 7.31 (1H, d, J = 2.3 Hz), 7.23-7.19 (1H, m), 2.89 (2H, q, J = 7.3 Hz), 1.30 (3H, t, J = 7.3 Hz). |
| 1-860 | 8.52 (1H, d, J = 1.8 Hz), 8.22 (2H, s), 8.02 (1H, dd, J1 = 8.2 Hz, J2 = 1.8 Hz), 7.63 (1H, d, J = 8.2 Hz), 7.29 (1H, d, J = 7.8 Hz), 3.38-3.29 (1H, m), 2.96-2.88 (1H, m), 1.39 (3H, t, J = 7.6 Hz). |
| 1-862 | 8.24 (1H, s), 8.23 (1H, d, J = 2.3 Hz), 8.11 (1H, d, J = 2.3 Hz), 8.03 (1H, dd, J1 = 8.2 Hz, J2 = 2.3 Hz), 7.64 (1H, d, J = 8.2 Hz), 7.61 (1H, d, J = 8.7 Hz), 7.52 (1H, dd, J1 = 8.5 Hz, J2 = 2.1 Hz), 3.38-3.29 (1H, m), 2.96-2.87 (1H, m), 1.36 (3H, t, J = 7.3 Hz). |
| 1-867 | 8.57 (1H, d, J = 1.8 Hz), 8.24 (1H, d, J = 1.8 Hz), 8.23 (1H, s), 8.18 (1H, dd, J1 = 8.2 Hz, J2 = 1.8 Hz), 8.00 (1H, dd, J1 = 8.5 Hz, J2 = 2.1 Hz), 7.61 (1H, d, J = 8.2 Hz), 7.27 (1H, d, J = 8.7 Hz), 3.19 (2H, q, J = 7.5 Hz), 1.27 (3H, t, J = 7.6 Hz). |
| 1-869 | 8.25-8.24 (2H, m), 8.11 (1H, d, J = 2.7 Hz), 8.01 (1H, dd, J1 = 8.2 Hz, J2 = 2.3 Hz), 7.71-7.68 (1H, m), 7.65-7.61 (2H, m), 3.20 (2H, q, J = 7.3 Hz), 1.27 (3H, t, J = 7.6 Hz). |
| 2-14 | 8.62 (1H, d, J = 3.2 Hz), 8.52 (1H, s), 8.28 (1H, d, J = 7.8 Hz), 7.82 (1H, t, J = 7.8 Hz), 7.55-7.47 (3H, m), 7.37 (1H, t, J = 7.6 Hz), 2.83 (2H, q, J = 7.3 Hz), 1.23 (3H, t, J = 7.3 Hz). |
| 2-30 | 8.79 (1H, s), 7.98 (1H, s), 7.85 (1H, d, J = 1.4 Hz), 7.73 (1H, dd, J1 = 8.2 Hz, J2 = 1.8 Hz), 7.27 (1H, d, J = 8.2 Hz), 2.88 (2H, q, J = 7.3 Hz), 1.27 (3H, t, J = 7.3 Hz). |
| 2-32 | 8.80 (1H, s), 7.99 (1H, s), 7.59 (1H, d, J = 8.7 Hz), 7.34 (1H, d, J = 1.8 Hz), 7.25-7.22 (1H, m), 2.92 (2H, q, J = 7.3 Hz), 1.30 (3H, t, J = 7.3 Hz). |
| 2-33 | 8.88 (1H, s), 8.01 (1H, s), 7.90 (1H, d, J = 2.3 Hz), 7.79 (1H, dd, J1 = 8.7 Hz, J2 = 2.3 Hz), 7.71 (1H, d, J = 8.7 Hz), 2.95 (2H, q, J = 7.3 Hz), 1.30 (3H, t, J = 7.3 Hz). |
| 2-90 | 8.93 (1H, dd, J1 = 4.6 Hz, J2 = 0.9 Hz), 8.42 (1H, s), 8.14 (1H, dd, J1 = 8.0 Hz, J2 = 1.1 Hz), 7.59-7.56 (2H, m), 7.51-7.44 (2H, m), 7.40 (1H, td, J1 = 7.7 Hz, J2 = 1.5 Hz), 2.78 (2H, q, J = 7.5 Hz), 1.22 (3H, t, J = 7.3 Hz). |
| 2-91 | 8.79 (1H, d, J = 5.0 Hz), 8.56 (1H, s), 8.52 (1H, s), 7.56-7.48 (3H, m), 7.47 (1H, d, J = 5.0 Hz), 7.39 (1H, td, J1 = 7.6 Hz, J2 = 1.5 Hz), 2.84 (2H, q, J = 7.5 Hz), 1.23 (3H, t, J = 7.3 Hz). |
| 2-95 | 8.80 (1H, d, J = 5.0 Hz), 8.58 (1H, s), 8.52 (1H, s), 7.69 (1H, dd, J1 = 7.8 Hz, J2 = 1.8 Hz), 7.53 (1H, dd, J1 = 8.0 Hz, J2 = 1.6 Hz), 7.49-7.45 (2H, m), 2.68 (2H, q, J = 7.3 Hz), 1.05 (3H, t, J = 7.3 Hz). |
| 2-96 | 8.79 (1H, d, J = 5.0 Hz), 8.53 (1H, s), 8.51 (1H, s), 7.48-7.45 (3H, m), 7.34 (1H, dd, J1 = 8.5 Hz, J2 = 2.1 Hz), 2.88 (2H, q, J = 7.5 Hz), 1.27 (3H, t, J = 7.6 Hz). |
| 2-97 | 8.80 (1H, d, J = 5.5 Hz), 8.59 (1H, s), 8.51 (1H, s), 7.59-7.58 (1H, m), 7.48-7.47 (3H, m), 2.82 (2H, q, J = 7.3 Hz), 1.22 (3H, t, J = 7.3 Hz). |
| 2-98 | 8.79 (1H, d, J = 5.0 Hz), 8.55 (1H, s), 8.34 (1H, d, J = 8.7 Hz), 7.48-7.37 (4H, m), 2.89 (2H, q, J = 7.5 Hz), 1.27 (3H, t, J = 7.3 Hz). |
| 2-99 | 8.79 (1H, d, J = 5.5 Hz), 8.52 (1H, s), 8.50 (1H, s), 7.50-7.47 (2H, m), 7.19 (1H, dd, J1 = 9.2 Hz, J2 = 2.7 Hz), 7.05 (1H, ddd, J1 = 9.6 Hz, J2 = 6.9 Hz, J3 = 1.8 Hz), 2.88 (2H, q, J = 7.3 Hz), 1.29 (3H, t, J = 7.3 Hz) |
| 2-100 | 8.79 (1H, d, J = 5.0 Hz), 8.54 (1H, s), 8.51 (1H, s), 7.63 (1H, s), 7.51-7.47 (2H, m), 7.39 (1H, d, J = 8.2 Hz), 2.88 (2H, q, J = 7.3 Hz), 1.27 (3H, t, J = 7.3 Hz). |

TABLE 5-continued

| Compound No. | $^1$H-NMR Spectrum (CDCl$_3$) σ ppm: |
|---|---|
| 2-102 | 8.79 (1H, d, J = 5.0 Hz), 8.54 (1H, s), 8.51 (1H, s), 7.82 (1H, d, J = 1.8 Hz), 7.70 (1H, dd, J1 = 8.2 Hz, J2 = 1.8 Hz), 7.47 (1H, dd, j1 = 5.0 Hz, J2 = 1.4 Hz), 7.24 (1H, d, J = 8.2 Hz), 2.86 (2H, q, J = 7.3 Hz), 1.26 (3H, t, J = 7.3 Hz). |
| 2-103 | 8.79 (1H, d, J = 5.0 Hz), 8.52-8.51 (2H, m), 7.46 (1H, d, J = 5.0 Hz), 7.40 (1H, d, J = 8.2 Hz), 7.35 (1H, s), 7.18 (1H, dd, J1 = 8.0 Hz, J2 = 1.1 Hz), 2.81 (2H, q, J = 7.3 Hz), 2.45 (3H, s), 1.22 (3H, t, J = 7.3 Hz). |
| 2-104 | 8.81 (1H, d, J = 5.0 Hz), 8.64 (1H, s), 8.51 (1H, s), 7.75 (1H, d, J = 1.4 Hz), 7.69-7.63 (2H, m), 7.49 (1H, dd, J1 = 5.5 Hz, J2 = 1.4 Hz), 2.94 (2H, q, J = 7.3 Hz), 1.31 (3H, t, J = 7.3 Hz). |
| 2-107 | 8.80 (1H, d, J = 5.0 Hz), 8.62 (1H, s), 8.52 (1H, s), 7.74 (1H, s), 7.68 (1H, d, J = 8.2 Hz), 7.62 (1H, dd, J1 = 8.2 Hz, J2 = 1.8 Hz), 7.49 (1H, d, J = 5.0 Hz), 2.93 (2H, q, J = 7.5 Hz), 1.29 (3H, t, J = 7.3 Hz). |
| 2-109 | 8.81 (1H, d, J = 5.0 Hz), 8.64 (1H, s), 8.52 (1H, s), 7.73 (1H, s), 7.70 (1H, d, J = 8.2 Hz), 7.61 (1H, d, J = 8.2 Hz), 7.49 (1H, d, J = 4.6 Hz), 2.91 (2H, q, J = 7.3 Hz), 1.28 (3H, t, J = 7.3 Hz). |
| 2-110 | 8.80 (1H, d, J = 5.0 Hz), 8.62 (1H, s), 8.52 (1H, s), 7.63 (1H, d, J = 8.2 Hz), 7.56 (1H, s), 7.49 (1H, dd, J1 = 5.0 Hz, J2 = 0.9 Hz), 7.44 (1H, dd, J1 = 8.2 Hz, J2 = 1.4 Hz), 4.25-4.13 (1H, m), 2.89 (2H, q, J = 7.5 Hz), 1.26 (3H, t, J = 7.3 Hz). |
| 2-111 | 8.81 (1H, d, J = 5.0 Hz), 8.64 (1H, s), 8.52 (1H, s), 7.73 (1H, s), 7.67 (2H, d, J = 8.2 Hz), 7.60 (1H, d, J = 8.2 Hz), 7.49 (1H, dd, J1 = 5.0 Hz, J2 = 0.9 Hz), 3.58 (3H, s), 2.89 (2H, q, J = 7.3 Hz), 1.27 (3H, t, J = 7.3 Hz). |
| 2-112 | 8.80 (1H, d, J = 5.5 Hz), 8.54 (1H, s), 8.52 (1H, d, J = 0.9 Hz), 7.56 (1H, d, J = 8.7 Hz), 7.48 (1H, dd, J1 = 5.3 Hz, J2 = 1.1 Hz), 7.31 (1H, d, J = 2.3 Hz), 7.21 (1H, ddd, J1 = 8.6 Hz, J2 = 1.2 Hz, J3 = 0.6 Hz), 2.90 (2H, q, J = 7.3 Hz), 1.29 (3H, t, J = 7.6 Hz). |
| 2-113 | 8.80 (1H, d, J = 5.0 Hz), 8.61 (1H, s), 8.51 (1H, s), 7.76 (1H, s), 7.64 (1H, dd, J1 = 8.2 Hz, J2 = 1.4 Hz), 7.60 (1H, d, J = 8.2 Hz), 7.48 (1H, d, J = 5.0 Hz), 2.92 (2H, q, J = 7.3 Hz), 1.28 (3H, t, J = 7.3 Hz). |
| 2-118 | 8.81 (1H, d, J = 5.0 Hz), 8.63 (1H, s), 8.51 (1H, s), 7.87 (1H, d, J = 2.3 Hz), 7.76 (1H, dd, J1 = 8.7 Hz, J2 = 2.3 Hz), 7.67 (1H, d, J = 8.7 Hz), 7.49 (1H, d, J = 4.1 Hz), 2.93 (2H, q, J = 7.3 Hz), 1.29 (3H, t, J = 7.3 Hz). |
| 2-120 | 8.80 (1H, d, J = 5.0 Hz), 8.58 (1H, s), 8.50 (1H, s), 7.98 (1H, .s), 7.64 (1H, s), 7.48 (1H, d, J = 5.0 Hz), 2.84 (2H, q, J = 7.5 Hz), 1.25 (3H, t, J = 7.3 Hz). |
| 2-121 | 8.80 (1H, d, J = 5.0 Hz), 8.57 (1H, s), 8.51 (1H, s), 7.65 (1H, d, J = 8.2 Hz), 7.48 (2H, d, J = 8.2 Hz), 2.69 (2H, q, J = 7.5 Hz), 1.06 (3H, t, J = 7.3 Hz). |
| 2-122 | 8.80 (1H, d, J = 5.0 Hz), 8.57 (1H, s), 8.51 (1H, s), 7.82 (1H, d, J = 8.2 Hz), 7.48 (1H, dd, J1 = 5.0 Hz, J2 = 0.9 Hz), 7.41 (1H, d, J = 8.7 Hz), 2.69 (2H, q, J = 7.5 Hz), 1.06 (3H, t, J = 7.3 Hz). |
| 2-123 | 8.80 (1H, d, J = 5.0 Hz), 8.57 (1H, s), 8.51 (1H, d, J = 0.9 Hz), 7.56 (1H, d, J = 8.2 Hz), 7.50 (1H, d, J = 2.3 Hz), 7.48 (1H, dd, J1 = 5.5 Hz, J2 = 1.4 Hz), 7.33 (1H, dd, J1 = 8.0 Hz, J2 = 2.1 Hz), 3.87 (2H, s), 2.88 (2H, q, J = 7.3 Hz), 1.27 (3H, t, , J = 7.3 Hz). |
| 2-125 | 8.80 (1H, d, J = 5.0 Hz), 8.56 (1H, s), 8.52 (1H, s), 7.55 (1H, d, J = 1.8 Hz), 7.53 (1H, d, J = 7.8 Hz), 7.47 (1H, dd, J1 = 5.0 Hz, J2 = 0.9 Hz), 7.39 (1H, dd, J1 = 8.0 Hz, J2 = 2.1 Hz), 4.65 (2H, s), 2.87 (2H, q, J = 7.5 Hz), 1.26 (3H, t, J = 7.3 Hz). |
| 2-126 | 8.79 (1H, d, J = 5.0 Hz), 8.55 (1H, s), 8.52 (1H, s), 7.56 (1H, d, J = 1.4 Hz), 7.51 (1H, d, J = 8.2 Hz), 7.47 (1H, dd, J1 = 5.0 Hz, J2 = 1.4 Hz), 7.36 (1H, dd, J1 = 8.2 Hz, J2 = 1.8 Hz), 4.82 (2H, s), 2.86 (2H, q, J = 7.3 Hz), 1.91 (1H, br), 1.24 (3H, t, J = 7.6 Hz). |
| 2-127 | 8.79 (1H, d, J = 5.0 Hz), 8.51 (1H, s), 7.46 (1H, dd, J1 = 5.3 Hz, J2 = 1.1 Hz), 7.40 (1H, d, J = 7.8 Hz), 7.03 (1H, dd, J1 = 8.2 Hz, J2 = 1.8 Hz), 2.80 (2H, q, J = 7.5 Hz), 2.01-1.95 (1H, m), 1.21 (3H, t, J = 7.3 Hz), 1.11-1.06 (2H, m), 0.81-0.77 |
| 2-128 | 8.79 (1H, d, J = 5.0 Hz), 8.56 (1H, s), 8.51 (1H, d, J = 0.9 Hz), 7.54 (1H, d, J = 2.3 Hz), 7.52 (1H, d, J = 8.2 Hz), 7.47 (1H, dd, J1 = 5.0 Hz, J2 = 0.9 Hz), 7.17 (1H, dd, J1 = 8.2 Hz, J2 = 1.8 Hz), 2.88 (2H, q, J = 7.5 Hz), 1.86 (2H, dd, J1 = 7.8 Hz, J2 = 5.0 Hz), 1.51 (2H, dd, J1 = 8.0 Hz, J2 = 5.7 Hz), 1.26 (3H, t, J = 7.3 Hz). |
| 2-129 | 8.80 (1H, d, J = 5.0 Hz), 8.61 (1H, s), 8.52 (1H, s), 8.28 (1H, d, J = 1.8 Hz), 8.13 (1H, s), 8.08 (1H, dd, J1 = 8.2 Hz, J2 = 1.4 Hz), 7.60 (1H, d, J = 8.2 Hz), 7.47 (1H, dd, J1 = 5.3 Hz, J2 = 1.1 Hz), 4.02 (3H, s), 2.96 (2H, q, J = 7.3 Hz), 1.28 (3H, t, J = 7.3 Hz). |
| 2-131 | 8.78 (1H, d, J = 5.0 Hz), 8.61 (1H, s), 8.50 (1H, br), 8.21 (1H, d, J = 1.8 Hz), 8.06-8.02 (1H, m), 7.64 (1H, d, J = 8.2 Hz), 7.46 (1H, dd, J1 = 5.0 Hz, J2 = 0.9 Hz), 2.95 (2H, q, J = 7.5 Hz), 2.68 (3H, s), 1.27 (3H, t, J = 7.3 Hz). |
| 2-132 | 8.79 (1H, d, J = 5.0 Hz), 8.57 (1H, s), 8.51 (1H, d, J = 0.9 Hz), 7.58 (1H, d, J = 8.2 Hz), 7.56 (1H, d, J = 2.3 Hz), 7.48 (1H, dd, J1 = 5.3 Hz, J2 = 1.1 Hz), 7.43 (1H, dd, J1 = 8.2 Hz, J2 = 1.8 Hz), 5.93 (2H, s), 2.87 (2H, q, J = 7.5 Hz), 1.25 (3H, t, J = 7.3 Hz). 19F NMR: −63.48 (3F, s), −64.84 (3F, s). |
| 2-134 | 8.80 (1H, d, J = 5.0 Hz), 8.57 (1H, s), 7.71 (1H, s), 7.63 (1H, d, J = 8.2 Hz), 7.48 (1H, d, J = 8.2 Hz), 7.44 (1H, d, J = 4.1 Hz), 2.93 (2H, q, J = 7.3 Hz), 2.62 (3H, s), 1.29 (3H, t, J = 7.3 Hz). |
| 2-135 | 8.80 (1H, d, J = 5.0 Hz), 8.57 (1H, s), 7.43 (1H, dd, J1 = 5.0 Hz, J2 = 1.4 Hz), 7.38 (1H, d, J = 8.7 Hz), 7.30-7.28 (1H, m), 7.22-7.19 (1H, m), 2.89 (2H, q, J = 7.3 Hz), 2.61 (3H, s), 1.29 (3H, t, J = 7.6 Hz). |
| 2-140 | 8.80 (1H, d, J = 5.0 Hz), 8.57 (1H, s), 8.51 (1H, s), 7.57-7.48 (3H, m), 7.45 (1H, dd, J1 = 5.3 Hz, J2 = 1.1 Hz), 7.39 (1H, td, J1 = 7.6 Hz, J2 = 1.4 Hz), 2.84 (2H, q, J = 7.3 Hz), 1.24 (3H, t, J = 7.3 Hz). |
| 2-143 | 8.80 (1H, d, J = 5.0 Hz), 8.55 (1H, s), 8.50 (1H, s), 7.82 (1H, d, J = 1.8 Hz), 7.70 (1H, dd, J1 = 8.2 Hz, J2 = 1.8 Hz), 7.46 (1H, dd, J1 = 5.0 Hz, J2 = 0.9 Hz), 7.24 (1H, d, J = 8.2 Hz), 2.86 (2H, q, J = 7.3 Hz), 1.26 (3H, t, J = 7.6 Hz). |
| 2-145 | 8.81 (1H, d, J = 5.0 Hz), 8.55 (1H, s), 8.51 (1H, s), 7.55 (1H, d, J = 8.2 Hz), 7.47 (1H, dd, J1 = 5.0 Hz, J2 = 1.4 Hz), 7.31 (1H, d, J = 2.3 Hz), 7.23-7.20 (1H, m), |

TABLE 5-continued

| Compound No. | $^1$H-NMR Spectrum (CDCl$_3$) σ ppm: |
|---|---|
| 2-147 | 8.87 (1H, d, J = 2.3 Hz)8.59 (1H, s), 8.40 (1H, d, J = 8.2 Hz), 8.05 (1H, dd, J1 = 8.2 Hz, J2 = 2.3 Hz), 7.56-7.48 (3H, m), 7.39 (1H, td, J1 = 7.6 Hz, J2 = 1.7 Hz), 2.85 (2H, q, J = 7.5 Hz), 1.24 (3H, t, J = 7.3 Hz). |
| 2-148 | 8.57 (1H, s), 8.44 (1H, d, J = 8.2 Hz), 7.97 (1H, t, J = 7.6 Hz), 7.61 (1H, dd, J1 = 7.8 Hz, J2 = 0.9 Hz), 7.54-7.46 (3H, m), 7.38-7.33 (1H, m), 2.84 (2H, q, J = 7.3 Hz), 1.23 (3H, t, J = 7.3 Hz). |
| 2-153 | 9.11 (1H, s), 8.66 (1H, d, J = 5.0 Hz), 8.30-8.25 (3H, m), 7.79 (1H, t, J = 7.6 Hz), 7.71 (1H, t, J = 7.6 Hz), 7.56 (1H, d, J = 7.8 Hz), 7.44 (1H, dd, J1 = 8.0 Hz, J2 = 4.8 Hz), 3.38-3.28 (1H, m), 2.97-2.88 (1H, m), 1.37 (3H, t, J = 7.1 Hz). |
| 2-169 | 8.81 (1H, s), 8.55 (1H, d, J = 1.8 Hz), 8.04 (1H, dd, J1 = 8.9 Hz, J2 = 2.5 Hz), 8.03 (1H, s), 7.31 (1H, d, J = 8.2 Hz), 3.42-3.33 (1H, m), 3.02-2.93 (1H, m), 1.40 (3H, t, J = 7.6 Hz). |
| 2-171 | 8.83 (1H, s), 8.13 (1H, d, J = 2.3 Hz), 8.04 (1H, s), 7.67 (1H, d, J = 8.7 Hz), 7.55 (1H, dd, J1 = 8.2 Hz, J2 = 2.3 Hz), 3.42-3.33 (1H, m), 3.02-2.93 (1H, m), 1.38 (3H, t, J = 7.3 Hz). |
| 2-172 | 8.90 (1H, s), 8.68 (1H, d, J = 2.7 Hz), 8.10 (1H, dd, J1 = 8.7 Hz, J2 = 2.3 Hz), 8.05 (1H, s), 7.75 (1H, d, J = 8.2 Hz), 3.48-3.39 (1H, m), 3.07-2.98 (1H, m), 1.41 (3H, t, J = 7.3 Hz). |
| 2-229 | 8.92 (1H, d, J = 4.6 Hz), 8.39 (1H, s), 8.25 (1H, d, J = 7.8 Hz), 8.17 (1H, d, J = 7.8 Hz), 7.78 (1H, t, J = 7.8 Hz), 7.69 (1H, t, J = 7.6 Hz), 7.57 (1H, d, J = 7.8 Hz), 7.50 (1H, dd, J1 = 8.0 Hz, J2 = 4.8 Hz), 3.30 (1H, m), 2.90-2.81 (1H, m), 1.33 (3H, t, J = 7.3 Hz). |
| 2-230 | 8.78 (1H, d, J = 5.0 Hz), 8.58 (1H, s), 8.46 (1H, s), 8.24 (1H, d, J = 7.8 Hz), 7.77-7.65 (2H, m), 7.56-7.47 (2H, m), 3.36-3.26 (1H, m), 2.94-2.84 (1H, m), 1.35 (3H, t, J = 7.6 Hz). |
| 2-234 | 8.79 (1H, d, J = 5.0 Hz), 8.51 (1H, s), 8.48 (1H, s), 7.67 (1H, dd, J1 = 7.8 Hz, J2 = 1.4 Hz), 7.60 (1H, t, J = 8.0 Hz), 7.48 (1H, dd, J1 = 5.5 Hz, J2 = 1.4 Hz), 7.41 (1H, dd, J1 = 7.8 Hz, J2 = 1.4 Hz), 3.82-3.73 (1H, m), 3.37-3.28 (1H, m), 1.45 (3H, t, J = 7.6 Hz). |
| 2-235 | 8.81 (1H, d, J = 5.5 Hz), 8.58 (1H, s), 8.48 (1H, s), 8.23 (1H, d, J = 2.3 Hz), 7.66 (1H, dd, J1 = 8.5 Hz, J2 = 2.5 Hz), 7.53-7.51 (2H, m), 3.40-3.31 (1H, m), 2.97-2.88 (1H, m), 1.39 (3H, t, J = 7.6 Hz). |
| 2-236 | 8.81 (1H, d, J = 5.0 Hz), 8.62 (1H, s), 8.48 (1H, s), 8.21 (1H, d, J = 8.7 Hz), 7.74 (1H, dd, J1 = 8.5 Hz, J2 = 2.1 Hz), 7.60 (1H, d, J = 1.8 Hz), 7.52 (1H, d, J = 5.0 Hz), 3.38-3.29 (1H, m), 2.96-2.88 (1H, m), 1.38 (3H, t, J = 7.6 Hz). |
| 2-237 | 8.82 (1H, d, J = 5.0 Hz), 8.55 (1H, s), 8.50 (1H, s), 8.10-8.08 (1H, m), 7.78-7.76 (2H, m), 7.51 (1H, dd, J1 = 5.3 Hz, J2 = 1.1 Hz), 3.26-3.17 (1H, m), 2.91-2.82 (1H, m), 1.31 (3H, t, J = 7.6 Hz). |
| 2-238 | 8.81 (1H, d, J = 5.0 Hz), 8.56 (1H, s), 8.48 (1H, s), 7.97 (1H, dd, J1 = 8.2 Hz, J2 = 2.7 Hz), 7.57 (1H, dd, J1 = 8.7 Hz, J2 = 4.1 Hz), 7.52 (1H, dd, J1 = 5.0 Hz, J2 = 0.9 Hz), 7.38 (1H, ddd, J1 = 9.4 Hz, J2 = 6.6 Hz, J3 = 2.1 Hz), 3.37-3.28 (1H, m), 2.94-2.85 (1H, m), 1.37 (3H, t, J = 7.3 Hz). |
| 2-239 | 8.78 (1H, d, J = 5.0 Hz), 8.58 (1H, s), 8.44 (1H, s), 8.33 (1H, d, J = 2.3 Hz), 7.78 (1H, dd, J = 8.5, 2.1 Hz), 7.50-7.48 (1H, m), 7.43 (1H, d, J = 8.7 Hz), 3.37-3.28 (1H, m), 2.94-2.85 (1H, m), 1.36 (3H, t, J = 7.3 Hz). |
| 2-241 | 8.81 (1H, d, J = 5.0 Hz), 8.58 (1H, s), 8.53 (1H, d, J = 2.3 Hz), 8.48 (1H, s), 8.02 (1H, dd, J1 = 8.2 Hz, J2 = 1.8 Hz), 7.52 (1H, dd, J1 = 5.0 Hz, J2 = 0.9 Hz), 7.29 (1H, d, J = 8.7 Hz), 3.40-3.32 (1H, m), 2.97-2.88 (1H, m), 1.40 (3H, t, J = 7.3 Hz). |
| 2-242 | 8.80 (1H, d, J = 5.0 Hz), 8.55 (1H, s), 8.49 (1H, s), 8.03 (1H, s), 7.51-7.43 (3H, m), 3.36-3.27 (1H, m), 2.94-2.85 (1H, m), 2.56 (3H, s), 1.37 (3H, t, J = 7.6 Hz). |
| 2-243 | 8.83 (1H, d, J = 5.0 Hz), 8.69 (1H, s), 8.60 (1H, d, J = 2.3 Hz), 8.49 (1H, s), 7.98 (1H, dd, J1 = 8.2 Hz, J2 = 1.8 Hz), 7.72 (1H, d, J = 8.2 Hz), 7.55 (1H, d, J = 5.5 Hz), 3.48-3.39 (1H, m), 3.01-2.93 (1H, m), 1.42 (3H, t, J = 7.3 Hz). |
| 2-245 | 8.91 (1H, d, J = 1.8 Hz), 8.82 (1H, d, J = 5.0 Hz), 8.67 (1H, s), 8.49 (1H, s), 8.36 (1H, dd, J1 = 8.2 Hz, J2 = 1.8 Hz), 7.66 (1H, d, J = 8.2 Hz), 7.53 (1H, dd, J1 = 5.0 Hz, J2 = 0.9 Hz), 4.48 (2H, q, J = 7.0 Hz), 3.45-3.36 (1H, m), 3.02-2.93 (1H, m), 1.47-1.42 (6H, m). |
| 2-246 | 8.83 (1H, d, J = 5.0 Hz), 8.68 (1H, s), 8.58 (1H, d, J = 1.8 Hz), 8.49 (1H, s), 7.96 (1H, dd, J1 = 8.2 Hz, J2 = 1.4 Hz), 7.73 (1H, d, J = 8.2 Hz), 7.54 (1H, dd, J1 = 5.0 Hz, J2 = 1.4 Hz), 3.46-3.37 (1H, m), 3.00-2.91 (1H, m), 1.42 (3H, t, J = 7.6 Hz). |
| 2-248 | 8.83 (1H, d, J = 5.0 Hz), 8.68 (1H, s), 8.56 (1H, d, J = 1.8 Hz), 8.50 (1H, s), 7.95 (1H, dd, J1 = 8.2 Hz, J2 = 1.8 Hz), 7.75 (1H, d, J = 8.2 Hz), 7.54 (1H, d, J = 3.7 Hz), 3.44-3.35 (1H, m), 3.01-2.92 (1H, m), 1.37 (3H, t, J = 7.3 Hz). |
| 2-249 | 8.82 (1H, d, J = 5.0 Hz), 8.67 (1H, s), 8.49 (1H, s), 8.29 (1H, d, J = 1.8 Hz), 7.83 (1H, d, J = 8.2 Hz), 7.69 (1H, d, J = 8.2 Hz), 7.53 (1H, d, J = 4.1 Hz), 4.41-4.29 (1H, m), 3.43-3.34 (1H, m), 2.99-2.90 (1H, m), 1.36 (3H, t, J = 7.6 Hz). |
| 2-250 | 8.83 (1H, d, J = 5.0 Hz), 8.68 (1H, s), 8.52-8.50 (2H, m), 7.92 (1H, d, J = 8.2 Hz), 7.71 (1H, d, J = 8.2 Hz), 7.53 (1H, dd, J1 = 5.0 Hz, J2 = 0.9 Hz), 3.61 (3H, s), 3.43-3.34 (1H, m), 3.01-2.02 (1H, m), 1.36 (3H, t, J = 7.3 Hz). |
| 2-251 | 8.80 (1H, d, J = 5.0 Hz), 8.51 (1H, s), 8.48 (1H, s), 7.71 (1H, d, J = 2.7 Hz), 7.50 (1H, d, J = 5.0 Hz), 7.46 (1H, d, J = 8.7 Hz), 7.16 (1H, dd, J1 = 8.7 Hz, J2 = 2.7 Hz), 3.98 (3H, s), 3.33-3.24 (1H, m), 2.91-2.83 (1H, m), 1.35 (3H, t, J = 7.6 Hz). |
| 2-252 | 8.82 (1H, d, J = 5.0 Hz), 8.60 (1H, s), 8.49 (1H, s), 7.63 (1H, d, J = 8.7 Hz), 7.54-7.51 (2H, m), 3.40-3.31 (1H, m), 2.97-2.88 (1H, m), 1.38 (3H, t, J = 7.6 Hz). |
| 2-253 | 8.82 (1H, d, J = 5.0 Hz), 8.66 (1H, s), 8.54 (1H, s), 8.49 (1H, s), 7.97 (1H, dd, J1 = 8.2 Hz, J2 = 1.8 Hz), 7.65 (1H, d, J = 8.2 Hz), 7.53 (1H, d, J = 5.0 Hz), 3.44-3.36 (1H, m), 3.02-2.93 (1H, m), 1.40 (3H, t, J = 7.6 Hz). |
| 2-258 | 8.83 (1H, d, J = 5.0 Hz), 8.68 (1H, s), 8.67 (1H, d, J = 2.3 Hz), 8.49 (1H, s), 8.08 (1H, dd, J1 = 8.7 Hz, J2 = 2.3 Hz), 7.71 (1H, d, J = 8.7 Hz), 7.54 (1H, d, J = 5.0 Hz), 3.47-3.38 (1H, m), 3.02-2.93 (1H, m), 1.42 (3H, t, J = 7.3 Hz). |
| 2-260 | 8.81 (1H, d, J = 5.0 Hz), 8.63-8.46 (3H, m), 7.68 (1H, s), 7.53 (1H, d, J = 4.1 Hz), 3.42-3.32 (1H, m), 2.97-2.88 (1H, m), 1.40 (3H, t, J = 7.3 Hz). |

TABLE 5-continued

| Compound No. | $^1$H-NMR Spectrum (CDCl$_3$) σ ppm: |
|---|---|
| 2-261 | 8.78 (1H, d, J = 5.0 Hz), 8.48 (1H, s), 8.47 (1H, s), 7.77 (1H, d, J = 8.7 Hz), 7.48 (1H, dd, J1 = 5.0 Hz, J2 = 0.9 Hz), 7.37 (1H, d, J = 8.7 Hz), 3.85-3.76 (1H, m), 3.38-3.29 (1H, m), 1.46 (3H, t, J = 7.6 Hz). |
| 2-262 | 8.78 (1H, d, J = 8.7 Hz), 8.48 (1H, s), 8, 47 (1H, s), 7.94 (1H, d, J = 8.2 Hz), 7.48 (1H, dd, J1 = 5.0 Hz, J2 = 1.4 Hz), 7.29 (1H, d, J = 8.7 Hz), 3.84-3.75 (1H, m), 3.38-3.29 (1H, m), 1.46 (3H, t, J = 7.6 Hz). |
| 2-263 | 8.82 (1H, d, J = 5.0 Hz), 8.62 (1H, s), 8.49 (1H, s), 8.18 (1H, d, J = 1.8 Hz), 7.76 (1H, dd, J1 = 8.2 Hz, J2 = 2.3 Hz), 7.63 (1h, d, J = 7.8 Hz), 7.53 (1H, dd, J1 = 5.0 Hz, J2 = 0.9 Hz), 3.97 (2H, s), 3.43-3.33 (1H, m), 2.96-2.87 (1H, m), 1.40 (3H, t, J = 7.6 Hz). |
| 2-267 | 8.80 (1H, d, J = 5.0 Hz), 8.53 (1H, s), 8.49 (1H, s), 7.91 (1H, d, J = 1.8 Hz), 7.50 (1H, dd, J1 = 5.0 Hz, J2 = 1.4 Hz), 7.42 (1H, d, J = 7.8 Hz), 7.33 (1H, dd, J1 = 8.2 Hz, J2 = 1.8 Hz), 3.34-3.25 (1H, m), 2.92-2.83 (1H, m), 2.13-2.07 (1H, m), 1.36 (3H, t, J = 7.6 Hz), 1.17-1.13 (2H, m), 0.92-0.83 (2H, m). |
| 2-268 | 8.82 (1H, d, J = 5.0 Hz), 8.60 (1H, s), 8.49 (1H, s), 7.91 (1H, d, J = 2.3 Hz), 7.86 (1H, dd, J1 = 8.2 Hz, J2 = 2.3 Hz), 7.59 (1H, d, J = 5.0 Hz), 7.52 (1H, dd, J1 = 5.0 Hz, J2 = 0.9 Hz), 3.39-3.30 (1H, m), 2.92-2.83 (1H, m), 1.94-1.90 (2H, m), 1.65-1.61 (2H, m), 1.37 (3H, t, J = 7.3 Hz). |
| 2-271 | 8.93 (1H, d, J = 1.8 Hz), 8.79 (1H, d, J = 5.0 Hz), 8.66 (1H, s), 8.46 (1H, s), 8.34 (1H, dd, J = 8.2 Hz, 1.8 Hz), 7.67 (1H, d, J = 8.2 Hz), 7.49 (1H, d, J = 5.0 Hz), 3.43-3.33 (1H, m), 3.02-2.92 (1H, m), 2.67 (3H, s), 1.40 (3H, t, J = 7.6 Hz). |
| 2-272 | 8.81 (1H, d, J = 5.0 Hz), 8.62 (1H, s), 8.48 (1H, s), 8.38 (1H, d, J = 1.8 Hz), 7.71 (1H, dd, J1 = 8.0 Hz, J2 = 2.1 Hz), 7.64 (1H, d, J = 7.8 Hz), 7.52 (1H, dd, J1 = 5.0 Hz, J2 = 1.4 Hz), 6.04 (2H, s), 3.43-3.34 (1H, m), 2.98-2.89 (1H, m), 1.38 (3H, t, J = 7.6 Hz). |
| 2-275 | 8.82 (1H, d, J = 5.0 Hz), 8.53 (1H, s), 8.05 (1H, d, J = 1.8 Hz), 7.57-7.54 (1H, m), 7.49-7.46 (2H, m), 3.21-3.12 (1H, m), 2.86-2.77 (1H, m), 1.27 (3H, t, J = 7.6 Hz). |
| 2-283 | 8.82 (1H, d, J = 5.0 Hz), 8.59 (1H, s), 8.53 (1H, d, J = 1.8 Hz), 8.46 (1H, s), 8.02 (1H, dd, J1 = 8.2 Hz, J2 = 2.3 Hz), 7.50 (1H, d, J = 3.7 Hz), 7.29 (1H, d, J = 8.2 Hz), 3.41-3.32 (1H, m), 2.97-2.88 (1H, m), 1.40 (3H, t, J = 7.3 Hz). |
| 2-285 | 8.83 (1H, d, J = 5.0 Hz), 8.61 (1H, s), 8.47 (1H, s), 8.12 (1H, d, J = 2.3 Hz), 7.63 (1H, d, J = 8.7 Hz), 7.54-7.51 (2H, m), 3.41-3.32 (1H, m), 2.97-2.88 (1H, m), 1.38 (3H, t, J = 7.6 Hz). |
| 2-288 | 8.65 (1H, s), 8.40 (1H, d, J = 8.2 Hz), 8.26-8.23 (1H, m), 8.00 (1H, t, J = 7.8 Hz), 7.78-7.73 (1H, m), 7.70-7.64 (2H, m), 7.59-7.56 (1H, m), 3.37-3.27 (1H, m), 2.95-2.86 (1H, m), 1.35 (3H, t, J = 7.6 Hz). |
| 2-294 | 8.71 (1H, s), 8.69 (1H, s), 8.28 (1H, dd, J1 = 8.0 Hz, J2 = 1.6 Hz), 7.86 (1H, s), 7.80 (1H, td, J1 = 7.6 Hz, J2 = 1.2 Hz), 7.71 (1H, td, J1 = 7.6 Hz, J2 = 1.4 Hz), 7.60 (1H, dd, J1 = 7.8 Hz, J2 = 1.4 Hz), 3.39-3.30 (1H, m), 2.98-2.90 (1H, m), 1.39 (3H, t, J = 7.3 Hz). |
| 2-297 | 8.67 (1H, s), 8.62 (1H, s), 8.57 (1H, d, J = 2.3 Hz), 8.19 (1H, dd, J1 = 8.2 Hz, J2 = 1.8 Hz), 7.83 (1H, s), 7.30-7.27 (1H, m), 3.36 (2H, q, J = 7.3 Hz), 1.32 (3H, t, J = 7.3 Hz). |
| 2-299 | 8.68 (1H, s), 8.65 (1H, s), 8.12 (1H, d, J = 2.7 Hz), 7.84 (1H, s), 7.70 (1H, dd, J1 = 8.0 Hz, J2 = 2.5 Hz), 7.65 (1H, d, J = 8.7 Hz), 3.38 (2H, q, J = 7.5 Hz), 1.32 (3H, t, J = 7.3 Hz). |
| 2-309 | 8.77 (1H, s), 8.58 (1H, d, J = 1.8 Hz), 8.21 (1H, dd, J1 = 8.0 Hz, J2 = 2.1 Hz), 8.00 (1H, s), 7.30 (1H, d, J = 8.2 Hz), 3.32 (2H, q, J = 7.5 Hz), 1.31 (3H, t, J = 7.6 Hz). |
| 2-311 | 8.80 (1H, s), 8.12 (1H, d, J = 2.7 Hz), 8.01 (1H, s), 7.73-7.70 (1H, m), 7.67 (1H, d, J = 8.7 Hz), 3.33 (2H, q, J = 7.5 Hz), 1.31 (3H, t, J = 7.3 Hz). |
| 2-312 | 8.83 (1H, s), 8.67 (1H, d, J = 2.3 Hz), 8.27 (1H, dd, J1 = 8.5 Hz, J2 = 2.5 Hz), 8.02 (1H, s), 7.76 (1H, d, J = 8.7 Hz), 3.39 (2H, q, J = 7.5 Hz), 1.34 (3H, t, J = 7.3 Hz). |
| 2-322 | 8.73 (1H, s), 8.52 (1H, s), 8.51 (1H, s), 8.39 (1H, d, J = 2.3 Hz), 7.98 (1H, dd, J1 = 8.5 Hz, J2 = 2.1 Hz), 7.44 (1H, d, J = 8.7 Hz), 3.30 (2H, q, J = 7.5 Hz), 1.30 (3H, t, J = 7.3 Hz). |
| 2-325 | 8.74 (1H, s), 8.54 (1H, s), 8.52 (1H, s), 8.11 (1H, d, J = 2.3 Hz), 7.70 (1H, dd, J1 = 8.9 Hz, J2 = 2.1 Hz), 7.64 (1H, d, J = 8.7 Hz), 3.30 (2H, q, J = 7.5 Hz), 1.30 (3H, t, J = 7.6 Hz). |
| 2-329 | 8.57 (1H, s), 8.40-8.39 (2H, m), 7.98 (1H, dd, J1 = 8.2 Hz, J2 = 1.8 Hz), 7.52 (1H, s), 7.42 (1H, d, J = 8.2 Hz), 3.33 (2H, q, J = 7.3 Hz), 1.31 (3H, t, J = 7.3 Hz). |
| 2-332 | 8.58 (1H, s), 8.39 (1H, s), 8.11 (1H, d, J = 2.3 Hz), 7.71-7.68 (1H, m), 7.62 (1H, d, J = 8.7 Hz), 7.53 (1H, s), 3.34 (2H, q, J = 7.5 Hz), 1.31 (3H, t, J = 7.6 Hz). |
| 2-357 | 8.48 (1H, s), 8.40 (1H, d, J = 2.3 Hz), 8.03 (1H, s), 7.97 (1H, dd, J1 = 8.2 Hz, J2 = 2.3 Hz), 7.45 (1H, d, J = 8.2 Hz), 6.95 (1H, s), 4.01 (3H, s), 3.28 (2H, q, J = 7.3 Hz), 1.30 (3H, t, J = 7.6 Hz). |
| 2-369 | 8.91 (1H, dd, J1 = 4.6 Hz, J2 = 0.9 Hz), 8.45 (1H, s), 8.28 (1H, dd, J = 7.8 Hz, J2 = 1.8 Hz), 8.16 (1H, dd, J1 = 8.0 Hz, J2 = 1.1 Hz), 7.86 (1H, td, J1 = 7.6 Hz, J2 = 1.7 Hz), 7.81 (1H, dd, J1 = 7.7 Hz, J2 = 1.5 Hz), 7.61 (1H, dd, J1 = 7.3 Hz, J2 = 1.4 Hz), 7.48 (1H, dd, J1 = 8.0 Hz, J2 = 4.8 Hz), 3.13 (1H, q, J = 7.5 Hz), 1.24 (3H, t, J = 7.6 Hz). |
| 2-370 | 8.80 (1H, d, J = 5.0 Hz), 8.56 (1H, s), 8.48 (1H, s), 8.28 (1H, dd, J1 = 7.6 Hz, J2 = 1.6 Hz), 7.87 (1H, td, J1 = 7.6 Hz, J2 = 1.8 Hz), 7.82 (1H, td, J1 = 7.7 Hz, J2 = 1.5 Hz), 7.57 (1H, dd, J1 = 7.6 Hz, J2 = 1.1 Hz), 7.49-7.48 (1H, m), 3.30 (2H, q, J = 7.5 Hz), 1.29 (3H, t, J = 7.3 Hz). |
| 2-374 | 8.78 (1H, d, J = 5.0 Hz), 8.49 (1H, s), 8.48 (1H, s), 7.83 (1H, dd, J1 = 8.2 Hz, J2 = 1.4 Hz), 7.71 (1H, t, J = 8.0 Hz), 7.47 (1H, dd, J1 = 5.0 Hz, J2 = 1.4 Hz), 7.43 (1H, dd, J1 = 7.8 Hz, J2 = 1.4 Hz), 3.60 (2H, q, J = 7.5 Hz), 1.43 (3H, t, J = 7.3 Hz). |
| 2-375 | 8.80 (1H, d, J = 5.0 Hz), 8.54 (1H, s), 8.47 (1H, s), 8.25 (1H, d, J = 2.7 Hz), 7.82 (1H, dd, J1 = 8.2 Hz, J2 = 2.3 Hz), 7.52 (1H, d, J = 8.2 Hz), 7.49 (1H, dd, J1 = 5.0 Hz, J2 = 0.9 Hz), 3.31 (2H, q, J = 7.5 Hz), 1.31 (3H, t, J = 7.6 Hz). |
| 2-376 | 8.80 (1H, d, J = 5.0 Hz), 8.57 (1H, s), 8.47 (1H, s), 8.21 (1H, d, J = 8.7 Hz), 7.78 (1H, dd, J1 = 8.5 Hz, J2 = 2.1 Hz), 7.59 (1H, d, J = 2.3 Hz), 7.49 (1H, dd, J1 = 5.3 Hz, J2 = 1.1 Hz), 3.30 (2H, q, J = 7.5 Hz), 1.29 (3H, t, J = 7.6 Hz). |
| 2-377 | 8.80 (1H, d, J = 5.0 Hz), 8.51 (1H, s), 8.49 (1H, s), 8.18 (1H, dd, J1 = 8.0 Hz, J2 = 1.6 Hz), 7.93 (1H, dd, J1 = 8.2 Hz, J2 = 1.4 Hz), 7.77 (1H, t, J = 8.2 Hz), 7.49 (1H, dd, J1 = 5.0 Hz, J2 = 1.4 Hz), 3.25 (2H, q, J = 7.5 Hz), 1.28 (3H, t, J = 7.3 Hz). |

TABLE 5-continued

| Compound No. | $^1$H-NMR Spectrum (CDCl$_3$) σ ppm: |
|---|---|
| 2-378 | 8.80 (1H, d, J = 5.5 Hz), 8.54 (1H, s), 8.47 (1H, s), 7.99 (1H, dd, J1 = 7.3 Hz, J2 = 2.7 Hz), 7.60-7.52 (2H, m), 7.49 (1H, dd, J1 = 5.0 Hz, J2 = 0.9 Hz), 3.29 (2H, q, J = 7.5 Hz), 1.30 (3H, t, J = 7.6 Hz). |
| 2-379 | 8.77 (1H, J = 5.0 Hz), 8.52 (1H, s), 8.45 (1H, s), 8.38 (1H, d, J = 2.3 Hz), 7.96 (1H, dd, J1 = 8.2 Hz, J2 = 2.3 Hz), 7.48-7.46 (1H, m), 7.42 (1H, d, J = 8.2 Hz), 3.29 (2H, q, J = 7.5 Hz), 1.29 (3H, t, J = 7.3 Hz). |
| 2-381 | 8.79 (1H, d, J = 5.0 Hz), 8.57 (1H, d, J = 1.8 Hz), 8.53 (1H, s), 8.46 (1H, s), 8.18 (1H, dd, J1 = 8.2 Hz, J2 = 1.8 Hz), 7.49 (1H, dd, J1 = 5.0 Hz, J2 = 1.4 Hz), 7.28 (1H, d, J = 8.2 Hz), 3.31 (2H, q, J = 7.3 Hz), 1.30 (3H, t, J = 7.6 Hz). |
| 2-382 | 8.79 (1H, d, J = 5.0 Hz), 8.52 (1H, s), 8.47 (1H, s), 8.06 (1H, d, J = 1.4 Hz), 7.63 (1H, dd, J1 = 8.0 Hz, J2 = 1.6 Hz), 7.47 (1H, d, J = 5.0 Hz), 7.44 (1H, d, J = 8.2 Hz), 3.27 (2H, q, J = 7.5 Hz), 2.59 (3H, s), 1.28 (3H, t, J = 7.3 Hz). |
| 2-383 | 8.81 (1H, d, J = 5.0 Hz), 8.61 (1H, s), 8.58 (1H, d, J = 1.8 Hz), 8.47 (1H, d, J = 0.9 Hz), 8.14 (1H, dd, J1 = 8.2 Hz, J2 = 1.8 Hz), 7.73 (1H, d, J = 8.2 Hz), 7.51 (1H, dd, J1 = 5.3 Hz, J2 = 1.6 Hz), 3.40 (2H, q, J = 7.5 Hz), 1.33 (3H, t, J = 7.3 Hz). |
| 2-384 | 8.79 (1H, d, J = 5.0 Hz), 8.50 (1H, s), 8.47 (1H, s), 7.84 (1H, br), 7.70 (1H, d, J = 2.7 Hz), 7.50 (1H, d, J = 5.0 Hz), 7.40 (1H, d, J = 8.7 Hz), 7.24 (1H, d, J = 3.2 Hz), 3.27 (2H, q, J = 7.5 Hz)1.27 (3H, t, J = 7.3 Hz). |
| 2-385 | 8.89 (1H, d, J = 1.8 Hz), 8.80 (1H, d, J = 5.0 Hz), 8.60 (1H, s), 8.50 (1H, dd, J1 = 7.8 Hz, J2 = 1.8 Hz), 8.48 (1H, s), 7.66 (1H, d, J = 7.6 Hz), 7.50 (1H, dd, J1 = 5.0 Hz, J2 = 0.9 Hz), 4.50 (2H, q, J = 7.2 Hz), 3.37 (2H, q, J = 7.5 Hz), 1.47 (3H, t, J = 7.1 Hz), 1.32 (3H, t, J = 7.3 Hz). |
| 2-386 | 8.81 (1H, d, J = 5.0 Hz), 8.61 (1H, s), 8.55 (1H, d, J = 1.8 Hz), 8.48 (1H, s), 8.13 (1H, dd, J1 = 8.2 Hz, J2 = 1.8 Hz), 7.74 (1H, d, J = 8.2 Hz), 7.51 (1H, dd, J1 = 5.0 Hz, J2 = 1.4 Hz), 3.37 (2H, q, J = 7.5 Hz), 1.32 (3H, t, J = 7.6 Hz). |
| 2-387 | 9.14 (1H, m), 8.90-8.87 (2H, m), 8.62 (1H, s), 8.32 (1H, s), 7.57 (1H, dd, J1 = 5.0 Hz, J2 = 0.9 Hz), 3.99 (2H, q, J = 7.5 Hz), 1.50 (3H, t, J = 7.6 Hz). |
| 2-388 | 8.81 (1H, d, J = 5.0 Hz), 8.63 (1H, s), 8.53 (1H, d, J = 2.3 Hz), 8.49 (1H, s), 8.12 (1H, dd, J1 = 8.0 Hz, J2 = 1.6 Hz), 7.76 (1H, d, J = 8.2 Hz), 7.52-7.50 (1H, m), 3.38 (2H, q, J = 7.3 Hz), 1.30 (3H, t, J = 7.3 Hz). |
| 2-389 | 8.81 (1H, d, J = 5.0 Hz), 8.61 (1H, s), 8.48 (1H, s), 8.31 (1H, d, J = 2.3 Hz), 7.98 (1H, dd, J1 = 8.2 Hz, J2 = 1.4 Hz), 7.69 (1H, d, J = 8.2 Hz), 7.50 (1H, dd, J1 = 5.0 Hz, J2 = 1.4 Hz), 4.41-4.29 (1H, m), 3.35 (2H, q, J = 7.5 Hz), 1.29 (3H, t, J = 7.3 Hz). |
| 2-390 | 8.81 (1H, d, J = 5.0 Hz), 8.61 (1H, s), 8.50 (2H, dd, J1 = 8.2 Hz, J2 = 1.4 Hz), 8.09 (1H, dd, J1 = 8.2 Hz, J2 = 1.4 Hz), 7.71 (1H, d, J = 8.7 Hz), 7.50 (1H, dd, J1 = 5.0 Hz, J2 = 0.9 Hz), 3.64 (3H, s), 3.37 (2H, q, J = 7.5 Hz), 1.30 (3H, t, J = 7.6 Hz). |
| 2-391 | 8.79 (1H, s), 8.51 (1H, s), 8.47 (1H, s), 7.73 (1H, d, J = 3.2 Hz), 7.48-7.46 (2H, m), 7.29 (1H, dd, J1 = 8.7 Hz, J2 = 3.2 Hz), 3.98 (3H, s), 3.24 (2H, q, J = 7.5 Hz), 1.28 (3H, t, J = 7.3 Hz). |
| 2-392 | 8.80 (1H, d, J = 5.0 Hz), 8.56 (1H, s), 8.47 (1H, s), 8.12 (1H, d, J = 2.7 Hz), 7.71-7.68 (1H, m), 7.64 (1H, d, J = 8.7 Hz), 7.50 (1H, dd, J1 = 5.0 Hz, J2 = 1.4 Hz), 3.32 (2H, q, J = 7.5 Hz), 1.30 (3H, t, J = 7.6 Hz). |
| 2-393 | 8.80 (1H, d, J = 5.0 Hz), 8.60 (1H, d, J = 0.9 Hz), 8.53 (1H, d, J = 1.8 Hz), 8.48 (1H, s), 8.13 (1H, dd, J1 = 8.2 Hz, J2 = 1.8 Hz), 7.64 (1H, d, J = 7.3 Hz), 7.50 (1H, d, J = 4.6 Hz), 3.36 (2H, q, J = 7.5 Hz), 1.31 (3H, t, J = 7.6 Hz). |
| 2-394 | 8.79 (1H, d, J = 5.0 Hz), 8.52 (1H, s), 8.47 (1H, s), 8.02 (1H, d, J = 2.3 Hz), 7.60 (1H, dd, J1 = 8.2 Hz, J2 = 2.3 Hz), 7.48 (1H, d, J = 5.0 Hz), 7.43 (1H, d, J = 8.2 Hz), 3.27 (2H, q, J = 7.5 Hz), 2.62 (3H, s), 1.29 (3H, t, J = 7.6 Hz). |
| 2-395 | 8.81 (1H, d, J = 5.0 Hz), 8.60 (1H, s), 8.48 (1H, s), 8.42 (1H, d, J = 1.8 Hz), 8.25 (1H, m, dd, J1 = 8.2 Hz, J2 = 1.8 Hz), 7.78 (1H, d, J = 8.2 Hz), 7.50 (1H, d, J = 3.7 Hz), 3.36 (2H, q, J = 7.2 Hz), 2.89 (3H, s), 1.32 (3H, t, J = 7.3 Hz). |
| 2-396 | 8.83-8.80 (2H, m), 8.62 (1H, s), 8.49 (1H, s), 8.44 (1H, d, J1 = 8.0 Hz, J2 = 2.1 Hz), 7.80 (1H, d, J = 7.8 Hz), 7.52 (1H, d, J = 3.7 Hz), 3.42 (2H, q, J = 7.5 Hz), 3.22 (3H, s), 1.35 (3H, t, J = 7.3 Hz). |
| 2-397 | 8.80 (1H, d, J = 5.0 Hz), 8.59 (1H, s), 8.47 (1H, s), 8.18 (1H, d, J = 2.7 Hz), 7.79 (1H, dd, J1 = 8.7 Hz, J2 = 2.7 Hz), 7.71 (1H, d, J = 8.2 Hz), 7.51 (1H, dd, J1 = 5.0 Hz, J2 = 0.9 Hz), 3.36 (2H, q, J = 7.5 Hz), 1.31 (3H, t, J = 7.6 Hz). |
| 2-398 | 8.81 (1H, d, J = 5.0 Hz), 8.66 (1H, d, J = 2.7 Hz), 8.60 (1H, s), 8.48 (1H, s), 8.24 (1H, dd, J1 = 8.7 Hz, J2 = 2.7 Hz), 7.72 (1H, d, J = 8.7 Hz), 7.51 (1H, d, J = 6.0 Hz), 3.39 (2H, q, J = 7.5 Hz), 1.33 (3H, t, J = 7.3 Hz). |
| 2-399 | 8.79 (1H, d, J = 5.0 Hz), 8.51 (1H, s), 8.47 (1H, s), 7.87 (1H, dd, J1 = 2.3 Hz, J2 = 0.9 Hz), 7.48-7.46 (3H, m), 5.33 (2H, s), 3.54 (3H, s), 3.25 (2H, q, J = 7.5 Hz), 1.28 (3H, t, J = 7.3 Hz). |
| 2-400 | 8.79 (1H, d, J = 5.0 Hz), 8.68 (1H, s), 8.56 (1H, s), 8.45 (1H, s), 7.64 (1H, s), 7.49 (1H, d, J = 4.6 Hz), 3.31 (2H, q, J = 7.5 Hz), 1.31 (3H, t, J = 7.3 Hz). |
| 2-401 | 8.78 (1H, d, J = 5.5 Hz), 8.48 (1H, s), 8.47 (1H, s), 7.91 (1H, d, J = 8.2 Hz), 7.48 (1H, d, J = 5.0 Hz), 7.39 (1H, d, J = 8.7 Hz), 3.63 (2H, q, J = 7.5 Hz), 1.44 (3H, t, J = 7.6 Hz). |
| 2-402 | 8.78 (1H, d, J = 5.0 Hz), 8.48 (1H, s), 8.47 (1H, s), 8.09 (1H, d, J = 8.2 Hz), 7.48 (1H, dd, J1 = 5.3 Hz, J2 = 1.6 Hz), 7.31 (1H, d, J = 8.7 Hz), 3.63 (2H, q, J = 7.5 Hz), 1.44 (3H, t, J = 7.3 Hz). |
| 2-403 | 8.80 (1H, d, J = 5.0 Hz), 8.56 (1H, s), 8.47 (1H, s), 8.21 (1H, d, J = 2.3 Hz), 7.91 (1H, dd, J1 = 8.0 Hz, J2 = 2.1 Hz), 7.63 (1H, d, J = 8.0 Hz), 7.49 (1H, dd, J1 = 5.0 Hz, J2 = 0.9 Hz), 4.00 (2H, s), 3.32 (2H, q, J = 7.3 Hz), 1.30 (3H, t, J = 7.3 Hz). |
| 2-404 | 8.81 (1H, d, J = 5.0 Hz), 8.63 (1H, s), 8.59-8.57 (1H, m), 8.48 (1H, s), 8.18 (1H, dd, J1 = 8.2 Hz, J2 = 2.3 Hz), 7.80 (1H, d, J = 8.2 Hz), 7.51 (1H, d, J = 5.0 Hz), 3.39 (2H, q, J = 7.5 Hz), 1.34 (3H, t, J = 7.3 Hz). |

TABLE 5-continued

| Compound No. | $^1$H-NMR Spectrum (CDCl$_3$) σ ppm: |
|---|---|
| 2-407 | 8.79 (1H, d, J = 5.0 Hz), 8.51 (1H, s), 8.47 (1H, s), 7.91 (1H, s), 7.48-7.47 (2H, m), 7.41 (1H, d, J = 8.2 Hz), 3.26 (2H, d, J = 7.0 Hz), 2.14-2.08 (1H, m), 1.28 (3H, t, J = 7.3 Hz), 1.23-1.18 (2H, m), 0.91-0.87 (2H, m). |
| 2-408 | 8.80 (1H, d, J = 5.0 Hz), 8.54 (1H, s), 8.47 (1H, s), 7.97 (1H, s), 7.93 (1H, d, J = 8.2 Hz), 7.58 (1H, d, J = 8.2 Hz), 7.49 (1H, d, J = 5.0 Hz), 3.29 (2H, q, J = 7.5 Hz), 1.29 (3H, t, J = 7.6 Hz). |
| 2-409 | 8.98 (1H, d, J = 1.8 Hz), 8.80 (1H, d, J = 5.0 Hz), 8.59 (1H, s), 8.54 (1H, dd, J1 = 8.2 Hz, J2 = 1.8 Hz), 8.48 (1H, s), 8.15 (1H, s), 7.62 (1H, d, J = 7.8 Hz), 7.48 (1H, dd, J1 = 5.0 Hz, J2 = 1.4 Hz), 4.04 (3H, s), 3.35 (2H, q, J = 7.5 Hz), 1.33 (3H, t, J = 7.3 Hz). |
| 2-410 | 9.01 (1H, d, J = 2.3 Hz), 8.80 (1H, d, J = 5.0 Hz), 8.64-8.62 (2H, m), 8.48 (1H, s), 7.71 (1H, d, J = 8.2 Hz), 7.49 (1H, d, J = 5.0 Hz), 4.48 (3H, s), 3.38 (2H, q, J = 7.5 Hz), 1.34 (3H, t, J = 7.6 Hz). |
| 2-411 | 8.90 (1H, d, J = 1.8 Hz), 8.76 (1H, d, J = 5.0 Hz), 8.59 (1H, s), 8.49 (1H, dd, J1 = 8.2 Hz, J2 = 1.8 Hz), 8.43 (1H, s), 7.66 (1H, d, J = 8.2 Hz), 7.45 (1H, dd, J = 4.1 Hz), 3.35 (2H, q, J = 7.3 Hz), 2.69 (3H, s), 1.30 (3H, t, J = 7.3 Hz). |
| 2-412 | 8.80 (1H, d, J = 5.0 Hz), 8.56 (1H, s), 8.47 (1H, d, J = 0.9 Hz), 8.37 (1H, d, J = 2.3 Hz), 7.89 (1H, dd, J1 = 8.2 Hz, J2 = 2.3 Hz), 7.64 (1H, d, J = 8.2 Hz), 7.49 (1H, dd, J1 = 5.3 Hz, J2 = 1.1 Hz), 6.05 (2H, s), 3.33 (2H, q, J = 7.3 Hz), 1.29 (3H, t, J = 7.6 Hz). |
| 2-414 | 8.55-8.52 (1H, m), 8.81 (1H, d, J = 5.0 Hz), 8.15 (1H, dd, J1 = 8.2 Hz, J2 = 1.4 Hz), 7.63 (1H, d, J = 8.2 Hz), 7.45 (1H, dd, J1 = 5.0 Hz, J2 = 1.4 Hz), 3.38 (2H, q, J = 7.3 Hz), 2.64 (3H, s), 1.31 (3H, t, J = 7.3 Hz). |
| 2-415 | 8.80 (1H, d, J = 5.0 Hz), 8.51 (1H, s), 8.12 (1H, d, J = 2.3 Hz), 7.73-7.70 (1H, m), 7.54 (1H, d, J = 8.7 Hz), 7.44 (1H, dd, J1 = 5.0 Hz, J2 = 0.9 Hz), 3.35 (2H, q, J = 7.3 Hz), 1.30 (3H, t, J = 7.3 Hz). |
| 2-416 | 8.82 (1H, d, J = 5.0 Hz), 8.55 (1H, d, J = 0.9 Hz), 8.07 (1H, d, J = 2.3 Hz), 7.74 (1H, d, J = 8.7 Hz), 7.70-7.67 (1H, m), 7.48 (1H, dd, J1 = 5.3 Hz, J2 = 1.1 Hz), 4.97 (2H, br), 3.39 (2H, q, J = 7.5 Hz), 3.31 (3H, s), 1.31 (3H, t, J = 7.3 Hz). |
| 2-420 | 8.80 (1H, d, J = 5.5 Hz), 8.57 (1H, s), 8.47 (1H, s), 8.28 (1H, dd, J1 = 7.6 Hz, J2 = 1.6 Hz), 7.87 (1H, td, J1 = 7.6 Hz, J2 = 1.8 Hz), 7.82 (1H, td, J1 = 7.7 Hz, J2 = 1.7 Hz), 7.57 (1H, dd, J1 = 7.3 Hz, J2 = 1.4 Hz), 7.47 (1H, d, J = 5.0 Hz), 3.31 (2H, q, J = 7.5 Hz), 1.29 (3H, t, J = 7.6 Hz). |
| 2-423 | 8.80 (1H, d, J = 5.0 Hz), 8.57 (1H, d, J = 1.8 Hz), 8.54 (1H, s), 8.45 (1H, s), 8.18 (1H, dd, J1 = 8.2 Hz, J2 = 1.8 Hz), 7.47 (1H, d, J = 3.7 Hz), 7.27 (1H, d, J = 8.2 Hz), 3.31 (2H, q, J = 7.5 Hz), 1.30 (3H, t, J = 7.6 Hz). |
| 2-425 | 8.81 (1H, d, J = 5.0 Hz), 8.57 (1H, s), 8.46 (1H, s), 8.12 (1H, d, J = 2.3 Hz), 7.69 (1H, dd, J1 = 8.5 Hz, J2 = 1.6 Hz), 7.63 (1H, d, J = 8.7 Hz), 7.48 (1H, d, J = 5.0 Hz), 3.32 (2H, q, J = 7.5 Hz), 1.31 (3H, t, J = 7.6 Hz). |
| 2-427 | 8.87 (1H, d, J = 2.3 Hz), 8.59 (1H, s), 8.36 (1H, d, J = 8.2 Hz), 8.28 (1H, dd, J1 = 7.6 Hz, J2 = 1.6 Hz), 8.06 (1H, dd, J1 = 8.5 Hz, J2 = 2.1 Hz), 7.87 (1H, td, J1 = 7.7 Hz, J2 = 1.7 Hz), 7.82 (1H, td, J1 = 7.6 Hz, J2 = 1.6 Hz), 7.57 (1H, dd, J1 = 7.6 Hz, J2 = 1.6 Hz), 3.31 (2H, q, J = 7.5 Hz), 1.28 (3H, t, J = 7.6 Hz). |
| 2-428 | 8.59 (1H, s), 8.39 (1H, d, J = 8.2 Hz), 8.24 (1H, dd, J1 = 7.6 Hz, J2 = 1.6 Hz), 7.97 (1H, t, J = 7.8 Hz), 7.86-7.76 (2H, m), 7.62 (1H, d, J = 6.9 Hz), 7.55 (1H, dd, J1 = 7.8 Hz, J2 = 1.4 Hz), 3.35 (2H, q, J = 7.5 Hz), 1.27 (3H, t, J = 7.6 Hz). |
| 2-434 | 8.87 (1H, d, J = 1.8 Hz), 8.60 (1H, s), 8.40 (1H, d, J = 8.2 Hz), 8.05 (1H, dd, J1 = 8.2 Hz, J2 = 2.3 Hz), 7.57-7.48 (3H, m), 7.38 (1H, dd, J1 = 7.6 Hz, J2 = 1.4 Hz), 2.78 (2H, t, J = 7.3 Hz), 1.58 (2H, sext, J = 7.3 Hz), 0.94 (3H, t, J = 7.3 Hz). |
| 2-445 | 8.89 (1H, d, J = 2.3 Hz), 8.63 (1H, s), 8.37 (1H, d, J = 8.2 Hz), 8.29 (1H, dd, J1 = 7.8 Hz, J2 = 1.4 Hz), 7.78 (1H, td, J1 = 7.7 Hz, J2 = 1.2 Hz), 7.70 (1H, td, J1 = 7.7 Hz, J2 = 1.7 Hz), 7.57 (1H, dd, J1 = 7.8 Hz, J2 = 0.9 Hz), 3.30-3.23 (1H, m), 2.91-2.84 (1H, m), 2.06-1.93 (1H, m), 1.93-1.77 (1H, m), 1.09 (3H, t, J = 7.3 Hz). |
| 2-447 | 8.88 (1H, s), 8.59 (1H, s), 8.36 (1H, d, J = 8.2 Hz), 8.27 (1H, dd, J1 = 7.8 Hz, J2 = 1.8 Hz), 8.06 (1H, dd, J1 = 8.2 Hz, J2 = 2.3 Hz), 7.86 (1H, td, J1 = 7.6 Hz, J2 = 1.7 Hz), 7.82 (1H, td, J1 = 7.7 Hz, J2 = 1.5 Hz), 7.57 (1H, dd, J1 = 7.8 Hz, J2 = 1.4 Hz), 3.25 (2H, t, J = 7.8 Hz), 1.74 (2H, sext, J = 7.8 Hz), 1.00 (3H, t, J = 7.3 Hz). |
| 2-484 | 8.88 (1H, s), 8.56 (1H, s), 8.40 (1H, d, J = 8.2 Hz), 8.07 (1H, dd, J1 = 8.2 Hz, J2 = 2.3 Hz), 7.82-7.80 (1H, m), 7.58-7.56 (3H, m), 3.34 (2H, q, J = 9.5 Hz). |
| 2-485 | 8.90 (1H, dd, J1 = 2.3 Hz, J2 = 0.9 Hz), 8.70 (1H, s), 8.44 (1H, dd, J1 = 7.8 Hz, J2 = 1.4 Hz), 8.40 (1H, d, J = 8.2 Hz), 8.09 (1H, dd, J1 = 8.2 Hz, J2 = 1.8 Hz), 7.84 (1H, td, J1 = 7.7 Hz, J2 = 1.5 Hz), 7.79 (1H, td, J1 = 7.6 Hz, J2 = 1.7 Hz), 7.64 (1H, dd, J1 = 7.8 Hz, J2 = 1.4 Hz), 4.37-4.26 (1H, m), 3.64-3.53 (1H, m). |
| 3-14 | 9.10 (1H, d, J = 2.3 Hz), 8.62 (1H, d, J = 5.0 Hz), 8.31 (1H, d, J = 8.2 Hz), 8.26 (1H, s), 7.56-7.48 (3H, m), 7.43-7.37 (2H, m), 2.84 (2H, q, J = 7.3 Hz), 1.24 (3H, t, J = 7.3 Hz). |
| 3-15 | 9.29 (1H, d, J = 1.8 Hz), 8.88 (1H, d, J = 1.4 Hz), 8.55 (1H, t, J = 1.8 Hz), 8.33 (1H, s), 7.57-7.50 (3H, m), 7.40 (1H, td, J1 = 7.6 Hz, J2 = 1.7 Hz), 2.85 (2H, q, J = 7.3 Hz), 1.25 (3H, t, J = 7.3 Hz). |
| 3-29 | 8.64 (1H, d, J = 4.6 Hz), 8.57 (1H, s), 7.85 (1H, t, J = 8.0 Hz), 7.76 (1H, t, J = 7.6 Hz), 7.69 (1H, t, J = 7.6 Hz), 7.56 (1H, d, J = 7.8 Hz), 7.31 (1H, dd, J1 = 7.6 Hz, J2 = 4.8 Hz), 3.39-3.30 (1H, m), 2.96-2.87 (1H, m), 1.37 (3H, t, J = 7.6 Hz). |
| 3-30 | 9.29 (1H, d, J = 1.8 Hz), 8.92 (1H, d, J = 0.9 Hz), 8.54 (1H, s), 8.36 (1H, s), 8.27 (1H, dd, J1 = 8.0 Hz, J2 = 1.6 Hz), 7.80 (1H, td, J1 = 7.7 Hz, J2 = 1.2 Hz), 7.72 (1H, td, J1 = 7.6 Hz, J2 = 1.4 Hz), 7.57 (1H, dd, J1 = 7.8 Hz, J2 = 0.9 Hz), 3.32 (1H, m), 2.93 (1H, m), 1.37 (3H, t, J = 7.6 Hz). |
| 3-45 | 9.26 (1H, d, J = 1.8 Hz), 8.86 (1H, d, J = 1.4 Hz), 8.49 (1H, s), 8.43 (1H, s), 8.22 (1H, dd, J1 = 7.8 Hz, J2 = 1.8 Hz), 7.86 (1H, td, J1 = 7.6 Hz, J2 = 1.7 Hz), 7.81 (1H, td, J1 = 7.6 Hz, J2 = 1.4 Hz), 7.59 (1H, dd, J1 = 7.8 Hz, J2 = 1.4 Hz), 3.27 (2H, q, J = 7.5 Hz), 1.26 (3H, t, J = 7.3 Hz). |
| 4-10 | 8.71 (1H, s), 8.32 (1H, s), 8.32 (1H, s), 7.83 (1H, d, J = 5.0 Hz), 7.56-7.49 (3H, m), 7.39 (1H, t, J = 7.6 Hz), 2.83 (2H, q, J = 7.3 Hz), 1.24 (3H, t, J = 7.3 Hz). |

TABLE 5-continued

| Compound No. | $^1$H-NMR Spectrum (CDCl$_3$) σ ppm: |
|---|---|
| 4-25 | 8.74 (2H, d, J = 5.0 Hz), 8.31 (1H, s), 8.26 (1H, d, J = 8.2 Hz), 7.81-7.79 (3H, m), 7.71 (1H, t, J = 7.6 Hz), 7.55 (1H, d, J = 8.2 Hz), 3.35-3.26 (1H, m), 2.96-2.87 (1H, m), 1.36 (3H, t, J = 7.3 Hz). |

<Formulation>

Specific examples of the method for formulating the compound of the present invention as an agricultural/horticultural insecticide or acaricide are described below in Formulation Examples 1 to 5.

Formulation Example 1: Dust

A dust containing 2 wt % of an active agent can be obtained by uniformly pulverizing and mixing a mixture of the compound (1-631) (2 parts by weight) of Synthesis Example 1, PAP (isopropylphosphoric acid ester) (1 part by weight) and clay (97 parts by weight). Furthermore, each dust can be obtained by the same method except for using the corresponding compound shown in Tables 1 to 4 in place of the compound of Synthesis Example 1.

Formulation Example 2: Wettable Powder

A wettable powder containing 20 wt % of an active agent can be obtained by uniformly pulverizing and mixing a mixture of the compound (1-631) (20 parts by weight) of Synthesis Example 1, sodium alkylbenzenesulfonate (3 parts by weight), polyoxyethylene alkylphenyl ether (5 parts by weight), and terra alba (72 parts by weight). Furthermore, each wettable powder can be obtained by the same method except for using the corresponding compound shown in Tables 1 to 4 in place of the compound of Synthesis Example 1.

Formulation Example 3: Emulsifiable Concentrate

An emulsifiable concentrate containing 30 wt % of an active agent can be obtained by mixing and dissolving the compound (1-631) (30 parts by weight) of Synthesis Example 1, methylnaphthalene (40 parts by weight), and polyoxyethylene alkylphenyl ether (30 parts by weight). Furthermore, each emulsifiable concentrate can be obtained by the same method except for using the corresponding compound shown in Tables 1 to 4 in place of the compound of Synthesis Example 1.

Formulation Example 4: Flowable Formulation

A flowable formulation containing 25 wt % of an active agent can be obtained by uniformly mixing a mixture of the compound (1-631) (25 parts by weight) of Synthesis Example 1, polyoxyethylene alkyl ether (1 part by weight), sodium alkylnaphthalenesulfonate (1 part by weight), xanthane gum (1 part by weight) and water (72 parts by weight). Furthermore, each flowable formulation can be obtained by the same method except for using the corresponding compound shown in Tables 1 to 4 in place of the compound of Synthesis Example 1.

Formulation Example 5: Granule

A granule containing 5 wt % of an active agent can be obtained by further adding water (15 parts by weight) to a mixture of the compound (1-631) (5 parts by weight) of Synthesis Example 1, sodium laurylsulfate (1 part by weight), calcium ligninsulfonate (5 parts by weight), bentonite (30 parts by weight) and clay (59 parts by weight), followed by kneading in a kneader, granulating in a granulator, and drying in a fluid drier. Furthermore, each granule can be obtained by the same method except for using the corresponding compound shown in Tables 1 to 4 in place of the compound (1-631) of Synthesis Example 1.

Specific examples of the evaluation for the control effect of the pest control agent according to the present invention obtained above are described below in Test Examples 1 to 5.

Test Example-1: *Spodoptera litura* Control Test

Cabbage seedlings grown in a cell tray were placed on a turntable, and 30 mL of a diluted emulsifiable concentrate (500 ppm) prepared according to Formulation Example 3 was uniformly sprayed thereon by means of a spray gun. After air drying, the seedlings were put in a plastic container having a cover perforated with air vents, and five *Spodoptera litura* at second instar larvae were released in each container, and the containers were placed in a constant temperature chamber at 25° C. (with lighting for 16 hours). Four days after the release, the number of surviving larvae was investigated, and the mortality rate (%) was calculated according to the following calculating formula (a). Test was conducted in duplicate.

Mortality rate (%)={1−(number of surviving larvae on investigation day in treatment plot/number of surviving larvae on investigation day in non-treatment plot)}×100   Formula (a):

As representative examples, compounds of Compound Nos. 1-75, 1-81, 1-82, 1-83, 1-85, 1-86, 1-87, 1-88, 1-91, 1-197, 1-229, 1-236, 1-243, 1-251, 1-255, 1-278, 1-305, 1-310, 1-319, 1-336, 1-354, 1-360, 1-361, 1-363, 1-364, 1-365, 1-366, 1-367, 1-369, 1-370, 1-475, 1-507, 1-513, 1-520, 1-528, 1-536, 1-552, 1-554, 1-555, 1-562, 1-587, 1-596, 1-631, 1-637, 1-638, 1-639, 1-640, 1-641, 1-642, 1-643, 1-644, 1-646, 1-647, 1-752, 1-784, 1-786, 1-790, 1-791, 1-798, 1-802, 1-805, 1-806, 1-809, 1-810, 1-815, 1-820, 1-823, 1-830, 1-831, 1-832, 1-833, 1-860, 1-862, 1-867, 1-869, 2-30, 2-32, 2-33, 2-91, 2-96, 2-97, 2-99, 2-100, 2-102, 2-107, 2-112, 2-113, 2-127, 2-134, 2-135, 2-140, 2-143, 2-145, 2-147, 2-169, 2-171, 2-172, 2-230, 2-234, 2-235, 2-236, 2-238, 2-239, 2-241, 2-246, 2-252, 2-261, 2-262, 2-267, 2-275, 2-283, 2-285, 2-295, 2-297, 2-299, 2-309, 2-311, 2-312, 2-322, 2-323, 2-325, 2-329, 2-330, 2-332, 2-351, 2-353, 2-367, 2-370, 2-374, 2-375, 2-376, 2-377, 2-378, 2-379, 2-381, 2-386, 2-388, 2-389, 2-392, 2-393, 2-397, 2-398, 2-401, 2-402, 2-407, 2-408, 2-409, 2-410, 2-411, 2-414, 2-415, 2-420, 2-423, 2-425, 2-427, 3-14, 3-15, 3-29, 3-30, 3-45, 4-10, and 4-25 showed a mortality rate of 80% or more.

Test Example-2: *Nilaparvata lugens* Control Test

Sprouted rice seedlings grown in a plastic cup were placed on a turntable, and 30 mL of a diluted emulsifiable concentrate (500 ppm) prepared according to Formulation Example 3 was uniformly sprayed thereon by means of a spray gun. After air drying, the seedlings were put in a polycarbonate-made plastic container having a cover provided with nylon gauze, and ten *Nilaparvata lugens* at fourth instar larvae were released in each container, and the containers were placed in a constant temperature chamber at 25° C. (with lighting for 16 hours). Five days after the release, the number of surviving larvae was investigated, and the mortality rate (%) was calculated according to the following calculating formula (a). Test was conducted in duplicate.

Mortality rate (%)={1−(number of surviving larvae on investigation day in treatment plot/number of surviving larvae on investigation day in non-treatment plot)}×100    Formula (a):

As representative examples, compounds of Compound Nos. 1-56, 1-83, 1-488, 1-578, 2-147, 2-409, 2-414, 2-427, 3-14, and 4-25 showed a mortality rate of 80% or more.

Test Example-3: *Aphis craccivora* Control Test

Three apterous adults of *Aphis craccivora* were released on each of broad bean (*Vicia faba*) seedlings grown in a plastic cup. One day after the release, the board bean seedlings were placed on a turntable, and 30 mL of a diluted emulsifiable concentrate (500 ppm) prepared according to Formulation Example 3 was uniformly sprayed thereon by means of a spray gun. After the treatment, the seedlings were placed in a constant temperature chamber at 25° C. (with lighting for 16 hours). Four days after the treatment, the number of parasitic adults and larvae was investigated, and the preventive value (%) was calculated according to the following calculating formula (b). Test was conducted in duplicate.

Preventive value (%)={1−(number of parasitic insects on investigation day in treatment plot/number of parasitic insects on investigation day in non-treatment plot)}×100    Formula (b):

As representative examples, compounds of Compound Nos. 1-26, 1-232, 1-275, 1-510, 2-91, 2-100, 2-140, 2-230, 2-370, 2-375, 2-379, 2-407, 2-408, 2-420, 2-423, 3-15, and 3-45 showed a preventive value of 80% or more.

Test Example-4: *Tetranychus urticae* Control Test

Ten female adults of *Tetranychus urticae* were released on each of bean seedlings grown in a plastic cup. One day after the release, the bean seedlings were placed on a turntable, and 30 mL of a diluted emulsifiable concentrate (500 ppm) prepared according to Formulation Example 3 was uniformly sprayed thereon by means of a spray gun. After the treatment, the seedlings were placed in a constant temperature chamber at 25° C. (with lighting for 16 hours). Eight days after the treatment, the number of surviving parasitic insects was investigated, and the preventive value (%) was calculated according to the following calculating formula (b). Test was conducted in duplicate.

Preventive value (%)={1−(number of parasitic insects on investigation day in treatment plot/number of parasitic insects on investigation day in non-treatment plot)}×100    Formula (b):

As representative examples, compound of Compound No. 1-834 showed a preventive value of 80% or more.

INDUSTRIAL APPLICABILITY

According to the present invention, a novel 1,2,3-triazole derivative offering an excellent insecticidal or acaricidal effect and an insecticide or acaricide containing the 1,2,3-triazole derivative can be provided.

While the invention has been described in detail and with reference to specific embodiments thereof, it will be apparent to one skilled in the art that various changes and modifications can be made therein without departing from the spirit and scope of the invention.

This application is based on Japanese Patent Application (Patent Application No. 2015-233791) filed on Nov. 30, 2015, the contents of which are incorporated herein by way of reference.

The invention claimed is:

1. A 1,2,3-triazole derivative represented by the following formula (1):

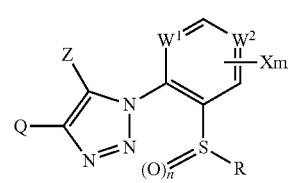

(1)

wherein in the formula (1):
R is an ethyl group;
n represents an integer of 0 to 2;
$W^1$ and $W^2$ are CH;
X is a hydrogen atom, a halogen atom, a cyano group, a C1-C6 alkyl group that may be substituted with a cyano group, a C3-C6 cycloalkyl group that may be substituted with a cyano group, a C1-C6 alkoxy group, a C1-C6 haloalkyl group that may be substituted with a cyano group, a C1-C6 haloalkoxy group, a C1-C6 alkylcarbonyl group, a C1-C6 alkylthio group, a C1-C6 alkylsulfinyl group, a C1-C6 alkylsulfonyl group, a C1-C6 haloalkylthio group, a C1-C6 haloalkylsulfinyl group, a C1-C6 haloalkylsulfonyl group, a C1-C6 alkylamino group, a (C1-C6 alkoxy)carbonyl group, a di(C1-C6 alkyl)amino group, a (C1-C6 alkyl)carbonylamino group, a (C1-C6 alkyl)carbonyl(C1-C6 alkyl) amino group, an N—(C1-C6 alkyl)carbamoyl group, an N,N'-di(C1-C6 alkyl)carbamoyl group, a pentafluorosulfanyl group, or an aryl group that may be substituted with a halogen atom;
m represents an integer of 1 to 4 and when m represents an integer of 2 or more, respective X may be the same or different;
Q is a pyridyl group that may be substituted with one or more groups selected from the group consisting of a halogen atom, a cyano group, a C1-C6 alkyl group that may be substituted with a cyano group, a C3-C6 cycloalkyl group that may be substituted with a cyano group, a C1-C6 alkoxy group, a C1-C6 haloalkyl group that may be substituted with a cyano group, a C1-C6 haloalkoxy group, a C1-C6 alkylthio group, a C1-C6 haloalkylthio group, a C1-C6 alkylsulfinyl group, a C1-C6 alkylsulfonyl group, a C1-C6 alkylcarbonyl group, a C1-C6 haloalkylcarbonyl group, and a pentafluorosulfanyl group; and
Z is a hydrogen atom, a halogen atom, or a C1-C6 alkyl group.

2. An insecticide or acaricide containing the 1,2,3-triazole derivative according to claim 1 as an active ingredient.

* * * * *